United States Patent [19]

Chen et al.

[11] Patent Number: 5,578,593
[45] Date of Patent: Nov. 26, 1996

[54] SPIRO PIPERIDINES AND HOMOLOGS PROMOTE RELEASE OF GROWTH HORMONE

[75] Inventors: Meng-Hsin Chen, Westfield; David B. R. Johnston, Warren; Ravi P. Nargund, East Brunswick; Arthur A. Patchett; James R. Tata, both of Westfield; Lihu Yang, Edison, all of N.J.

[73] Assignee: Merck & Co., Inc., Rahway, N.J.

[21] Appl. No.: 146,848

[22] Filed: Nov. 3, 1993

Related U.S. Application Data

[63] Continuation-in-part of Ser. No. 989,322, Dec. 11, 1992, abandoned.

[51] Int. Cl.[6] .................... A61K 31/55; A61K 31/44; C07D 401/00; C07D 471/00
[52] U.S. Cl. .................. 514/212; 514/222.2; 514/278.8; 514/247; 514/278; 514/825; 540/543; 544/6; 544/70; 544/230; 546/17; 546/18
[58] Field of Search ........................... 546/205, 206, 546/17, 18; 540/543; 544/6, 70, 230; 514/825, 278, 212, 222.2, 228.8, 247

[56] References Cited

FOREIGN PATENT DOCUMENTS

| | | |
|---|---|---|
| 0144230A3 | 6/1985 | European Pat. Off. . |
| 0431943A2 | 6/1991 | European Pat. Off. . |
| 0513974A1 | 11/1992 | European Pat. Off. . |

OTHER PUBLICATIONS

*Chemical Abstract* vol. 116, No. 2,0938d, Baldwin et al, (1991), Prep. of anylheterocyclspiropiperidines as class III antiarlythias and enhoties.

*Primary Examiner*—C. Warren Ivy
*Assistant Examiner*—Raymond Covington
*Attorney, Agent, or Firm*—J. Eric Thies; David L. Rose

[57] ABSTRACT

There are disclosed certain novel compounds identified as spiro piperidines and homologs which promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone. Growth hormone releasing compositions containing such spiro compounds as the active ingredient thereof are also disclosed.

17 Claims, No Drawings

SPIRO PIPERIDINES AND HOMOLOGS PROMOTE RELEASE OF GROWTH HORMONE

CROSS REFERENCE TO RELATED APPLICATIONS

This application is a continuation-in-part of our application Serial No. 07/989,322 filed 11 Dec. 1992, now abandoned.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth s hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carded with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptide analogs for promoting the release of growth hormone which are stable in a variety of physiological environments and which may be administered parenterally, nasally or by the oral route.

SUMMARY OF THE INVENTION

The instant invention covers certain spiro piperidine compounds and homologs thereof which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the spiro compounds. It is a further object of this invention to describe procedures for the preparation of such compounds. A still further object is to describe the use of such compounds to increase the secretion of growth hormone in humans and animals. A still further object of this invention is to describe compositions containing the spiro piperidine compounds and homologs thereof for the use of treating humans and animals so as to increase the level of growth hormone secretions. Further objects will become apparent from a reading of the following description.

DESCRIPTION OF THE INVENTION

The novel spiro piperidines and homologs of the instant invention are best described in the following structural formulas I and II:

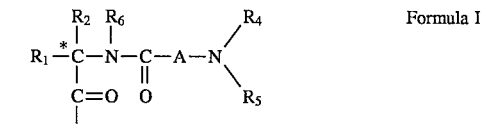

Formula I

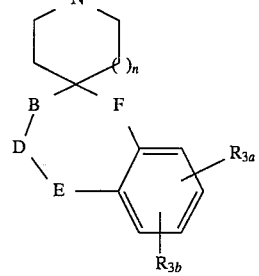

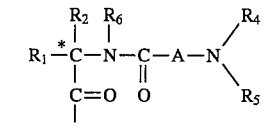

Formula II

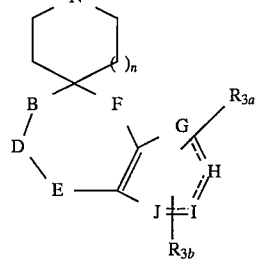

$R_1$ is $C_1$–$C_{10}$ alkyl, aryl, aryl ($C_1$–$C_6$ alkyl) and $C_3$–$C_7$ cycloalkyl ($C_1$–$C_6$alkyl) or $C_1$–$C_5$alkyl-K-$C_1$–$C_5$ alkyl, aryl($C_0$–$C_5$alkyl)-K-($C_1$–$C_5$ alkyl), $C_3$–$C_7$ cycloalkyl($C_0$–$C_5$ alkyl)-K-($C_1$–$C_5$ alkyl) where K is O, S(O)$_m$, N(R$_2$)C(O), C(O)N(R$_2$), OC(O), C(O)O, —CR$_2$=CR$_2$- or —C≡C— where the aryl groups are defined below and $R_2$ and the alkyl groups may be futher substituted by 1–5 halogen, S(O)$_m$R$_{2a}$, 1 to 3 of OR$_{2a}$ or C(O)OR$_{2a}$ and the aryl groups may be further substituted by phenyl, phenoxy, halophenyl, 1 to 3 of $C_1$–$C_6$ alkyl, 1 to 3 of halogen, 1 to 2 of OR$_2$, methylenedioxy, S(O)$_m$R$_2$, 1 to 2 of CF$_3$, OCF$_3$, nitro, N(R$_2$)(R$_2$), N(R$_2$)C(O)(R$_2$), C(O)OR$_2$, C(O)N(R$_2$)(R$_2$), SO$_2$N(R$_2$)(R$_2$), N(R$_2$)SO$_2$ aryl or N(R$_2$)SO$_2$R$_2$ R$_2$ is hydrogen, C$_1$–C$_6$ alkyl, C$_3$–C$_7$ cycloalkyl, and where two C$_1$–C$_6$ alkyl groups are present on one atom, they may be optionally joined to form a C$_3$-C$_8$ cyclic ting optionally including oxygen, sulfur or NR$_{2a}$;

R$_{2a}$ is hydrogen or C$_1$–C$_6$ alkyl;

R$_{3a}$ and R$_{3b}$ are independently hydrogen, halogen, C$_1$–C$_6$ alkyl, OR$_2$, cyano, OCF$_3$, methylenedioxy, nitro, S(O)$_m$R, CF$_3$ or C(O)OR$_2$, and when R$_{3a}$ and R$_{3b}$ are in an ortho arrangement they may be joined to form a C$_5$ to C$_8$ aliphatic or aromatic ring optionally icluding 1 or 2 heteroatoms selected from oxygen,sulfer, or nitrogen;

R$_4$ and R$_5$ are independently hydrogen, C$_1$–C$_6$ alkyl, substituted C$_1$–C$_6$ alkyl where the substituents may be 1 to 5 halo, 1 to 3 hydroxy, 1 to 3 C$_1$–C$_{10}$ alkanoyloxy, 1 to 3 C$_1$–C$_6$ alkoxy, phenyl, phenoxy, 2-furyl, C$_1$–C$_6$ alkoxycarbonyl, S(O)$_m$(C$_1$–C$_6$ alkyl); or R$_4$ and R$_5$ can be taken together to form —(CH$_2$)$_r$L$_a$(CH$_2$)$_s$— where L$_a$ is C(R$_2$)$_2$, O, S(O)$_m$ or N(R$_2$), r and s are independently 1 to 3 and R$_2$ is as defined above;

R$_6$ is hydrogen or C$_1$–C$_6$ alkyl;

A is:

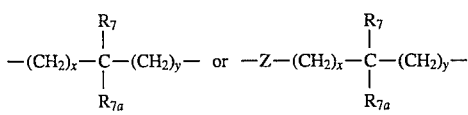

where x and y are independently 0–3;

Z is N—R$_2$ or O;

R$_7$ and R$_{7a}$ are independently hydrogen, C$_1$–C$_6$ alkyl, trifluoromethyl, phenyl, substituted C$_1$–C$_6$ alkyl where the substituents are imidazolyl, phenyl, indolyl, p-hydroxyphenyl, OR$_2$, S(O)$_m$R$_2$, C(O)OR$_2$, C$_3$–C$_7$ cycloalkyl, N(R$_2$)(R$_2$), C(O)N(R$_2$)(R$_2$); or R$_7$ and R$_{7a}$ can independently be joined to one or both of R$_4$ and R$_5$ groups to form alkylene bridges between the terminal nitrogen and the alkyl portion of the R$_7$ or R$_{7a}$ groups, wherein the bridge contains 1 to 5 carbons atoms;

B, D, E, and F are independently C(R$_8$)(R$_{10}$), or C=O, such that one or two of B,D,E, or F may be optionally missing to provide a 5, 6, or 7 membered ring; or B and D or D and E taken together may be CR$_8$=CR$_{10}$, where CR$_8$=CR$_{10}$ may include a benzofusion in which R$_8$ and R$_{10}$ ethylene units are linked to form a phenyl ring;

R$_8$ and R$_{10}$ are independently hydrogen, R$_2$, (CH$_2$)$_q$aryl, (CH$_2$)$_q$O(R$_2$), (CH$_2$)$_q$O(CH$_2$)$_t$aryl, (CH$_2$)$_q$OC(O)R$_2$, (CH$_2$)$_q$OC(O)(CH$_2$)$_t$aryl, (CH$_2$)$_q$OC(O)N(R$_2$)(R$_2$), (CH$_2$)$_q$OC(O)N(R$_2$)(CH$_2$)$_t$aryl, (CH$_2$)$_q$C(O)R$_2$, (CH$_2$)$_q$C(O)(CH$_2$)$_t$aryl, (CH$_2$)$_q$C(O)OR$_2$, (CH$_2$)$_q$C(O)O(CH$_2$)$_t$aryl, (CH$_2$)$_q$C(O)N(R$_2$)(R$_2$), (CH$_2$)$_q$C(O)N(R$_2$)(CH$_2$)$_t$aryl, (CH$_2$)$_q$N(R$_2$)(R$_2$), (CH$_2$)$_q$N(R$_2$)(R$_9$), (CH$_2$)$_q$S(O)$_m$R$_2$, (CH$_2$)$_q$S(O)$_m$(CH$_2$)$_t$aryl, (CH$_2$)$_q$SO$_2$N(R$_2$)(R$_2$), (CH$_2$)$_q$SO$_2$N(R$_2$)(CH$_2$)$_t$aryl, (CH$_2$)$_q$(1H-tetrazol-5-yl), (CH$_2$)$_q$C(O)NHSO$_2$R$_2$, (CH$_2$)$_q$C(O)NHSO$_2$(CH$_2$)$_t$aryl, (CH$_2$)$_q$SO$_2$NHC(O)R$_2$, (CH$_2$)$_q$SO$_2$NHC(O)(CH$_2$)$_t$aryl, (CH$_2$)$_q$SO$_2$NH(CH$_2$)$_t$aryl, (CH$_2$)$_q$SO$_2$NH—C≡N and the (CH$_2$)$_t$ may be substituted by 1 to 2 C$_{1-4}$ alkyl and the R$_2$, (CH$_2$)$_q$ and aryl groups may optionally be substituted by 1 to 5 halogen, 1 to 3OR$_{2a}$, C(O)OR$_{2a}$, C(O)O(CH$_2$)$_t$aryl, 1 to 3 C$_1$–C$_4$ alkyl, C(O)N(R$_{2a}$)(R$_{2a}$), SO$_2$N(R$_{2a}$)(R$_{2a}$), S(O)$_m$R$_{2a}$, N(R$_{2a}$)(R$_{2a}$), 1 to 2 CF$_3$, or 1H-tetrazol-5-yl;

R$_9$ is R$_2$, (CH$_2$)$_q$ aryl, C(O)R$_2$, C(O)(CH$_2$)$_t$ aryl, C(O)N(R$_2$)(R$_2$), C(O)N(R$_2$)(CH$_2$)$_t$ aryl, C(O)OR$_2$, C(O)O(CH$_2$)$_t$ aryl, S(O)$_2$N(R$_2$)(R$_2$), SO$_2$N(R$_2$)(CH$_2$)$_t$ aryl, SO$_2$R$_2$ or SO$_2$(CH$_2$)$_t$ aryl and the (CH$_2$)$_t$ may be substituted by 1 to 2 C$_1$–C$_4$ alkyl and the R$_2$, (CH$_2$)$_q$ and aryl groups may optionally be substituted by 1 to 5 halogen, 1 to 3 OR$_{2a}$, C(O)OR$_{2a}$, C(O)O(CH$_2$)$_t$ aryl, 1 to 3 C$_1$–C$_4$ alkyl, C(O)N(R$_{2a}$)(R$_{2a}$), SO$_2$N(R$_{2a}$)(R$_{2a}$), S(O)$_m$R$_{2a}$, N(R$_{2a}$)(R$_{2a}$) or 1 to 2 CF$_3$.

m is 0 to 2;

n is 1 or 2;

q is 0 to 3;

t is 0 to 3; and

G, H, I and J are carbon, nitrogen, sulfur or oxygen atoms, such that at least one is a heteroatom and one of G, H, I or J may be optionally missing to afford 5 or 6 membered heterocyclic aromatic rings; and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, ethinyl, propenyl, butadienyl, hexenyl and the like.

The alkoxy groups specified above are intended to include those alkoxy groups of the designated length in either a straight or branched configuration which may optionally contain double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propinyloxy, isobutenyloxy, hexenyloxy and the like.

The term "halogen" is intended to include the halogen atom fluorine, chlorine, bromine and iodine.

The term "aryl" is intended to include phenyl and naphthyl and aromatic residues of 5- and 6-membered rings with 1 to 3 heteroatoms or fused 5 or 6 membered bicyclic rings with 1 to 3 heteroatoms of nitrogen, sulfur or oxygen. Examples of such heterocyclic aromatic rings are pyridine, thiophene, furan, benzothiophene, tetrazole, indole, N-methylindole, dihydroindole, indazole, N-formylindole, benzimidazole, thiazole, pyrimidine, and thiadiazole.

Certain of the above defined terms may occur more than once in the above formula and upon such occurrence each term shall be defined independently of the other.

Preferred compounds of the instant invention are:

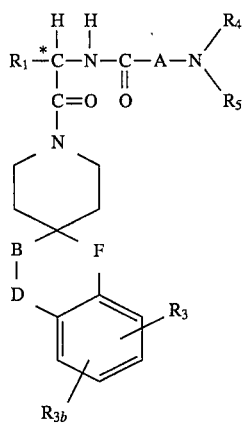

Formula III where $R_1$ is $C_1$–$C_{10}$ alkyl, aryl ($C_1$–$C_4$ alkyl), $C_3$–$C_6$ cycloalkyl ($C_1$–$C_4$ alkyl), ($C_1$–$C_4$ alkyl)-K-($C_1$–$C_4$ alkyl), aryl($C_0$–$C_5$alkyl)-K-($C_1$–$C_4$ alkyl), ($C_3$–$C_7$cycloalkyl)($C_0$–$C_5$ alkyl)-K-($C_1$–$C_4$alkyl) where K is O, S(O)$_m$, —CR$_2$=CR$_2$— or —C≡C—; or N(R$_2$)C(O) where $R_2$ and the alkyl groups may be further substituted by 1 to 7 halogen, S(O)$_m$C$_1$–C$_4$alkyl, 1 to 2 OR$_2$ or C(O)OR$_{2a}$ and the aryl groups may be further substituted by 1 to 2 $C_1$–$C_4$ alkyl, 1 to 2 halogen, OR$_2$, CF$_3$, OCF$_3$, methylenedioxy, S(O)$_m$R$_{2a}$, SO$_2$N(R$_{2a}$)(R$_{2a}$) or N(R$_{2a}$)SO$_2$R$_{2a}$;

$R_2$ is hydrogen, $C_1$–$C_6$ alkyl, $C_3$–$C_7$cycloalkyl, and, if two $C_1$–$C_6$ alkyl groups are present on one atom, they may be optionally joined to form a $C_4$–$C_6$ cyclic ring optionally including oxygen, sulfur or NR$_{2a}$;

$R_{2a}$ is hydrogen or $C_1$–$C_6$ alkyl;

$R_{3a}$ and $R_{3b}$ are independently hydrogen, halogen, $C_1$–$C_4$ alkyl, OR$_2$, methylenedioxy, nitro, S(O)$_m$C$_1$–C$_4$alkyl, CF$_3$ or C(O)OR$_2$;

$R_4$ and $R_5$ are independently hydrogen, $C_1$–$C_6$ alkyl, substituted $C_1$–$C_6$ alkyl where the substituents may be 1 to 5 halo, 1 to 2 hydroxy, 1 to 2 $C_1$–$C_6$ alkanoyloxy, 1 to 2 $C_1$–$C_6$ alkyloxy or S(O)$_m$(C$_1$–C$_4$ alkyl);

A is:

$$-(CH_2)_x-\underset{\underset{R_{7a}}{|}}{\overset{\overset{R_7}{|}}{C}}-(CH_2)_y-$$

or $$-N(R_2)-(CH_2)_x-\underset{\underset{R_{7a}}{|}}{\overset{\overset{R_7}{|}}{C}}-(CH_2)_y-$$

where x and y are independently 0–3;

$R_7$ and $R_{7a}$ are independently hydrogen, $C_1$–$C_4$ alkyl, substituted $C_1$–$C_4$ alkyl where the substituents are from 1 to 3 fluoro or imidazolyl, phenyl, indolyl, S(O)$_m$C$_1$–C$_4$alkyl, C(O)OR$_2$ or $R_7$ and $R_{7a}$ can independently be joined to one or both of the $R_4$ and $R_5$ groups to form alkylene bridges between the terminal nitrogen and the alkyl portion of the $R_7$ or $R_{7a}$ groups, wherein the bridges contains 1 to 3 carbon atoms;

B, D and F are independently C(R$_8$)(R$_{10}$) or C=O, such that one of B, D or F may be optionally missing to provide a 5 or 6 membered ring; or B and D taken together may be CR$_8$=CR$_{10}$ and CR$_8$=CR$_{10}$ may include a benzofusion in which R$_8$ and R$_{10}$ ethylene units are linked to form a phenyl ring;

$R_8$ and $R_{10}$ are independently hydrogen, R$_2$, (CH$_2$)$_q$ aryl, (CH$_2$)$_q$OR$_2$, (CH$_2$)$_q$O(CH$_2$)$_t$aryl (CH$_2$)$_q$OC(O)R$_2$, (CH$_2$)$_q$C(O)OR$_2$, (CH$_2$)$_q$C(O)O(CH$_2$)$_t$ aryl, (CH$_2$)$_q$C(O)N(R$_2$)(R$_2$), (CH$_2$)$_q$C(O)N(R$_2$)(CH$_2$)$_t$ aryl, (CH$_2$)$_q$N(R$_2$)C(O)R$_2$, (CH$_2$)$_q$N(R$_2$)C(O)(CH$_2$)$_t$ aryl, (CH$_2$)$_q$N(R$_2$)C(O)N(R$_2$)(R$_2$), (CH$_2$)$_q$N(R$_2$)C(O)N(R$_2$)(CH$_2$)$_t$ aryl, (CH$_2$)$_q$N(R$_2$)SO$_2$R$_2$, (CH$_2$)$_q$N(R$_2$)SO$_2$(CH$_2$)$_t$ aryl, (CH$_2$)$_q$S(O)$_m$R$_2$, (CH$_2$)$_q$S(O)$_m$(CH$_2$)$_t$ aryl, (CH$_2$)$_q$S(O)$_m$N(H)CN, (CH$_2$)$_q$(1H-tetrazol-5-yl), (CH$_2$)$_q$C(O)NHSO$_2$R$_2$, (CH$_2$)$_q$C(O)NHSO$_2$(CH$_2$)$_t$ aryl, (CH$_2$)$_q$SO$_2$NH(CH$_2$)$_t$ aryl, (CH$_2$)$_q$SO$_2$NHC(O)R$_2$, (CH$_2$)$_q$SO$_2$NHC(O)CH$_2$)$_t$ aryl and the (CH$_2$)$_t$ and (CH$_2$)$_q$ may be substituted by 1 to 2 $C_1$–$C_2$ alkyl and the R$_2$ and aryl groups may optionally be substituted by 1 to 2 halogens, OR$_{2a}$, C(O)OR$_{2a}$,C(O)O(CH$_2$)$_t$ aryl, S(O)$_m$C$_1$–C$_4$ alkyl, 1 to 2 $C_1$–$C_3$ alkyl or 1H-tetrazol-5-yl;

m is 0 to 2;

q is 0 to 3;

t is 0 to 3; and the aryl group is phenyl, napthyl, pyridyl, thienyl, furanyl, indolyl, N-methyl indolyl, thiazolyl, or pyrimidinyl and the pharmaceutically acceptable salts and individual diasteromers thereof.

Still further preferred compounds are realized when F is not present in Formula III.

Thus, more preferred compounds of the instant invention are realized in structural Formula IV.

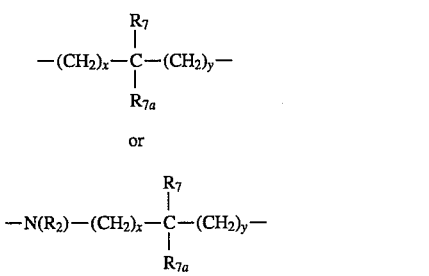

IV $R_1$ is $C_1$–$C_{10}$ alkyl, aryl ($C_1$–$C_4$ alkyl), $C_5$–$C_6$cycloalkyl ($C_1$–$C_4$ alkyl) or ($C_1$–$C_4$ alkyl)-K-$C_1$–$C_2$alkyl-, aryl($C_0$–$C_2$alkyl)-K-($C_1$–$C_2$ alkyl), $C_3$–$C_6$cycloalkyl ($C_0$–$C_2$alkyl)-K-($C_1$–$C_2$alkyl), where K is O,S(O)$_m$ and the aryl groups may be further substituted by 1 to 2 $C_1$–$C_4$ alkyl, 1 to 2 OR$_2$, C(O)OR$_2$, S(O)$_m$R$_2$ or 1 to 3 halogen;

$R_2$ is hydrogen, $C_1$–$C_4$ alkyl, $C_3$–$C_6$ cycloalkyl, and, if two $C_1$–$C_4$ alkyls are present on one atom, they may be optionally joined to form a $C_5$–$C_6$ cyclic ring optionally including oxygen or NR$_{2a}$;

$R_{2a}$ is hydrogen or $C_1$–$C_4$ alkyl;

$R_{3a}$ and $R_{3b}$ are independently hydrogen, halogen, $C_1$–$C_4$ alkyl, hydroxy, C(O)OR$_2$, hydroxy, $C_1$–$C_4$ alkoxy, S(O)$_m$C$_1$–C$_4$ alkyl or CF$_3$;

$R_4$ and $R_5$ are independently hydrogen, $C_1$–$C_4$ alkyl, substituted $C_1$–$C_4$ alkyl where the substituents may be 1 to 2 hydroxy or S(O)$_m$ ($C_1$–$C_3$alkyl);

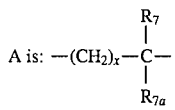

where x is 0 or 1;

R$_7$ and R$_{7a}$ are independently hydrogen, C$_1$–C$_3$ alkyl; or R$_7$ and R$_{7a}$ can independently be joined to one or both of the R$_4$ and R$_5$ groups to form alkylene bridges between the terminal nitrogen and the alkyl portion of the R$_7$ or R$_{7a}$ groups to form 5 or 6 membered rings containing the terminal nitrogen;

B and D are independently C(R$_8$)(R$_{10}$), C=O, or B and D taken together may be CR$_8$=CR$_{10}$;

R$_8$ and R$_{10}$ are independently hydrogen, R$_2$, (CH$_2$)$_q$ aryl, (CH$_2$)$_q$OR$_2$, (CH$_2$)$_q$O(CH$_2$)$_t$ aryl, (CH$_2$)$_q$OC(O)R$_2$, (CH$_2$)$_q$C(O)OR$_2$, (CH$_2$)$_q$C(O)O(CH$_2$)$_t$ aryl, (CH$_2$)$_q$C(O)N(R$_2$)(R$_2$), (CH$_2$)$_q$C(O)N(R$_2$)(CH$_2$)$_t$ aryl, (CH$_2$)$_q$N(R$_2$)C(O)R$_2$, (CH$_2$)$_q$N(R$_2$)C(O)(CH$_2$)$_t$aryl, (CH$_2$)$_q$N(R$_2$)C(O)N(R$_2$)(R$_2$), (CH$_2$)$_q$N(R$_2$)C(O)N(R$_2$)(CH$_2$)$_t$ aryl, (CH$_2$)$_q$N(R$_2$)SO$_2$R$_2$, (CH$_2$)$_q$N(R$_2$)SO$_2$(CH$_2$)$_t$ aryl, (CH$_2$)$_q$S(O)$_m$R$_2$, (CH$_2$)q(1H-tetrazol-5-yl), (CH$_2$)$_q$C(O)NHSO$_2$R$_2$, (CH$_2$)$_q$C(O)NHSO$_2$(CH$_2$)$_t$ aryl, (CH$_2$)$_q$SO$_2$NH(CH$_2$)$_t$ aryl, (CH$_2$)$_q$SO$_2$NHC(O)R$_2$, (CH$_2$)$_q$SO$_2$NHC(O)CH$_2$)$_t$ aryl and the (CH$_2$)$_t$ and (CH$_2$)$_q$ may be substituted by 1 to 2 C$_1$–C$_2$ alkyl and the R$_2$ and aryl groups may optionally be substituted by 1 to 2 halogens, OR$_{2a}$, C(O)OR$_{2a}$, C(O)O(CH$_2$)$_t$ aryl, S(O)$_m$R$_{2a}$, 1 to 2 C$_1$–C$_3$ alkyl or 1H-tetrazol-5-yl;

m is 0 to 2;

q is 0 to 2;

t is 0 to 2; and aryl is phenyl, pyridyl, indolyl, N-methyl indolyl, or pyrimidinyl or thienyl and the pharmaceutically acceptable salts and individual diastereomers thereof.

Most preferred compounds of the instant invention are realized in structural formula V.

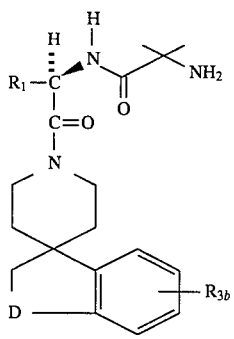

Formula V

R$_1$ is

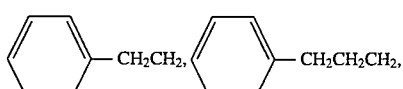

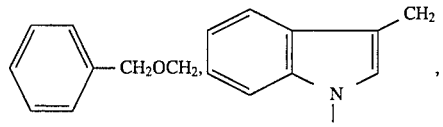

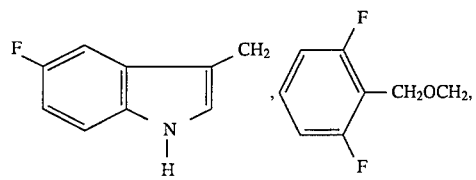

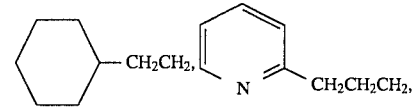

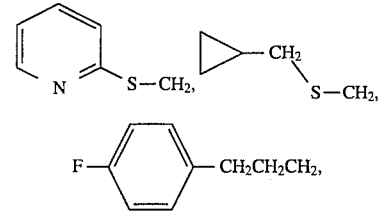

R$_{3a}$ is H, fluoro;

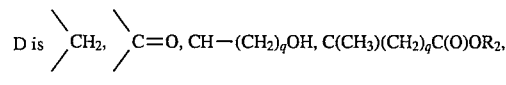

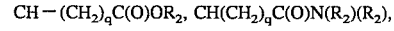

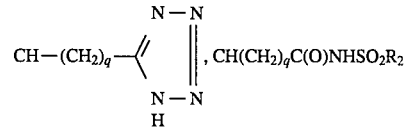

R$_2$ is H or C$_1$–C$_4$ alkyl;

q is 0, 1, 2;

and the pharmaceutically acceptable salts and individual diastereomers thereof.

Representative preferred growth hormone releasing compounds of the present invention include the following:

1. N-[1(R)-[(2,3-Dihydrospiro[1H-indene-1,4'-piperidin]-1'-yl)carbonyl]-2-(1H-indol-3-yl)ethyl]-2-amino-2-methylpropanamide 2. N-[1(RS)-[(2,3-Dihydrospiro[1H-indene-1,4'-piperidin]-1'-yl)carbonyl]-2-(5-fluoro-1H-indol-3-yl)ethyl]-2-amino-2-methylpropanamide 3. N-[1(RS)-[(2,3-Dihydro-3-oxospiro[1H-indene-1,4'-piperidin]-1'-yl)-carbonyl]-2-(1H-indol-3-yl)ethyl]-2-amino-2-methylpropanamide 4. N-[1(RS)-[(2,3-Dihydro-3(RS)-hydroxyspiro[1H-indene-1,4'-piperidin]-1'-yl)carbonyl]-2-(1H-indol-3-yl)ethyl]-2-amino-2-methylpropanamide 5. N-[1(R)-[(2,3-Dihydro-6-fluorospiro[1H-indene-1,4'-piperidin]-1'-yl) carbonyl]-2-(indol-3-yl)ethyl]-2-amino-2-methylpropanamide 6. N-[1(R)-[(2,3-Dihydrospiro[1H-indene-1,4'-piperidin]-1'-yl)carbonyl]-2-(phenylmethyloxy)ethyl]-2-amino-2-methylpropanamide 7. N-[1(R)-[(2,3-Dihydro-3-oxospiro[1H-indene-1,4'-piperidin]-1'-yl)carbonyl]-2-(phenylmethyloxy)ethyl]-2-amino-2-methylpropanamide 8. N-[1(R)-[(2,3-Dihydro-3(RS)-hydroxyspiro[1H-indene-1,4'-piperidin]-1'-yl) carbonyl]-2-(phenylmethyloxy)ethyl]-2-amino-2-methylpropanamide 9. N-[1(R)-[(2,3-Dihydrospiro[1H-indene-1,4'-piperidin]-1'-yl)carbonyl]-2-(2',6'-difluorophenylmethyloxy)ethyl]-2-amino-2-methylpropanamide 10. N-[1(RS)-[(2,3-Dihydro-3(RS)-hydroxyspiro[1H-indene-1,4'-piperidin]-1'-yl) carbonyl]-3-phenylpropyl]-2-amino-2-methylpropanamide 11. N-[1(R)-[(2,3-Dihydro-3-oxospiro[1H-indene-1,4'-piperidin]-1'-yl)carbonyl]-3-cyclohexylpropyl]-2-amino-2-methylpropanamide 12. N-[1(R)-[(2,3-Dihydro-3-(RS)-hydroxyspiro[1H-indene-1,4'-piperidin]-1'-yl) carbonyl]-3-cyclohexylpropyl]-2-amino-2-methylpropanamide 13. N-[1(R)-[(2,3-Dihydro-3-oxospiro[1H-indene-1,4'-piperidin]-1'-yl)carbonyl]-4-phenylbutyl]-2-amino-2-methylpropanamide 14. N-[1(R)-[(2,3-Dihydro-3(RS)-hydroxyspiro[1H-indene-1,4'-piperidin]-1'-yl) carbonyl]-4-phenylbutyl]-2-amino-2-methylpropanamide 15. 1'-[2(R)-[(2-amino-2-methyl-1-oxopropyl)amino]-3-(indole-3-yl)-1-oxopropyl]-2,3-dihydrospiro[1H-indene-1,4'-piperidine]-3-carboxylic acid;

16. 1'[2(R)-[(2-amino-2-methyl-1-oxopropyl)amino]-3-(indole-3-yl)-1-oxopropyl]-2,3-dihydrospiro[1H-indene-1,4'-piperidine-3-carboxylic acid ethyl ester;

17. 1'-[2(R)-[(2-amino-2-methyl-1-oxopropyl)amino]-5-phenyl-1-oxopentyl]-2,3-dihydrospiro[1H-indene-1,4'-piperidine]-3-carboxylic acid;

18. 1'-[2(R)-[(2-amino-2-methyl-1-oxopropyl)amino]-5-phenyl-1-oxopentyl]-2,3-dihydrospiro[1H-indene-1,4'-piperidine]-3-carboxylic acid ethyl ester;

19. 1'-[2(R)-[(2-amino-2-methyl-1-oxopropyl)amino]-3-(indole-3-yl)-1-oxopropyl]-2,3-dihydrospiro[1H-indene-1,4'-piperidine]-3-acetic acid;

20. 1'-[2(R)-[(2-amino-2-methyl-1-oxopropyl)amino]-3-(indole-3-yl)-1-oxopropyl]-2,3-dihydrospiro[1H-indene-1,4'-piperidine]-3(R)-acetic acid;

21. 1'-[2(R)-[(2-amino-2-methyl-1-oxopropyl)amino]-3-(indole-3-yl)-1-oxopropyl]-2,3-dihydrospiro[1H-indene-1,4'-piperidine]-3(S)-acetic acid;

22. 1'-[2(R)-[(2-amino-2-methyl-1-oxopropyl)amino]-3-(indole-3-yl)-1-oxopropyl]-2,3-dihydrospiro[1H-indene-1,4'-piperidine]-3-acetic acid ethyl ester;

23. 1'-[2(R)-[(2-amino-2-methyl-1-oxopropyl)amino]-3-(indole-3-yl)-1-oxopropyl]-2,3-dihydrospiro[1H-indene-1,4'-piperidine]-3(R)-acetic acid ethyl ester;

24. 1'-[2(R)-[(2-amino-2-methyl-1-oxopropyl)amino]-3-(indole-3-yl)-1-oxopropyl]-2,3-dihydrospiro[1H-indene-1,4'-piperidine]-3(S)-acetic acid ethyl ester;

25. 1'-[2(R)-[(2-amino-2-methyl-1-oxopropyl)amino]-3-(5-fluoroindole-3-yl)-1-oxopropyl]-2,3-dihydrospiro[1H-indene-1,4-piperidine]-3-acetic acid;

26. 1'-[2(R)-[(2-amino-2-methyl-1-oxopropyl)amino]-3-(5-fluoroindole-3-yl)-1-oxopropyl]-2,3-dihydrospiro[1H-indene-1,4-piperidine]-3(R)-acetic acid;

27. 1'-[2(R)-[(2-amino-2-methyl-1-oxopropyl)amino]-3-(5-fluoroindole-3-yl)-1-oxopropyl]-2,3-dihydrospiro[1H-indene-1,4-piperidine]-3(S)-acetic acid;

28. 1'-[2(R)-[(2-amino-2-methyl-1-oxopropyl)amino]-3-(5-fluoroindole-3-yl)-1-oxopropyl]-2,3-dihydrospiro[1H-indene-1,4'-piperidine]-3-acetic acid ethyl ester;

29. 1'-[2(R)-[(2-amino-2-methyl-1-oxopropyl)amino]-3-(5-fluoroindole-3-yl)-1-oxopropyl]-2,3-dihydrospiro[1H-indene-1,4'-piperidine]-3(R)-acetic acid ethyl ester;

30. 1'-[2(R)-[(2-amino-2-methyl-1-oxopropyl)amino]-3-(5-fluoroindole-3-yl)-1-oxopropyl]-2,3-dihydrospiro[1H-indene-1,4'-piperidine]-3(S)-acetic acid ethyl ester;

31. 1'-[2(R)-[(2-amino-2-methyl-1-oxopropyl)amino]3-(phenylmethoxy)-1-oxopropyl]-2,3-dihydrospiro[1H-indene-1,4'-piperidine]-3-acetic acid;

32. 1'-[2(R)-[(2-amino-2-methyl-1-oxopropyl)amino]-3-(phenylmethoxy)-1-oxopropyl]-2,3-dihydrospiro[1H-indene-1,4'-piperidine]-3-acetic acid ethyl ester;

33. 1'-[2(R)-[(2-amino-2-methyl-1-oxopropyl)amino]-3-(2,6-difluorophenylmethoxy)-1-oxopropyl]-2,3-dihydrospiro[1H-indene-1,4'-piperidine]-3-acetic acid;

34. 1'-[2(R)-[(2-amino-2-methyl-1-oxopropyl)amino]-3-(2,6-difluorophenylmethoxy)-1-oxopropyl]-2,3-dihydrospiro[1H-indene-1,4'-piperidine]-3-acetic acid ethyl ester;

35. 1'-[2(R)-[(2-amino-2-methyl-1-oxopropyl)amino]-3-(5-fluoroindole-3-yl)-1-oxopropyl]-2,3-dihydro-6-fluorospiro[1H-indene-1,4'-piperidine]-3-acetic acid;

36. 1'-[2(R)-[(2-amino-2-methyl-1-oxopropyl)amino]-3-(5-fluoroindole-3-yl)-1-oxopropyl]-2,3-dihydro-6-fluorospiro[1H-indene-1,4'-piperidine]-3-acetic acid ethyl ester;

37. 1'-[2(R)-[(2-amino-2-methyl-1-oxopropyl)amino]-5-phenyl-1-oxopentyl]-2,3-dihydrospiro[1H-indene-1,4'-piperidine]-3-propanoic acid;

38. 1'-[2(R)-[(2-amino-2-methyl-1-oxopropyl)amino]-5-phenyl-1-oxopentyl]-2,3-dihydrospiro[1H-indene-1,4'-piperidine]-3-propionic acid ethyl ester;

39. 1'-[2(R)-[(2-amino-2-methyl-1-oxopropyl)amino]-5-phenyl-1-oxopentyl]-2,3-dihydrospiro[1H-indene-1,4'-piperidine]-3-acetic acid;

40. 1'-[2(R)-[(2-amino-2-methyl-1-oxopropyl)amino]-5-phenyl-1-oxopentyl]-2,3-dihydrospiro[1H-indene-1,4'-piperidine]-3(S)-acetic acid;

41. 1'-[2(R)-[(2-amino-2-methyl-1-oxopropyl)amino]-5-phenyl-1-oxopentyl]-2,3-dihydrospiro[1H-indene-1,4'-piperidine ]-3(R)-acetic acid;

42. 1'-[2(R)-[(2-amino-2-methyl-1-oxopropyl)amino]-5-phenyl-1-oxopentyl]-2,3-dihydrospiro[1H-indene-1,4'-piperidine]-3-acetic acid ethyl ester;

43. 1'-[2(R)-[(2-amino-2-methyl-1-oxopropyl)amino]-5-phenyl-1-oxopentyl]-2,3-dihydrospiro[1H-indene-1,4'-piperidine]-3(S)-acetic acid ethyl ester;

44. 1'-[2(R)-[(2-amino-2-methyl-1-oxopropyl)amino]-5-phenyl-1-oxopentyl]-2,3-dihydrospiro[1H-indene-1,4'-piperidine]-3(R)-acetic acid ethyl ester;

45. N-Ethyl-1'-[2(R)-[(2-amino-2-methyl-1-oxopropyl)amino]-5-phenyl-1-oxopentyl]-2,3-dihydrospiro[1H-indene-1,4'-piperidine]-3-acetamide;

46. N-Ethyl-1'-[2(R)-[(2-amino-2-methyl-1-oxopropyl)amino]-5-phenyl-1-oxopentyl]-2,3-dihydrospiro[1H-indene-1,4'-piperidine ]-3(S)-acetamide;

47. N-Ethyl-1'-[2(R)-[(2-amino-2-methyl-1-oxopropyl)amino]-5-phenyl-1-oxopentyl]-2,3-dihydrospiro[1H-indene-1,4'-piperidine ]-3-acetamide;

48. 1'-[2(R)-[(2-amino-2-methyl-1-oxopropyl)amino]-5-phenyl-1-oxopentyl]-2,3-dihydro-6-fluorospiro[1H-indene-1,4'-piperidine]-3-acetic acid;

49. 1'-[2(R)-[(2-amino-2-methyl-1-oxopropyl)amino]-5-phenyl-1-oxopentyl-2,3-dihydro-6-fluorospiro[1H-indene-1,4'-piperidine]-3-acetic acid ethyl ester;

50. 1'-[2(R)-[(2-amino-2-methyl-1-oxopropyl)amino]-5-phenyl-1-oxopentyl]-2,3-dihydrospiro[1H-indene-1,4'-piperidine]-3-propanoic acid;

51. 1'-[2(R)-[(2-amino-2-methyl-1-oxopropyl)amino]-5-phenyl-1-oxopentyl]-2,3-dihydrospiro[1H-indene-1,4'-piperidine]-3-propanoic acid ethyl ester;

52. 1'-[2(R)-[(2-amino-2-methyl-1-oxopropyl)amino]-3-(indole-3-yl)-1-oxopropyl]-2,3-dihydro-6-fluorospiro[1H-indene-1,4'-piperidine]-3-acetic acid.

and pharmaceutically acceptable salts and individual diastereomers (where unspecified) thereof.

Representative examples of the nomenclature employed are given below:

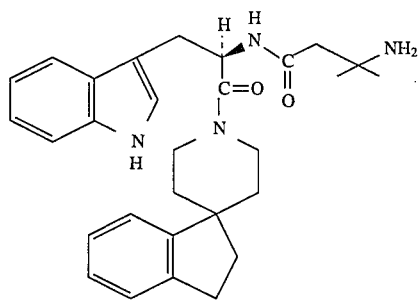

N-[1(R)-[(2,3-Dihydrospiro[1H-indene-1,4'-piperidin]-1'-yl)carbonyl]-2-(1H-indol-3-yl)ethyl]-3-amino-3-methylbutanamide

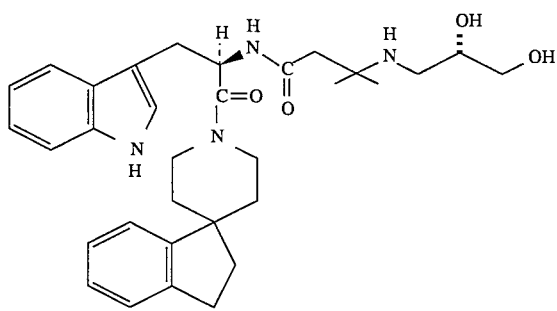

N-[1(R)-[(2,3-Dihydrospiro[1H-indene-1,4'-piperidin]-1'-yl)carbonyl]-2-(1H-indol-3-yl)ethyl]-3-[[2(R),3-dihydroxypropyl]amino]-3-methylbutanamide

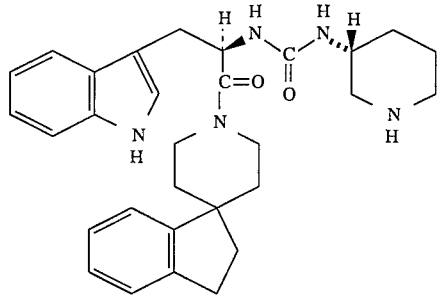

N-[1(R)-[(3,4-Dihydrospiro[1(2H)-naphthalene-1,4'-piperidin]-1'-yl)carbonyl]-2-(indol-3-yl)ethyl]-N'-[3-(R)-piperidinyl]urea

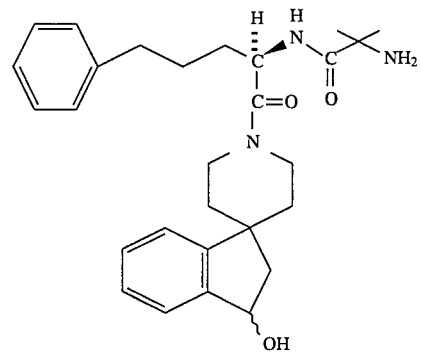

N-[1(R)-[(2,3-Dihydro-3(RS)-hydroxyspiro[1H-indene-1,4'-piperidin]-1'-yl)carbonyl]-4-phenylbutyl]-2-amino-2-methylpropanamide

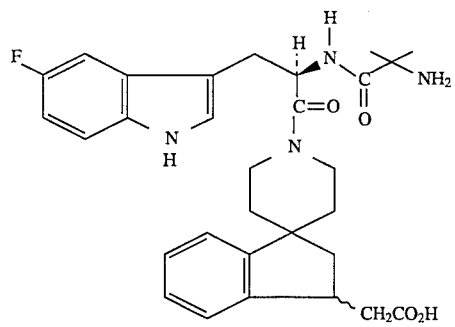

1'-[2(R)-[(2-amino-2-methyl-1-oxopropyl)amino]-3-(5-fluoroindole-3-yl)-1-oxopropyl]-2,3-dihydrospiro[1H-indene-1,4'-piperidine]-3-acetic acid

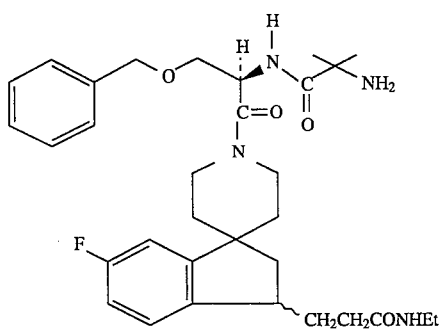

N-Ethyl-1'-[2(R)-[(2-amino-2-methyl-1-oxopropyl)amino]-3-(phenylmethoxy)-1-oxopropyl]-2,3-dihydro-6-fluorospiro[1H-indene-1,4'-piperidine]-3-propanamide Throughout the instant application, the following abbreviations are used with the following meanings:

| | |
|---|---|
| BOC | t-butyloxycarbonyl |
| BOCON | 2-(tert-butoxycarbonylamino)-2-phenyl-acetonitrile |
| BOP | Benzotriazol-1-yloxy tris/dimethylamino)-phosphonium hexafluorophosphate |
| CBZ | Benzyloxycarbonyl |
| DCC | Dicyclohexylcarbodiimide |
| DIBALH | Diisobutyl aluminum hydride |
| DMF | N,N-dimethylformamide |
| EDC | 1-(3-dimethylaminopropyl)-3-ethylcarbodi-imide hydrochloride |
| FAB-MS | Fast atom bombardment-mass spectroscopy |
| GHRP | Growth hormone releasing peptide |
| HOBT | Hydroxybenztriazole |
| LAH | Lithium aluminum hydride |
| HPLC | High pressure liquid chromatography |
| MHz | Megahertz |
| MPLC | Medium pressure liquid chromatography |
| NMM | N-Methylmorpholine |
| NMR | Nuclear Magnetic Resonance |
| PLC | Preparative layer chromatography |
| PCC | Pyridinium chlorochromate |
| Ser | Serine |
| TFA | Trifluoroacetic acid |
| THF | Tetrahydrofuran |
| TLC | Thin layer chromatography |
| TMS | Tetramethylsilane |

The compounds of the instant invention all have at least one asymmetric center as noted by the asterisk in the structural Formulas I and II above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the ambit of the instant invention. In the case of the asymmetric center represented by the asterisk, it has been found that the absolute stereochemistry of the more active and thus more preferred isomer is shown in Formula Ia. This preferred absolute configuration applies to Formulas I and II. With the $R_2$ substituent as hydrogen, the special configuration of the asymmetric center corresponds to that in a D-amino acid. In most cases this is also designated an R-configuration although this will vary according to the values of $R_1$ and $R_2$ used in making R— or S— stereochemical assignments.

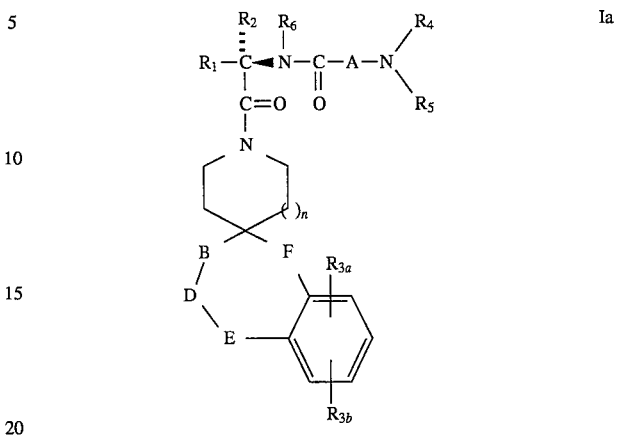

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The preparation of compounds I and II of the present invention can be carded out in sequential or convergent synthetic routes. Syntheses detailing the preparation of the compounds of Formula I and II in a sequential manner are presented in the following reaction schemes.

The protected amino acid derivatives 1 are, in many cases, commercially available where the protecting group L is, for example, BOC or CBZ groups. Other protected amino acid derivatives 1 can be prepared by literature methods. Many of the spiro piperidines and spiroazepines (n=2) of formula 2 and 2a are known in the literature and can be derivatized on the aryl groups by standard means, such as halogenation, nitration, sulfonylation, etc. Alternatively, various aryl substituted spiro piperidines and azepinescan be prepared following literature methods using derivatized aryl intermediates. Many spiroazepine intermediates (n=2 in Formula I) are also known. Novel spiroazepines can be prepared as illustrated in Scheme 23. They may be used in the schemes shown below in place of piperidine intermediates to afford compounds of Formulas I and II where n=2.

Intermediates of formulas 3 and 3a can be synthesized as described in Scheme 1. Coupling of spiro compounds of formula 2 and 2a to protected amino acids of formula 1, wherein L is a suitable protecting group, is conveniently carded out in an inert solvent such as dichloromethane by a coupling reagent such as DCC or EDC in the presence of HOBT. Alternatively, the coupling can also be effected with a coupling reagent such as BOP in an inert solvent such as dichloromethane. Separation of unwanted side products, and purification of intermediates is achieved by chromatography on silica gel, employing flash chromatography (W. C. Still, M. Kahn, and A. Mitra *J. Org. Chem.* 1978, 43, 2923), MPLC or preparative TLC.

SCHEME 1

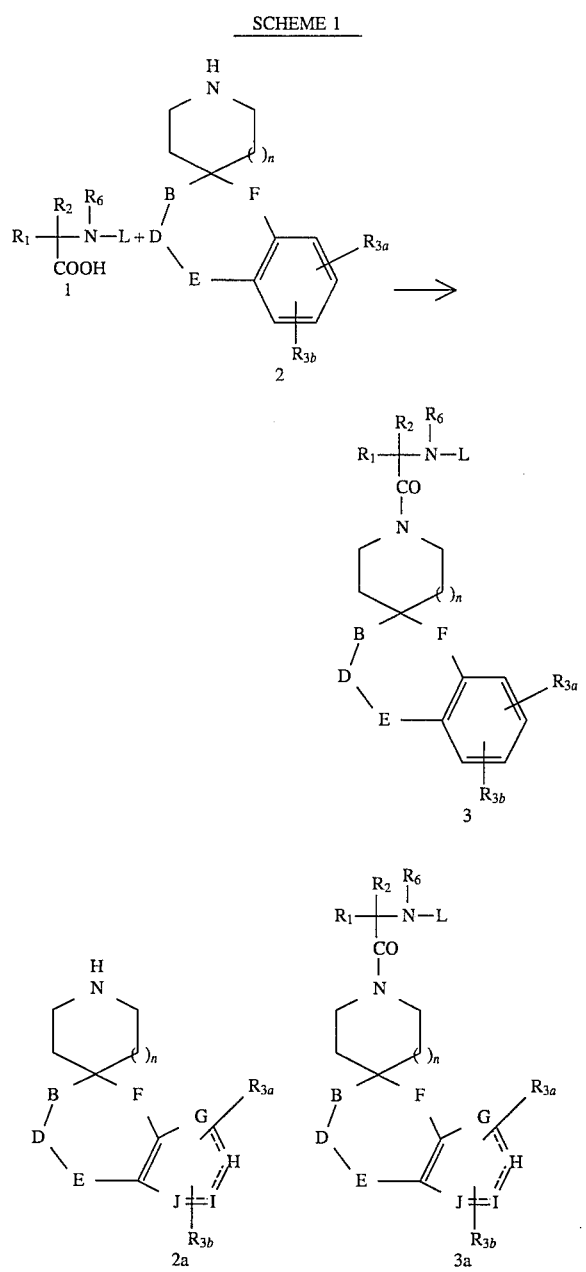

Conversion of 3 and 3a to intermediates 4 and 4a can be carried out as illustrated in Scheme 2. Removal of benzyloxycarbonyl groups can be achieved by a number of methods known in the art; for example, catalytic hydrogenation with hydrogen in the presence of palladium or platinum catalyst in a protic solvent such as methanol. In cases where catalytic hydrogenation is contraindicated by the presence of other potentially reactive functionality, removal of benzyloxy carbonyl groups can also be achieved by treatment with a solution of hydrogen bromide in acetic acid. Removal of BOC protecting groups is carried out in a solvent such as methylene chloride or methanol, with a strong acid, such as hydrochloric acid or trifluoroacetic acid. Conditions required to remove other protecting groups which may be present can be found in Greene, T; Wuts, P. G. M. *Protective Groups in Organic Synthesis*, John Wiley & Sons, Inc., New York, N.Y. 1991.

SHCEME 2

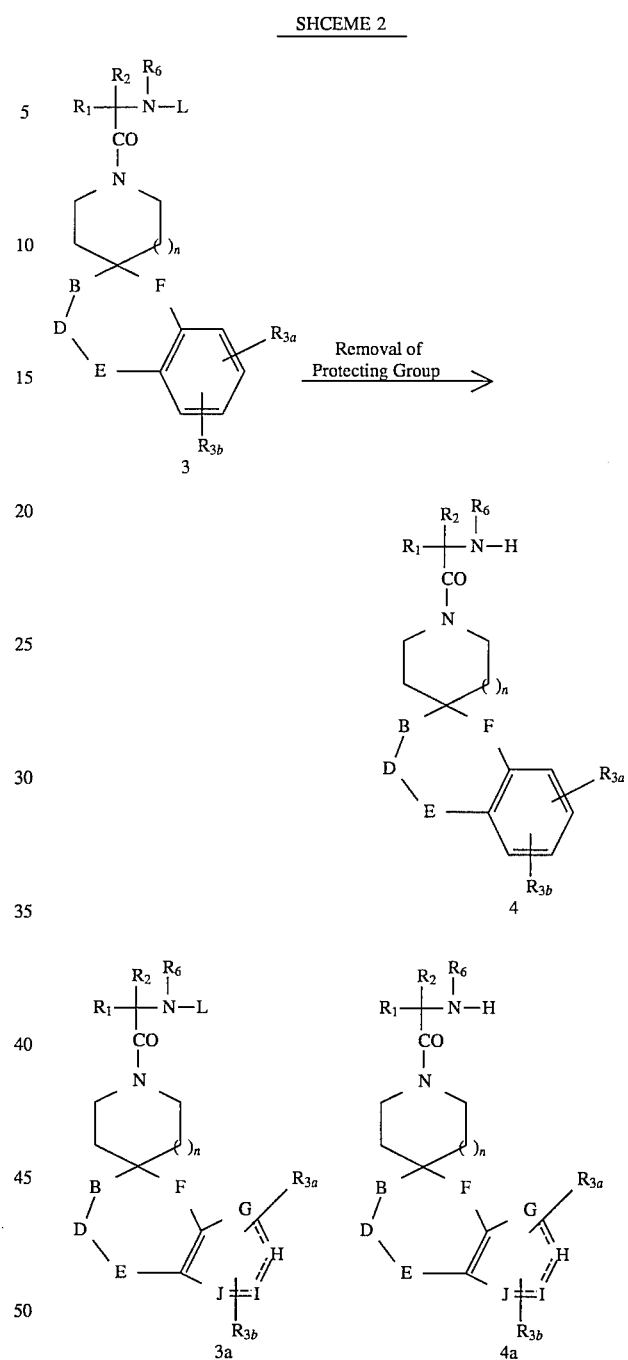

Intermediates of formula 5 and 5b, wherein A is a methylene or a substituted methylene group, can be prepared as shown in Scheme 3 by coupling of intermediates of formula 4 and 4a to amino acids of formula 6, once again, in an inert solvent such as dichloromethane by a coupling reagent such as EDC or DCC in the presence of HOBT. These amino acids 6 are known amino acids or amino acids readily synthesized by methods known to those skilled in the art. Alternatively, the coupling can also be effected with a coupling reagent such as BOP in an inert solvent such as dichloromethane. Also if $R_4$ or $R_5$ is a hydrogen then amino acids of formula 7 are employed in the coupling reaction, wherein L is a protecting group as defined above, to give 5a and 5c. Deprotection of 5a and 5c (L=protecting group) can be carried out under conditions known in the art.

SCHEME 3

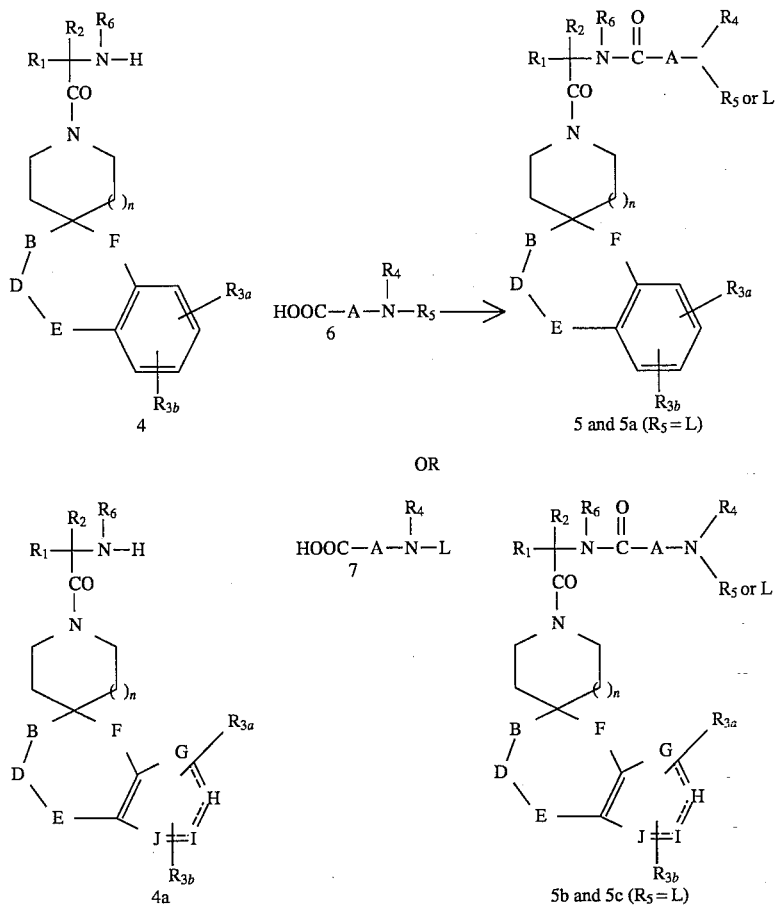

Compounds of formula I and II wherein $R_4$ and/or $R_5$ is a hydrogen can be further elaborated to new compounds I and II (preferred side chain $R_4$ or $R_5$=$CH_2$—$CH(OH)$—$CH_2X$, wherein X=H or OH) which are substituted on the amino group as depicted in Scheme 4. Reductive amination of I and II with an aldehyde is carded out under conditions known in the art; for example, by catalytic hydrogenation with hydrogen in the presence of platinum, palladium, or nickel catalysts or with chemical reducing agents such as sodium cyanoborohydride in an inert solvent such as methanol or ethanol. Alkylation to yield amino alcohols can also be accomplished via an epoxide opening reaction.

SCHEME 4

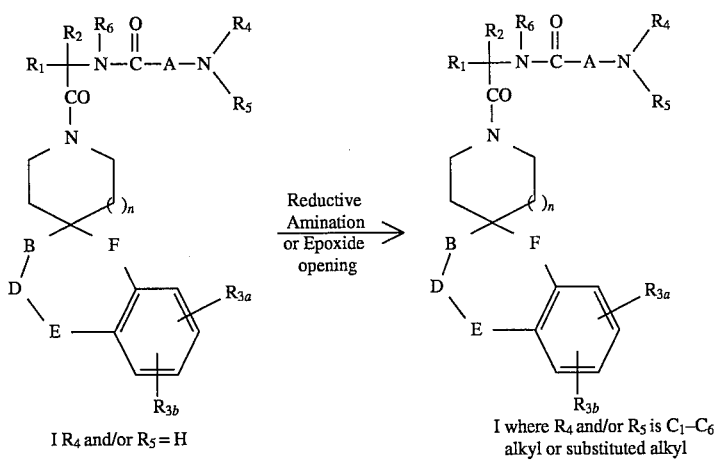

-continued
SCHEME 4

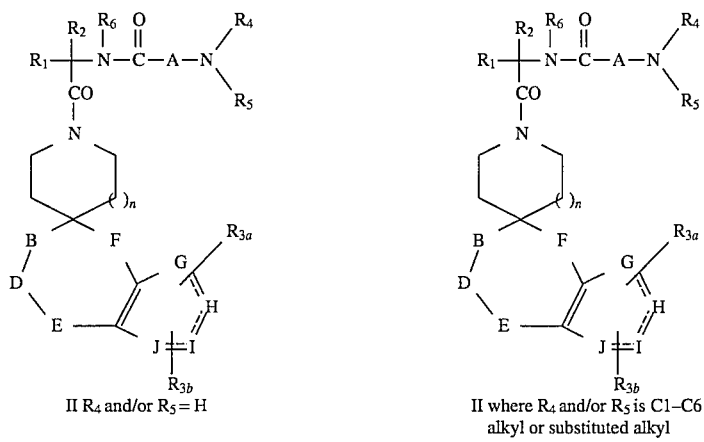

Compounds of formula I and II, wherein A is $N(R_2)$—$(CH_2)_z$—$C(R_7)(R_{7a})$—$(CH_2)_y$, can be prepared as shown in Scheme 5 by reacting 4 or 4a with reagents 8, wherein X is a good leaving group such as Cl, Br, I, imidazole. Alternatively, 4 and 4a can be reacted with an isocyanate of formula 9 in an inert solvent such as 1,2-dichloroethane. If $R_4$ or $R_5$ is hydrogen in the final product, the reagents 8 and 9 will bear a removable L protecting group in place of $R_5$.

The compounds I and II of the present invention can also be prepared in a convergent manner as described in reaction Schemes 6, 7 and 8:

The protected amino acid derivatives 10 are, in many cases, commercially available where M=methyl, ethyl, or benzyl esters. Other ester protected amino acids can be prepared by classical methods familiar to those skilled in the art. Some of these methods include the reaction of a protected amino acid with a diazoalkane and removal of a

SCHEME 5

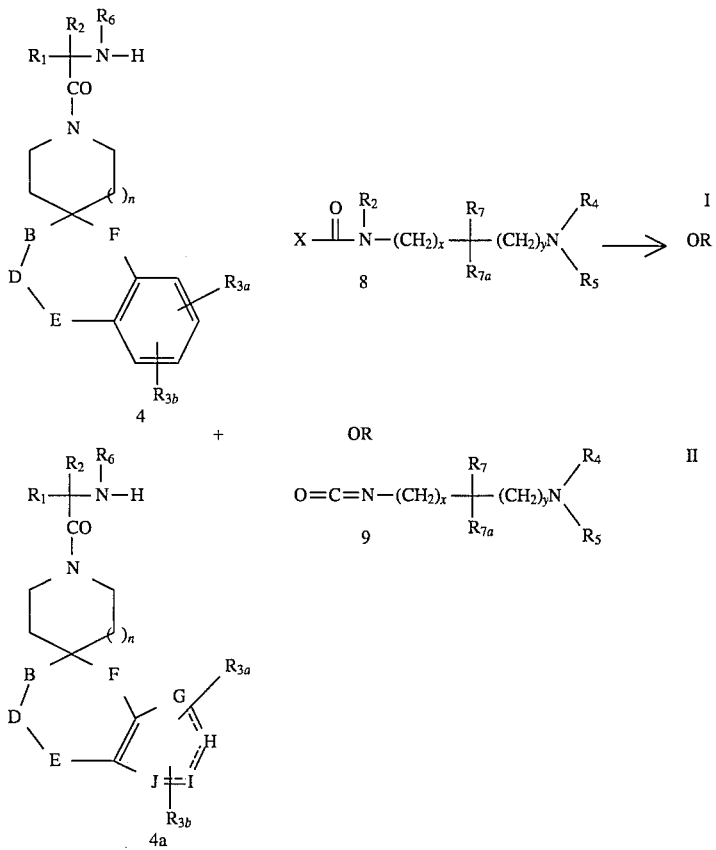

protecting group L, the reaction of an amino acid with an appropriate alcohol in the presence a strong acid like hydrochloric acid or p-toluenesulfonic acid. Synthetic routes for the preparation of new amino acids are described in Schemes 11, 12 and 13.

Intermediates of formula 11 and 11a, can be prepared as shown in Scheme 6 by coupling of amines 10 to amino acids 6 and/or 7, wherein L is a protecting group, as described above in Scheme 3. When a urea linkage is present in 11 or 11a, it can be introduced as illustrated in Scheme 5.

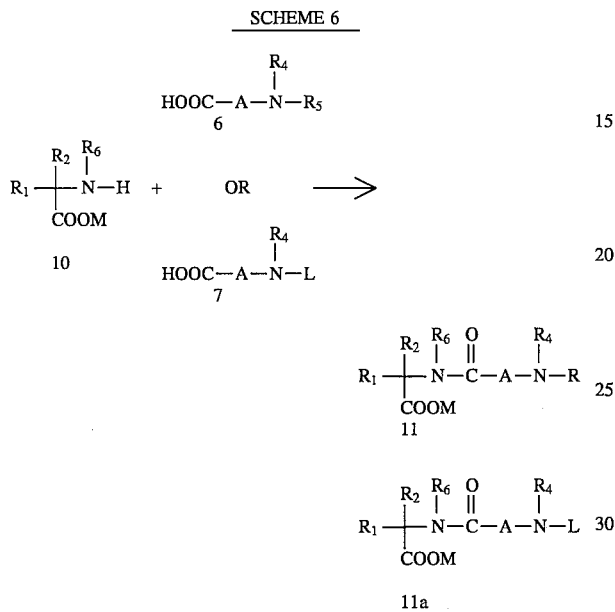

Conversion of the ester 11 or 11a to intermediate acids 12 or 12a can be achieved by a number of methods known in the art as described in Scheme 7; for example, methyl and ethyl esters can be hydrolyzed with lithium hydroxide in a protic solvent like aqueous methanol. In addition, removal of benzyl group can be accomplished by a number of reductive methods including hydrogenation in the presence of platinum or palladium catalyst in a protic solvent such as methanol. An allyl ester can be cleaved with tetrakis-triphenylphosphine palladium catalyst in the presence of 2-ethylhexanoic acid in a variety of solvents including ethyl acetate and dichloromethane (see *J. Org. Chem.* 1982, 42, 587).

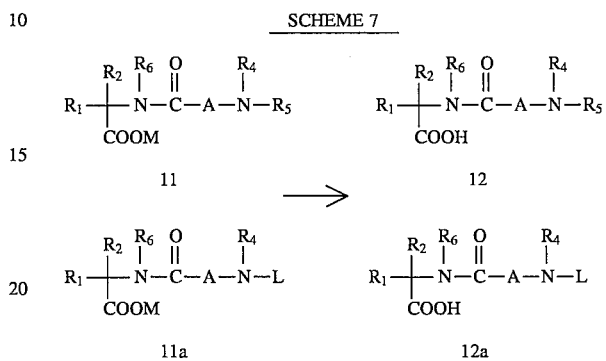

Acid 12 or 12a can then be elaborated to 5 & 5a and 5b & 5c as described in Scheme 8. Coupling of spiro compounds of formula 2 and 2a to acids of formula 12 or 12a, wherein L is a suitable protecting group, is conveniently carded out in an inert solvent such as dichloromethane by a coupling reagent such as dicylohexyl carbodiimide (DCC) or EDC in the presence of 1-hydroxybenztriazole (HOBT). Alternatively, the coupling can also be effected with a coupling reagent such as benzotriazol-1-yloxytris(dimethylamino) phosphonium hexafluorophosphate ("BOP") in an inert solvent such as dichloromethane. Transformation of 5a & 5c to I and II is achieved by removal of the protecting group L. When $R_4$ and/or $R_5$ is H, substituted alkyl groups may be optionally added to the nitrogen atom as described in Scheme 4.

SCHEME 8

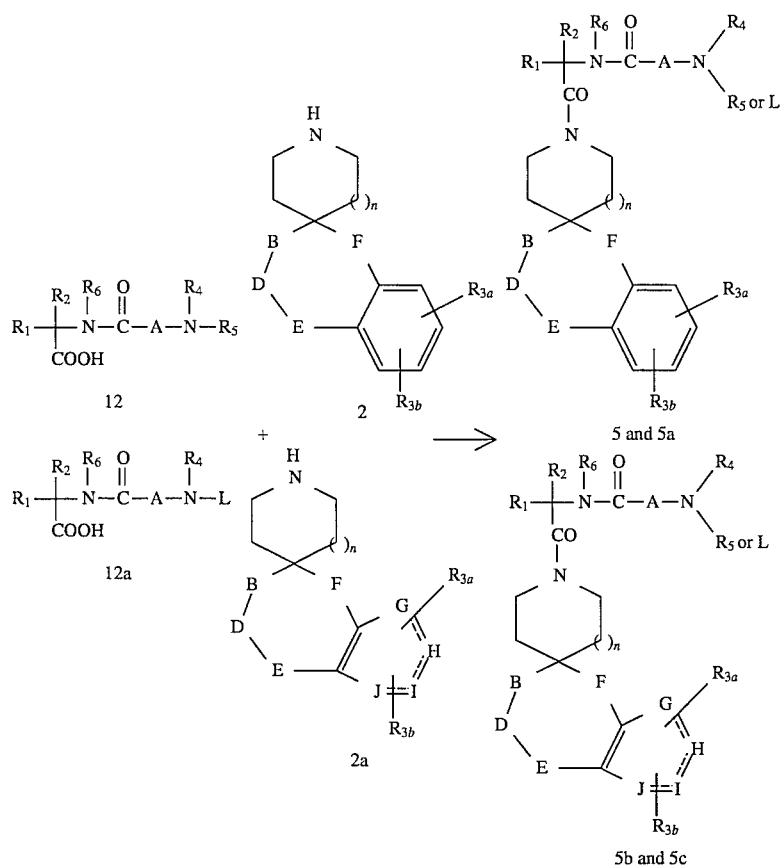

The preparation of oxygenated spiroindanyl intermediates is illustrated in Scheme 9. Hydroboration of the protected spiroindene followed by oxidative workup with pyridinium chlorochromate provides the spiroindanone 14. The amino protecting group (L), which for example is a t-butoxycarbonyl or benzyloxy-carbonyl group is removed under acidic and/or reducing conditions to provide the spiroindanone 15 which can then be incorporated into a growth hormone secretagogue via the chemistry detailed in Schemes 1 and 8, utilizing generic intermediates 2 and 2a.

Alkylation alpha to the ketone of the spiroindanone intermediate can be readily accomplished employing a variety of bases and alkylating agents. For example treatment of 14 with excess sodium hydride in an inert solvent such as tetrahydrofuran followed by excess methyl iodide produces 16.

Spiroindane intermediates containing hydroxyl substituents are easily prepared from the spiroindanone 14 The reduction of the ketone can be accomplished with reducing agents, for example sodium borohydride. The protecting group (L) can then be removed as noted above and the resulting hydroxyspiroindane can be employed in the chemistry described in Schemes 1 and 8. Alternatively the secretagogues that contain a hydroxyspiroindane function can be obtained from the secretagogues containing the spiroindanone by reducing the ketone as the final step in the synthesis.

Chiral hydroxy spiroindanes can be prepared by methods well known to those skilled in the an including the use of chiral reducing agents such as (S)-tetrahydro-1-methyl-3,3-diphenyl-1H,3H-pyrrolo[1,2,c][1,3,2]oxazaborole (Corey et al., J. Am. Chem. Soc. 1987, 109, 5551). Determination of absolute stereochemistry can be achieved by a number of methods including x-ray crystallography of a suitable crystalline derivative. Derivatization with Mosher's acid may provide a suitable derivative. Alkylation and acylation of hydroxyspiroindane 18 is readily carried out with a base and the desired alkylation or acylation agent. Urethanes are formed by reacting 18 with organic isocyanates or with sodium isocyanate.

SCHEME 9

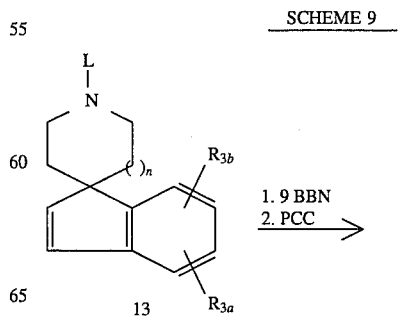

-continued
SCHEME 9

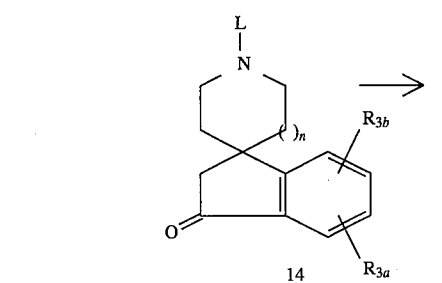

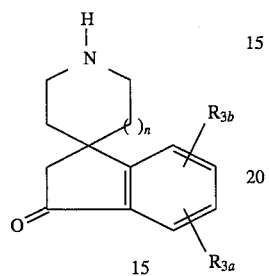

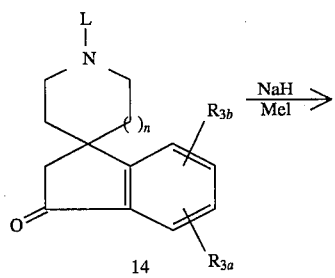

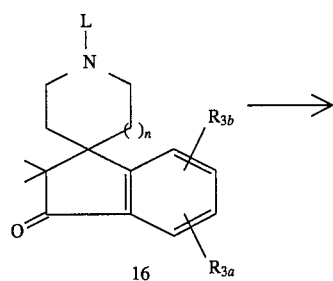

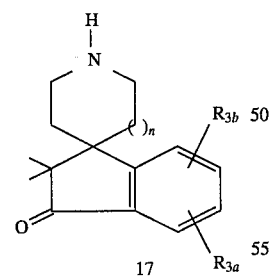

-continued
SCHEME 9

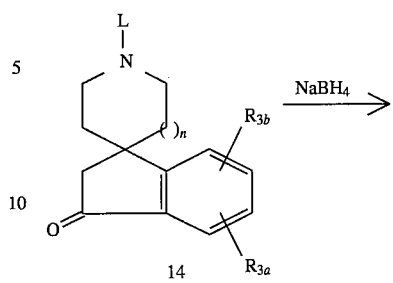

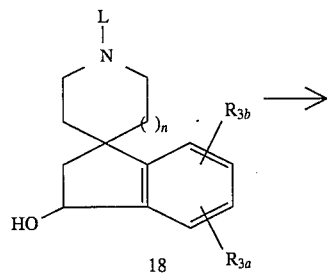

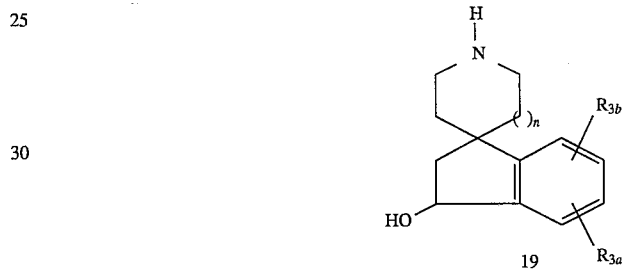

The spiroindanone intermediates 14 can also serve as convenient starting materials for the incorporation of amines onto the spiroindanes, see Scheme 10. Formation of the oxime of the spiroindanone with hydroxylamine hydrochloride in a suitable solvent such as ethanol in the presence of sodium hydroxide followed by reduction of the oxime provides the amine 21. The amino group of 21 can be easily alkylated, acylated, sulfonylated or reacted with isocyanates by methods commonly known to those skilled in the art.

Chiral aminospiroindanes are available by numerous methods including resolution of the racemates by the classical methods. For example resolution can be achieved by the formation of diastereomeric salts of the racemic amines with optically active acids such as D- and L-tartaric acid. The determination of the absolute stereochemistry can be accomplished in a number of ways including X-ray crystallography of a suitable crystalline derivative such as a D- or L-tartaric acid salt.

SCHEME 10

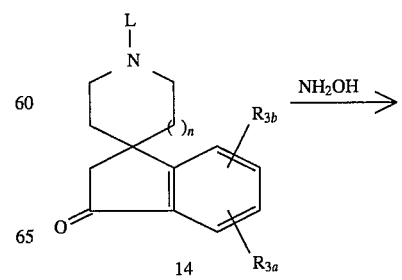

SCHEME 10 -continued

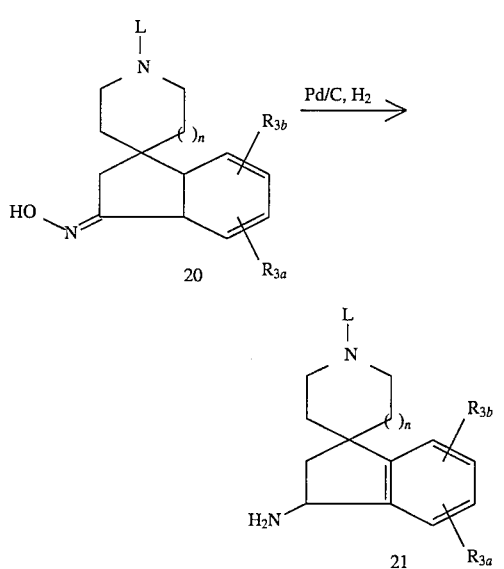

The compounds of formulas I and II of the present invention are prepared from a variety of substituted natural and unnatural amino acids such as those of formulas 22 and 6 and 7 where A is a substituted methylene group.

The preparation of these intermediates is accomplished by classical methods familiar to those skilled in the art (Williams, R. M. "*Synthesis of Optically Active α-Amino Acids*" Pergamon Press: Oxford, 1989; Vol. 7). When it is desirable to synthesize these intermediates in optically pure form, some established methods include: (1) asymmetric electrophilic amination of chiral enolates (*J. Am. Chem. Soc.* 1986, 108, 6394–6395, 6395–6397, and 6397–6399), (2) asymmetric nucleophilic amination of optically active carbonyl derivatives, (*J. Am. Chem. Soc.* 1992, 114, 1906; *Tetrahedron Lett.* 1987, 28, 32), (3) diastereoselective alkylation of chiral glycine enolate synthons (*J. Am. Chem. Soc.* 1991, 113, 9276; *J. Org. Chem.* 1989, 54, 3916), (4) diastereoselective nucleophilic addition to a chiral electrophilic glycinate synthon (*J. Am. Chem. Soc.* 1986, 108, 1103), (5) asymmetric hydrogenation of prochiral dehydroamino acid derivatives ("*Asymmetric Synthesis, Chiral Catalysis*; Morrison, J. D., Ed; Academic Press: Orlando, Fla., 1985; Vol 5), and (6) enzymatic syntheses (*Angew. Chem. Int. Ed. Engl.* 1978, 17, 176). D,L-Amino acids as their amino or carboxyl protected intermediates can be resolved by crystallization of salts derived from optically active acids or amines. β-Amino acids can be prepared, for example by the hydrolysis of substituted β-lactams as described in U.S. Pat. No. 5,206, 237.

For example, alkylation of the enolate of diphenyloxazinone 23 (*J. Am. Chem. Soc.* 1991, 113, 9276) with cinnamyl bromide in the presence of sodium bis(trimethylsilyl)amide proceeds smoothly to afford 24 which is converted into the desired (D)-2-amino-5-phenylpentanoic acid 25 by removing the N-t-butyloxycarbonyl group with trifluoroacetic acid and hydrogenation over a PdCl₂ catalyst (Scheme 11)

SCHEME 11

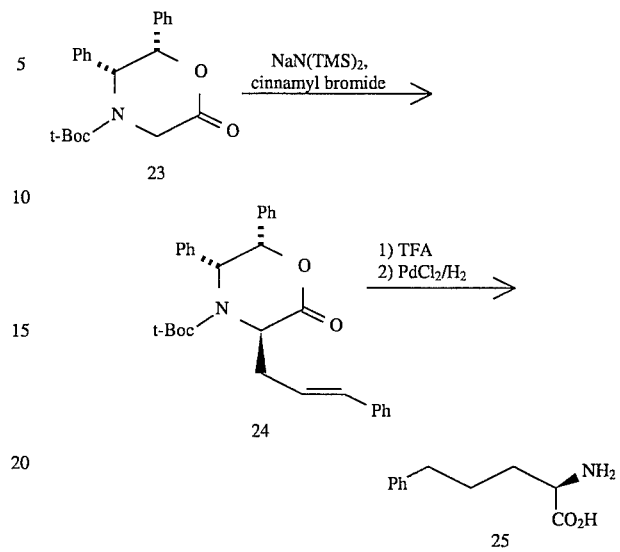

Intermediates of formula 22 which are O-benzyl-(D)-serine derivatives 27 are conveniently prepared using a known procedure from suitably substituted benzyl halides and N-protected-(D)-serine 26. The protecting group L is conveniently a BOC or a CBZ group. Benzylation of 26 can be achieved by a number of methods well known in the literature including deprotonation with two equivalents of sodium hydride in an inert solvent such as DMF followed by treatment with one equivalent of a variety of benzyl halides (*Synthesis* 1989, 36) as shown in Scheme 12.

SCHEME 12

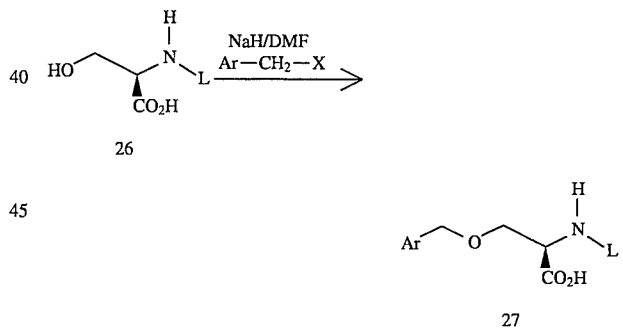

The O-alkyl-(D)-serine derivatives are also prepared using this procedure and an alkyl halide.

The alkylation of N-protected-(D)-cysteine 45 is carried out by the procedure described in the (D)-serine derivative synthesis and illustrated below with $R_{1a}$-X where X is a leaving group such as halides and mesyloxy groups as shown in Scheme 13.

SCHEME 13

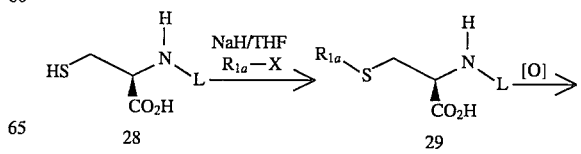

-continued
SCHEME 13

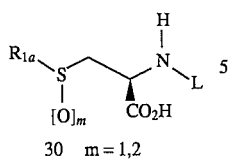

30  m = 1,2

The oxidation of the cysteine derivatives 29 to the sulfoxide 30 (m=1) and the sulfone 30 (m=2) can be accomplished with many oxidizing agents. (For a review of the oxidation of sulfides see *Org. Prep. Proced. Int.* 1982, 14, 45.) Sodium periodate (*J. Org. Chem.* 1967, 32, 3191) is often used for the synthesis of sulfoxides and potassium hydrogen persulfate (OXONE) (*Tetrahedron Lett.* 1981, 22, 1287) is used for the synthesis of sulfones.

Hence, a variety of substituted amino acids may be incorporated into a growth hormone secretagogue via the chemistry detailed in Schemes 1 and 8. The secretagogues that contain a sulfoxide or a sulfone functional group can also be prepared from the cysteine secretagogues by using sodium periodate or OXONE®. Alternatively hydrogen peroxide may be used as the oxidizing reagent in the last step of the synthesis as shown in Scheme 14. The sulfoxide 32 (m=1) and sulfone 32 (m=2) analogs can be separated by preparative thin layer chromatography.

SCHEME 14

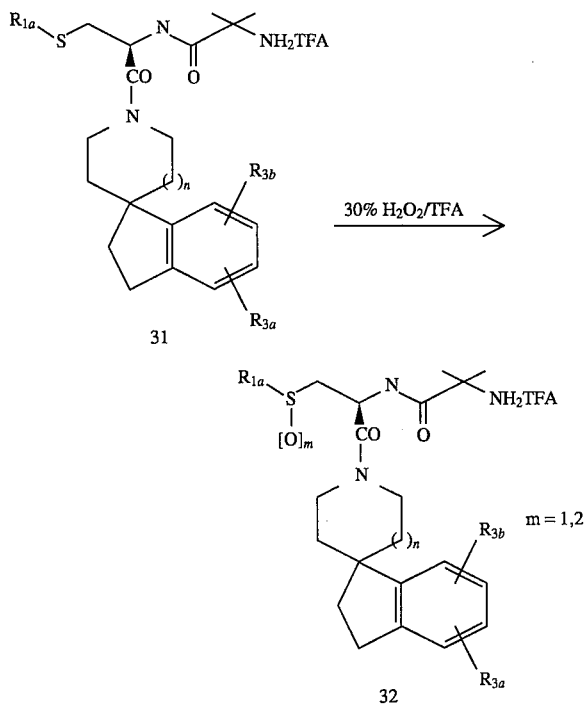

Removal of amino protecting groups can be achieved by a number of methods known in the art; as described above and in *Protective Groups in Organic Synthesis* T. W. Greene, John Wiley and Sons, New York 1981.

Compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatogrphy (HPLC) or by recrystallization.

Homologation of the spiroindanone 14 provides easy access to spiroindanyl intermediates containing acid and ester groups. This chemistry is described in Scheme 15 below. Treatment of 14 with a base in an inert solvent such as THF followed by the addition of a triflating agent provides the enol triflate. Carboxylation of the enol triflate according to the procedure of Cacchi, S. *Tetrahedron Letters*, 1985, 1109–1112 provides the ester 34. The protecting group can then be removed as described above and the resulting amine can be incorporated into a secretagogue via the chemistry depicted in Schemes 1 and 8. A secretagogue containing an acid function is readily available via saponification of the ester group as the final step of the synthesis.

Saponification of the ester of 34 provides an acid which can be conveniently derivatized as for example reaction with an amine in the presence of a coupling agent such as EDC gives amides which can then be incorporated into secretagogues following the chemistry detailed in Schemes 1 and 8.

Hydrogenation of 34 using a palladium catalyst in an inert solvent provides the saturated compounds which can then either be derivatized as above or carried on to the final products via the chemistry described in Schemes 1 and 8. The ester may also be reduced to a primary alcohol with LAH and to a aldehyde with DIBALH. Reductive alkylation of the aldehyde with ammonium acetate and sodium cyanoborohydride affords an amino methyl analog. These hydroxymethyl and aminomethyl analogs may then be further reacted to afford additional growth hormone secretagogues of the general formula I. Chiral acids are available by a variety of methods known to those skilled in the art including asymmetric catalytic hydrogenation and resolution of a pair of diastereomeric salts formed by reaction with a chiral amine such as D or L α-methylbenzylamine. The absolute stereochemistry can be determined in a number of ways including X-ray crystallography of a suitable crystalline derivative.

SCHEME 15

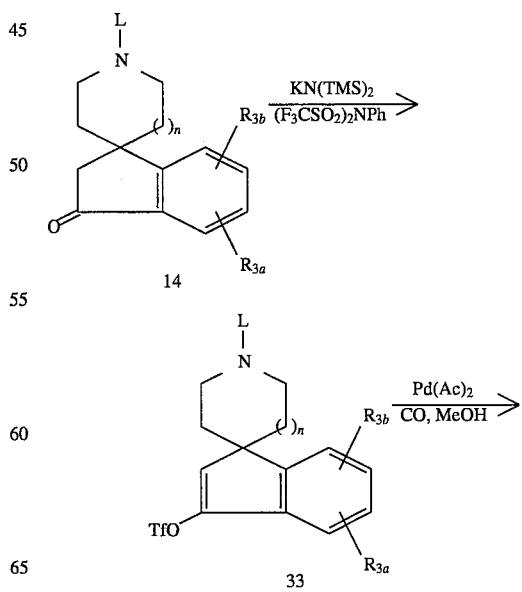

31
-continued
SCHEME 15

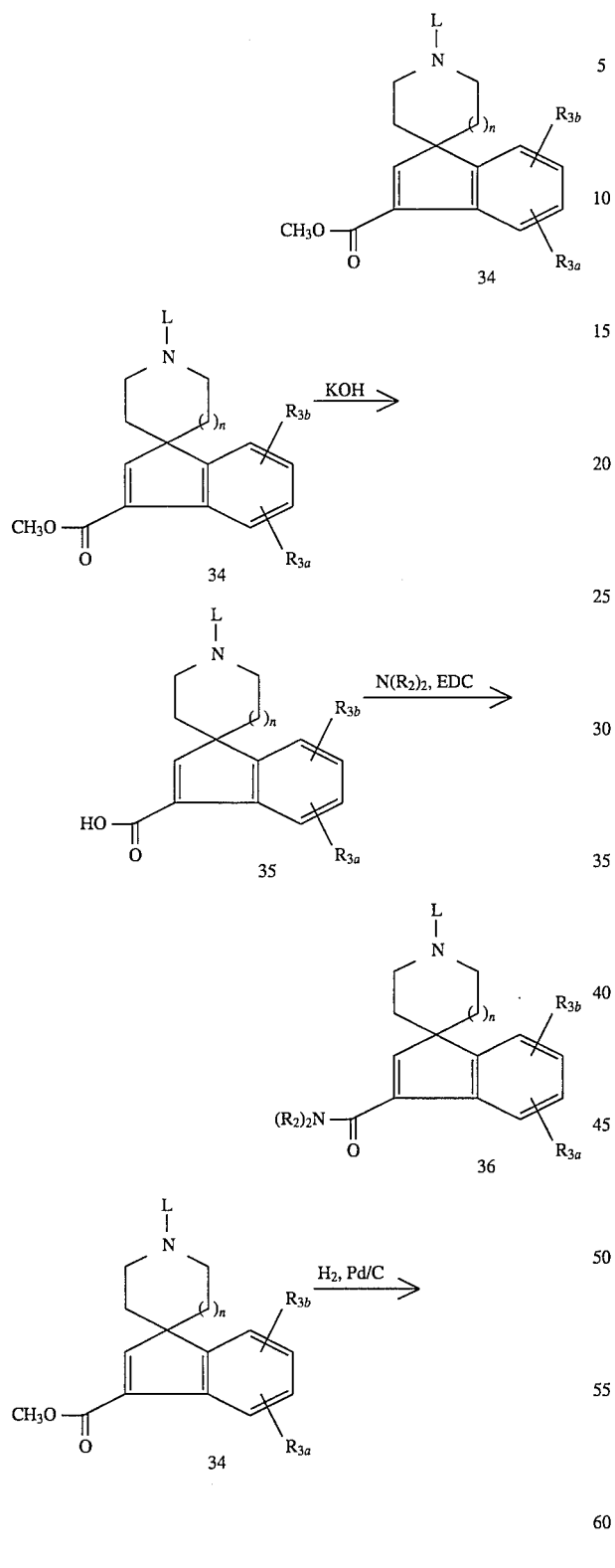

32
-continued
SCHEME 15

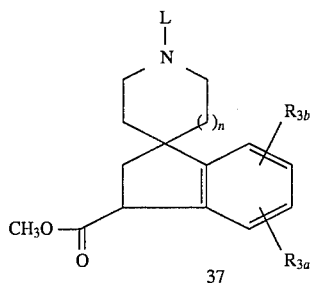

Spiroindane intermediates, for incorporation into growth hormone secretagogues, can be further elaborated in the benzylic position by the chemistry detailed in the following schemes.

Homologs of ester 37 can be conviently prepared by a variety of methods known to those skilled in the art igncluding the displacement of an activated alcohol such as tosylate 38 by a malonate nucleophile followed by decarboxylation or a cuprate reaction followed by the adjustment of the chain length or oxidation state as appropiate, see scheme 16 below.

SCHEME 16

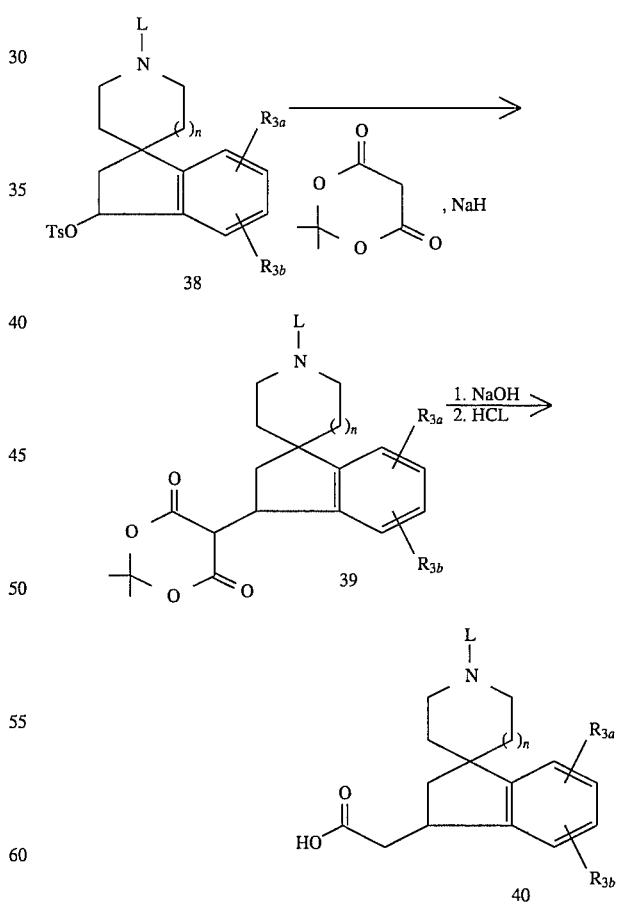

SCHEME 16 -continued

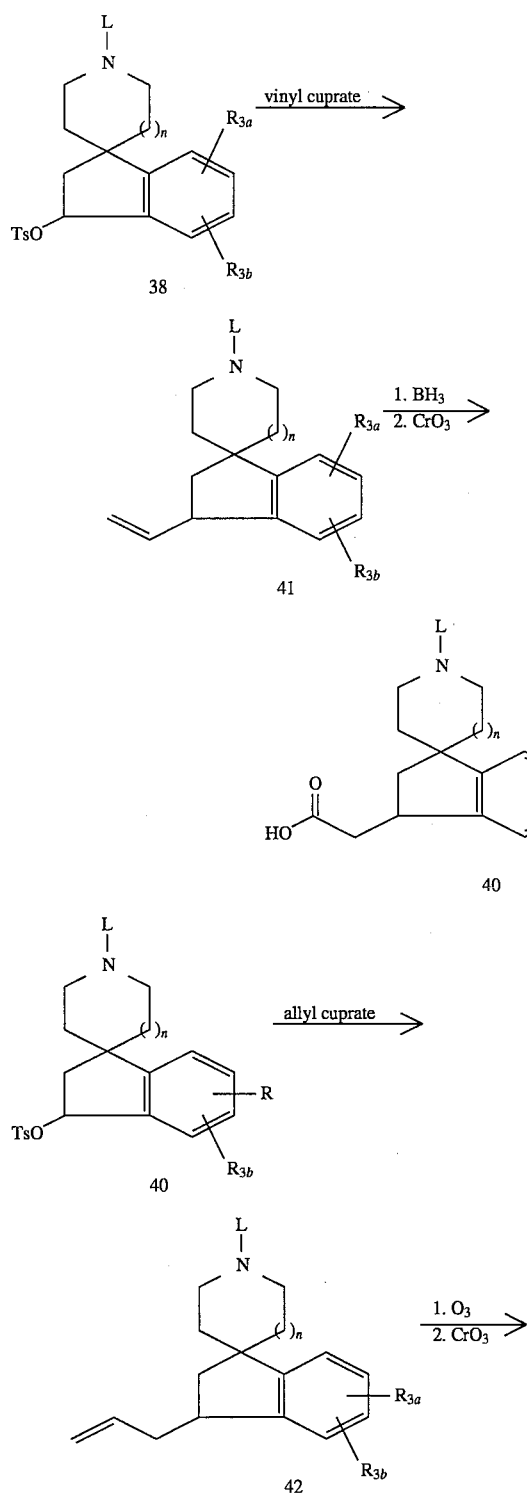

Alternatively the reaction of spiroindanone 14 with Wittig or Emmons reagents also provides access to homologs of ester 37. The chemistry is described in scheme 17 below. Treatment of triethylphosphonoacetate with a base in an inert solvent such as THF followed by the addition of ketone 14 provides the unsaturated ester 43. Hydrogenation of 43 using a palladium catalyst in an inert solvent provides the saturated ester 44. The protecting group can then be removed as described above and the resulting amine can be incorporated into a secretagogue via the chemistry described in Schemes 1 and 8. A secretagogue containing an acid function can be obtained via saponification of the ester function as the final step of the synthesis.

SCHEME 17

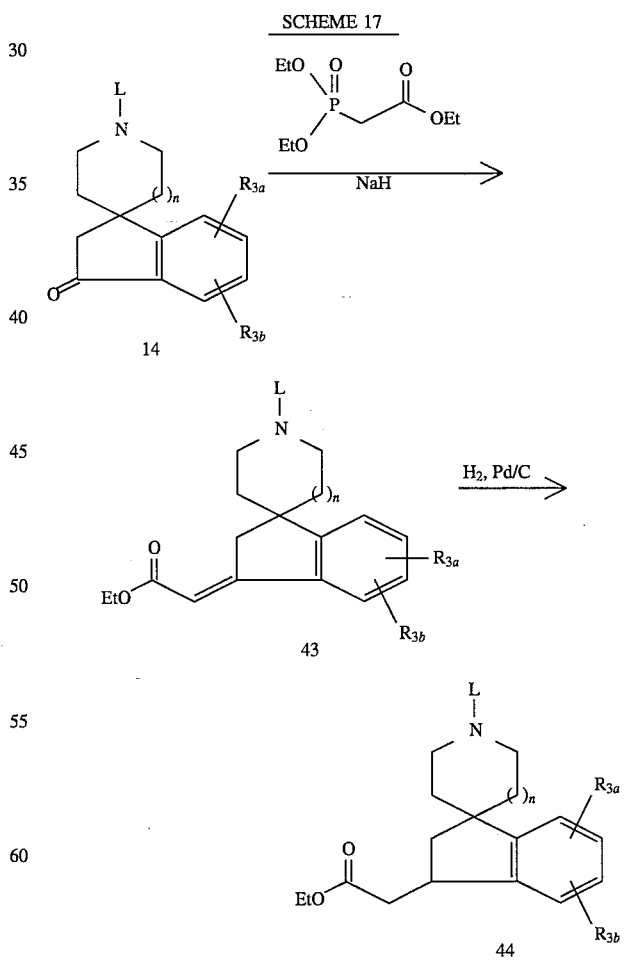

Chiral esters and acids are available by a variety of methods known to those skilled in the art including asymmetric catalytic hydrogenation, chomatographic resolution of a pair of diasteromers, and via crystallization of salts formed from chiral amines such as D or L-α-methylbenzylamine. The absolute stereochemistry can be determined in a number of ways including X-ray crystallography of a suitable crystalline derivative.

The ester can be reduced to an alcohol by treatment with LAH and to an aldehyde with DIBALH. Reductive alkylation of the aldehyde with ammonium acetate and sodium cyanoborohydride affords an amino methyl analog. These hydroxymethyl and aminomethyl analogs may then be further reacted to afford additional growth hormone secretagogues of the general formula 1.

Saponification of ester 44 provides an acid which can be conviently derivatized as for example reaction with an amine in the presence of a coupling reagent such as EDC gives amides which can be incorporated into a secretagogue as detailed in Schemes 1 and 8.

Homologation of ester 44 is possible using a variety of methods known to those skilled in the art including the method described in J. Org. Chem. 1992, 57 7194–7208.

A variety of acid equivalents can also be incorporated into the spiroindane intermediates for example acylsulfonamides are readily available from acids such as 35 and 40. Treatment of the spiroindane acid with a base in an inert solvent such as THF followed by the addition of oxalyl chloride provides an acid chloride which is then treated with a sodium salt of a sulfonamide. The protecting group can then be removed using chemistry described above and the resulting amine can be incorporated into a secretagogue using chemistry depicted in Schemes 1 and 8.

SCHEME 18

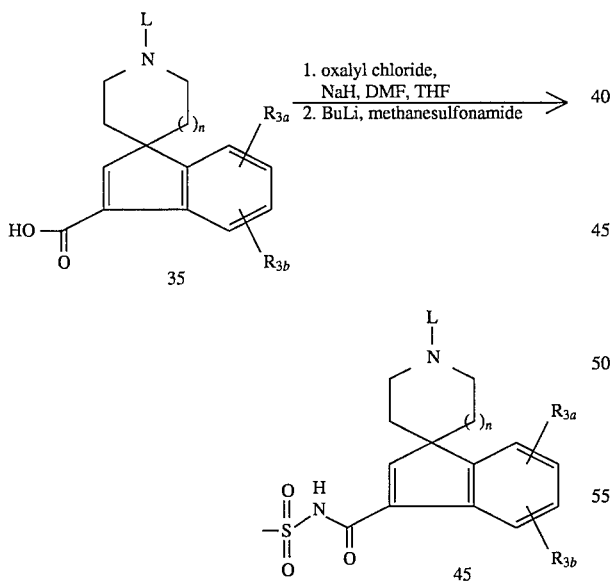

Tetrazole spiroindane intermediates are available from nitriles of both the shorter and longer homolog series. For example the reaction of enol triflate 33 with a cyanide anion and a palladium catalyst in the presence of an inert solvent such as toluene provides the unsaturated nitrile which can be converted into the tetrazole by reaction with trimethylstannyl azide in an inert solvent at elevated temperatures. Reduction of the indene double bond in 45 and 47 with catalysts such as Pd/C in ethanol affords the corresponding saturated analogs.

SCHEME 19

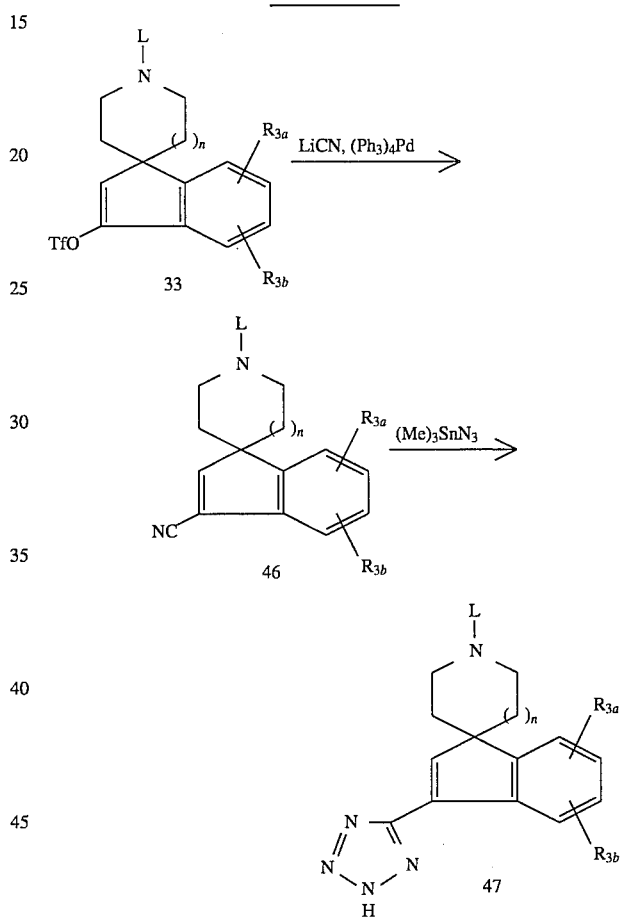

Esters such as 37 can be conviently acylated or alkylated next to the ester function by treatment with a variety of bases and alkylating or acylating agents. For example reaction of 37 with potassium bis(trimethylsilylamide) in an inert solvent such as THF followed by the addition of ethyl chloroformate provides 48 in good yield. Removal of the protecting group and incorporation into the secretagogues can be accomplished as described above.

SCHEME 20

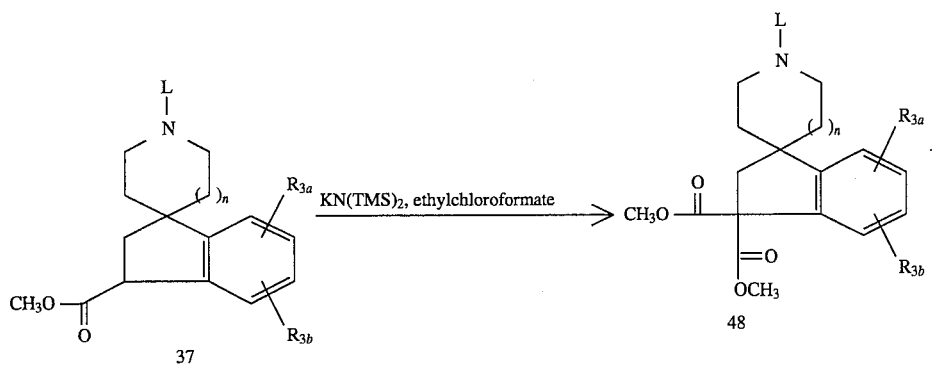

Further substitution at the benzylic position of the spiroindanes is readily carded out via the tosylate of alcohol 18. Displacement of the tosylate with a variety of nucleophiles is possible. For example treatment of tosylate 38 with sodium thiomethoxide in DMSO provides the sulfide 49. The protecting group can be removed as above and the resulting amine can be incorporated into the secretagogues employing chemistry described in Schemes 1 and 8. Alternatively the sulfide can be oxidized to the sulfoxide or sulfone by treatment with the appropriate oxidizing agent prior to deprotection or as the final step in the synthesis.

SCHEME 21

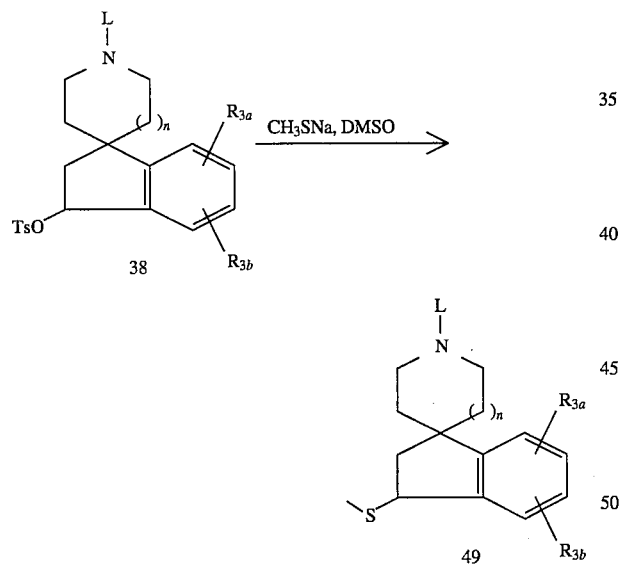

The incorporation of aryl and heteroaryl groups into the benzylic position of spiroindanes is most coveniently carded out via the enol triflate 33. Palladium catalysed reaction of the enol triflate with a variety of aryl or heteroarylstannanes in an inert solvent such as toluene provides the desired intermediates. For example 2-trimethylstannylpyridine reacts with 33 in the presence of a catalytic amount of tetrakis(triphenylphosphene)palladium in toluene at refux to give the coupled product 50. Alternativiely the enol triflate 33 can be converted into the vinyl stannane 51 by reaction with hexamethylditin and a palladium catalyst in an inert solvent such as toluene. The vinyl stannane can then be coupled with a variety of aryl or hetero aryl bromides or triflates, for example coupling to 2-bromo-3-carbomethoxy-pyridine provides 52. The protecting group L can be removed from the coupled products using chemistry described above and the resulting amine can be included in the secretagogues as described in Schemes 1 and 8.

SCHEME 22

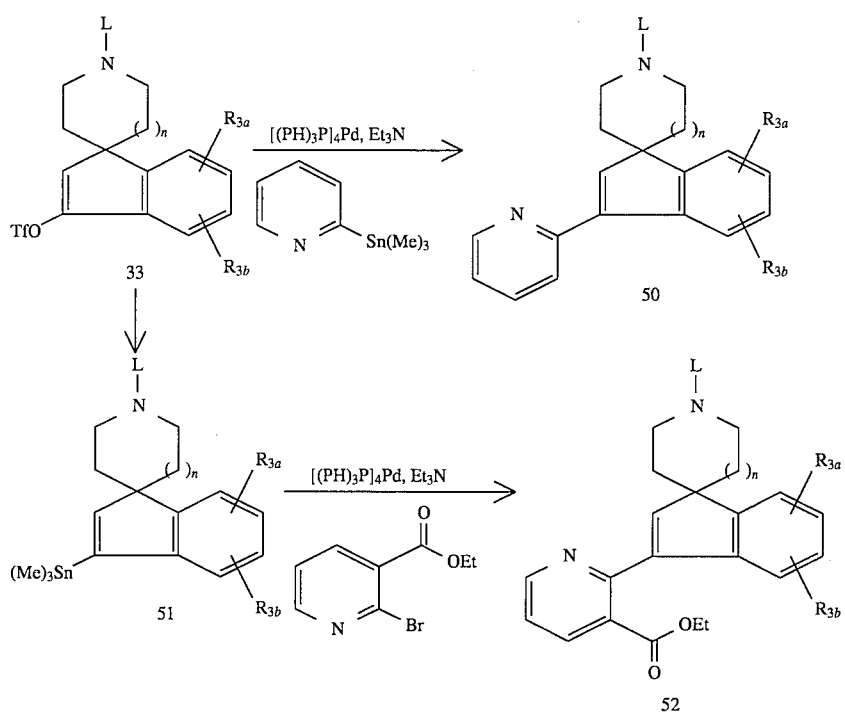

The spiropiperidine ring of the growth hormone secretagogues can be replaced with a spiroazepine ring. Alkylation of indene with dibromide 53, prepared as described in J. Am. Chem. Soc. 1990, 9001–9003, and base in an inert solvent such as THF followed by acid treatment provides ketone 54. Ring expansion of the ketone can be accomplished using a variety of methods including treatment of the ketone with hydrazoic acid in an inert solvent such as chloroform. The lactam can then be reduced to an amine be reaction with LAH in an inert solvent such as THF. The resulting amine can be incorporated into a secretagogue by employing the chemistry depicted in Schemes 1 and 8 and the indene double bond in 56 may be reduced or further substituted as described herein for spiroindenylpiperidines and their L protected derivatives.

SCHEME 23

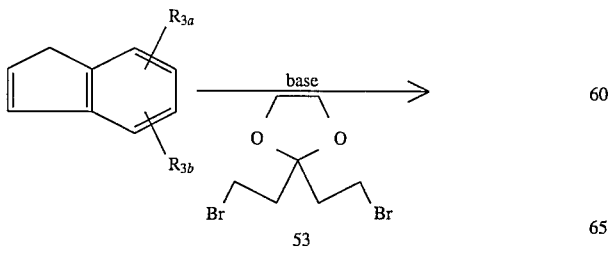

-continued
SCHEME 23

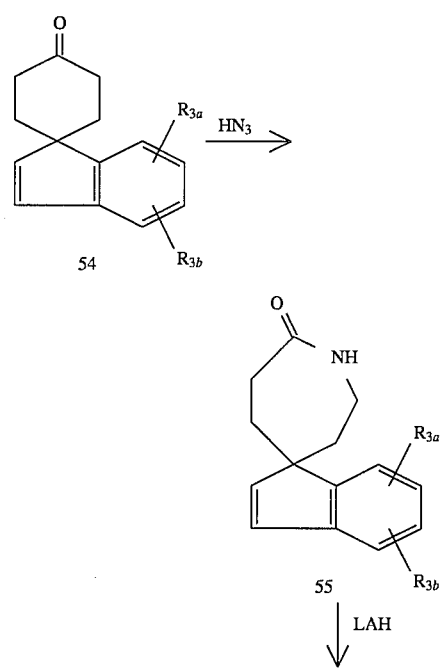

-continued
SCHEME 23

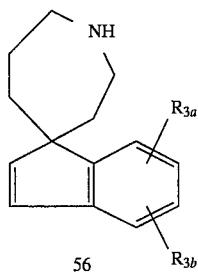

Alternative spiro compounds are readily prepared from 1-indanones. For example the 1-indanone 57 can be alkylated in the presence of a base, such as sodium hydride or lithium or potassium bis(trimethylsilyl)amide with the protected bis 2-haloethyl amine, where L is a defined protecting group such as methyl, benzyl, t-Boc, or Cbz, etc., and Y could be Cl, Br, I, in an inert solvent such as THF or DMF to yield the spiropiperidine 58. The protecting group could be removed by procedures described above to yield formula 59 The ketone functionality may be reduced to an alcohol using sodium borohydride or may be fully reduced to a methylene also employing conditions known to those skilled in the art. For example, reduction of the ketone with sodium borohydride, followed by catalytic hydrogenation yielded compound 60. Removal of the protecting group L yielded general structure 61. The spiropiperidines of structure 59 or 60 can then be incorporated into a growth hormone secretagogue via the chemistry described above. Alternatively, the ketone can be reduced after the incorporation into the secretagogue.

It is noted that the order of-carrying out the foregoing reaction schemes may be varied to facilitate the reaction or to avoid unwanted reaction products.

The growth hormone releasing compounds of Formula I and II are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I and II can also be employed to investigate the possible negative or positive feedback effects of some of the pituitary hormones, e.g., growth hormone and endorphin peptides, on the pituitary to modify growth hormone s release. Of particular scientific importance is the use of these compounds to elucidate the subcellular mechanisms mediating the release of growth hormone.

The compounds of Formula I and II can be administered to animals, including man, to release growth hormone in vivo. For example, the compounds can be administered to commercially important animals such as swine, cattle, sheep

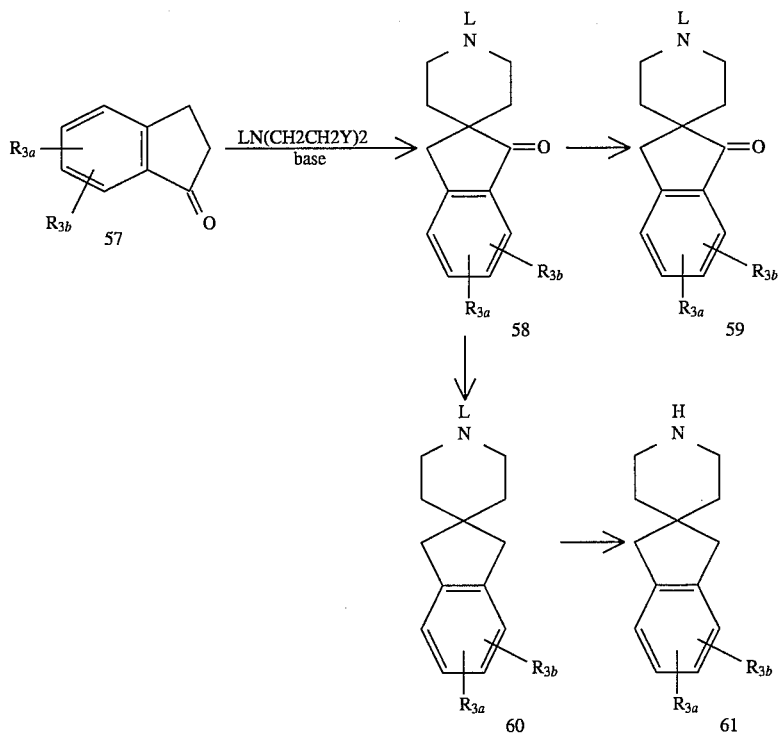

and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I and II can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carder or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the catabolic side effects or with other pharmaceutically active materials wherein the combination enhances efficacy and minimizes side effects.

Growth promoting and anabolic agents include, but are not limited to, TRH, diethylstilbesterol, estrogens, β-agonists, theophylline, anabolic steroids, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the growth hormone secretagogues of this invention is in combination with other growth hormone secretagogues such as the growth hormone releasing peptides GHRP-6, GHRP-1 as described in U.S. Pat. Nos. 4,411,890 and publications WO 89/07110, WO 89/07 111 and B-HT920 as well as hexarelin and the newly discovered GHRP-2 as described in WO 93/04081 or growth hormone releasing hormone (GHRH, also designated GRF) and its analogs or growth hormone and its analogs or somatomedins including IGF-1 and IGF-2 or α-adrenergic aginists such as clonidine or serotonin 5HTID agonists such as sumitriptan or agents which inhibit somatostatin or its release such as physostigmine and pyridostigmine.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; treating growth hormone deficient adults; prevention of catabolic side effects of glucocorticoids, treatment of osteoporosis, stimulation of the immune system, acceleration of wound healing, accelerating bone fracture repair, treatment of growth retardation, treating acute or chronic renal failure or insufficiency, treatment of physiological short stature, including growth hormone deficient children, treating short stature associated with chronic illness, treatment of obesity and growth retardation associated with obesity, treating growth retardation associated with Prader-Willi syndrome and Turner's syndrome; accelerating the recovery and reducing hospitalization of bum patients or following major surgery such as gastrointestinal surgery; treatment of intrauterine growth retardation, skeletal dysplasia, hypercortisonism and Cushings syndrome; replacement of growth hormone in stressed patients; treatment of osteochondrodysplasias, Noonans syndrome, sleep disorders, Alzheimer's disease, delayed wound healing, and psychosocial deprivation; treatment of pulmonary dysfunction and ventilator dependency; attenuation of protein catabolic response after a major operation; treating malabsorption syndromes, reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; to stimulate thymic development and prevent the age-related decline of thymic function; adjunctive therapy for patients on chronic hemodialysis; treatment of immunosuppressed patients and to enhance antibody response following vaccination; improvement in muscle strength, mobility, maintenance of skin thickness, metabolic homeostasis, renal hemeostasis in the frail elderly; stimulation of osteoblasts, bone remodelling, and cartilage growth; treatment of neurological diseases such as peripheral and drug induced neuropathy, Guillian-Barre Syndrome, amyotrophic lateral sclerosis, multiple sclerosis, cerebrovascular accidents and demyelinating diseases; stimulation of the immune system in companion animals and treatment of disorders of aging in companion animals; growth promotant in livestock; and stimulation of wool growth in sheep.

It will be known to those skilled in the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N. A. T., Role of Bisphosphonates in Metabolic Bone Diseases. *Trends in Endocrinol. Metab.*, 1993, 4, 19–25. Bisphosphonates with these utilities include alendronate, tiludronate, dimethyl—APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carder such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the disclosed invention.

EXAMPLE 1

N-[1(R,S)-[2,3-dihydrospiro[1H-indene-1,4'-piperidin]-1'yl)carbonyl]-2-(indazol-3-yl)ethyl]-2-amino-2-methylpropanamide hydrochloride Step A:

[1(R,S)-[2,3-dihydrospiro[1H-indene-1,4'piperidin]-1'yl)carbonyl]-2-(indazol-3-yl)ethyl]carbamic acid 1,1-dimethylethyl ester To a mixture of 81 mg (0.265 mmol) of DL-2-amino-3-(3-indazole)propionic acid (J. Am. Chem. Soc., 1952,2009), 74 mg (0.33 mmol) of 3,4-dihydrospiro[1H-indene-1,4'-piperidine]hydrochloride [Chambers, et al, J. Med. Chem., 1992, 35, 2036] 45 mg (0.33 mmol) of HOBT, and 0.047 ml (0.33 mmol) of NMM in 1.0 ml of dichloromethane and 0.5 ml of DMF was added 63 mg (0.33 mmol) of EDC. The reaction mixture was stirred at room temperature over night and then poured into ethyl acetate, washed sequentually with saturated aqueous sodium bicarbonate and brine. The organic layer was dried over anhydrous sodium sulfate filtered and then concentrated. Purification by flash chromatography (silica gel, dichloromethane/ethyl acetate 3:1) gave 42 mg (34%) of the title compound.

$^1$H NMR (200 MHz, CDCl$_3$,60/40 mixture of conformers): 7.80–7.65 (m, 1H), 7.50–7.31 (m, 2H), 7.22–7.04 (m,5H), 6.81–6.60 (m, 1H), 5.88–5.72 (m, 1H), 5.26–5.08 (m, 1H), 4.58–4.38 (m, 1H), 3.92–3.70 (m,1H), 3.51–3.38 (m, 2H), 3.10 (dt; ⅔H), 2.90–2.56 (m, 3⅔H), 1.92–1.58 (m, 3H), 1.51–1.12 (m, 1⅔H),0.78 (dt, ⅓H)

Step B:

N-[1(R,S)-[2,3-dihydrospiro[1H-indene-1,4'-piperidin]-1'yl)carbonyl]-2-(indazol-3-yl)ethyl]-2-[[1,1-dimethylethyloxy)carbonyl]amino-2-methylpropanamide A solution of 37 mg (0.078 mmol) of the intermediate obtained in Step A in a 1:1 mixture of trifluroacetic acid and dichloromethane with 0.050 ml of anisole was stirred at room temperature for 1 hour. The solution was concentrated and azeotroped with toluene. The residue was dissolved in dichloromethane and cooled to 0° C. To this solution was added 18.5 mg (0.091 mmol) of Boc alpha methyl alanine, 12.2 mg (0.091 mmol) of HOBT, 0.013 ml (0.091 mmol) of NMM, and 17.3 mg (0.091 mmol) of EDC. The mixture was stirred at room temperature for 16 hours. The solution was then diluted with ethyl acetate and then washed with saturated sodium bicarbonate followed by brine. The organic layer was dried over sodium sulfate and concentrated. Purification by flash chromatography (silica gel, dichloromethane/ethyl acetate 2:1) gave 29 mg (69%) of the title compound.

$^1$H NMR (400 MHz, CD$_3$OD, 2:1 mixture of conformers) 7.83 (d, ⅔H), 7.74 (d,⅓H), 7.54–7.34 (m, 2H), 7.18–7.07 (m, 5 1/H), 6.60–6.51 (m, ⅔H), 5.48–5.40 (m, 1H), 4.33–4.28 (m, ⅔H), 3.89–3.81 (m, ⅓H), 3.79–3.71 (m, ⅔H), 3.10-(dt, ⅔H), 2.84 (t, ⅔H), 2.78 (t, 1H), 2.69–2.61 (m, 4/3), 1.92 t, 1H),1.90–1.80 (m, ⅔H), 1.67 (dt,⅓H), 1.44 (s, 8H), 1.38 (s, 4H), 1.29 (s, 2H), 1.24 (s, 1H), 1.30–1.18 (m,⅔H), 1.10–1.09 (m, ⅓H), 0.41 (dt, ⅔H).

Step C:

N-[1(R,S)-[2,3-dihydrospiro[1H-indene-1,4'-piperidin]-1'yl)-carbonyl]-2-(indazol-3-yl)ethyl]-2-amino-2-methylpropanamide hydrochloride A solution of 1.3N HCl/methanol and 26 mg (0.046 mmol) of the intermediate obtained from Step B was stirred at room temperature for 3 hours and then concentrated. Purification by flash chromatography (silica gel, dichoromethane/methanol/ammonium hydroxide 94:5:1) gave 18.3 mg (85%) of the free amine. The free amine was dissolved in 0.5 ml of 1.3N HCl/methanol and then concentrated to provide the title compound.

$^1$H NMR (400 MHz CD$_3$OD, 60/40 mixture of rotatomers): 7.78 (t, 1H), 7.63–7.51 (m, 2H), 7.25 (t,1H), 7.17–7.04 (m, 4⅖H), 6.65 (d, ⅗H), 5.48–5.35 (m, 1H), 4.42 (d, ⅖H), 4.33 (d, ⅗H), 3.91–3.81 (m, 1H), 3.65–3.41 (m, 2H), 3.16 (t, ⅗H), 2.90 (t, ⅖H ), 2.88 (t, 1H), 2.72 (t, 1H), 2.77–2.68 (m, 1H), 2.02–1.95 (m, 4H), 1.81 (dt, ⅖H), 1.68 (dt, ⅖H), 1.58 (s, 3H), 1.49 s, 2H), 1.39 (s, 1H), 1.30–1.23 (m, 2H), 1.05 (dt, ⅗H), 0.73 (dt, ⅗H). FAB-MS: m/e 460 (m+1).

EXAMPLE 2

N-[1(R,S)-[2,3-dihydrospiro[1H-indene-1,4'-piperidin]-1'-yl)carbonyl]-2-(benzothien-3-yl)ethyl]-2-amino-2-methylpropanamide hydrochloride Step A:

[1(R,S)-[2,3-dihydrospiro[1H-indene-1,4'-piperidin]-1'yl)carbonyl]-2-(benzothien-3-yl)ethyl]carbamic acid 1,1-dimethylethyl ester The title compound (371 mg, 48%) was prepared from 500 mg (1.56 mmol) of (RS)-N[t-butyloxycarbonyl)-3-benzothienylglycine (Int. J. Peptitde Protein Res. 29, 1987, 118) and 348 mg (1.56 mmol) of 3,4-dihydrospiro[1H-indene-1,4'-piperidine]hydrochloride according to the procedure described in Example 1 (Step A).

$^1$H NMR (200 MHz, CDCl$_3$, mixture of conformers): 7.90–7.71 (m,2H), 7.5–7.0 (m, 6⅓H), 6.8–6.7 (m, ⅔H), 5.71–5.50 (m, 1H), 5.20–5.01 (m, 1H), 4.5–4.4 (m, 2H), 3.5–3.1 (m, 1H), 3.05–2.55 (m, 4H), 1.9–1.1 (m, 3⅔H), 0.9–0.8 (m, ⅔H), 0.25 (dt, ⅔H).

Step B:

N-[1(R,S)-[2,3-dihydrospiro[1H-indene-1,4'-piperidin]-1'-yl)carbonyl]-2-(benzothien-3-yl)ethyl]-2-[[1,1-dimethylethyloxy)carbonyl]amino]-2-methylpropanamide A solution of 358 mg (0.729 mmol) of the intermediate obtained in Step A in a 1:1 mixture of trifluroacetic acid and dichloromethane was stirred for 1 hour. The solution was concentrated and azeotroped from toluene. A 200 mg (0.512 mmol) portion of the residue was reacted with 104 mg (0.512 mmol) of BOC α-methyl alanine according to the procedure described in Example 1 Step B to give 172 mg (58%) of the title compound.

$^1$H NMR (400 CDCl$_3$, 60:40 mixture of conformers): 8.05 (d, ⁶⁄₁₀H), 7.95 (d, ⁴⁄₁₀H), 7.83–7.81 (m, 1H), 7.42–7.11 (m, 6⁴⁄₁₀H), 5.41–5.36 (m, ⁶⁄₁₀H), 5.30–5.21 (m,⁴⁄₁₀H), 4.93–4.92 (bs, 1H), 4.42–4.38 (m, 1H), 3.40–3.11 (m, 3H), 2.88 (dt, ⁶⁄₁₀H), 2.50 (dt, ⁴⁄₁₀H), 2.12 (dt, ⁴⁄₁₀H), 1.90–1.65 (m, 2H), 1.51–1.43 (m, 15H), 1.40–1.30 (m, ⁴⁄₁₀H), 1.13 (dt, 1H), 0.86–0.81 (m, 1H), 0.2 (dt, ⁶⁄₁₀).

Step C:

N-[1(R,S)-[2,3-dihydrospiro[1H-indene-1,4'-piperidin]-1'-yl)-carbonyl]-2-(benzothien-3-yl)ethyl]-2-amino-2-methylpropanamide hydrochloride A solution of 30 mg (0.052 mmol) of the intermediate from Step B in a 1:1 mixture of trifluroacetic acid and dichloromethane was stirred for 1 hour and then concentrated and stripped. The residue was diluted with dichloromethane and washed with saturated sodium bicarbonate, dried over sodium sulfate and concentrated. Purification by flash chromatography (silica gel, dichloromethane/acetone 1:1) gave 17 mg (69%) of the amine. The amine was dissolved in methanol and 1.0 equivalent of 4N HCl was added. The solution was concentrated and azeotroped with methanol to give 18 mg of the title compound.

$^1$H NMR (400 MHz, CD$_3$OD, 3:1 mixture of conformers): 7.95–7.85 (m, 2H), 7.46–7.36 (m, 3H), 7.18–7.08 (m, 3H), 6.74 (d, 1H), 5.38–5.32 (m, 2H), 4.45–4.30 (m, 1H), 3.80–3.65 (m, 1H), 3.15–3.01 (m, 1H), 2.86–2.62 (m, 3H), 1.96–1.91 (m, 2H), 1.80–1.71 (m, 1⅓H), 1.60–1.4 (m, 6H), 1.38–1.30 (m, 1H), 1.11–1.0 (m, 1H), 0.50–0.39 (m, 1⅔H), FAB-MS:m/e 476 (m+1).

EXAMPLE 3

N-[1(R,S)-[2,3-dihydrospiro[1H-indene-1,4'-piperidin]-1'-yl)carbonyl]-2-(3',4'-dichlorophenylethyl)-2-amino-2-methylpropanamide hydrochloride Step A:

N-[1(R,S)-[2,3-dihydrospiro[1H-indene-1,4'-piperidin]-1'-yl)-carbonyl]-2-(3',4'-dichlorophenylethyl)carbamic acid 1,1-dimethylethyl ester 1.63 g of the title compound was prepared from 2.2 g (6.6 mmol) of N-t-butoxycarbonyl-3'4'dichlorophenylglycine (Int. J. Peptide Protein Res. 30, 1987, 13) and 1.48 g (6.60 mmol) of 3,4-dihydrospiro-[1H-indene-1,4'-piperidine]hydrochloride according to the procedure described in Example 1 (Step A).

Step B:

N-[1(R,S)-[2,3-dihydrospiro[1H-indene-1,4'-piperidin]-1'-yl)carbonyl]-2-(3',4'dichlorophenylethyl)-2-[[1,1-dimethylethyloxycarbonyl]amino]-2-methylpropanamide A solution of 1.6 g (3.1 mmol) of the intermediate from Step A in a 1:1 mixture of trifluoroaceteic acid and dichloromethane was stirred for 1 hour concentrated and azeotroped from toluene. A 250 mg (0.484 mmol) portion of the residue was reacted with 108 mg (0.533 mmol) of N-BOC α-methyl alanine according to the procedure described in Example 1 (Step B) to give 171 mg (60%) of the title compound.

Step C:

N-[1(R,S)-[2,3-dihydrospiro[1H-indene-1,4'-piperidin]-1'-yl)carbonyl]-2-(3',4'dichlorophenylethyl)-2-amino-2-methylpropanamide hydrochloride A solution of 40 mg (0.068 mmol) of the intermediate from Step B in a 1.3N HCl methanol was stirred for 2 hours and then concentrated and azeotroped from toluene. Purification by flash chromatography (silica gel, dichloromethane/methanol/ammonium hydroxide 94:5:1) gave the amine. The amine was dissolved in HCl/methanol and stripped to give 26 mg (73%) of the title compound as a white solid.

$^1$H NMR (400 MHz, CD$_3$OD, 60/40 mixture of conformers): 7.52–7.43 (m, 2H), 7.32–7.06 (m, 4H), 6.93 (d, 1H), 5.20–5.13 (m, 1H), 4.48–4.44 (m, 1H), 4.05–3.95 (m, 1H), 3.25–2.75 (m, 5⅗H), 2.13–2.02 (m, 2H), 1.85–1.60 (m, ⅘H), 1.58–1.40 (m, 3H), total 6H, 1.55 (s)+1.53 (s)+1.48 (s),+1.42 (s,), 1.03 (dt, ⅗H). FAB-MS: m/e 489 (m+1).

EXAMPLE 4

N-[1(R,S)-[(2,3-dihydro-3-oxospiro[1H-indene-1,4'-piperidin]1'-yl)carbonyl]-2-(indol-3-yl)ethyl]-2-amino-2-methylpropanamide hydrochloride Step A:

1'-(t-butyloxycarbonyl)-3,4-dihydro-3-oxospiro[1H-indene-1,4'-piperidine]

To a solution of 661 mg (2.31 mmol) of 1'-(t-butyloxycarbonyl)spiro[1H-indene-1,4'-piperidine][prepared by the method of Chambers, et al, J. Med. Chem., 1992, 35, 2036] in 5.0 ml of THF was added 5.8 ml (1.0M THF, 2.9 mmol)

of 9-BBN. The reaction mixture was heated at 70° C. until TLC analysis indicated that the starting material was consumed. The solution was concentrated and the residue was dissolved in dichloromethane. The solution was cooled to 0° C. and 4.1 g (19.2 mmol) of PCC was added slowly over 15 minutes. The reaction mixture was warmed to room temperature and then to reflux for 30 minutes. The solution was then diluted with ether and filtered through a pad of a mixture of celite and florisil. Purification by flash chromotgraphy (silica gel, hexane/ethyl acetate, 4:1) gave 326 mg (47%) of the title compound.

$^1$H NMR (200 MHz, CDCl$_3$): 7.75–7.60 (m, 2H), 7.50–7.44 (m, 2H), 4.30–4.15 (m, 2H), 2.85 (dt, 2H), 2.63 (s, 2H), 1.98 (dt, 2H), 1.53–1.40 (m, 2H), 1.49 (s, 9H).

Step B:

spiro[1H-indene-1,4'-piperidin]-3(2H)-one Trifluoroacetamide

A solution of the intermediate from Step A in a 1:1:0.5 mixture of trifluoroacetic acid, dichloromethane and anisole was stirred for 1 hour and then concentrated and azeotroped from toluene to give the title compound.

$^1$H NMR (200 MHz, CDCl$_3$): 7.81–7.70 (m, 1H), 7.62–7.45 (m, 2H), 7.22–7.15 (m, 1H), 3.72–3.58 (m, 2H), 3.29–3.04 (m, 2H), 2.70 (s, 2H), 2.47 (dt, 2H), 1.85–1.75 (m, 2H).

Step C:

(2R)-[[-2-[[1,1-dimethylethoxy)carbonyl]amino]-2,2-dimethyl-1-oxoethyl]amino]-1H-indole-3-propanoic acid benzyl ester To 5.0 g (16.5 mmol) of the commercially available N-tBOC-D-tryptophan in 100 mL of chloroform was added 1.80 mL (16.5 mmol) of benzyl alcohol, 0.20 g (1.65 mmol) of 4-N,N-dimethylamino pyridine (DMAP), and 3.20 g of EDC and stirred for 16 h. The reaction mixture was poured into 100 mL of water and the organic layer was seperated. The aqueous was further extracted with 2×100 mL of chloroform. The combined organics were washed with 50 mL of 10% aqueous citric acid, 100 mL of 10% aqueous sodium bicarbonate solution, dried over anhydrous magnesium sulfate, filtered and concentrated to give a thick oil.

To a solution of this oil in 10 mL of dichloromethane was added 20 mL of trifluoroacetic acid and stirred for 1 h. The reaction mixture was concentrated, basified carefully with saturated aqueous sodium bicarbonate solution, and extracted with chloroform (2×100 mL). The combined organics were washed with brine (100 mL), dried over potassium carbonate, filtered, and concentrated to give 5.46 g of the amine as a brown oil which was used without purification.

To 5.46 g of the above product in 100 mL of chloroform was added 3.40 g (22.2 mmol) of HOBT, 4.60 g (22.2 mmol) of N-BOC-α-methyl alanine, and 5.32 g (28.0 mmol) of EDC and stirred for 16 h. The reaction mixture was poured into 100 mL of water and the organic layer was seperated. The aqueous was further extracted with 2×100 mL of chloroform. The combined organics were washed with 50 mL of 10% aqueous citric acid, 100 mL of 10% aqueous sodium bicarbonate solution, dried over anhydrous magnesium sulfate, filtered and concentrated to give 6.94 g of the product as a thick oil. Flash chromatography (200 g SiO$_2$; hexane-ethyl acetate as eluent) gave 4.75 g of the desired material as a colorless foam.

$^1$H NMR(CDCl$_3$, 200 MHz) δ8.48 (bs, 1H), 7.54 (bd, 1H), 7.38–7.23 (m, 3H), 7.19 (bd, 2H), 7.15–7.00 (m, 1H), 6.90 (d, 1H), 6.86 (d, 1H), 5.06 (bs, 2H), 4.95 (ddd, 1H), 3.30 (2dd, 2H), 1.40 (s, 15H).

Step D:

(2R)-[[-2-[[1,1-dimethylethoxy)carbonyl]amino]-2,2-dimethyl-1-oxoethyl]amino]-1H-indole-3-propanoic acid To a solution of 4.75 g of the material from step B in 100 mL of ethanol was added 1.0 g of 10% Pd/C and stirred at RT under a H$_2$ balloon for 18 h. The catalyst was filtered off through a pad of celite and washed with ethyl acetate. The filtrate was concentrated to give 2.96 g of the acid as a colorless foam.

$^1$H NMR (CDCl$_3$, 200 MHz) δ8.60 (bs, 1H), 7.55 (d, 1H), 7.26–6.90 (m, 3H), 6.88 (bd, 1H), 4.80 (m, 1H), 3.32 (2dd, 2H), 1.37 (s, 3H), 1.35 (s, 12H).

Step E:

N-[1(R,S)-[(2,3-dihydro-3-oxospiro[1H-indene-1,4'-piperidin]-1'-yl)carbonyl]-2-(indol-3-yl)ethyl]-2-[[1,1-dimethylethyloxycarbonylamino-2-methylpropanamide The title compound (763 mg, 1.33 mmol) was prepared from 720 mg (2.39 mmol) of the intermediate from Step B and 929 mg (2.39 mmol) of the intermediate from Step D according to the procedure described for Example 1 (Step A).

$^1$H NMR (400 MHz, CD$_3$OD, 2:1 mixture of conformers): 7.7–7.54 (m, 3H), 7.45–7.39 (m, 2⅓H), 7.23 (s, ⅔H), 7.17–7.07 (m, 2⅓H), 6.93–6.91 (m, ⅔H), 5.33–5.29 (m, ⅔H), 5.26–5.24 (m, ⅓H), 4.48–4.43 (m, 1H), 3.85–3.72 (m,1H), 3.19–3.12 (m, 1H), 2.99–2.92 (dt, ⅔H) 2.60–2.36 (m, 2⅔H), 2.20–1.89 (m,⅔H), 1.45–1.38 (m, 15H), 1.3.1–1.21 (m, 1H), 1.12 (dt, ⅔H), 0.80–0.76 (m, ⅔H), 0.10 (dt, ⅔H).

Step F:

N-[1(R,S)-[(2,3-dihydro-3-oxospiro[1H-indene-1,4'-piperdin]-1'-yl)carbonyl]-2-(indol-3-yl)ethyl]-2-amino-2-methylpropanamide hydrochloride A solution of 121 mg (0.211 mmol) of the intermediate from Step E in a 1:1:0.1 mixture of dichloromethane, trifluroacetic acid and anisole was stirred for 30 minutes and then concentrated and azeotroped from toluene. Purification by flash chromatography (silica gel, dichloromethane/methanol/ammonium hydroxide 94:4:1) gave the amine. A 26 mg portion of this amine was dissolved in dioxane and 1.0 equivalent of 4N HCl was added. The solution was concentrated to give the title compound.

$^1$H NMR (400 MHz, CD$_3$OD, 3/1 mixture of conformers): 7.70–7.64 (m, 2H), 7.59–7.53 (m, 1H), 7.47–7.35 (m, 2⅓H), 7.23 (s, ⅔H), 7.17–6.98 (m, 3H), 5.28–5.24 (m, ⅔H), 5.18 (t,⅓H), 4.56–4.50 (m, ⅓H), 4.47–4.32 (m, ⅔H), 3.87–3.83 (m, 1H), 3.39–3.30 (m, ⅔H), 3.29–3.18 (m, 1⅔H), 2.98 (dt, ⅔H). 2.59–2.44 (m, 2H), 2.10 (dt, ⅓H), 1.85 (dt, ⅓H), 1.63 (s, 1H), 1.62 (s, 2H), 1.61 (s, 2H), 1.51 (s, 1H), 1.50–1.34 (m, ⅔H), 1.27–1.26 (m, ⅔H), 1.10 (dt, ⅔H).

EXAMPLE 5

N-[1(R,S)-[(2,3-dihydro-3(R,S)-hydroxyspiro[1H-indene-1,4'-piperidin]-1'-yl)carbonyl]-2-(indol-3-yl)ethyl]-2-amino-2-methylpropanamide hydrochloride Step A:

N-[1(R,S)-[(2,3-dihydro-3(R,S)-hydroxyspiro[1H-indene-1,4'-piperidin]-1'-yl)carbonyl]-2-(indol-3-yl)ethyl]-2-amino-2-methylpropanamide hydrochloride To a solution of 34 mg (0.072 mmol) of the intermediate from Example 4 (Step F) in methanol was added 3.9 mg (0.108 mmol) of sodium borohydride. After stirring for 24 hours TLC analysis indicated that some starting material remained so another 1.0 mg of sodium borohyride was added. After 2 more hours of stirring the s reaction mixture was concentrated and the residue was dissolved in chloroform and 1N NaOH. The layers were separated and the aqueous layer was extracted with chloroform 3 times. The combined organic layers were dried over sodium sulfate and concentrated. Purification by flash chromatography (silica gel, dichloromethane/methanol/ammonium hydroxide 94:4:1) gave 26.2 mg (77%) of the free amine. An 8 mg portion of this amine in dioxane was treated with 1.0 equivalent of 1.0N HCl and concentrated to give the title compound.

$^1$H NMR (400 MHz, CD$_3$OD, 1:1 mixture of diastereomers, 2:1 mixture of conformers): 7.63–7.01 (m, 8⅓H), 6.70–6.60 (m, ⅔H), 5.40–5.02 (m, 2H), 4.40–4.31 (m, 1H), 3.75–3.65 (m, 1H), 3.36–3.32 (m, ⅓H), 3.27–3.14 (m, 1H), 3.08–2.98 (m, ⅔H), 2.68–2.56 (m, 1⅓H), 2.38–2.25 (m, 1H), 1.94 (dt, ⅙H), 1.75 (dt, ⅙H), 1.73–1.65 (m, 1H), 1.60–1.49 (m, 6H), 1.44–0.75 (m, 3⅔H), 0.30 (dt, ⅓H), 0.08 (dt, ⅓H). FAB-MS: m/e 475 (m+1).

EXAMPLE 6

N-[1(R,S)-[(2,3-dihydro-3-oxospiro[1H-indene-1,4'-piperidin]-1'-yl)-carbonyl]-2-phenylpropyl]-2-amino-2-methylpropanamide hydrochloride Step A:

N-[1(R,S)-[(2,3-dihydro-3-oxospiro[1H-indene-1,4'-piperidin]-1'-yl)carbonyl]-2-phenylpropyl]carbamic acid 1,1-dimethylethyl ester The title compound (336 mg, 0.70 mmol) was prepared from 306 mg (0.965 mmol) of the intermediate from Example 4 (Step B) and 295 mg (1.06 mmol) of N-BOc-d-HomoPhe according to the procedure described for Example I (Step A).

$^1$H NMR (400 MHz, CD$_3$OD, mixture of conformers): 7.69–7.58 (m, 3H), 7.46–7.41 (m, 1H), 7.25–7.13 (m, 4H), 6.95–6.05 (m, 1H), 4.61–4.49 (m, 2H), 3.82–3.64 (m, 1H), 3.20–3.13 (m, 1H), 2.80–2.61 (m, 5H), 2.11 (dt, 1H), 2.00–1.85 (m, 3H), 1.54 (dt, 1H), 1.48–1.45 (m, 9H).

Step B:

N-[1(R,S)-[(2,3-dihydro-3-oxospiro[1H-indene-1,4'-piperidin]-1'-yl)carbonyl]-2-phenylpropyl]-2-[[1,1-dimethylethyloxycarbonyl]amino]-2-methylpropanamide The title compound (236 mg, 0.431 mmol) was prepared from 316 mg (0.665 mmol) of the intermediate from Step A and 148 mg (0.731 mmol) of Boc alpha methyl alanine according to the procedure described in Example 1 (Step A).

Step C:

N-[1(R,S)-[(2,3-dihydro-3-oxospiro[1H-indene-1,4'-piperidin]-1'-yl)carbonyl]-2-phenylpropyl]-2-amino-2-methylpropanamide hydrochloride The title compound was prepared from the intermediate from Step B according to the procedure described in Example 4 (Step F).

$^1$H NMR (400 MHz, CD$_3$OD): 7.73–7.58 (m, 3H), 7.47 7.42 (m, 1H), 7.29–7.15 (m, 5H), 4.81–4.75 (m, 1H), 4.58–4.54 (m, 1H), 3.72–3.56 (m, 1H), 3.24–3.18 (m, 1H), 2.85–2.60 (m, 5H), 2.16–1.88 (m, 4H), 1.66–1.62 (m, 6H), 1.61–1.42 (m, 2H).

EXAMPLE 7

N-[1(R,S)-[(2,3-dihydro-3(RS)-hydroxyspiro[1H-indene-1,4'-piperidin]-1'-yl)carbonyl]-2-phenylpropyl]-2-amino-2-methylpropanamide hydrochloride Step A:

N-[1(R,S)-[(2,3-dihydro-3(RS)-hydroxyspiro[1H-indene-1,4'-piperidin]-1'-yl)carbonyl]-2-phenylpropyl]-2-amino-2-methylpropanamide hydrochloride The title compound (53.8 mg, 0.11 mmol) was prepared from 76 mg (0.170 mmol) of the intermediate from Example 6 (Step C) according to the procedure described in Example 5 (Step A).

$^1$H NMR (400 MHz, CD$_3$OD, 1:1 mixture of diastereomers): 7.38–7.12 (m, 9H), 5.21–5.17 (m, 1H), 4.83–4.74 (m, 1H), 4.48–4.42 (m, 1H), 3.66–3.62 (m, ½H), 3.55–3.45 (m, ½H), 3.23–3.12 (m, 2H), 2.80–2.75 (m, 1H), 2.68–2.30 (m, 1H), 2.1–1.78 (m, 3H), 1.70–1.55 (m, 10H), 1.45–1.31 (m, 1H).

EXAMPLE 8

N-[1(R,S)-[(2,3-dihydro-3-(RS)-hydroxyspiro[1H-indene-1,4'-piperidin]-1'-yl)carbonyl]-2-(phenylmethyloxy)ethyl]-2-amino-2-methylpropanamide hydrochloride Step A:

N-[1(R,S)-[(2,3-dihydro-3-(RS)-hydroxyspiro[1H-indene-1,4'-piperidin]-1'-yl)carbonyl]-2-(phenylmethyloxy)ethyl]-2-amino-2-methylpropanamide hydrochloride The title compound (46.5 mg, 0.092 mmol) was prepared from 66 mg (0.140 mmol) of N-[1(R,S)-[(2,3-dihydro-3-oxospiro[1H-indene-1,4'-piperidin]-1'yl)carbonyl]-2-(phenylmethyloxy)ethyl]-2-amino-2-methylpropanamide hydrochloride according to the procedure described in Example 5 (Step A).

$^1$H NMR (400 MHz, CD$_3$OD, 1:1 mixture of diastereomers and a 3:1 mix of conformers): 7.39–7.15 (m, 8⅔H), 6.89–6.82 (m, ⅓H), 5.23–5.14 (m, 2H), 4.58–4.48 (m, 3H), 4.10–4.00 (m, 1H), 3.80–3.71 (m, 2H), 3.31–3.29 (m, 1H), 2.90–2.85 (m, 1H), 2.58–2.52 (m, 1H), 2.12–2.05 (dt, ⅙H), 1.95–1.79 (m, 1H), 1.62+1.61+1.58+1.57 (s, 6H total), 1.46–1.40 (m, 1H).

EXAMPLE 9

N-[1(R,S)-[(2,3-dihydro-2,2-dimethyl-3-oxospiro[1H-indene-1,4'-piperidin]-1'-yl)carbonyl]-2-(phenylmethyloxy)ethyl]-2-amino-2-methylpropanamide hydrochloride Step A:

1'-(t-butyloxycarbonyl)3,4-dihydro-2,2-dimethyl-3-oxospiro[1H-indene-1,4'-piperidine]

To a solution of 307 mg (1.01 mmol) of the intermediate from Example 4 (Step A) was added 91 mg (3.03 mmol) of sodium hydride. The mixture was stirred for 20 minutes and then 0.198 ml (3.03 mmol) of methyl iodide was added. The solution was stirred over night. The reaction was quenched with water and the aqueous layer was extracted with ethyl acetate, dried over magnesium sulfate, and concentrated. Purification by flash chromatography (silica gel, hexane/ethyl acetate 3:1) gave 258 mg (0.77 mmol) of the title compound.

$^1$H NMR (200 MHz, CDCl$_3$) 7.70–7.61 (m, 2H), 7.58 (dt, 1H), 7.38 (dt, 1H), 3.85–3.70 (m, 2H), 3.56–3.40 (m, 2H), 1.92–1.55 (m, 4H), 1.47 (s, 9H), 1.11 (s, 6H).

Step B:

N-[1(R,S)-[(2,3-dihydro-2,2-dimethyl-3-oxospiro[1H-indene-1,4'-piperidin]-1'-yl)carbonyl]-2-(phenylmethyloxy)ethyl]-2-t-buytloxycarbonylamine The title compound (288 mg, 0.56 mmol) was prepared from the intermediate obtained from Step A (248 mg, 0.753 mmol) according to the procedure described for Example 1 (Step B) except that O-Benzyl-N-BOC-d-Ser (267 mg, 0.90 mmol) was used instead of N-BOC α-methyl alanine.

$^1$HNMR (200 MHz, CDCl$_3$ mixture of conformers): 7.81–7.21 (m, 9H), 5.58–5.50 (m, 1H), 4.98–4.86 (m, 1H), 4.56–4.50 (m, 1H), 4.20–3.40 (m, 5H), 1.92–1.25 (m, 6H), 1.52+1.49 (s, 9H), 1.14+1.12+0.98+0.90 (s, 6H total)

Step C:

N-[1(R,S)-[(2,3-dihydro-2,2-dimethyl-3-oxospiro[1H-indene-1,4'-piperidin]-1'-yl)carbonyl]-2-(phenylmethyloxy)ethyl]-2-[[1,1dimethylethyloxycarbonyl]amino]-2-methylpropanamide The title compound (209 mg, 0.425 mmol) was prepared from the intermediate obtained from Step B (238 mg, 0.47 mmol) and Boc a-methyl alanine (119.1 mg, 0.577 mmol) according to the procedure described for Example 1 (Step B).

Step D:

N-[1(R,S)-[(2,3-dihydro-2,2-dimethyl-3-oxospiro[1H-indene-1,4'-piperidin]-1'-yl)carbonyl]-2-(phenylmethyloxy)ethyl]-2-amino-2-methylpropanamide hydrochloride The title compound (57.6 mg, 0.109 mmol) was prepared from the intermediate obtained from Step C (78 mg, 0.131 mmol) according to the procedure described for Example 4 (Step F).

$^1$H NMR (400 MHz, CD$_3$OD, 1:1 mixture of conformers): 7.82 (d, ½H), 7.71–7.68 (m, 2½H), 7.46 (t, 1H), 7.35–7.29 (m, 5H), 5.18–5.14 (m, 1H), 4.56 (s, 2H), 3.94–3.61 (m, 7H), 2.00–1.75 (m, 3H), 1.60–1.58 (m, 6H), 1.11+1.10+1.05+1.00 (s, 6H total).

EXAMPLE 10

N-[1(R,S)-[(2,3-dihydro-2,2-dimethyl-3-(RS)-hydroxyspiro[1H-indene-1,4'-piperidin]-1'-yl)carbonyl]-2-(phenylmethyloxy)ethyl]-2-amino-2-methylpropanamide hydrochloride Step A:

N-[1(R,S)-[(2,3-dihydro-2,2-dimethyl-3-(RS)-hydroxyspiro[1H-indene-1,4'-piperidin]-1'-yl)carbonyl]-2-(phenylmethyloxy)ethyl]-2-amino-2-methylpropanamide hydrochloride The title compound (16.1 mg, 0.030 mmol) was prepared from the intermediate obtained from Example 9, Step D (25 mg, 0.047 mmol) according to the procedure described for Example 5 (Step A) except that a large excess of sodium borohydride was used instead of a slight excess.

$^1$H NMR (400 MHz, CD$_3$OD, 1:1 mixture of diastereomers and a mixture of conformers): 7.50–7.20 (m, 9H), 5.19–5.10 (m, 1H), 4.85–4.71 (m, 1½H), 4.62–4.52 (m, ½H), 4.35–4.26 (m, ½H), 4.18–4.05 (m, ½H), 4.01–3.90 (m, ½H), 3.85–3.65 (m, 2H), 3.48–3.35 (m, 1H), 3.10–3.00 (m, ½H), 1.95–1.68 (m, 2H), 1.60–1.57 (m, 6H), 1.52–1.28 (m, 2H), 1.04+1.03+0.94+0.91+0.75+0.713+0.71+0.64 (s, 6H total).

EXAMPLE 11

N-[1(R,S)-[(2,3-dihydro-4-(RS)-hydroxyspiro[1H--indene-1,4'-piperidin]-1'-yl)carbonyl]-2-(indol-3-yl)ethyl]-2-amino-2-methylpropanamide hydrochloride Step A:

1'-(t-butyloxycarbonyl)3,4-dihydro-2(RS)-hydroxyspiro[-1,4'-piperidine]

To a solution of 197 mg (0.721 mmol) of spiroindene in 2 ml of THF at 0° C. was added 0.793 ml (0.793 mmol) of borane tetrhydrofuran complex. The solution was stirred at room temperature for 16 hours and then cooled to 0° C. The reaction was quenched with methanol and then 4.2 equivalents of aqueous sodium hydroxide was added followed by 4.2 equivalents of hydrogen peroxide. The mixture was stirred over night at room temperature and then extracted with ethyl acetate. The organic layer was dried over sodium sulfate and concentrated. Purifcation by flash chromatography (silica gel, hexane/ethyl acetate 3:1) gave 71 mg (0.234 mmol) of the title compound and 43 mg (0.143 mmol) of 1'-(t-butyloxycarbonyl)3,4-dihydro-3(RS)-hydroxyspiro[1H-indene-1,4'-piperidine].

$^1$HNMR (400 MHz, CDCl$_3$): 7.28–7.15 (m, 4), 4.49–4.42 (m, 1H), 3.99–3.85 (m, 2H), 3.30 (dd, 1H), 3.25–3.15 (m, 2H), 2.85 (d, 1H), 2.05–2.00 (m, 1H), 1.85–1.78 (m, 1H), 1.75–1.51 (m, 2H), 1.49 (s, 9H).

Step B:

N-[1(R,S)-[(2,3-dihydro-2-(RS)-hydroxyspiro[1H--indene-1,4'-piperidin]-1'-yl)carbonyl]-2-(indol-3-yl)ethyl]carbamic acid 1,1-dimethylethyl ester The title compound (31 mg, 0.054 mmol) was prepared from the intermediate from Step A (38 mg, 0.125 mmol) and a (48.7 mg, 0.125 mmol) according to the procedure described for Example 1 (Step A).

Step C:

N-[1(R,S)-[(2,3-dihydro-3-(RS)-hydroxyspiro[1H-indene-1,4'-piperidin]-1'-yl)carbonyl]-2-(indol-3-yl)ethyl]-2-amino-2-methylpropanamide hydrochloride The title compound (17.1 mg, 0.33 mmol) was prepared from the intermediate obtained from Step B (25 mg, 0.43 mmol) according to the procedure described for Example 4 (Step F).

$^1$H NMR (400 MHz, CD$_3$OD, 1:1 mixture of diastereomers and 60:40 mixture of conformers): 8.30 (m, ⅗H), 8.29–8.25 (m, ⅖H), 7.64–7.54 (m, 1H), 7.44 (d, ⅖H), 7.35–7.32 (m, 1H), 7.19–7.00 (m, 5H), 6.66–6.63 (m, ⅗H), 5.48–5.19 (m, 1H), 4.31–4.15 (m, 2H), 3.77–3.71 (m, ⅖H), 3.58–3.52 (m, ⅗H), 3.25–2.90 (m, 4H), 2.95–2.67 (m, 1H), 2.00–1.95 (m, 1H), 1.85–1.78 (m, 1⅗H), 1.61–1.59 (m, 4⅖H), 1.32–1.21 (m, ⅖H), 1.1–0.85 (m, ⅗H), 0.40–0.35 (m, ³⁄₁₀H), 0.20–0.10 (m, ³⁄₁₀H). FAB-MS:m/e 475 (m+1).

EXAMPLE 12

N-[1(R,S)-[(2,3-dihydro-3,4-(RS,SR)-dihydroxyspiro[1H-indene-1,4'-piperidin]-1'-yl)carbonyl]-2-(indol-3-yl)ethyl]-2-amino-2-methylpropanamide hydrochloride Step A:

1'-(t-butyloxycarbonyl)3,4-dihydro-2,3(RS,SR)-dihydroxyspiro[1H-indene-1,4'-piperidine]

A solution of 300 mg (1.05 mmol) of the spiroindane was cannulated into a mixture of 27 mg (0.105 mmol) of OsO$_4$ and 135 mg (1.16 mmol) N-methyl morpholine-N-oxide in 1 ml of acetone with several drops of water. The reaction was stirred for 2 hours and then quenched with saturated sodium bicarbonate. The solution was poured into a 1:1 mixture of ether and water. The layers were separated and the aqueous layer was extracted with ether. The combined organic layers were dried over sodium sulfate and concentrated. Purification by flash chromatography (silica gel, hexane/ethyl acetate 60:40) gave 247 mg (47%) of the title compound.

$^1$H NMR (400 MHz, CDCl$_3$) 7.41–7.39 (m, 1H), 7.29–7.24 (m, 2H), 7.19–7.17 (m, 1H), 5.13 (d, 1H), 4.30–4.28 (m, 2H), 3.97–3.90 (m, 2H), 3.21–3.10 (m, 1H), 1.65–1.52 (m, 1H), 1.46 (s, 9H).

Step B:

3,4-dihydro-2,3(RS,SR)-dihydroxyspiro[1H-indene-1,4'-piperidine]hydrochloride

The title compound (73 mg, 0.21 mmol) was prepared from the intermediate obtained from Step A according to the procedure described in Example 4 (Step B).

Step C:

N-[1(R,S)-[(2,3-dihydro-3,4-(RS,SR)-dihydroxyspiro[1H-indene-1,4'-piperidin]-1'-yl)carbonyl]-2-(indol-3-yl)ethyl]-carbamic acid 1,1dimethylethyl ester The title compound was prepared in 50% yield from the intermediate obtained in Step B and Boc-d-Trp according to the procedure described in Example 1 (Step A).

Step D:

N-[1(R,S)-[(2,3-dihydro-3,4-(RS,SR)-dihydroxyspiro[1H-indene-1,4'-piperidin]-1'-yl)carbonyl]-2-(indol-3-yl)ethyl]-2-[[1,1-dimethylethyloxycarbonyl]amino]-2-methylpropanamide The title compound was prepared in 61% yield from the intermediate obtained in Step C and N-Boc alpha methyl alanine according to the procedure described in Example 1 (Step B).

Step E:

N-[1(R,S)-[(2,3-dihydro-3,4-(RS,SR)-dihydroxyspiro[1H-indene-1,4'-piperidin]-1'-yl)carbonyl]-2-(indol-3-yl)ethyl]-2-amino-2-methylpropanamide hydrochloride The title compound was prepared in 79% yield from the intermediate obtained in Step D according to the procedure described in Example 1 (Step C).

$^1$H NMR (400 MHz, CD$_3$OD, 1:1 mixture of diastereomers and a 2:1 mixture of conformers): 7.63–7.61 (m, 1H), 7.43 (d, ⅓H), 7.35–7.03 (m, 7H), 6.66 (m, ⅓H), 5.30–5.16 (m, 1H), 5.05–5.00 (m, ⅓H), 4.25–4.15 (m, 2H), 3.81–3.45 (m, 2H), 3.30–2.91 (m, 4⅔H), 2.05–1.70 (m, 1⅓H), 1.60 (s, 5H), 1.55–1.45 (m, 1H), 1.49 (s 1H), 1.45–1.25 (m, 2H), 1.05 (dt, ⅓H), 0.90 (dt, ⅔H), 0.35 (dt, ⅓H), 0.13 (dt, ⅓H). FAB-MS m/e 491 (m+1).

EXAMPLE 13A

N-[1(R)-[(1-oxospiro[indane-2,4'-piperidine]-1'-yl)carbonyl]-2-(indol-3-yl)-ethyl]-2-amino-2-methyl-propanamide hydrochloride Step A:

1-oxospiro[indane-2,4'-piperidine]-1'-carboxylic acid1,1-dimethylethyl ester

To a stirred solution of 1-indanone (1.0 g, 7.6 mmol) and bis(2-bromoethyl)t-butyl carbamate (2.5 g, 7.6 mmol) in DMF (30 ml) at room temperature under Ar, was added sodium hydride (60% in mineral oil, 0.912 g, 22.8 mmol). The reaction mixture was stirred for two hours at room temperature and was then poured into ice water. The solution was extracted with ethyl acetate and dried over Na$_2$SO$_4$. Evaporation and purification by flash chromatography eluting with 20–40% ethyl acetate in hexane afforded 2.01 g of product.

$^1$H NMR (400 MHz, CDCl$_3$): δ7.73 (d, J=7.6 Hz, 1H), 7.58 (t, J=7.6 Hz, 1H), 7.43 (d, J=7.6 Hz, 1H), 7.35 (t, J=7.6 Hz, 1H), 4.10 (td, J=13.7 Hz, 3.6 Hz, 2H), 3.04 (s, 2H), 2.97 (dt, J=13.7 Hz, 3 Hz, 2H), 1.87 (dt, J=13 Hz, 4.3 Hz, 2H), 1.44 (s, 9H), 1.34 (d, J=13 Hz, 2H). EI MS calc. for C$_{18}$H$_{23}$NO$_3$, 301; found 301 (M+, 5%), 244, 228, 200, 145, 57(100%).

Step B:

spiro[indan-2,4'-piperidine]-1-one, hydrochloride

To a solution of the product from Step A (53 mg) in methanol (2 ml) as added concentrated hydrochloric acid (2 ml). The mixture was stirred at room temperature for three hours and evaporated in vacuo to afford the product (46 mg).

$^1$H NMR (400 MHz), CD$_3$OD) δ7.71 (d, J=7.5 Hz, 1H), 7.70 (t, J=7.5 Hz, 1H), 7.57 (d, 7.5 Hz, 1H), 7.44 (t, J=7.5 Hz, 1H), 3.57–3.52 (m, 2H), 3.29–3.24 (m, 2H), 3.22 (s,

2H), 2.13–2.05 (m, 2H), 1.80–1.72 (m, 2H). EI MS calc. for $C_{13}H_{15}NO$, 201; found 201 (M+, 15%), 145.

Step C:

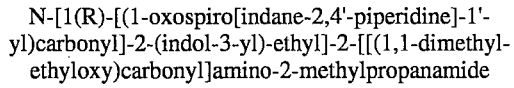

N-[1(R)-[(1-oxospiro[indane-2,4'-piperidine]-1'-yl)carbonyl]-2-(indol-3-yl)-ethyl]-2-[[(1,1-dimethyl-ethyloxy)carbonyl]amino-2-methylpropanamide Prepared by the procedure described in Example 18, Step A, from the intermediate from the previous step.

$^1$H NMR (400 MHz, CDCl$_3$) δ8.51, 8.47 (2br.s, 1H), 7.80–7.05 (m, 10H), 5.34–5.18 (2m, 1H), 5.05 (br.s, 1H), 4.50–4.42, 4.15–4.10 (2m, 1H), 3.60–3.50 (m), 3.42–3.35 (m), 1.49 (s, 3H), 1.47 (s, 3H), 1.42 (s, 9H), 1.12–1.08 (m), 0.62 (br.d, J=12.7 Hz), 0.45–0.28 (br.m). FAB-MS calc. for $C_{35}H_{40}N_4O_5$, 572; found 573 (M+H).

Step D:

N-[1(R)-[(1-oxospiro[indane-2,4'-piperidine]-1'-yl)carbonyl]-2-(indol-3-yl)-ethyl ]-2-amino-2-methylpropanamide hydrochloride Prepared by the procedure described in Example 19, Step C, from the intermediate from the previous step.

$^1$H NMR (400 MHz, CD$_3$OD) δ7.67–7.48 (m, 4H), 7.46–7.36 (m, 2H), 7.14–6.99 (m, 3H), 5.25–5.19 (m, 1H), 4.33, 4.15 (2dm, J=13.7 Hz, 1H) 3.85–3.70 (m, 1H), 3.30–2.80 (m), 1.70–1.60 (m), 1.61, 1.58, 1.51 (3s, 6H), 1.50–1.40, 1.39–1.25, 1.20–1.15, 1.03–0.80 (m). FAB-MS calc. for $C_{28}H_{37}N_4O_3$, 472; found (M+H).

EXAMPLE 13B

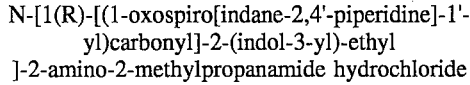

N-[1(R)-[(1-hydroxyspiro[indane-2,4'-piperidine]-1'-yl)carbonyl]-2-(indol-3-yl)-ethyl]-2-amino-2-methylpropanamide To a stirred solution of the title compound from Example 13A (50 mg) in methanol (4 ml) at 0° was added NaBH$_4$ (15 mg). One drop of 3N HCl was added after 30 minutes and the mixture was evaporated to dryness. The compound was taken up in 10% methanol in dichloromethane and purified by prep-TLC eluting with 10% methanol in dichloromethane to give the product (31.8 mg).

$^1$H NMR (400 MHz, CD$_3$OD) δ7.61–6.99 (m, 9h),5.17–5.11 (m, 1H0, 4.60, 4.57, 4.39, 4.23 (4s, 1H), 4.04 (td), 3.91 (td), 3.67–3.58 (m), 3.53 (td), 3.48–3.38 (m), 3.30–3.05 (m), 300–2.80 (m), 2.7–2.56 (m), 2.30 (d,=15 Hz), 2.21 (d, J=15 Hz), 1.70–1.62 (m), 1,56–1.49 (m), 1.40–1.15 (m), 1.29, 1.28, 1.27, 1.27, 1.25 (5s, 6H), 1.15–0.88 (m), 0.56–0.50 (m), 0.54–0.38 (m). FAB-MS calc. for $C_{28}H_{34}N_4)_3$, 475; found 476 (M+H).

EXAMPLE 14

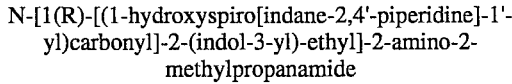

N-[1(R)-[(spiro[indane-2,4'-piperidine]-1'-yl)carbonyl]-2-(indol-3-yl)-ethyl]-2-amino-2-methylpropanamide hydrochloride Step A:

Spiro[indane-2,4'-piperidine]-1'-carboxylic acid, 1,1-dimethylethyl ester

To a stirred solution of 1-oxospiro[indane-2,4'-piperidine]-1'-carboxylic acid, 1,1-dimethylethyl ester (250 mg) in ethanol (5 ml)at 0° was added NaBH$_4$ (50 mg). The mixture was stirred for 3 hours and then evaporated to remove the ethanol. The residue was partitioned between acidic brine and ethyl acetate. The organic layer was dried (Na$_2$SO$_4$) and evaporated to afford an alcohol. The alcohol was hydrogenated at 1000 psi in ethanol (5 ml) in the presence of 10% Pd/C (40 mg) at room temperature for 16 hours. The mixture was filtered through celite to remove the catalyst, evaporated to dryness and purified by flash column eluting with 10–20% ethyl acetate in hexane to afford the product.

$^1$H NMR (400 MHz, CDCl$_3$) δ7.17–7.10 (m, 4H), 3.44–3.41 (m, 4H), 2.80 (s, 4H), 1.57–1.55 (m, 4H), 1.45 (s, 9H). EI MS calc. for $C_{18}H_{25}N_2O_2$, 287; found 287 (M+, 5%), 231, 142, 57 (100%).

Step B:

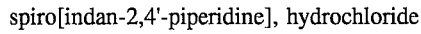

spiro[indan-2,4'-piperidine], hydrochloride

To a solution of the product from Step A (64 mg) in methanol (2 ml) was added concentrated hydrochloric acid (2 ml). The mixture was stirred at room temperature for three hours and then evaporated in vacuo to afford the product (43 mg).

Step C:

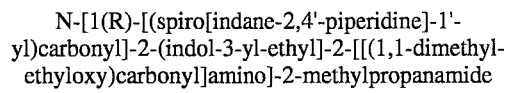

N-[1(R)-[(spiro[indane-2,4'-piperidine]-1'-yl)carbonyl]-2-(indol-3-yl-ethyl]-2-[[(1,1-dimethyl-ethyloxy)carbonyl]amino]-2-methylpropanamide Prepared by the procedure described in Example 18, Step A, from the intermediate from the previous step.

$^1$H NMR (400 MHz, CDCl$_3$) δ8.20 (br.s, 1H), 7.66 (d, J=7.7 Hz, 1H), 7.34 (d, J=8 Hz, 1H), 7.24–7.07 (m, 8H), 5.23–5.18 (m, 1H), 5.00 (br.s, 1H), 3.60–3.52 (m, 1H), 3.30–3.05 (m, 4H), 2.95–2.88 (m, 1H), 2.66 (d, J$_{AB}$=16 Hz, 1H), 2.61 (J$_{BA}$=16 Hz, 1H), 2.48 (d, J$_{AB}$=16 Hz, 1H), 2.36 (d, J$_{BA}$=16 Hz, 1H), 1.80–1.70 (m, 1H), 1.48 (s, 3H), 1.45 (s, 3H), 1.42 (s, 9H), 1.25–1.06 (m, 1H). FAB-MS calc. for $C_{33}H_{42}N_4O_4$, 558; found 559 (M+H).

Step D:

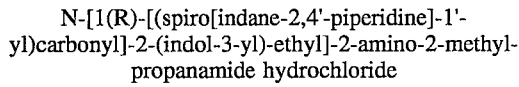

N-[1(R)-[(spiro[indane-2,4'-piperidine]-1'-yl)carbonyl]-2-(indol-3-yl)-ethyl]-2-amino-2-methyl-propanamide hydrochloride Prepared by the procedure described in Example 14, Step B, from the intermediate from the previous step.

$^1$H NMR (400 MHz, CD$_3$OD) δ7.56 (d, J=7.8 Hz, 1H), 7.38 (d, J=8.3 Hz, 1H), 7.13–7.00 (m, 7H), 5.17 (dd, J=6 Hz, 9 Hz, 1H), 3.70–3.60 (m, 1H), 3.30–3.13 (m, 5H), 2.68 (s, 2H), 2.49 (d, J$_{AB}$=5.8 Hz, 1H), 2.40 (d, J$_{BA}$=5.8 Hz, 1H), 2.40 (d, J$_{BA}$=5.8 Hz, 1H), 1.59 (s, 3H), 1.54 (s, 3H), 1.40–1.15 (m, 3H), 1.04–0.96 (m, 1H). FAB-MS calc. for $C_{28}H_{34}N_4O_2$, 495; found 496 (M+H).

EXAMPLE 15

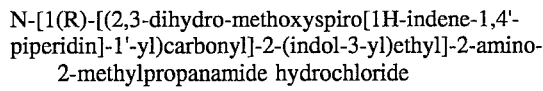

N-[1(R)-[(2,3-dihydro-methoxyspiro[1H-indene-1,4'-piperidin]-1'-yl)carbonyl]-2-(indol-3-yl)ethyl]-2-amino-2-methylpropanamide hydrochloride Step A:

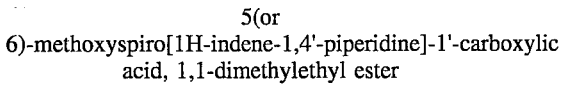

5(or 6)-methoxyspiro[1H-indene-1,4'-piperidine]-1'-carboxylic acid, 1,1-dimethylethyl ester 5(or 6)-Methoxyindene (500 mg; 3.42 mmol) was put into a 50 mL round bottom flask and set under an argon atmosphere. The material was then dissolved in THF (4 mL). While stirring, the solution was cooled to −5° C. and 1M Lithium bis(trimethylsilyl)amide in THF (6.84 mL, 6.84 mmol) was added dropwise over a 15 minute period. After stirring for an additional 15 minutes, the solution was transferred by cannula to another solution of bis(2-chloroethyl)t-butyl carbamate (780 mg, 3.21 mmol) in THF (3 mL), cooled to −5° C. The transfer was done over a 15 minute period. The mixture was then stirred for 2 hours at −5° C. and for an additional 30 minutes at room temperature. TLC analysis indicated that all starting material was gone. The reaction mixture was concentrated to give a dark brown residue. Purification by column chromatography gave pure desired product. (683 mg, 63%).

$^1$H NMR (400 MHz, CDCl$_3$): The product exists as a mixture of two regioisomers (2:1): δ7.241–7.180 (m), 6.877–6.705 (m), 4.140 (br. s), 3.800 (s), 3.574 (s), 3.075 (d), 1.984–1.910 (m), 1.600 (s), 1.452, (s), 1.309 (d). FAB-MS calc. for C$_{19}$H$_{25}$NO$_3$ 315; found 315 (M+H, 24%), [260.0 (M+H-100, 100%) loss of t-Boc group].

Step B:

2,3-Dihydro-5(or 6)-methoxyspiro[1H-indene-1,4'-piperidine]1'-carboxylic acid, 1,1-dimethylethyl ester The intermediate from the previous step (680 mg, 2.25 mmol), 10% was hydrogenated using palladium on carbon (40 mg) in ethanol (40 mL) at 1 atmosphere. Filtration and evaporation gave the product (40 mL). Yield: 700 mg (98%)

$^1$H NMR (400 MHz, CDCl$_3$): The product exists as a mixture of two regioisomers (2:1): δ7.092 (d), 7.014 (d), 6.747–6.656 (m), 4.063 (br. s), 3.765 (s), 3.577 (s), 2.935–2.801 (m), 2.058–2.009 (m), 1.467 (s), 1.464–1.443 (m). FAB-MS calc. for C$_{19}$H$_{27}$NO$_3$ 317; found 317 (M+H, 10%), [262.0 (M+H-56, 100%) loss of tert-butyl group].

Step C:

2,3-Dihydro-5(or 6)-methoxyspiro[1H-indene-1,4'-piperidine]

To a solution of the intermediate from the previous step (700 mg, 2.21 mmol) in dichloromethane (4 mL) was added trifluoroacetic acid (4 mL). The solution was stirred at room temperature for 30 minutes. The reaction mixture was evaporated and then saturated sodium bicarbonate was added. Then the mixture was washed with brine, dried over magnesium sulfate and concentrated to give the desired product. Yield: 435.5 mg (91%). FAB-MS calc. for C$_{14}$H$_{19}$NO 217; found 218 (M+H, 100%).

Step D:

N-[1(R)-[(2,3-dihydro-5(or 6)-methoxyspiro[1H-indene-1,4'-piperidin]-1'-yl)carbonyl]-2-(indol-3-yl)ethyl]-2-[[(1,1-dimethylethyloxy)carbonyl]amino]-2-methylpropanamide To a stirred solution of 2,3-Dihydro-5(or 6)-methoxyspiro [1H-indene-1,4'-piperidine], (50 mg, 0.23 mmol), α(R)-[[2-[[(1,1-dimethylethoxy)-carbonyl]amino]-2,2-dimethyl-1-oxoethyl]amino]-1H-indole-3-propanoic acid (95 mg, 0.24 mmol) Example 4, Step D, HOBT (40 mg, 0.24 mmol), in CH$_2$Cl$_2$ was added EDC (88 mg 0.46 mmol). The mixture was stirred overnight and washed with brine. The organic layer was dried, evaporated and purified by flash column to give product (97.5 mg, 72%).

$^1$H NMR (400 MHz, CDCl3): The product exists as a mixture of two conformers (2:1): δ8.186 (s), 8.071 (s), 7.755 (t), 7.594 (d), 7.372–7.010 (4m), 6.690–6.673 (m), 6.238 (d), 5.243–5.190 (m), 5.031–4.955 (m), 4.437–4.386 (m), 3.755, 3.732, 3.726 (3s), 3.622 (s), 3.304–3.150 (m), 2.912 (t), 2.748–2.495 (2m), 2.083–1.575 (2m), 1.498, 1.478, 1.465, 1.427 (4s), 1.369 (s), 1.285–1.230 (m), 0.047 (s). FAB-MS calc. for C$_{34}$H$_{44}$N$_4$O$_5$ 588; found 589 (M+H, 28%).

Step E:

N-[1(R)-[(2,3-dihydro-5(or 6)methoxyspiro[1H-indene-1,4'-piperidin]-1'-yl)carbonyl]-2-(indol-3-yl)ethyl]-2-amino-2-methyl propanamide hydrochloride To a stirred solution of the intermediate from the previous step (35 mg, 0.06 mmol) in ethanol (2 ml) was added concentrated HCl (2 ml). The mixture was stirred at room temperature for 1 hour and then evaporated to a foam (29.6 mg, 95%).

$^1$H NMR (400 MHz, CD$_3$OD): The product exists as a mixture of two conformers (2:1): δ7.646–6.625 (6m), 5.282–5.161 (m), 4.326 (d), 3.705 (d), 3.361–3.125 (m), 3.061 (t), 2.826–2.597 (m), 1.953–1.802 (m), 1.655–1.548 (5s), 1.505 (d), 1.377–1.198 (2m), 0.997–0.831 (2m), 0.320–0.111 (m). FAB-MS calc. for C$_{29}$H$_{36}$N$_4$O$_3$ 488; found 489 (M+H, 66%).

EXAMPLE 16

N-[1(R)-[(2,3-dihydro-5(or 6)-hydroxyspiro[1H-indene-1,4'-piperidin]-1'-yl)carbonyl]-2-(indol-3-yl)ethyl]-2-amino-2-methyl-propanamide hydrochloride Step A:

N-trifluoroacetyl-2,3-dihydro-5(or 6)-methoxyspiro[1H-indene-1,4'-piperidine]

To a solution of intermediate from Example 15, Step C (200 mg, 0.92 mmol) in dichloromethane (4 mL) was added of triethylamine (192 mg, 1.84 mmol) and trifluoroacetic anhydride (300 mg, 1.12 mmol). The reaction was stirred for 4 hours, until TLC analysis indicated that the reaction was complete. The solution was concentrated and the residue was purified by column chromatography to give the desired product. Yield: 145.6 mg (50.5%).

$^1$H NMR (400 MHz, CDCl$_3$): The product exists as a mixture of two regioisomers (2:1): δ7.112 (d, ⅔H), 7.010 (d, ⅓H), 6.761–6.721 (m, 1⅓H), 6.638 (d, ⅔H), 4.551–4.513 (m, 1H), 3.992 (d, 1H), 3.778 (s, 3H), 3.286–3.353 (m, 1H), 3.005–2.851 (m, 3H), 2.313–2.027 (m, 2H), 1.866–1.778 (m, 2H), 1.659–1.603 (m, 2H). FAB-MS calc. for C$_{16}$H$_{18}$NO$_2$F$_3$ 313; found 314 (M+H, 100%).

Step B:

N-trifluoroacetyl-2,3-dihydrospiro[1H-indene-1,4'-piperidin]-5(or 6)-ol

To a stirred solution of the material from the previous step (125 mg, 0.4 mmol) in dry dichloromethane (3 mL) under an argon atmosphere was added 1M BBr$_3$ in dichloromethane (0.8 mL, 0.8 mmol). The reaction was stirred for 1.5 hours and then poured into salt water and extracted with dichloromethane. The organic layer was dried over magnesium sulfate and concentrated to give the desired product (113.7 mg, 95%). FAB-MS calc. for C$_{15}$H$_{16}$NO$_2$F$_3$ 299; found 300 (M+H, 100%).

Step C:

2,3-Dihydrgspiro[1H-inden-1,4'-piperidine]-5(or 6)-ol

To a solution of the intermediate from the previous step (94 mg, 0.31 mmol) in methanol (5 mL) was added 3N NaOH (35 drops). The reaction was stirred for 1 hour. The solution was then concentrated several times from toluene to give the desired product (60.5 mg, 94%) which was used without further purification.

$^1$H NMR (CD$_3$OD): δ7.008 (d, 1H), 6.637–6.611 (m, 2H), Hidden 4.826 (s, 1H), 3.411 (d, 2H), 3.210–3.164 (m, 2H), 2.866–2.820 (m, 2H), 2.144–2.007 (m, 4H), 1.750–1.710 (m, 1H), 1.278 (s, 2H).

Step D:

N-[1(R)-[(2,3-dihydro-5(or 6)-hydroxyspiro[1H-indene-1,4'-piperidin]-1'-yl)carbonyl]-2-(indol-3-yl)ethyl]-2-[[(1,1-dimethylethyloxy)carbonyl]amino]-2-methylpropanamide Prepared by the procedure described in Example 15, Step D. The intermediate from the previous step (60 mg, 0.26 mmol), α(R)-[[2-[[(1,1-dimethylethoxy)carbonyl]amino]-2,2-dimethyl-1-oxoethyl]amino]-1H-indole-3-propanoic acid (138 mg, 0.35 mmol), HOBT (50 mg, 0.37 mmol), and EDC (136 mg, 0.71 mmol). Reaction time: 10 hours. Yield: 141.2 mg (81%).

Step E:

N-[1(R)-[(2,3-dihydro-5(or 6)-hydroxyspiro[1H-indene-1,4'-piperidin]-1'-yl)carbonyl]-2-(indol-3-yl)ethyl]-2-amino-2-methylpropanamide hydrochloride TYhe title compound was prepared by the procedure described in Example 15, Step E using the intermediate from previous step, (20 mg, 0.34 mmol), methanol (3 mL), and concentrated HCl (3 ml). Reaction time: 3 hours. Yield: 17 mg (95%).

$^1$H NMR (400 MHz CD$_3$OD): Compound exists as a mixture of two conformers (2:1): δ7.619–6.234 (8m, 7), 5.293–5.170 (m, 1H), 4.322 (dt, 1H), 3.727 (d, 5/6), 3.338–3.122 (2m, 4⅓H), 2.987 (t, ⅓H), 2.785–2.570 (2m, 2⅔H), 1.961–1.801 (m, 2H), 1.648–1.567 (5s, 5H), 1.507 (d, 2H), 1.381–1.203 (m, 4H), 0.977–0.873 (2m, 2⅔H), 0.193 (dt, 1/3H). FAB-MS calc. for C$_{28}$H$_{34}$N$_4$O$_4$ 474; found 475 (M+H, 78%).

EXAMPLE 17

N-[1(R)-[(Spiro[9H-fluorene-9,4'-piperidin]-1'-yl)-carbonyl]-2-(indol-3-yl)ethyl]-2-amino-2-methylpropanamide hydrochloride Step A:

Spiro[9H-fluorene-9,4'-piperidine]-1'-carboxylic acid, 1,1-dimethylethyl ester Fluorene (1 g, 6.02 mmol) was put into a 100 mL dry round bottom flask. The material was dissolved with THF (5 mL) under argon. While stirring, the solution was cooled to −5° C. and 1M Lithium bis(trimethylsilyl)amide in THF (12.04 mL, 12.04 mmol) was added dropwise over a 10 minute period. After stirring for an additional 15 minutes, the solution was transferred by cannula to another solution of bis(2-chloroethyl)-t-butyl carbamate (1.35 g, 5.60 mmol) in THF (3 mL) and cooled to −5° C. The transfer was done over a 15 minute period. The mixture was then stirred for 2 hours at −5° C. and for an additional 30 minutes at room temperature. TLC analysis indicated that all of the starting material was gone. The reaction mixture was concentrated to give a black residue. Purification by column chromatography gave the product (1.310g, 65%).

$^1$H NMR(400 MHz, CDCl$_3$): δ7.767 (d, 2H), 7.600 (d, 2H), 7.396–7.278 (m, 4H), 3.832 (t, 4H), 1.855 (t, 4H), 1.525 (s, 9H). FAB-MS calc. for C$_{22}$H$_{25}$NO$_2$ 335; 336 (M+H, 8%) [280 (M+H, 100% ) loss of tert-butyl group].

Step B:

Spiro[9H-fluorene-9,4'-piperidine]

The title compound was prepared by the procedure described in Example 15, Step C using the intermediate from the previous step (1 g, 2.98 mmol)and trifluoroacetic acid (4 mL). Reaction time: 1 hour. Yield: 610.3 mg (87%). FAB-MS calc. for C$_{17}$H$_{17}$N 235; found 236 (M+H, 100%).

Step C:

N-[1(R)-[(spiro[9H-fluorene-9,4'-piperidin]-1'-yl)carbonyl]-2-(indol-3-yl)ethyl]-2-[[(1,1-dimethylethyloxy)carbonyl]amino]-2-methylpropanamide The title compound was prepared by the procedure described in Example 15, Step D using the intermediate from the previous step (275 mg, 1.162 mmol), α(R)-[[2-[[(1,1-dimethylethoxy)carbonyl]amino]-2,2-dimethyl-1-oxoethyl]amino]-1H-indole-3-propanoic acid (453 mg, 1.16 mmol), HOBT (156 mg, 1.16 mmol), and EDC (223 mg, 1.16 mmol). Reaction time: 30 minutes.

Yield: 371 mg (53%).

$^1$H NMR (400 MHz, CDCl$_3$): δ8.225 (br. s, 1H), 7.698–7.159 (m, 13H), 6.610 (d, 1H), 5.348–5.265 (m, 1H), 5.020 (br. s, 1H), 3.988–3.905 (m, 1H), 3.595–3.502 (m, 2H) 3.365–3.296 (m, 1H), 3.189 (t, 1H), 1.718–1.655 (m, 1H), 1.545, 1.518, (2s, 6H), 1.611–1.281 (m, 3H), 1.467 (s, 9H), 0.932–0.865 (m, 1H). FAB-MS calc. for C$_{37}$H$_{42}$N$_4$O$_4$ 606; found 607 (M+H, 23%).

Step D:

N-[1(R)-spiro[9H-fluorene-9,4'-piperidin]-1'-yl)carbonyl]-2-(indol-3-yl)ethyl]-2-amino-2-methylpropanamide hydrochloride The title compound was prepared by the procedure described in Example 15, Step E using the intermediate from the previous step (320 mg, 0.49 mmol), methanol (5 mL) and concentrated HCl (5 ml). Reaction time: 40 minutes. Yield: 229 (85.5%).

$^1$H NMR (400 MHz, CD$_3$OD): δ7.710 (t, 2H), 7.645 (d, 1H), 7.546 (d, 1H), 7.481 (d, 1H), 7.345–7.075 (m, 8H), 6.878 (d, 1H), 5.308–5.265 (m, 1H), 3.811–3.694 (m, 4H), 3.401–3.212 (m, 4H), 1.669, 1.612 (2s, 6H), 1.677–1.285 (m, 4 H). FAB-MS calc. for C$_{32}$H$_{34}$N$_4$O$_2$ 506; found 507 (M+H, 54%).

EXAMPLE 18

N-[1(R)-[(spiro[1H-indene-1,4'-piperidin]-1'-yl)carbonyl]-2-(indol-3-yl)ethyl]-2-amino-2-methylpropanamide hydrochloride Step A:

N-[1(R)-[(spiro[1H-indene-1,4'-piperidin]-1'-yl)carbonyl]-2-(indol-3-yl)ethyl]-2-[[(1,1-dimethylethyloxy)carbonyl]amino ]-2-methylpropanamide To a stirred solution of α(R)-[[2-[[(1,1-dimethylethoxy)carbonyl]amino]-2,2-dimethyl-1-oxoethyl]amino]-1H-indole-3-propanoic acid (50 mg, 0.13 mmol), (Example 4, Step D) spiro[1H-indene-1,4'-piperidine]hydrochloride (28.5 mg, 0.13 mmol) (Chambers, M. et al, J. Med. Chem. 1992, 35, 2033–2039), HOBT (17.3 mg, 0.13 mmol) and N-methylmorpholine (14.1 μL, 0.13 mmol) in dichloromethane (5 mL) at room temperature was added EDC (49.3 mg, 0.26 mmol). The reaction mixture was stirred for four hours and poured into a mixture of brine (10 mL) and HCl (3N, 1 mL). The mixture was extracted with ethyl acetate (20 mL) and the organic extract was dried ($MgSO_4$) and evaporated. The residue was purified by silica gel column eluting with a solvent gradient of 40–60% ethyl acetate in hexane to give the product (63.6 mg, 89%).

$^1$H NMR (400 MHz, $CDCl_3$): compound exists as a mixture of conformers (ratio 2:1): δ8.28, 8.24 (2 br. s, 1H), 7.74, 7.62 (2d, 7.7 Hz, 1H), 7.62, 7.39 (2d, 8.0 Hz, 1H), 7.30–7.10 (m, 7H), 6.68–6.30 (m, 2H), 5.35–5.20 (2m, 1H), 5.00 (br. s, 1H), 4.45–4.36 (m, 1H), 3.62, 3.53 (br. d, 14 Hz, 1H), 3.30–3.00 (m, 2H), 2.86–2.71 (m, 1H), 2.42–2.23 (m, ⅓H), 1.71 (v. br. s, 2H), 1.51, 1.49, 1.47 (3s, 6H), 1.44, 1.43, (2s, 9H), 1.40–1.07 (m, 2H), 0.88, 0.72 (2 br. d, 1H), 0.42 (dt, 4 Hz, 12 Hz, ⅓H).

Step B:

N-[1(R)-[(spiro[1H-indene-1,4'-piperidin]-1'-yl)carbonyl]-2-(indol-3-yl)ethyl]-2-amino-2-methyl-propanamide trifluoroacetic acid salt To a stirred solution of the intermediate prepared in Step A (60 mg, 0.11 mmol) in dichloromethane (1 mL) was added TFA (1 mL). The reaction mixture was stirred at room temperature for 30 minutes and TLC showed that all of the starting material was gone. 10 mL of toluene was added and the mixture was evaporated in vacuo. This procedure was repeated twice to give the title compound.

$^1$H NMR (400 MHz, $CD_3OD$): compound exists as a mixture of conformers (ratio 2:1): δ8.35, 8.29 (2:1, 2 d, 6 Hz, 1H), 7.64, 7.56 (2:1, 2 d, Hz, 1H), 7.46, 7.38 (2:1, 2 d, 8 Hz, 1H), 7.27–7.02 (m, 6H), 6.83–6.80 (m, ⅔H), 6.77 (d, 5.7 Hz, ⅔H), 6.71 (d, 5.7 Hz, ⅓H), 6.68 (d, 5.7 Hz, ⅔H), 6.55 (d, 5.7 Hz, ⅓H), 5.30–5.20 (2 m, 1H), 4.17–4.21 (2 br. m, 1H), 3.88–3.78 (2 br. m 1H), 3.40–3.18 (m, 2H), 3.05–2.08 (2m, 1H), 2.91–2.81 (2m, 1H), 1.63,1.62,1.61, 1.52 (4 s, 6H), 1.18–1.15 (m, 1H), 1.08–0.95 (m, 1H), 0.68–0.61 (dd, ⅔), 0.49–0.40 (dt, ⅔H). FAB-MS: calc. for $C_{28}H_{32}N_4O_2$, 456; found 457 (M+H, 100% ).

EXAMPLE 19

N-[1(R)-[(3,4-dihydrospiro[naphthalene-1(2H),4'-piperidin]-1'-yl)carbonyl]-2-(indol-3-yl)ethyl]-2-amino-2-methylpropanamide hydrochloride Step A:

N-[1(R)-[(3,4-dihydrospiro[naphthalene-1(2H),4'-piperidin]-1'-yl)carbonyl]-2-(indol-3-yl)ethyl]-2-[[(1,1-dimethylethyloxy)carbonyl]amino]]-2-methylpropanamide This intermediate was prepared from α(R)-[[2-[[(1,1-dimethylethoxy)carbonyl]amino]-2,2-dimethyl-1-oxoethyl]amino]-1H-indole-3-propanoic acid and 3,4-dihydrospiro[naphthalene-1(2H),4'-piperidine (Chambers, M. et al, J. Med. Chem. 1992, 35, 2033–2039) by the procedure described in Example 15, Step D.

$^1$H NMR (400 MHz, $CDCl_3$): compound exists as a mixture of conformers (ratio 2:1): d 8.20 (br. s, 1H), 7.77, 7.59 (2d, 8 Hz, 1H), 7.36–6.95 (m, 8⅓H), 6.45 (d, 8 Hz, ⅔H), 5.36–5.19 (2 m, 1H), 5.00 (br. s, 1H), 4.36 (br. d, 13 Hz, 1H), 3.47 (md, 8 Hz, 1H), 3.39–3.10 (m, 2H), 3.02–2.96 (dt, 2,8 Hz, ⅔H), 2.71–2.60 (m, 3H), 3.02–2.96 (dt, 2,8 Hz, ⅓H), 2.35–2.24 (m, ⅓H), 2.90–1.55 (m, 7H), 1.50, 1.48, 1.47 (3 s, 6H), 1.43 (s, 9H), 1.40–1.20 (m, 2H) 0.98–0.80 (m, 2H), 0.48–0.38 (m, ⅓H). FAB-MS: calc. for $C_{34}H_{44}N_4O_4$, 572; found 573 (M+H, 20%).

Step B:

N-[1(R)-[(3,4-dihydrospiro[naphthalene-1(2H),4'-piperidin]-1'-yl)carbonyl]-2-(indol-3-yl)ethyl]-2-amino-2-methylpropanamide hydrochloride To a stirred solution of the intermediate prepared in step A (50 mg, 0.087 mmol) in methanol (2 mL) was added concentrated hydrochloric acid (2 mL). The reaction mixture was stirred at room temperature for one hour and 10 mL of toluene was added and the mixture was evaporated in vacuo. This procedure was repeated twice to give the title compound (41.2 mg, 100%).

$^1$H NMR (400 MHz, $CD_3OD$): compound exists as a mixture of conformers (ratio 2:1): δ8.30, 8.25 (2 d, 8.6, ⅓H), 7.62–7.53 (2d, 7.9, 1H), 7.41,7.36 (2 d, 8.2, 1H), 7.25–6.90 (m, 7H), 6.49 (d, 8.9, ⅔H), 5.30–5.13 (2 m, 1H), 4.34–4.20 (m, 1H), 3.70–3.60 (m, 1H), 3.38–3.08 (m, 2H), 2.72–2.55 (m, 4H), 2.04–1.96 (dt, ⅓H), 1.85–1.79 (dt, ⅔H), 1.60, 1.51 (2 s, 6H), 1.40–1.16 (m, 2H), 0.95 (br. md, 12 Hz, ⅔H), 0.49–0.40 (dt, 4.5, 12, ⅔H). FAB-MS: calc. for $C_{29}H_{36}N_4O_2$, 472; found 473 (M+1,80%).

EXAMPLE 20

N-[1(R)-[(2,3-dihydrospiro[1H-indene-1,4'-piperidin]-1'-yl)carbonyl]-2-(1H-indol-3-yl)ethyl]-3-amino-3-methylbutanamide hydrochloride Step A:

N-[1(R)-[spiro[1H-indene-1,4'-piperidin]-1'-yl-carbonyl]-2-(1H-indol-3-yl)ethyl]carbamic benzyl ester To a solution of N-benzyloxycarbonyl-(D)-tryptophan (1.69 g, 5.0 mmole) in 70 mL of chloroform at room temperature was added spiro[1H-indene-1,4'-piperidine]hydrochloride (J. Med. Chem. 1992, 35, 2033)(1.21 g, 5.5 mmole), triethylamine (0.73 mL, 5.25 mmole) followed by 1-hydroxybenzotriazole hydrate (0.74 g, 5.5 mmole) and 1-(3-dimethylaminopropyl)-3-ethylcarbodiimide hydrochloride (1.05 g, 5.5 mmole). After 12 hours at room temperature, the mixture was diluted with methylene chloride and then washed sequentially with water and brine. The organic layer was dried over sodium sulfate, filtered and concentrated. The residue was purified by chromatatron (hexanes/ethyl acetate=1/1) to give 2.01 g (79%) of the title compound.

$^1$H NMR (200 MHz, $CDCl_3$, mixture of conformers): 8.14 (m, 1H), 7.75–7.08 (m, 14H), 6.67 (m, 2H), 5.89 (m, 1H), 5.14 (s, 2H), 5.06 (m, 1H), 4.46 (m, 1H), 3.63 (m, 1H), 3.32–2.50 (m, 4H), 1.83 (m, 1H), 1.40–0.5 (m, 3H).

Step B:

1'-[2(R)-amino-3-(1H-indol-3-yl)-1-oxopropyl]-2,3-dihydrospiro[1H-indene-1,4-piperidene]

The intermediate obtained from Step A (2.01 g, 3.98 mmole) was dissolved in 40 mL methanol and hydrogenated over Pd(OH)$_2$ on carbon at one atmosphere for 16 hours. The mixture was filtered through Celite and the filtrate concentrated under vacuum. The residue was purified by chromatatron (methylene chloride/methanol/ammonium hydroxide=10/1/0.1) to give 1.41 g (95%) of the title compound.

$^1$H NMR (400 MHz, CDCl$_3$, mixture of conformers): 8.43 (s, 1H), 7.61 (d, 8 Hz, ⅔H), 7.54 (d, 8 Hz, ⅓H), 7.36 (d, 8 Hz, 1H), 7.19–6.70 (m, 7H), 4.55 (t, 12 Hz, 1H), 4.13 (m, 1H), 3.70 (m, 1H), 3.15 (m, 1H), 3.03 (m, 1H), 2.94–2.65 (m, 4H), 1.92 (m, 2H), 1.74 (m, 1H), 1.52–1.10 (m, 2⅓H), 0.65 (td, 13, 4 Hz, ⅔H).

Step C:

N-[1(R)-[(2,3-dihydrospiro[1H-indene-1,4'-piperidin]-1'-yl)carbonyl]-2-(1H-indol-3-yl)ethyl]-3-amino-3-methylbutanamide hydrochloride Prepared from the intermediate obtained from Step B (373 mg, 1.0 mmole) and 3-t-butyloxycarbonylamino-3-methylbutanoic acid (238 mg, 1.1 mmole) by the procedure described in Example 20, Step A (without triethylamine). The crude product was purified by chromatatron (methylene chloride/methanol=20/1). The purified compound in 3 mL methanol was added hydrochloride in ethyl ether at room temperature. The reaction was stirred for 0.5 hours and concentrated. The title compound was precipitated out from methanol and ethyl ether solution (346 mg, 68%).

$^1$H NMR (400 MHz, CD$_3$OD, mixture of conformers): 7.64 (d, 8 Hz, ⅔H), 7.56 (d, 8 Hz, ⅓H), 7.40 (d, 8 Hz, ⅔H), 7.35 (d, 8 Hz, ⅓H), 7.18–7.01 (m, 6⅓H), 6.62 (d, 7 Hz, ⅔H), 5.27 (m, 1 H), 4.34 (d, 13 Hz, 1H), 3.73 (m, 1H), 3.27–3.02 (m, 3H), 2.83–2.51 (m, 5H), 1.93–1.62 (m, 2⅓H), 1.37 (s, 4H), 1.36 (s, 2H), 1.45–0.84 (m, 3H), 0.17 (td, 13, 4 Hz, ⅔H). FAB-MS: 473 (M+1).

EXAMPLE 21

N-[1(R)-[(2,3-dihydrospiro[1H-indene-1,4'-piperidin]-1'-yl)carbonyl]-2-(1H-indol-3-yl)ethyl]-2-amino-2-methylpropanamide hydrochloride Prepared from the intermediate obtained from Example 20, Step B (1.86 g, 5.0 mmole), and N-benzyloxycarbonyl-2-methylalanine (1.3 g, 5.5 mole) by the procedure described in Example 20, Step A (without triethylamine). The crude product was purified by chromatatron (hexanes/ethyl acetate=1/1). The purified compound was dissolved in 50 mL of methanol and hydrogenated under the conditions which were described in Example 20, Step B to give the desired free base. To the free base in 5 mL methanol was added hydrochloridic acid/dioxane (4.0M, 1.37 mL, 5.5 mmole) at 0° C. The solution was concentrated to dryness. The title compound was precipitated from a s methanol and ethyl ether solution (1.7 g, 69%).

$^1$H NMR (400 MHz, CD$_3$OD, mixture of conformers): 7.62 (d, 8 Hz, ⅗H), 7.55 (d, 8 Hz, ⅖H), 7.41 (d, 8 Hz, ⅗H), 7.36 (d, 8 Hz, ⅖H), 7.19–7.01 (m, 6⅖H), 6.63 (d, 7 Hz, ⅖H), 5.24, (m, 1H), 4.33 (m, 1H), 3.71 (m, 1H), 3.36–2.60 (m, 6H), 1.88 (m, 2H), 1.61 (s, 5H), 1.50 (s, 1H), 1.80–1.22 (m, 2⅕H), 0.99 (td, 13, 4 Hz, ⅗H), 0.89 (d, 8Hz, ⅖H), 0.21 (td, 13,4 Hz, ⅗H). FAB-MS: 459(M+1).

EXAMPLE 22

N-[1(R)-[(2,3-dihydrospiro[1H-indene-1,4'-piperidin]-1'-yl)carbonyl]-2-(1H-indol-3-yl)ethyl]-3(R)-nipecotamide hydrochloride Prepared from the intermediate obtained from Example 20, Step B (205 mg, 0.5 mmole), and t-butyloxycarbonyl-(D)-nipecotic acid (Recueil, 1951, 70, 899) (115 mg, 0.5 mmole) by the procedure described in Example 20, Step C (use 1,3-dicyclohexyl-carbodiimide instead of EDC, without triethylamine) to give the title compound (124 mg, 48%).

$^1$H NMR (400 MHz, CD$_3$OD, mixture of conformers): 7.63 (d, 8 Hz, ⅔H), 7.55 (d, 8 Hz, ⅓H), 7.40 (d, 8 Hz, ⅔H), 7.36 (d, 8 Hz, ⅓ Hz), 7.18–7.01 (m, 6⅓H), 6.61 (d, 7 Hz, ⅔H), 5.22, (m,1H), 4.34 (d, 11 Hz, 1H), 3.70 (m, 1H), 3.27–2.64 (m, 11H), 2.02–1.65 (m, 7H), 1.22 (m, 1H), 0.98 (td, 13, 4 Hz, ⅔H), 0.85 (dd, 13,2 Hz, ⅔H), 0.15 (td, 13, 4 Hz, ⅔H). FAB-MS: 485 (M+1).

EXAMPLE 23

N-[1(R)-[(2,3-dihydrospiro[1H-indene-1,4'-piperidin]-1'-yl)carbonyl]-2-(1H-indol-3-yl)ethyl]-[3-[2(R)-hydroxylpropyl]-amino]-3-methylbutanamide hydrochloride Step A:

O-(tetrahydropyranyl)-(R)-lactaldehyde

To a solution of methyl (R)-lactate (1.0 mL, 10.48 mmole) in 5 mL dihydropyran was added a drop of concentrated hydrochloric acid at room temperature. After 1 hour stirring, the mixture was concentrated and purified by chromatatron (hexanes/ethyl acetate=3/1) to give 1.49 g (75%). A 500 mg (2.65 mmole) portion of the residue in 10 mL of toluene was added diisobutyl-aluminum hydride (1N, 3.45 mL), at –78° C. After 1.5 hours stirring at –78° C., the reaction was quenched with methanol at low temperature, the mixture was poured into 5% aqueous citric acid and extracted with ethyl ether (2×). The organic layers were washed with water, brine and dried over sodium sulfate, filtered and concentrated. The residue (*J. Org. Chem.* 1988, 53, 4098) was carried to the next step without purification.

$^1$H NMR (400 MHz, CDCl$_3$): 9.63 (d, 2 Hz, 1H), 4.69 (m, ½H), 4.62, (m, ½H), 4.21 (q, 7 Hz, ½H), 3.98–3.83 (m, 1½H), 3.49 (m, 1H), 1.85–1.49 (m, 6H), 1.43 (d, 7 Hz, 3/2H), 1.25 (d, 7 Hz, 3/2H).

Step B:

N-[1(R)-[(2,3-dihydrospiro[1H-indene-1,4'-piperidin]-1'-yl)carbonyl]-2-(1H-indol-3-yl)ethyl]-[3-[2(R)-hydroxylpropyl]-amino]-3-methylbutanamide hydrochloride To a stirred solution of the intermediate obtained from Example 20, Step C (140 mg, 0.27 mmole), in 3 mL anhydrous methanol was added the intermediate obtained from this Example, Step A (217 mg, 1.37 mg), sodium acetate (112 mg, 1.37 mmole) at room temperature. After stirring for 1 hour, sodium cyanoborohydride 1N solution in tetrahydrofuran (0.54 mL, 0.54 mmole) was added. The reaction mixture was stirred at room temperature for 16 hours. The solution was diluted with chloroform and washed with water, brine, and dried over sodium sulfate, filtered and concentrated. The residue was purified by chromatatron (methylene chloride/methanol/ammonium hydroxide=10/1/

0.1) to give 140 mg (84%) of solid.

To a solution of the reductive aminoylation solid (260 mg, 0.42 mmole) in 5 mL methanol was added 9N hydrochloric acid (0.5 mL) at room temperature. After 1 hour, the mixture was concentrated to dryness. The title compound was precipitated out from a methanol and ethyl ether solution (180 mg, 75%).

$^1$H NMR (400 MHz, CD$_3$OD, mixture of conformers): 7.63 (d, 8 Hz, ⅔H), 7.55 (d, 8 Hz, ⅓H), 7.40 (d, 8 Hz, ⅔H), 7.35 (d, 8 Hz, ⅓H), 7.18–7.01 (m, 6⅓H), 6.62 (d, 7 Hz, ⅔H), 5.27 (m, 1H), 4.33 (m, 1H), 3.98 (m, 1H), 3.72 (m, 1H), 3.27–3.03, (m, 3H), 2.85–2.60 (m, 7H), 1.93–1.65 (m, 3H), 1.39–1.23 (m, 10H), 1.00 (td, 13, 4 Hz, ⅔H), 0.88 (dd, 14, 2 Hz, ⅔H), 0.20 (td, 13, 4 Hz, ⅔H). FAB-MS: 532 (M+1).

EXAMPLE 24

N-[1(R)-[(2,3-dihydrospiro[1H-indene-1,4'-piperidin]-1'-yl)carbonyl]-2-(1H-indol-3-yl)ethyl]-[2-[2(R)-hydroxylpropyl]-amino]-2-methylpropanamide hydrochloride Prepared from the intermediate obtained from Example 21 (11 mg, 0.022 mmole), and the intermediate obtained from Example 23, Step A (16 mg, 0.1 mmole) by the procedure described in Example 23, Step B to give (7.9 mg, 65%) of the title compound.

$^1$H NMR (400 MHz, CD$_3$OD, mixture of conformers): 7.62 (d, 8 Hz, ⅔H), 7.56 (d, 8 Hz, ⅓H), 7.40 (d, 8 Hz, ⅔H), 7.36 (d, 8 Hz, ⅓H), 7.19–7.01 (m, 6⅓H), 6.68 (d, 7 Hz, ⅔H), 5.25 (m, 1H), 4.36 (m, 1H), 3.98–3.73 (m, 2H), 3.27–3.07 (m, 3H), 2.88–2.58 (m, 5H), 1.96–1.70 (m, 3H), 1.62–0.94 (m, 11⅓H), 0.34 (td, 13, 4 Hz, ⅔H). FAB-MS: 517 (M+1).

EXAMPLE 25

N-[1(R)-[(2,3-dihydrospiro[1H-indene-1,4'piperidin]-1'-yl)carbon yl]-2-(1H-indol-3-yl)ethyl]-[2(R,S)-amino]-(2-hydroxymethyl)propanamide hydrochloride Step A:

N-(t-butoxycarbonyl)-α-methylserine benzyl ester

To a solution of α-methylserine (1.19 g, 10.0 mmole) in 12 mL 1N aqueous sodium hydroxide was added di-t-butyldicarbonate (2.75 mL, 12.0 mmole) in 12 mL 1.4-dioxane at room temperature. After 24 hours, the mixture was diluted with ethyl acetate and acidified with 0.5N hydrochloric acid to pH=2.0. The organic layer was dried over sodium sulfate, filtered and concentrated. To the residue in 10 mL of methanol was added potassium carbonate (1.38 g, 10.0 mmole) in 5 mL of water. The resulting mixture was concentrated to dryness under vacuum to give the potassium salt which was suspended in 30 mL of N,N-dimethylformamide with benzyl bromide (1.3 mL, 11.0 mmole). The mixture was stirred at room temperature for 18 hours and diluted with ethyl ether, washed with water (5×), and brine. The organic layer was dried over magnesium sulfate, filtered and concentrated. The residue was purified by chromatatron (hexanes/ethyl acetate=2/1) to give 1.81 g (60%) of title compound.

$^1$H NMR (200 MHz, CDCl$_3$): 7.35 (s, 5H), 5.28 (br. s, 1H), 5.20 (s, 2H), 4.02 (d, 12 Hz, 1H), 3.78 (d, 12 Hz, 1H), 1.48 (s, 3H), 1.41 (s, 9H).

Step B:

2,2-dimethyl-3-(t-butyloxycarbonyl)-4-methyl-oxazolidine-4-carboxylic acid

To a solution of the intermediate obtained in this Example, Step A (1.81 g, 6.05 mmole) in 20 mL methylene chloride was added dimethoxypropane (3.7 mL, 30.2 mmole) and a catalytic amount of p-toluenesulfonic acid (20 mg). After 20 hours at room temperature, the reaction was diluted with methylene chloride and washed with saturated aqueous sodium bicarbonate, and brine. The organic layer was dried over sodium sulfate, filtered and concentrated, the residue was purified by chromatatron (hexanes/ethyl acetate=5/1). Debenzylation was following the procedure which was described in Example 20, Step B (use 10% Pd on carbon instead of Pd(OH)$_2$) to give 0.99 g (65%) of the title compound.

$^1$H NMR (400 MHz, CD$_3$OD mixture of conformers): 4.09 (d, 9 Hz, 1H), 3.83 (d, 9 Hz, 1H), 1.58–1.50 (m, 9H), 1.47 (s, 3H), 1.42 (s, 6H).

Step C:

N-[1(R)-[(2,3-dihydrospiro[1H-indene-1,4'-piperidin]-1'-yl)carbonyl]-2-(1H-indol-3-yl)ethyl]-[2(R,S)-amino]-(2-hydroxymethyl)propanamide hydrochloride Prepared from the intermediate obtained from Example 20, Step B (37 mg, 0.1 mmole), and the intermediate obtained from this Example, Step B (26 mg, 0.105 mmole) by the procedure described in Example 20, Step C (use DCC instead of EDC, use 9N hydrochloric acid instead of hydrochloride in ethyl ether) to give 33 mg (64%) of the title compound.

$^1$H NMR (400 MHz, CD$_3$OD, mixture of conformers and diastereomers): 7.65–7.01 (m, 8⅓H), 6.64 (m, ⅔H), 5.27 (m, 1H), 4.33 (m, 1H), 3.96–3.50 (m, 3H), 3.28–2.61 (m, 6H), 1.90–0.80 (m, 8⅓H), 0.3–0.05 (m, ⅔H). FAB-MS: 475 (M+1).

EXAMPLE 26

N-[1(R)-[(spiro[1H-indene-1,4'-piperidin]-1'-yl)carbonyl]-2-phenyl-ethyl]-2-amino-2-methylpropanamide hydrochloride Step A:

[1(R)-[(spiro[1H-indene-1,4'-piperidin]-1-'yl)carbonyl]-2-phenylethyl]carbamic acid 1,1-dimethylethyl ester Prepared from t-butyloxycarbonyl-(D)-phenylalanine (0.933 g, 3.52 mmole) by the procedure described in Example 20, Step A to give 1.46 g (96%) of the title compound.

$^1$H NMR (200 MHz, CDCl$_3$ mixture of conformers): 7.38–7.05 (m, 10H), 6.69 (m, 1H), 5.43 (m, 1H), 4.95 (m, 1H), 4.59 (m, 1H), 3.78 (m, 1H), 3.24–2.62 (m, 4H), 1.92–0,85 (m, 4H), 1.44 (s, 9H).

Step B:

N-[1(R)-[(spiro[1H-indene-1,4'-piperidin]-1-yl)carbonyl]-2-phenylethyl]-[2-[(1,1-dimethylethyloxy)carbonyl]amino]-2-methylpropanamide To a solution of the intermediate obtained from this Example, Step A (1.45 g, 3.35 mmole) in 5 mL methanol was added hydrogen chloride in ethyl ether at room temperature for 1 hour. The solution was concentrated to give a pale solid (1.18 g, 95%). To a portion (74 mg, 0.24 mmole) of the solid in 1 mL chloroform was added t-butyloxycarbonyl-α-methylalanine (43 mg, 0.21 mmole), 1-hydroxybenzotriazole (28 mg, 0.21 mmole), and 1,3-dicyclohexylcarbodiimide (43 mg, 0.21 mmole). After 4 hours at room temperature, the mixture was diluted with methylene chloride and washed with water and brine. The organic layer was concentrated and purified by chromatatron (hexanes/ethyl acetate=2/1) to give the title compound.

Step C:

N-[1(R)-[(spiro[1H-indene-1,4'-piperidin]-1'-yl)carbonyl]-2-phenylethyl]-2-amino-2-methylpropanamide hydrochloride To the intermediate obtained from this Example, Step B in 0.5 mL of methanol was added hydrogen chloride in ethyl ether at room temperature. The reaction was stirred for 1 hour and concentrated. The title compound was precipitated from a methanol and ethyl ether solution (64 mg, 70%).

$^1$H NMR (400 MHz, CD$_3$OD mixture of conformers): 7.41–7.12 (m, 9H), 6.88 (t, 6 Hz, 1H), 6.78 (dd, 10, 6 Hz, 1H), 4.52 (m, 1H), 4.02 (m, 1H), 3.39 (m, 1H), 3.29–2.99 (m, 3H), 2.09 (td, 13, 4 Hz, ½H), 1.95 (td, 13, 4 Hz, ½H), 1.60 (m, 1H), 1.62 (s, ⅔H), 1.59 (s, ⅔H), 1.52 (s, ⅔H), 1.46 (s, ⅔H), 1.34–1.09 (m, 2H). FAB-MS: 418 (M+1).

EXAMPLE 27

N-[1(R)-[(2,3-dihydrospiro[1H-indene-1,4'-piperidin]-1'-yl)carbonyl]-2-phenylethyl]-2-amino-2-methylpropanamide hydrochloride Prepared from the intermediate obtained from Example 26, Step C (31 mg, 0.068 mmole) by the procedure described in Example 20, Step B (use 10% Pd on carbon instead of Pd(OH)$_2$ to give 30 mg (97%) of the title compound.

$^1$H NMR (400 MHz, CD$_3$OD mixture of conformers): 7.38–6.92 (m, 9H), 5.16 (m, 1H), 4.44 (m, 1H), 3.91 (m, 1H), 3.21–2.78 (m, 6H), 2.04 (m, 2H), 1.88–1.30 (m, 3½H), 1.60 (s, ⅔H), 1.58 (s, ⅔H), 1.51 (s, ⅔H), 1.44 (s, ⅔H), 0.92 (td, 13, 4 Hz, ½H). FAB-MS: 420 (M+1).

EXAMPLE 28

N-[1(R,S)-[(2,3-dihydrospiro[1H-indene-1,4'-piperidin]-1'-yl)carbonyl]-2-[(5-hydroxy)-1H-indol-3-yl]ethyl]-2-amino-2-methylpropanamide hydrochloride Step A:

t-butyloxycarbonyl-5-hydroxytryptophan

To a solution of 5-hydroxytryptophan (2.2 g, 10.0 mmole) in 22 mL of 1N aqueous sodium hydroxide was added di-t-butyl-dicarbonate (2.61 g, 12 mmole) in 22 mL dioxane at room temperature. After 16 hours, the mixture was diluted with ethyl acetate and acidified with 5% citric acid. The organic layer was dried over sodium sulfate, filtered and concentrated to give 1.6 g (50%) of the title compound.

Step B:

[1(R,S)-[(spiro[1H-indene-1,4'-piperidin]-1'-yl)carbonyl]-2-[(5-hydroxy)-1H-indol-3-yl]ethyl]carbamic acid 1,1-dimethylethyl ester Prepared from the intermediate obtained from this Example, Step A (1.6 g, 5.0 mmole) by the procedure described in Example 20, Step A (use DCC instead of EDC).

$^1$H NMR (400 MHz, CDCl$_3$ mixture of conformers): 7.28–6.42 (m, 11), 4.97 (m, 1H), 4.43 (m, ⅔H), 4.26 (m, ⅓H), 3.78 (m, 1H), 3.20–2.74 (m, 4H), 1.75 (m, 1H), 1.47 (s, 6H), 1.44 (s, 3H), 1.30–0.35 (m, 3H).

Step C:

N-[1(R,S)-[(2,3-dihyrospiro[1H-indene-1,4'-piperidin]-1'-yl)carbonyl]-2-[(5-hydroxy)-1H-indol-3-yl]ethyl]-[2-[(1,1-dimethylethyloxy)carbonyl]amino]-2-methylpropanamide Prepared from the intermediate obtained from this Example, Step B (228 mg, 0.46 mmole) by the procedure described in Example 26, Step C followed by the procedures described in Example 27 and Example 26, Step B.

$^1$H NMR (400 MHz, CDCl$_3$ mixture of conformers): 8.01 (d, 1 Hz, ⅔H) 7.97 (d, 1 Hz, ⅓H), 7.28–6.98 (m, 6H), 5.22 (m, 1H), 5.10 (s, ⅓H), 5.08 (s, ⅔H), 4.44 (m, 1H), 3.52 (m, 1H), 3.14–2.33 (m, 6H), 1.84 (m, 1H), 1.64 (m, 1H), 1.50–0.90 (m, 18 ⅓H), 0.37 (td, 13,4 Hz, ⅔H).

Step D:

N-[1(R,S)-[(2,3-dihydrospiro[1H-indene-1,4'-piperidin]-1'-yl)carbonyl]-2-[(5-hydroxy)-1H-indol-3-yl]ethyl]-2-amino-2-methylpropanamide hydrochloride Prepared from the intermediate obtained from this Example, Step C (20.0 mg, 0.034 mmole) by the procedure described in Example 26, Step C to give 15 mg (84%) of the title compound.

$^1$H NMR (400 MHz, CD$_3$OD mixture of conformers): 7.28–6.71 (m, 8H), 5.24 (m, 1H), 4.42 (m, 1H), 3.80 (m, 1H), 3.31–2.70 (m, 6H), 1.96 (m, 2H), 1.72–0.96 (m, 3⅓H), 1.65 (s, 5H), 1.32 (s, 1H), 0.33 (td, 13, 4 Hz, ⅔H). FAB-MS: 475 (M+1).

EXAMPLE 29

N-[1(R)-[(2,3-dihydrospiro[1H-indene-1,4'-piperidin]-1'-yl)carbonyl]-2-(1H-indol-3-yl)ethyl]-[3-[2(R)-3-dihydroxylpropyl]amino]-3-methylbutanamide hydrochloride Prepared from the intermediate obtained from Example 20, Step C (220 mg, 0.43 mmole) and (R)-1,2-isopropylideneglyceraldehyde (*Tetrahedron* 1985, 41, 3117) (280 mg, 2.15 mmole) by the procedure described in Example 23, Step B to give 116 mg (46%) of title compound.

$^1$H NMR (400 MHz, CD$_3$OD mixture of conformers): 7.68 (d, 8 Hz, ⅔H), 7.58 (d, 8 Hz, ⅓H), 7.45 (d, 8 Hz, ⅔H), 7.38 (d, 8 Hz, ⅓H), 7.23–7.05 (m, 6⅓H), 6.66 (d, 7 Hz, ⅔H), 5.33 (m, 1H), 4.39 (m, 1H), 3.92 (m, 1H), 3.68 (m, 3H), 3.29–2.65 (m, 10H), 1.96–1.65 (m, 2H), 1.45 (s, 2H), 1.44 (s, 2H), 1.43 (s, 1H), 1.34 (s, 1H), 1.50–0.87 (m, 3⅓H), 0.24 (td, 13, 4 Hz, ⅔H). FAB-MS: 547 (M+1).

EXAMPLE 30

N-[1(R,S)-[(2,3-dihydrospiro[1H-indene-1,4'-piperidin]-1'-yl)carbonyl]-2-[(5-methoxy)-1H-indol-3-yl]ethyl]-2-amino-2-methylpropanamide hydrochloride To the intermediate obtained from Example 28, Step C (124 mg, 0.21 mole) dissolved in 4 mL of N,N-dimethylformamide was added cesium carbonate (136 mg, 0.42 mmole) and iodomethane (20 μl, 0.32 mmole) at room temperature. After 12 hours, the reaction was diluted with ethyl ether, washed with water (5×), and brine. The organic layer was purified by Pre-TLC (hexanes/ethyl acetate=1/1). Deprotection following the procedure which was described in Example 26, Step C gave 49 mg (44%) of the title compound.

$^1$H NMR (400 MHz, CD$_3$OD mixture of conformers): 7.29 (d, 8 Hz, ⅔H), 7.25 (d, 8 Hz, ⅓H), 7.16–6.63 (m, 7H), 5.21 (m, 1H), 4.63 (br. s, 1H), 4.43 (br. d, 13 Hz, 1H), 3.82 (s, 1H), 3.80 (s, 2H), 3.73 (m, 1H), 3.17–2.61 (m, 6H), 1.92–1.72 (m, 2H), 1.61 (s, 5H), 1.52 (s, 1H), 1.43–0.89 (m, 3⅓H), 0.23 (td, 13, 4 Hz, ⅔H). FAB-MS: 489 (M+1).

EXAMPLE 31

N-[1(R)-[(2,3-dihydrospiro[1H-indene-1,4'-piperidin]-1'-yl)carbonyl]-2-(1H-indol-3-yl)ethyl]-N'-[3-(R)-piperidinyl]urea hydrochloride Step A:

N-[1(R)-[(2,3-dihydrospiro[1H-indene-1,4'-piperidin]-1'-yl)carbonyl]-2-(1H-indol-3-yl)ethyl]-N'-[[1-(1,1-dimethylethyloxy)carbonyl]-3-(R)-piperidinyl]urea To a solution of t-butyloxycarbonyl-(D)-nipecotic acid (*Recueil*, 1951, 70, 899) (92.0 mg, 0.4 mmole) in 4 mL acetone was added triethylamine (84 μL, 0.6 mmole), and ethyl chloroformate (46 μL, 0.48 mmole) at 0° C. After 1 hour stirring, sodium azide (78 mg, 1.2 mmole) in 1 mL water was added to the reaction mixture. The resulting mixture was stirred for another 1 hour at room temperature and then poured into methylene chloride and washed with water and brine. The organic layer was dried over magnesium sulfate, filtered and concentrated. The residue was dissolved in 2 mL of toluene and heated to 90° C. for ½ hour and then the intermediate obtain from Example 20, Step B was added. After 1 more hour stirring at 90° C., the reaction mixture was concentrated under vacuum. The residue was purified by chromatatron (methylene chloride/methanol=20/1) to give 188 mg (78%) of the title compound.

$^1$H NMR (400 MHz, CDCl$_3$ mixture of conformers): 8.28 (d, 1 Hz, 1H). 7.72 (d, 8 Hz, ⅔H), 7.58 (d, 8 Hz, ⅓H), 7.37–7.06 (m, 7⅓H), 6.49 (m, ⅔H), 5.25 (m, 2H), 4.38 (m, 1H), 3.76–3.52 (m, 4H), 3.24–2.42 (m, 8H), 1.93–0.94 (m, 18⅓H), 0.23 (m, ⅔H).

Step B:

N-[1(R)-[(2,3-dihydrospiro[1H-indene-1,4'-piperidin]-1'-yl)carbonyl]-2-(1H-indol-3-yl)ethyl]-N'-[3-(R)-piperidinyl]urea hydrochloride Prepared from the intermediate obtained from this Example, Step A (188 mg, 0.31 mmole) by the procedure described in Example 26, Step C to give 62 mg (31%) of the title compound.

$^1$H NMR (400 MHz, CD$_3$OD mixture of conformers): 7.64 (d, 8 Hz, ⅔H), 7.52 (d, 8 Hz, ⅓H), 7.39 (d, 8 Hz, ⅔H), 7.35 (d, 8 Hz, ⅓H), 7.17–7.01 (m, 6⅓H), 6.61 (d, 7 Hz, ⅔H), 5.13 (t, 8 Hz, ⅔H), 5.04 (t, 8 Hz, ⅓), 4.35 (m, 1H), 3.84 (m, 1H), 3.36–2.62 (m, 10H), 2.03–1.22 (m, 8H), 1.00 (td, 13, 4 Hz, ⅔H), 0.83 (m, ⅔H), 0.13 (td, 13, 4 Hz, ⅔H). FAB-MS: 500 (M+1).

EXAMPLE 32

N-[1(R)-[(2,3-dihydrospiro[1H-indene-1,4'-piperidin]-1'-yl)carbonyl]-2-(1H-indol-3-yl)ethyl-2-(R)-amino-3-(imidazol-4-yl)propanamide dihydrochloride Prepared from the intermediate obtained from Example 20, Step B (37.0 mg, 0.1 mmole), and t-butyloxycarbonyl-(D)-histidine (30.0 mg, 0.11 mmole) by the procedure described in Example 25, Step C to give 35 mg (60%) of the title compound.

$^1$H NMR (400 MHz, CD$_3$OD mixture of conformers): 8.98 (s, ⅔H), 8.94 (s, ⅓H), 7.63–7.01 (m, 9⅓H), 6.60 (d, 7 Hz, ⅔H), 5.17 (t, 8 Hz, ⅔H), 5.10 (t, 8 Hz, ⅓H), 4.43 (m, 1H), 4.30 (m, 1H), 3.68–3.03 (m, 6H), 2.83–2.40 (m, 3H), 1.92–1.62 (m, 3H), 1.43–0.85 (m, 2⅓H), 0.11 (td, 13, 4 Hz, ⅔H). FAB-MS: 511 (M+1).

EXAMPLE 33

N-[1(R)-[(2,3-dihydrospiro[1H-indene-1,4'-piperidin]-1'-yl)carbonyl]-2-(1H-indol-3-yl)ethyl]-N'-(2-amino-2-methyl)propyl urea hydrochloride Step A:

N-[1(R)-[(2,3-dihydrospiro[1H-indene-1,4'-piperidin]-1'-yl)carbonyl]-2-(1H-indol-3-yl)ethyl]-N'-[[2-(1,1-dimethylethyloxy)carbonyl]amino]-2-methyl]propyl urea Prepared from the intermediate obtained from Example 20, Step B (175 mg, 0.47 mmole), and 3-t-butyloxycarbonylamino-3-methylbutanoic acid (217 mg, 1.0 mmole) by the procedure described in Example 31, Step A to give 253 mg (92%) of the title compound.

$^1$H NMR (300 MHz, CDCl$_3$ mixture of conformers): 8.35 (s, 1H), 7.71–7.03 (m, 8⅓H), 6.56 (m, ⅔H), 6.18 (m, 1H), 5.73 (m, 1H), 5.26 (m, 2H), 4.38 (m, 1H), 3.71 (m, 1H), 3.48–2.53 (m, 8H), 1.88–1.65 (m, 2H), 1.43 (s, 3H), 1.41 (s, 6H), 1.25 (s, 6H), 1.54–0.95 (m, 3⅓H), 0.33 (m, ⅔H).

Step B:

N-[1(R)-[(2,3-dihydrospiro[1H-indene-1,4'-piperidin]-1'-yl)carbonyl]-2-(1H-indol-3-yl)ethyl]-N'-(2-amino-2-methyl)propyl urea hydrochloride Prepared from the intermediate obtained from this Example, Step A (253 mg, 0.43 mg) by the procedure described in Example 31, Step B to give 63 mg (28%) of the title compound.

$^1$H NMR (300 MHz, CD$_3$OD mixture of conformers): 7.69 (d, 8 Hz, ⅔H), 7.58 (d, 8 Hz, ⅓H), 7.46–7.05 (m, 7⅓H), 6.67 (d, 7 Hz, ⅔), 5.15 (m, 1H), 4.42 (m, 1H), 3.75 (m, 1H), 3.49–2.69 (m, 8H), 2.21–0.85 (m, 5⅓H), 1.35 (s, 6H), 0.18 (td, 13, 4 Hz, ⅔H). FAB-MS: 488 (M+1).

EXAMPLE 34

N-[1(R,S)-[(2,3-dihydrospiro[1H-indene-1,4'-piperidin]-1'-yl)carbonyl]-2-(1H-indol-3-yl)ethyl]-N'-[3(R,S)-aminoquinuclidine]urea hydrochloride Prepared from the intermediate obtained from Example 20, Step B and quinuclidine-3-carboxylic acid (*J. Chem. Soc. Chem. Commun.* 1991, 760) by the procedure described in Example 31, Steps A and B to give the title compound.

$^1$H NMR (400 MHz, CD$_3$OD mixture of diastereomers and conformers): 7.65 (m, ⅔H), 7.53 (t, 8 Hz, ⅓H), 7.39 (d, 8 Hz, ⅔H), 7.35 (m, ⅓H), 7.17–7.01 (m, 6⅓H), 6.62 (d, 7 Hz, ⅔H), 5.12 (m, 1H), 4.33 (m, 1H), 4.08 (m, 1H), 3.91 (m, 2H), 3.36–2.57 (m, 11H), 2.15–1.70 (m, 7⅔H), 1.42 (m, ⅓H), 1.28 (d, 13 Hz, 1H), 1.02 (td, 13, 4 Hz, ⅔H), 0.85 (m, ⅔H), 0.17 (td, 13, 4 Hz, ⅔H).

EXAMPLE 35

N-[1(R,S)-[(2,3-dihyrospiro[1H-indene-1,4'-piperidin]-1'-yl)carbonyl]-2-(5-methyl-1H-indol-3-yl)ethyl]-2-amino-2-methylpropanamide trifluoroacetate Step A:

1'-[2(R,S)-amino-3-(5-methyl-1H-indol-3-yl)-1-oxopropyl]-2,3-dihydrospiro[1H-indene-1,4'-piperidine]trifluoroacetate Prepared from 5-methyltryptophan (218 mg, 1.0 mmole) by the procedure described in Example 28, Step A and B (use EDC instead of DCC, use 3,4-dihydrospiro[1H-indene-1,4'-piperidine]hydrochloride (*J. Med. Chem.* 1992, 35, 2033) instead of spiro[1H-indene-1,4'-piperidine]hydrochloride). The resulting residue in a 2:1 mixture of methylene chloride and trifluoroacetic acid was stirred at room temperature for 1 hour. The solution was concentrated and azeotroped with toluene to give 307 mg (79%) of the title compound $^1$H NMR (400 MHz, CDCl$_3$ mixture of conformers): 8.37 (s, ½H), 8.34 (s, ½H), 7.35–6.73 (m, 7H), 4.50 (m, 1H), 4.13 (m, 1H), 3.75 (m, ½H), 3.61 (m, ½H), 3.12–2.67 (m, 6H), 2.42 (s, 3/2H), 2.40 (s, 3/2H), 1.97–1.13 (m, 5½H), 0.71 (m, ½H).

Step B:

N-[1(R,S)-[(2,3-dihyrospiro[1H-indene-1,4'-piperidin]-1'-yl)carbonyl]-2-(5-methyl-1H-indol-3-yl)ethyl]-2-amino-2-methylpropanamide trifluoroacetate Prepared from the intermediate obtained from this Example, Step A (307 mg, 0.79 mmole) and t-butyloxycarbonyl-α-methylalanine (237 mg, 1.0 mmole) by the procedure described in Example 20, Step C (use trifloroacetic acid and methylene chloride mixture instead of hydrochloride in ethyl ether) to give 215 mg (46%) of the title compound.

$^1$H NMR (400 MHz, CD$_3$OD mixture of conformers): 7.40–6.94 (m, 7⅓H), 6.23 (d, 8 Hz, ⅔H), 5.21 (m, 1H), 4.33 (m, 1H), 3.71 (m, 1H), 3.26–2.59 (m, 6H), 2.41 (s, 1H), 2.39 (s, 2H), 1.87 (m, 2H), 1.70–1.22 (m, 2H), 1.60 (s, 5H), 1.56 (s, ⅔H), 1.52 (s, ⅓H), 1.01 (td, 13, 4 Hz, ⅔H), 0.87 (m, ⅔H), 0.23 (td, 13, 4 Hz, ⅔H). FAB-MS: 473 (M+1).

EXAMPLE 36

N-[1(R,S)-[(2,3-dihyrospiro[1H-indene-1,4'-piperidin]-1'-yl)carbonyl]-2-(5-bromo-1H-indol-3-yl)ethyl]-2-amino-2-methylpropanamide trifluoroacetate Prepared from 5-bromotryptophan (283 mg, 1.0 mmole) by the procedure described in Example 35, Step A and B to give 307 mg (47%) of the title compound.

$^1$H NMR (400 MHz, CD$_3$OD mixture of conformers): 7.78 (d, 2 Hz, ⅔H), 7.69 (d, 2 Hz, ⅓H), 7.35–7.03 (m, 6⅓H), 6.63 (d, 7 Hz, ⅔H), 5.17 (m, 1H), 4.36 (m, 1H), 3.70 (m, 1H), 3.34–2.63 (m, 6H), 1.90 (m, 2H), 1.75–0.96 (m, 3⅓H), 1.62 (s, 1H), 1.61 (s, 2H), 1.60 (s, 2H), 1.51 (s, 1H), 0.28 (td, 13, 4 Hz, ⅔Hz). FAB-MS: 538 (M+1).

EXAMPLE 37

N-[1(R)-[(2,3-dihydrospiro[1H-indene-1,4'-piperidin]-1'-yl)carbonyl]-2-(1H-indol-3-yl)ethyl]-N'-2-(N,N-dimethylamino)ethyl urea hydrochloride To a solution of 1,1-carbonyldiimidazole (162 mg, 1.0 mmole) in 2 mL tetrahydrofuran was added N,N-dimethylethylenediamine (109 μL, 1.0 mmole) at room temperature. After 10 minutes, the intermediate obtained from Example 20, Step B (37 mg, 0.1 mmole) was added to the reaction mixture. The resulting mixture was stirred at room temperature for 12 hours and then concentrated. The residue was purified by chromatatron (methylene chloride/methanol/ammonium hydroxide=10/1/0.1). The purified compound was acidified with hydrochloride in ethyl ether to give 25 mg (48%) of the title compound.

$^1$H NMR (400 MHz, CD$_3$OD mixture of conformers): 7.63 (d, 8 Hz, ⅔H), 7.53 (d, 8 Hz, ⅓H), 7.40 (d, 8 Hz, ⅔H), 7.36 (d, 8 Hz, ⅓H), 7.18–7.01 (m, 6⅓H), 6.62 (d, 7 Hz, ⅔H), 5.13 (t, 8 Hz, ⅔H), 5.04 (t, 8 Hz, ⅓H), 4.35 (m, 1H), 3.85 (t, 6 Hz, 1H), 3.68 (m, 1H), 3.50 (m, 2H), 3.25–2.57 (m, 8H), 2.98 (s, 2H), 2.93 (s, 3/2H), 2.92 (s, 3/2H), 2.90 (s, ½H), 2.88 (s, ½H), 1.93–1.67 (m, 2H), 1.42–1.22 (m, 2H), 1.00 (td, 13, 4 Hz, ⅔H), 0.84 (m, ⅔H), 0.14 (td, 13, 4 Hz, ⅔H). FAB-MS: 488 M+1).

EXAMPLE 38

N-[1(R)-[(2,3-dihydrospiro[1H-indene-1,4'-piperidin]-1'-yl)carbonyl]-3-cyclohexypropyl]-2-amino-2-methylpropanamide hydrochloride Step A:

t-butyloxycarbonyl-(D)-hexahydrohomophenylalanine

A solution of t-butyloxycarbonyl-(D)-homophenylalanine (100 mg, 0.358 mmole) in 1 mL acetic acid was hydrogenated over PtO$_2$ at one atmosphere for 16 hours. The mixture was filtered through Celite and the filtrate concentrated and azeotroped with toluene.

$^1$H NMR (400 MHz, CDCl$_3$): 5.03 (d, 8 Hz, 1H), 4.22 (m, 1H), 1.82 (m, 1H), 1.64 (m, 6H), 1.41 (s, 9H), 1.20 (m, 6H), 0.84 (m, 2H).

Step B:

[1(R)-[(2,3-dihydrospiro[1H-indene-1,4'-piperidin]-1'-yl)carbonyl]-3-cyclohexylpropyl]carbamic acid 1,1-dimethylethyl ester Prepared from the intermediate obtained from this Example, Step A and 3,4-dihydrospiro[1H-indene-1,4'-piperidine]hydrochloride (88 mg, 0.394 mmole) by the procedure described in Example 20, Step A to give 110 mg (67%) of the title compound.

$^1$H NMR (200 MHz, CDCl$_3$ mixture of conformers): 7.18 (m, 4H), 5.48 (d, 8 Hz, 1H), 4.62 (m, 2H), 3.90 (m, 1H), 3.28 (m, 1H), 2.98–2.81 (m, 3H), 2.09 (t, 8 Hz, 2H), 1.75–1.54 (m, 10H), 1.45 (s, ½H), 1.44 (s, ½H), 1.20 (m, 8H), 0.98 (m, 1H).

Step C:

N-[1(R)-[(2,3-dihydrospiro[1H-indene-1,4'-piperidin]-1'-yl)carbonyl]-3-cyclohexylpropyl]-2-amino-2-methylpropanamide hydrochloride Prepared from the intermediate obtained from this Example, Step B (110 mg, 0.24 mmole) by the procedure described in Example 26, Step B and C (use EDC instead of DCC) to give 29 mg (25%) of the title compound.

$^1$H NMR (400 MHz, CD$_3$OD mixture of conformers): 7.14 (m, 4H), 4.85 (m, 1H), 4.48 (m, 1H), 3.99 (m, 1H), 3.37 (m, 1H), 2.94 (m, 3H), 2.16 (m, 2H), 1.95–1.73 (m, 10H), 1.63 (s, 1H), 1.61 (s, ⅔H), 1.60 (s, ⅔H), 1.55 (s, 2H), 1.28–0.89 (m, 9H). FAB-MS: 440 (M+1).

EXAMPLE 39

N-[1(R)-[(2,3-dihydrospiro[1H-indene-1,4'-piperidin]-1'-yl)carbonyl]-2-(cyclohexylmethyloxy)ethyl]-2-amino-2-methylpropanamide hydrochloride Prepared from N-t-butyloxycarbonyl-O-benzyl-(D)-serine (100 mg, 0.339 mmole) by the procedure described in Example 38, Step A, B, and C to give 36 mg (21%) of the title compound.

$^1$H NMR (400 MHz, CD$_3$OD mixture of conformers): 7.14 (m, 4H), 5.14 (m, 1H), 4.47 (m, 1H), 4.10 (m, 1H), 3.65 (m, 2H), 3.30–3.25 (m, 3H), 2.92 (m, 3H), 2.15 (m, 2H), 1.91–1.55 (m, 9H), 1.63 (s, 1H), 1.60 (s, 2H), 1.59 (s, 3H), 1.28–0.93 (m, 6H). FAB-MS: 456 (M+1).

EXAMPLE 40

N-[1(R)-[(2,3-dihydrospiro[1H-indene-1,4'-piperidin]-1'-yl)carbonyl]-2-(4'-fluorophenylmethyloxy)ethyl]-2-amino-2-methylpropanamide hydrochloride Step A:

[1(R)-[(2,3-dihydrospiro[1H-indene-1,4'-piperidin]-1'-yl)carbonyl]-2-(4'-fluorophenylmethyloxy)ethyl]carbamic acid 1,1-dimethylethyl ester Oil free sodium hydride (prepared from 60% oil dispersion of sodium hydride by washing with hexanes (3×), 144 mg, 6.0 mmole) suspension in 10 mL N,N-dimethylformamide was added N-t-butyloxycarobnyl-(D)-serine (553 mg, 2.7 mmole) in 5 mL N,N-dimethylformamide at room temperature. When no more gas evolves 4-fluorobenzyl chloride (323 μL, 2.7 mmole) was added, and the mixture was stirred at room temperature for 18 hours. The reaction was poured into 0.5N hydrochloric acid and then extracted with ethyl acetate (3×). The organic layer was washed sequentially with water (5×), brine and dried over sodium sulfate, filtered and concentrated. A portion (290 mg, 0.926 mmole) of the residue was reacted with 3,4-dihydrospiro[1H-indene-1,4'-piperidine]hydrochloride (238 mg, 1.02 mmole) according to the procedure described in Example 20, Step A to give 268 mg (60%) of the title compound.

$^1$H NMR (200 MHz, CDCl$_3$ mixture of conformers): 7.37–6.62 (m, 8H), 5.58 (m, 1H), 4.93 (m, 1H), 4.67–4.48 (m, 3), 3.97 (m, 1H), 3.64 (m, 2H), 3.20 (m, 1H), 2.92 (m, 3H), 2.03 (m, 2), 1.81–1.48 (m, 4H), 1.45 (s, 9H).

Step B:

N-[1(R)-[(2,3-dihydrospiro[1H-indene-1,4'-piperidin]-1'-yl)carbonyl]-2-(4'-fluorophenylmethyloxy)ethyl]-2-amino-2-methylpropanamide hydrochloride Prepared from the intermediate obtained from this Example, Step A (268 mg, 0.556 mmole) by the procedure described in Example 26, Step B and Step C (using EDC instead of DCC) to give 196 mg (70%) of the title compound.

$^1$H NMR (400 MHz, CD$_3$OD mixture of conformers): 7.40–7.05 (m, 7½H), 6.79 (d, 7 Hz, ½H), 5.17 (t, 6 Hz, 1H), 4.52 (m, 3H), 4.02 (m, 1H), 3.72 (m, 2H), 3.28 (m, 1H), 2.90 (m, 3H), 2.09 (m, 2H), 1.89–1.50 (m, 4H), 1.62 (s, ⅔H), 1.59 (s, ⅔H), 1.58 (s, 3H). FAB-MS: 468 M+1).

EXAMPLE 41

N-[1(R)-[(2,3-dihydrospiro[1H-indene-1,4'-piperidin]-1'-yl)carbonyl]-2-(4'-chlorophenylmethyloxy)ethyl]-2-amino-2-methylpropanamide hydrochloride Step A:

[1(R)-[(2,3-dihydrospiro[1H-indene-1,4'-piperidin]-1'-yl)carbonyl]-2-(4'-chlorophenylmethyloxy)ethyl]carbamic acid 1,1-dimethylethyl ester Prepared from 4-chlorobenzyl chloride by the procedure described in Example 40, Step A.

$^1$H NMR (400 MHz, CDCl$_3$ mixture of conformers): 7.38–7.08 (m, 7½H), 6.68 (m, ½H), 5.58 (d, 8 Hz, 1/2H), 5.52 (d, 8 Hz, ½H), 4.90 (m, 1H), 4.65–4.42 (m, 3H), 3.94 (m, 1H), 3.61 (m, 2H), 3.15 (m, 1H), 2.87 (m, 3H), 2.02 (m, 2H), 1.80–1.46 (m, 4H), 1.43 (s, ⅔H), 1.42 (s, ⅔H).

Step B:

N-[1(R)-[(2,3-dihydrospiro[1H-indene-1,4'-piperidin]-1'-yl)carbonyl]-2-(4'-chlorophenylmethyloxy)ethyl]-2-amino-2-methylpropanamide hydrochloride Prepared from the intermediate obtained from Step A (92 mg, 0.18 mmole) by the procedure described in Example 26, Step B and Step C (using EDC instead of DCC) to give 58 mg (55%) of the title compound.

$^1$H NMR (400 MHz, CD$_3$OD mixture of conformers): 7.36–7.09 (m, 7½H), 6.78 (m, ½H), 5.18 (m, 1H), 4.52 (m, 3H), 4.04 (m, 1H), 3.74 (m, 2H), 3.28 (m, 1H), 2.90 (m, 3H), 2.09 (m, 2H), 1.90–1.52 (m, 4H), 1.63 (s, ⅔H), 1.60 (s, ⅔H), 1.58 (s, 3H). FAB-MS: 484.8 M+1).

EXAMPLE 42

N-[1(R)-[(2,3-dihydrospiro[1H-indene-1,4'-piperidin]-1'-yl)carbonyl]-2-(2',6'-difluorophenylmethyloxy)ethyl]-2-amino-2-methylpropanamide hydrochloride Step A:

[1(R)-[(2,3-dihydrospiro[1H-indene-1,4'-piperidin]-1'-yl)carbonyl]-2-(2',6'-difluorophenylmethyloxy)ethyl]carbamic acid 1,1-dimethylethyl ester Prepared from 2,6-diflorobenzyl bromide by the procedure described in Example 40, Step A.

$^1$H NMR (200 MHz, CDCl$_3$ mixture of conformers): 7.27–6.88 (m, 7H), 5.54 (m, 1H), 4.90 (m, 1H), 4.64 (m, 3H), 4.01 (m, 1H), 3.64 (m, 2H), 3.21 (m, 1H), 2.93 (m, 3H), 2.06 (m, 2H), 1.83–1.40 (m, 4H), 1.45 (s, 9H).

Step B:

N-[1(R)-[(2,3-dihydrospiro[1H-indene-1,4'-piperidin]-1'-yl)carbonyl]-2-(2',6'-difluorophenylmethyloxy)ethyl]-2-amino-2-methylpropanamide hydrochloride Prepared from the intermediate obtained from this Example, Step A (400 mg, 0.8 mole) by the procedure described in Example 26, Step B and Step C (using EDC instead of DCC) to give 293 mg (70%) of the title compound.

$^1$H NMR (400 MHz, CD$_3$OD mixture of conformers): 8.25 (d, 7 Hz, ½H), 8.19 (d, 7 Hz, ½H), 7.39 (m, 1H), 7.19–6.95 (m, 6H), 5.15 (m, 1H), 4.66 (d, 16 Hz, 2H), 4.45 (m, 1H), 4.03 (m,.1H), 3.76 (m, 2H), 3.28 (m, 1H), 2.91 (m, 3H), 2.11 (m, 3H), 1.88–1.48 (m, 4H), 1.61 (s, 1H), 1.57 (s, 5H). FAB-MS: 486 M+1).

EXAMPLE 43

N-[1(R)-[(2,3-dihydrospiro[1H-indene-1,4'-piperidin]-1'-yl)carbonyl]-2-(2',6'-dichlorophenylmethyloxy)ethyl]-2-amino-2-methylpropanamide hydrochloride Step A:

[1(R)-[(2,3-dihydrospiro[1H-indene-1,4'-piperidin]-1'-yl)carbonyl]-2-(2',6'-dichlorophenylmethyloxy)ethyl]carbamic acid 1,1-dimethylethyl ester Prepared from α,2,6-trichlorotoluene by the procedure described in Example 40, Step A.

$^1$H NMR (400 MHz, CDCl$_3$ mixture of conformers): 7.32–7.07 (m, 6½H), 6.79 (d, 6 Hz, ½H), 5.57 (d, 8 Hz, ½H), 5.51 (d, 8 Hz, ½ Hz), 4.89 (m, 1H), 4.76 (m, 2H), 4.58 (m, 1H), 3.95 (m, 1H), 3.72 (m, 1H), 3.61 (m, 1H), 3.12 (m, 1H), 2.85 (m, 3H), 2.01 (m, 2H), 1.78–1.26 (m, 4H), 1.42 (s, ½H), 1.41 (s, ½H).

Step B:

N-[1(R)-[(2,3-dihydrospiro[1H-indene-1,4'-piperidin]-1'-yl)carbonyl]-2-(2',6'-dichlorophenylmethyloxy)ethyl]-2-amino-2-methylpropanamide hydrochloride Prepared from the intermediate obtained from this Example, Step A by the procedure described in Example 26, Step B and Step C (using EDC instead of DCC).

$^1$H NMR (400 MHz, CD$_3$OD mixture of conformers): 7.43–7.11 (m, 6½H), 6.84 (m, ½H), 5.16 (t, 6 Hz, 1H), 4.84 (d, 10 Hz, 2H), 4.46 (m, 1H), 4.04 (m, 1H), 3.80 (m, 2H), 3.26 (m, 1H), 2.89 (m, 3H), 2.08 (m, 2H), 1.88–1.43 (m, 4H), 1.61 (s, 1H), 1.59 (s, 5H). FAB-MS: 519 (M+1).

EXAMPLE 44

N-[1(R)-[(2,3-dihydrospiro[1H-indene-1,4'-piperidin]-1'-yl)carbonyl]-2-(5'-[2'-chlorothiophene]methyloxy)ethyl]-2-amino-2-methylpropanamide Step A:

[1(R)-[(2,3-dihydrospiro[1H-indene-1,4'-piperidin]-1'-yl)carbonyl]-2-(5'-[2'-chlorothiophene]methyloxy)ethyl]carbamic acid 1,1-dimethylethyl ester Prepared from 2-chloro-(5-chloromethyl)-thiophene by the procedure described in Example 40, Step A.

$^1$H NMR (200 MHz, CDCl$_3$ mixture of conformers): 7.20–6.93 (m, 4H), 6.77 (s, 2H), 5.57 (m, 1H), 4.90 (m, 1H), 4.60 (m, 3H), 3.97 (m, 1H), 3.64 (m, 2H), 3.22 (m, 1H), 2.89 (m, 3H), 2.08 (m, 1H), 1.82–1.40 (m, 4H), 1.44 (br. s, 9H).

Step B:

N-[1(R)-[(2,3-dihydrospiro[1H-indene-1,4'-piperidin]-1'-yl)carbonyl]-2-(5'-[2'-chlorothiophene]methyloxy)ethyl]-2-amino-2-methylpropanamide Prepared from the intermediate obtained from this Example, Step A by the procedure described in Example 26, Step B and Step C (using EDC instead of DCC). The crude product was purified by Prep TLC (methylene chloride/methanol/ammonium hydroxide=10/1/0.1) to give free base.

$^1$H NMR (400 MHz, CD$_3$OD mixture of conformers): 7.19–7.10 (m, 4H), 6.98–6.85 (m, 2H), 5.14 (t, 6 Hz, 1H), 4.67 (s, 1H), 4.62 (s, 1H), 4.47 (m, 1H), 4.04 (m, 1H), 3.72 (m, 2H), 3.27 (m, 1H), 2.93 (m, 3), 2.13 (m, 2), 1.93–1.28 (m, 4H), 1.57 (s, ⅔H), 1.55 (s, ⅔H), 1.53 (s, 3H). FAB-MS: 490 (M+1).

EXAMPLE 45

N-[1(R)-[(2,3-dihydrospiro[1H-indene-1,4'-piperidin]-1'-yl)carbonyl]-2-(1'-naphthalenemethyloxy)ethyl]-2-amino-2-methylpropanamide hydrochloride Step A:

[1(R)-[(2,3-dihydrospiro[1H-indene-1,4'-piperidin]-1'-yl)carbonyl]-2-(1'-naphthalenemethyloxy)ethyl]carbamic acid 1,1-dimethylethyl ester Prepared from 1-chloromethylnaphthalene by the procedure described in Example 40, Step A.

$^1$H NMR (400 MHz, CDCl$_3$ mixture of conformers): 8.10 (m, 1H), 7.82 (m, 2H), 7.56–7.38 (m, 4H), 7.17–7.01 (m, 3½H), 6.22 (d, 7 Hz, ½H), 5.60 (m, 1H), 5.14 (s, 1H), 5.03–4.83 (m, 2H), 4.75 (m, 1H), 3.88–3.62 (m, 3H), 3.08–2.58 (m, 4H), 1.98–1.10 (m, 6H), 1.42 (s, 9H).

Step B:

N-[1(R)-[(2,3-dihydrospiro[1H-indene-1,4'-piperidin]-1'-yl)carbonyl]-2-(1'-naphthalenemethyloxy)ethyl]-2-amino-2-methylpropanamide hydrochloride Prepared from the intermediate obtained from this Example, Step A (180 mg, 0.34 mmole) by the procedure described in Example 26, Step B and Step C (using EDC instead of DCC) to give 117 mg (64%) of the title compound.

$^1$H NMR (400 MHz, CD$_3$OD mixture of conformers): 8.14 (m, 1H), 7.88 (m, 2H), 7.50 (m, 4H), 7.11 (m, 3½H), 6.36 (d, 7 Hz, ½H), 5.11 (t, 6 Hz, ½H), 5.03 (d, 12 Hz, 1H), 5.02 (s, 1H), 4.96 (d, 12 Hz, 1H), 4.37 (m, 1H), 3.88–3.77 (m, 3H), 3.19–2.67 (m, 4H), 1.96 (m, 2H), 1.78–1.18 (m, 4H), 1.59 (s, ⅔H), 1.58 (s, ⅔H), 1.55 (s, ⅔H), 1.53 (s, ⅔H). FAB-MS: 500 (M+1).

EXAMPLE 46

N-[1(R)-[(2,3-dihydrospiro[1H-indene-1,4'-piperidin]-1'-yl)carbonyl]-1-phenylmethyl]-2-amino-2-methylpropanamide hydrochloride Step A:

[1(R)-[(2,3-dihydrospiro[1H-indene-1,4'-piperidin]-1'-yl)carbonyl]-1-phenylmethyl]carbamic acid 1,1-dimethylethyl ester Prepared from t-butyloxycarbonyl-(D)-phenylglycine (251 mg, 1.0 mmole) by the procedure described in Example 38, Step B to give 364 mg (84%) of the title compound.

$^1$H NMR (400 MHz, CDCl$_3$ mixture of conformers): 7.43–7.25 (m, 5H), 7.17–7.07 (m, 3½H), 6.69 (d, 6 Hz, ½H), 6.15 (d, 7 Hz, 1H), 5.62 (d, 8 Hz, ½H), 5.57 (d, 8 Hz, ½H), 4.64 (m, 1H), 3.82 (m, 1H), 3.15 (td, 12, 2 Hz, ½H), 2.83 (m, 3½H), 2.00–1.48 (m, 5H), 1.40 (s, 9H), 1.10 (d, 13 Hz, ½H), 0.66 (td, 13,4 Hz, ½H).

Step B:

N-[1(R)-[(2,3-dihydrospiro[1H-indene-1,4'-piperidin]-1'-yl)carbonyl]-1-phenylmethyl]-2-amino-2-methyylpropanamide hydrochloride Prepared from the intermediate obtained from this Example, Step A (364 mg, 0.84 mmole) by the procedure described in Example 26, Step B and Step C (using EDC instead of DCC) to give 270 (75%) of the title compound.

$^1$H NMR (400 MHz, CD$_3$OD mixture of conformers): 7.52–7.37 (m, 5H), 7.17–7.04 (m, 3½H), 6.69 (m ½H), 5.95 (m, 1H), 4.54 (m, 1H), 3.84 (m, 1H), 3.29 (m, ½H), 2.94–2.82 (m, 3½H), 2.09–1.80 (m, 3H), 1.66 (s, 1H), 1.65 (s, 2H), 1.55 (s, 1H), 1.53 (s, 2H), 1.50 (m, 2H), 1.12 (m, ½H), 0.71 (td, 13, 4 Hz, ½H). FAB-MS: 406 (M+1).

EXAMPLE 47

N-[1(R)-[(2,3-dihydrospiro[1H-indene-1,4'-piperidin]-1'-yl)carbonyl]-2-(cyclopropylmethyloxy)ethyl]-2-amino-2-methylpropanamide hydrochloride Step A:

[1(R)-[(2,3-dihydrospiro[1H-indene-1,4'-piperidin]-1'-yl)carbonyl]-2-(cyclopropylmethyloxy)ethyl]carbamic acid 1,1-dimethylethyl ester Prepared from cyclopropylmethyl bromide by the procedure described in Example 40, Step A.

$^1$H NMR (400 MHz, CDCl$_3$ mixture of conformers): 7.21–7.04 (m, 4H), 5.52 (t, 9 Hz, 1H), 4.86 (m, 1H), 4.60 (m, 1H), 4.07 (m, 1H), 3.61 (m 1H), 3.54 (t, 7 Hz, 1H), 3.27 (m, 3H), 2.92 (t, 7 Hz, 2H), 2.86 (m, 1H), 2.08 (m, 2H), 1.92–1.75 (m, 2H), 1.57 (d, 13 Hz, 2H), 1.43 (s, ⅔H), 1.41 (⅔H), 0.98 (m, 1H), 0.47 (m, 2H), 0.16 (m, 2H).

Step B:

N-[1(R)-[(2,3-dihydrospiro[1H-indene-1,4'-piperidin]-1'-yl)carbonyl]-2-(cyclopropylmethyloxy)ethyl]-2-amino-2-methylpropanamide hydrochloride Prepared from the intermediate obtained from this Example, Step A (196 mg, 0.447 mmole) by the procedure in Example 26, Step B and Step C (using EDC instead of DCC) to give 142 mg (71%) of the title compound.

$^1$H NMR (400 MHz, CD$_3$OD mixture of conformers): 7.20–7.09 (m, 4H), 5.14 (m, 1H), 4.49 (m, 1H), 4.10 (m, 1H), 3.70 (m, 2H), 3.40–3.31 (m, 3H), 2.94 (t, 7 Hz, 3H), 2.15 (m, 2H), 1.93 (td, 13, 4 Hz, 1H), 1.76 (m, 1H), 1.65–1.56 (m, 2H), 1.63 (s, ⅔H), 1.61 (s, ⅔H), 1.59 (s, 3H), 1.04 (m, 1H), 0.51 (d, 8 Hz, 2H), 0.21 (m, 2H). FAB-MS: 414 (M+1).

EXAMPLE 48

N-[1(R)-[(2,3-dihydrospiro[1H-indene-1,4'-piperidin]-1'-yl)carbonyl]-2-(1H-indol-3-yl)ethyl]-2(S)-amino-(2-hydroxymethyl)propanamide Step A:

Methyl (2R,4S)-2-t-butyl-3-formyl-oxazolidine-4-methyl-4-carboxylic acid

Prepared from (l)-serine methyl ester hydrochloride by the procedure described in *Tetrahedron Lett.* 1984, 25, 2545 to give the title compound.

$^1$H NMR(200 MHz, CD$_3$OD, 1:1 mixture of conformers): 8.43 (s, ½H), 8.30 (s, ½H), 5.23 (s, 1/2H), 4.88 (s, ½H), 4.63 (d, 9 Hz, ½H), 4.25 (d, 9 Hz, ½H), 3.74 (s, ⅔H), 3.71 (s, ⅔H), 3.57 (d, 9 Hz, 1H), 1.65 (s, ⅔H), 1.63 (s, ⅔H), 0.98(s, 4H), 0.85 (s, 5H). FAB-MS calculated for C$_{11}$H$_{19}$NO$_4$ 229; found 230 (M+H).

Step B:

(2R,4S)-2-t-butyl-3-formyl-oxazolidine-4-methyl-4-carboxylic acid

A solution of 37 mg of lithium hydroxide in 5 ml water was added to a room temperature solution of 160 mg of the intermediate prepared in this Example, Step A in 10 ml of 1:1 THF-methanol and stirred for 16 hours. The organic solvents were removed under vacuum and the residue was partitioned between 100 ml ethyl ether and 20 ml of 1N NaHSO$_4$ (aq). The organic layer was dried over anhydrous magnesium sulfate, filtered and concentrated to give 129.6 mg (86%) of the title compound.

¹H NMR(200 MHz, CD₃OD, 3:2 mixture of conformers): 8.44 (s, 0.4H), 8.31 (s, 0.6H), 5.22 (s, 0.6H), 5.02 (s, 0.4H), 4.62 (d, 9 Hz, 06H), 4.32 (d, 9 Hz, 0.4H), 3.82 (d, 9 Hz, 0.4H), 3.67 (d, 9 Hz, 0.6H), 1.69 (s, 1.8H), 1.66 (s,1.2H), 1.02 (s, 3.5H), 0.91 (s, 5.5H). FAB-MS calculated for $C_{10}H_{17}NO_4$ 215; found 215.9 (M+H).

Step C:

N-[1(R)-[(2,3-dihydrospiro[1H-indene-1,4'-piperidin]-1'-yl)carbonyl]-2-(1H-indol-3-yl)ethyl]-2(S)-amino-(2-hydroxymethyl)propanamide Isobutylchloroformate and triethylamine were added to a 0° C. solution of the intermediate prepared in this Example, Step B in CH₂Cl₂, stirred for 2 hours and then added to a solution of 39.2 mg of the intermediate obtained from Example 20, Step B in CH₂Cl₂. After 10 minutes the solution was poured into 50 ml of ethyl ether and washed sequentially with 1N NaHSO₄ (aq), water, saturated aqueous NaHCO₃ and brine. The organic phase was dried over anhydrous MgSO₄, filtered and concentrated. The compound was purified by MPLC (silica gel, 50% to 100% ethyl acetate in hexane, linear gradient over 750 ml) to give 20.9 mg (35%) of the desired intermediate. This material was dissolved in 1 ml methanol, treated with 1 ml concentrated aqueous HCl and refluxed for 15 minutes. The solution was cooled to room temperature and the solvents were removed under vacuum. Purification by flash chromatography (silica gel, eluting with MeOH, NH₄OH(aq.), CH₂Cl₂) to afford 11.2 mg (68%) of the title compound.

¹H NMR (200 MHz, CD₃OD, 1:1 mixture of conformers): 0.12 (m, ½H), 0.83 (m, 1H), 1.18 (s, 1H), 1.21 (m, 1H), 1.24 (s, 2H), 1.5–1.8 (m 1H), 2.35–2.85 (m, 3.5H), 2.98 (m, 0.5H), 3.19 (t, 8 Hz, 2H), 3.38 (m, 1H), 3.65 (m, 1H), 3.8 (m, 1H), 4.25–4.4 (m, 1H), 5.15–5.3 (m, 1H), 6.61 (d, 6 Hz, 1H), 7–7.2 (m, 6H), 7.37 (m, 1H), 7.56 (d, 7 Hz, ½H), 7.80 (d, 7 Hz, ½H). FAB-MS calculated for $C_{28}H_{34}N_4O_3$ 474; found 475.7 (M+H). Microanalysis calculated for $C_{28}H_{34}N_4O_3 \cdot {}^{8}\!/_{10} H_2O$ C 68.91, H 7.15, N 11.48; found C 69.01, H 7.27, N 11.20.

EXAMPLE 49

N-[1(R)-[(2,3-dihydrospiro[1H-indene-1,4'-piperidin]-1'-yl)carbonyl]-2-(1H-indol-3-yl)ethyl]-3(R)-amino-(3-hydroxymethyl)butanamide trifluoroacetate Step A:

[(2R,4R)-2-t-butyl-3-formyl-4-methyl-oxazolidin-4-yl]acetic acid

To a 0° C. solution of 2.37 g of the intermediate prepared in Example 48, Step B in 55 ml methylene chloride was added t0.57 ml of isobutylchloroformate and 1.69 ml triethylamine. After stirring for 2 hours, the solution was added to a 0° C. etheral solution of diazomethane and the solution was stirred for 16 hours while gradually warming to room temperature. The solution was concentrated under reduced pressure and the residue was dissolved in 50 ml methanol. This solution was irradiated by a 250 watt ultra-violet lamp for 4 hours and then concentrated under vacuum. Purification by flash chromatography (silica gel, 1:2 ethyl acetate/hexane) to afford 1.11 g (63%) of this intermediate. This methyl ester was hydrolyzed by the procedure given in Example 63, Step B to give 1.04 g (99%) of the title compound.

¹H NMR (200 MHz, CDCl₃, 1:1 mixture of conformers): 0.97 (s, 4.5H), 0.99 (s, 4.5H), 1.58 (s, 1.5H), 1.59 (s, 1.5H), 2.64 (d, 5 Hz, 0.5H), 2.72 (d, 6 Hz, 0.5H), 2.92 (d, 16 Hz, 0.5H), 3.39 (d, 16 Hz, 0.5H), 3.62 (d, 9 Hz, 0.5H), 3.90 (d, 9 Hz, 0.5H), 4–4.25 (m, 1H), 4.88 (b s, 1H), 4.96 (s, 0.5H), 5.10 (s, 0.5H), 8.32 (s, 0.5H), 8.44 (s, 0.5H). FAB-MS calculated for $C_{11}H_{19}NO_4$ 292; found 292.9 (M+H).

Step B:

N-[1(R)-[(2,3-dihydrospiro[1H-indene-1,4'-piperidin]-1'-yl)carbonyl]-2-(1H-indol-3-yl)ethyl]-3(R)-amino-(3-hydroxymethyl)butanamide trifluoroacetate EDC was added to a 0° C. solution containing 43 mg of the intermediate prepared in this Example, Step A, 81 mg of the intermediate obtained from Example 20, Step B and HOBt in 2.5 ml CH₂Cl₂. The solution was stirred for 48 hours while gradually warming to room temperature and then poured into 150 ml of ethyl acetate and washed sequentially with 1N NaHSO₄ (aq.), water, saturated aqueous NaHCO₃ and brine. The organic phase was dried over anhydrous MgSO₄ and then filtered and concentrated. Purified by MPLC (20×150 mm silica gel, 60–100% ethyl acetate in hexanes, linear gradient over 750 ml) to afford 79.7 mg of the desired intermediate. This material was dissolved in 13.5 ml of methanol, diluted with 13.5 ml 6N aqueous HCl and then stirred for 24 hours. The methanol was removed under vacuum and the solution was diluted with 300 ml of water and then stirred for 24 hours. The solvent was removed under vacuum and the material was purified by reversed-phase MPLC (C8, 10×240 mm, 25–100% methanol in water, 0.1% TFA) to afford 49.5 mg (61%) of the title compound.

¹H NMR(400 MHz, CD₃OD, 1:1 mixture of conformers): 0.12 (dt, 13, 4 Hz, 1H), 0.84 (dd, 13, 2 Hz, ½H), 0.98 (dt, 13, 4 Hz, 1/2H), 1.22 (m, 1H), 1.32 (s, 3H), 1.36–1.75 (m, 1H), 1.8–1.95 (m, 2H), 2.5–2.83 (m, 5H), 3.01 (dt, 13, 2 Hz, ½H), 3.15–3.34 (m, 2H), 3.47–3.60 (m, 1.5H), 3.68–3.78 (m, 1H), 4.31 (m, 1H), 5.18–5.28 (m, 1H), 6.60 (d, 7 Hz, ½H), 7.0–7.14 (m, 5.5H), 7.18 (s, 1H), 7.36 (d, 8 Hz, ½H), 7.40 (d, 8 Hz, ½H), 7.55 (d, 8 Hz, ½H), 7.63 (d, 8 Hz, 1/2H). FAB-MS calculated for $C_{29}H_{36}N_4O_3$ 488; found 489.9 (M+H). Microanalysis calculated for $C_{31}H_{37}N_4O_5F_3 \cdot 1.85 H_2O$ C 58.64, H 6.30, N 8.82; Found C 58.70, H 5.93, N 8.49.

EXAMPLE 50

N-[1(R)-[(2,3-dihydrospiro[1H-indene-1,4'-piperidin]-1'-yl)carbonyl]-2-(1H-indol-3-yl)ethyl]-[[3(R)-[2(R)-hydroxylpropyl]amino]-3-hydroxymethyl]butanamide trifluoroacetate A mixture of 211 mg of the compound prepared in Example 49, Step B, 166 mg of the intermediate obtained from Example 23, Step A, 144 mg of anhydrous sodium acetate and 44 mg sodium cyanoborohydride in 2 ml methanol was stirred for 16 hours. A 10 ml portion of 3N aqueous HCl was added and the solution was stirred for 5 hours. The solvents were removed under vacuum and the material was purified by reversed-phase MPLC (C8, 25×310 mm, eluting with 1:1 methanol/water, 0.1% TFA) to afford 51.5 mg (22%) of the title compound.

¹H NMR(400 MHz, CD₃OD, 1:1 mixture of conformers): 0.13 (dt, 13, 4 Hz, ½H), 0.85 (dd, 13, 2 Hz, ½H), 0.96 (dt, 13, 4 Hz, ½H), 1.2–1.42 (m, 8H), 1.7–1.95 (m, 2.5H), 2.55–2.88 (m, 7.5H), 2.95–3.25 (m, 2.5H), 3.5–3.70 (m, 3H), 3.98 (m, 1H), 4.32–4.35 (m, 1H), 5.18–5.28 (m, 1H), 6.60 (d, 8 Hz, ½H), 7.0–7.15 (m, 6H), 7.18 (s, ½H), 7.36 (d, 8 Hz, ½H), 7.40 (d, 8 Hz, ½H), 7.54 (d, 8 Hz, ½H), 7.63 (d, 8 Hz, ½H). FAB-MS calculated for $C_{32}H_{43}N_4O_4$ 547; found 548.0 (M+H).

EXAMPLE 51

N-[1(R)-[(2,3-dihydrospiro[1H-indene-1,4'-piperidin]-1'-yl)carbonyl]-2-(1H-indol-3-yl)ethyl]-[[3(R)-[2(R),3-dihydroxylpropyl]amino]-3-hydroxymethyl]butanamide trifluoroacetate A mixture of 35 mg of the compound prepared in Example 49, Step B, 38 mg of (R)-1,2-isopropylideneglyceraldehyde, 24 mg of anhydrous sodium acetate and 4 mg sodium cyanoborohydride in 2 ml methanol was stirred for 16 hours. A 4 ml portion of 3N aqueous HCl was added and the solution was stirred for 5 hours. The solvents were removed under vacuum and the material was purified by reversed-phase MPLC (C8, 10×240 mm, eluting with 3:7 acetonitrile/water, 0.1% TFA) to afford 2.2 mg (5.6%) of the title compound.

$^1$H NMR(400 MHz, $CD_3OD$, 1:1 mixture of conformers): 0.13 (dt, 13, 4 Hz, ½H), 0.8–1.02 (m, 2H), 1.2–1.45 (m, 5H), 1.55–1.95 (m, 2.5H), 2.5–2.3 (m, 1H), 3.55–3.80 (m, 4H), 3.91 (m, 1H), 4.34 (m, 1H), 5.18–5.30 (m, 1H), 6.60 (d, 7 Hz, ½H), 7.0–7.15 (m, 6H), 7.18 (s, ½H), 7.36 (d, 8 Hz, ½H), 7.40 (d, 8 Hz, ½H), 7.54 (d, 8 Hz, ½H), 7.62 (d, 8 Hz, ½H). FAB-MS calculated for $C_{32}H_{42}N_4O_5$ 562; found 563.9 (M+H).

EXAMPLE 52

N-[1(R)-[(2,3-dihydrospiro[1H-indene-1,4'-piperidin]-1'-yl)carbonyl]-2-(1H-indol-3-yl)ethyl]-2-(R)-amino-(2-hydroxymethyl)propanamide hydrochloride Step A:

Methyl (2S,4R)-2-t-butyl-3-formyl-oxazolidine-4-methyl-4-carboxylic acid

Prepared from (D)-serine methyl ester by the procedure described in Example 48, Step A.

$^1$H NMR(200 MHz, $CD_3OD$, 1:1 mixture of conformers): 8.43 (s, ½H), 8.30 (s, ½H), 5.23 (s, ½H), 4.88 (s, ½H), 4.63 (d, 9 Hz, ½H), 4.25 (d, 9 Hz, ½H), 3.74 (s, 3/2H), 3.71 (s, 3/2H), 3.57 (d, 9 Hz, 1H), 1.65 (s, 3/2H), 1.63 (s, 3/2H), 0.98(s, 4H), 0.85 (s, 5H).

Step B:

(2S,4R)-2-t-butyl-3-formyl-oxazolidine-4-methyl-4-carboxylic acid

The title compound (2.36 g, 84%) was prepared from 2.97 g of the intermediate prepared in this Example, Step A according to the procedure described in Example 48, Step B.

$^1$H NMR(200 MHz, $CD_3OD$, 3:2 mixture of conformers): 8.44 (s, 0.4H), 8.31 (s, 0.6H), 5.22 (s, 0.6H), 5.02 (s, 0.4H), 4.62 (d, 9 Hz, 0.6H), 4.32 (d, 9 Hz, 0.4H), 3.82 (d, 9 Hz, 0.4H), 3.67 (d, 9 Hz, 0.6H), 1.69 (s, 1.8H), 1.66 (s, 1.2H), 1.02 (s, 3.5H), 0.91 (s, 5.5H). FAB-MS calculated for $C_{10}H_{17}NO_4$ 215; found 216 (M+H).
Step C:

1'-[2(R)-amino-3-(1H-indol-3-yl)-1-oxopropyl]-2,3-dihydrospiro[1H-indene-1,4'-piperidene]hydrochloride To the intermediate obtained from Example 20, Step B, was added hydrogen chloride in ether at room temperature. After concentration, the title compound was obtained.
Step D:

N-[1(R)-[(2,3-dihydrospiro[1H-indene-1,4'-piperidin]-1'-yl)carbonyl]-2-(1H-indol-3-yl)ethyl]-2-(R)-amino-(2-hydroxymethyl)propanamide hydrochloride EDC was added to a room temperature solution containing 340 mg of the intermediate prepared in this Example, Step B, 536 mg of the intermediate obtained from this Example, Step C, NMM and HOBt in 15 ml of 3:1 $CH_2Cl_2$/THF. The solution was stirred for 16 hours while gradually warming to room temperature and then poured into 700 ml of ethyl acetate and washed sequentially with saturated aqueous $NaHCO_3$ and brine. The organic phase was dried over anhydrous $MgSO_4$ and then filtered and concentrated. Purified by flash chromatography (25×150 mm silica gel, 70% ethyl acetate in $CH_2Cl_2$) to afford 312.5 mg (42%) of the desired intermediate. This material was dissolved in 10 ml of methanol, treated with 10 ml of concentrated aqueous HCl and then refluxed for ½ hour. The solvents were removed under vacuum and the material was purified by flash chromatography (silica gel, 25×150 mm, methanol, $NH_4OH$ (aq.), $CH_2Cl_2$) to afford 174.4 mg (67%) of the intermediate. This material was dissolved in 1 ml methanol, treated with 2 ml of 1.3N aqueous HCl followed by concentration under reduced pressure to afford the title compound.

$^1$H NMR(400 MHz, $CD_3OD$, 1:1 mixture of conformers): 0.22 (dt, 13, 4 Hz, ½H), 0.89 (t, 7 Hz, ½H), 1.01 (dt, 13, 4 Hz, ½H), 1.2–1.3 (m, 1H), 1.4 (m, ½H), 1.43 (s, 1.5H), 1.53 (s, 2H), 1.66 (dt, 13, 4 Hz, ½H), 1.76–1.96 (m, 2H), 2.6–2.85 (m, 3.5H), 3.04 (dt, 13, 3 Hz, ½H), 3.15–3.34 (m, 2H), 3.69–3.79 (m, 2H), 3.95 (m, 1H), 4.39 (m, 1H), 5.25 (m, 1H), 6.64 (d, 7 Hz, ½H), 7.0–7.15 (m, 6H), 7.19 (s, ½H), 7.36 (d, 8 Hz, ½H), 7.41 (d, 8 Hz, ½H), 7.54 (d, 8 Hz, ½H), 7.63 (d, 8 Hz, ½H), 8.33 (d, 7 Hz, 1/2H). FAB-MS calculated for $C_{28}H_{34}N_4O_3$ 474; found 475.7 M+H).

EXAMPLE 53

N-[1(R)-[(2,3-dihydrospiro[1H-indene-1,4'-piperidin]-1'-yl)carbonyl]-2-(1H-indol-3-yl)ethyl]-[[2(R)-[2(R),3-dihydroxylpropyl]amino]-2-hydroxymethyl]propanamide trifluoroacetate The title compound (10 mg, 29%) was prepared from 24 mg of the intermediate obtained in Example 52, Step D according to the procedure described in Example 51.

$^1$H NMR(400 MHz, $CD_3OD$, 1:1 mixture of conformers): 0.27 (dt, 13, 4 Hz, ½H), 0.92 (m, ½H), 1.04 (dt, 13, 4 Hz, ½H), 1.3 (m, 1H), 1.4–1.6 (m, 1H), 1.46 (s, 1.5H), 1.57 (s, 1.5H), 1.7–1.95 (m, 2H), 2.65–3.34 (m, 8H), 3.5–4.0 (m, 7H), 4.36 (m, 1H), 5.27 (m, 1H), 6.65 (d, 8 Hz, ½H), 7.0–7.13 (m, 6H), 7.19 (s, ½H), 7.36 (d, 8 Hz, ½H), 7.40 (d, 8 Hz, ½H), 7.55 (d, 8 Hz, ½H), 7.63 (d, 8 Hz, ½H). FAB-MS calculated for $C_{31}H_{30}N_4O_5$ 548; found 549.9 (M+H).

EXAMPLE 54

N-[1(R)-[(2,3-dihydrospiro[1H-indene-1,4'-piperidin]-1'-yl)carbonyl]-2-(1H-indol-3-yl)ethyl]-3(R,S)-quinuclidine carboxamide Dicyclohexylcarbodiimide was added to a 0° C. mixture of quinuclidine-3-carboxylic acid (*J. Chem. Soc. Chem.*

Commun. 1991, 760), the intermediate obtained from Example 52, Step C, HOBt and NMM in 2 ml 1:1 THF/CH$_2$Cl$_2$. The solution was stirred for 16 hours while gradually warming to room temperature. The solvents were removed under vacuum and the residue was dissolved in 2 ml CH$_2$Cl$_2$ and then filtered through Celite. The compound was purified by flash chromatography (20×40 mm, silica gel, methanol, NH$_4$OH (aq.), CH$_2$Cl$_2$) to provide the title compound.

$^1$H NMR (200 MHz, CD$_3$OD): 0.2 (m, ½), 0.8–2.2 (m, 10.5H), 2.0–3.8 (m, 13H), 3.35 (m, 1H), 5.26 (m, 1H), 6.6 (m, 1H), 7.0–7.2 (m, 6H), 5.38 (m, 1H), 7.55 (d, 7 Hz, ½H), 7.63 (d, 8 Hz, ½H). FAB-MS calculated for C$_{32}$H$_{38}$N$_4$O$_2$ 510; found 511.9 (M+H).

EXAMPLE 55

N-[1(R,S)-[(2,3-dihydrospiro[1H-indene-1,4'-piperidin]-1'-yl)-carbonyl]-2-(5-fluoro-1H-indol-3-yl)ethyl]-2-amino-2-methylpropanamide hydrochloride Step A:

[1(R,S)-[(2,3-dihydrospiro[1H-indene-1,4'-piperidin]-1'-yl)-carbonyl]-2-(5-fluoro-1H-indol-3-yl)ethyl]carbamic acid 1,1-dimethylethyl ester To a room temperature solution of 1 g of 5-fluoro-(d,l)-tryptophan in 90 ml 3:1 THF/water was added 1.5 g sodium bicarbonate and 6.2 ml of t-butyldicarbonate. After stirring for 3 days, the THF was stripped off and the mixture was poured into 500 ml of 0.1N aqueous sodium hydroxide. This solution was washed 3 times with hexanes, acidified with 1N NaHSO$_4$ (aq.) and then extracted with ethyl acetate. The organic layer was dried over anhydrous MgSO$_4$, filtered and concentrated to afford 1.5 g (100%) of the desired intermediate. To a room temperature solution of 520 mg of this compound in 15 ml 3:1 CH$_2$Cl$_2$/THF was added 397 mg of 3,4-dihydrospiro[1H-indene-1,4'-piperidine]hydrochloride, EDC, HOBT, and NMM. This solution was stirred for 16 hours and then poured into 700 ml ethyl acetate and washed sequentially with saturated aqueous NaHCO$_3$ and brine. The organic phase was dried over anhydrous MgSO$_4$, filtered and concentrated. The material was purified by flash chromatography (25× 150 mm, silica gel, 40% ethyl acetate in hexanes) to provide 650 mg (82%) of the title compound.

$^1$H NMR (200 MHz, CDCl$_3$): 0.46 (dt, 13, 4 Hz, 1/2H), 1.0–1.35 (m, 2.5H), 1.45 (s, 9H), 1.6–1.95 (m, 3H), 2.5–2.75 (m, 1H), 2.82 (t, 8 Hz, 2H), 2.89–3.05 (m, 1H), 3.14 (t, 8 Hz, 2H), 3.66 (m, 1H), 4.47 (m, 1H), 4.95 (m, 1H), 5.58 (m, 1H), 6.65 (m, ½H), 6.89–7.4 (m, 7.5H), 8.19 (m, 1H). FAB-MS calculated for C$_{29}$H$_{34}$N$_3$O$_3$F 491; found 492.8 (M+H).

Step B:

N-[1(R,S)-[(2,3-dihydrospiro[1H-indene-1,4'-piperidin]-1'-yl)carbonyl]-2-(5-fluoro-1H-indol-3-yl)ethyl]-2-amino-2-methylpropanamide hydrochloride A solution of 299 mg of the intermediate obtained from this Example, Step A in 5 ml 1:1 TFA/CH$_2$Cl$_2$ was stirred for 1 hour. The solution was concentrated under vacuum and azeotroped 2 times from toluene. The residue was dissolved in 10 ml CH$_2$Cl$_2$ and cooled to 0° C. EDC, HOBt, NMM and 185 mg of t-butyloxycarbonyl-α-methylalanine were added and the solution was stirred for 16 hours while gradually warming to room temperature. The solution was poured into 300 ml of ethyl acetate and washed sequentially with 1N NaHSO$_4$ (aq.), water, saturated NaHCO$_3$ (aq.) and brine. The organic phase was dried over anhydrous MgSO$_4$, filtered and concentrated. The material was purified by flash chromatography (25×150 mm, silica gel, 60% ethyl acetate in hexanes) to provide 354 mg (100%) of the desired intermediate. A solution of this material in 10 ml methanol was treated with 10 ml concentrated aqueous HCl and stirred for 1 hour. The solution was concentrated to give 325 mg (100%) of the title compound.

$^1$H NMR (200 MHz, CD$_3$OD): 0.28 (dt, 14, 4 Hz, 1/2H), 1.05 (m, 1H), 1.3 (m, 1H), 1.4–1.67 (m, 7H), 1.7–1.95 (m, 2.5H), 2.6–2.88 (m, 3.5H), 3.0–3.35 (m, 2.5H), 3.76 (m, 1H), 4.45 (m, 1H), 5.2 (m, 1H), 6.64 (d, 7 Hz, ½H), 6.89 (dt, 9, 3 Hz, 1H), 7.05–7.4 (m, 6.5H). FAB-MS calculated for C$_{28}$H$_{33}$N$_4$O$_2$F 476; found 477.7 M+H). 3.0–3.35 (m, 2.5H), 3.76 (m, 1H), 4.45 (m, 1H), 5.2 (m, 1H), 6.64 (d, 7 Hz, ½H), 6.89 (dt, 9, 3 Hz, 1H), 7.05–7.4 (m, 6.5H). FAB-MS calculated for C$_{28}$H$_{33}$N$_4$O$_2$F 476; found 477.7 M+H).

EXAMPLE 56

N-[1(R)-[(2,3-dihydrospiro[1H-indene-1,4'-piperidin]-1'-yl)carbonyl]-2-(phenlmethyloxy)ethyl]-N'-[3-(R)-piperidinyl]urea trifluoroacetate Isobutylchloroformate was added to a solution of t-butyloxycarbonyl-(D)-nipecotic acid and triethylamine in 5 ml acetone. After stirring for ½ hour, a solution of 280 mg of sodium azide in 1 ml water was added and stirred an additional ½ hour. The solution was poured into 100 ml ethyl ether and washed with water. The organic phase was dried over MgSO$_4$, filtered, concentrated and azeotroped twice from toluene. The residue was dissolved in 5 ml toluene and the solution was heated to 90° C. for ½ hour and then cooled to room temperature. A solution prepared by stirring 167 mg of the intermediate obtained from Example 63, step A in 2 ml 1:1 TFA/CH$_2$Cl$_2$ for ½ hour, then azeotroping from toluene and redissolving in 1 ml CH$_2$Cl$_2$ and 0.05 ml triethylamine was added to the toluene solution. After 15 minutes, the solution was poured into 100 ml ether and washed with 1N NaHSO$_4$ (aq.) followed by water. The organic phase was dried over anhydrous MgSO$_4$, filtered and concentrated. The material was purified by MPLC (20×150 mm, silica gel, 0–10% methanol in CH$_2$Cl$_2$, linear gradient over 500 ml) to give 182 mg (85%) of the desired intermediate. A solution of 180 mg of this material in 10 ml 1:1 TFA/CH$_2$Cl$_2$ was stirred for ½ hour and then concentrated and azeotroped from toluene to give 176 mg (96%) of the title compound.

$^1$H NMR (400 MHz, CD$_3$OD): 1.45–2.1 (m, 10), 2.85–3.01 (m, 5H), 3.2–3.4 (m, 3H), 3.62–3.73 (m, 2.5H), 3.83 (m, 1H), 4.01 (bt, 8 Hz, 1H), 4.47–4.57 (m, 3H), 4.98 (m, 1H), 6.67 (d, 8 Hz, ½H), 7.05–7.2 (m, 4H), 7.29–7.4 (m, 4.5H). FAB-MS calculated for C$_{29}$H$_{38}$N$_4$O$_3$ 490; found 491.8 M+H).

EXAMPLE 57

N-[1(R)-[(2,3-dihydrospiro[1H-indene-1,4'-piperidin]-1'-yl)carbonyl]-2-(phenylmethyloxy)ethyl]-N'-(2-amino-2-methyl)propyl urea trifluoroacetate Prepared from the intermediate obtained from the Example 63, Step A and 3-t-butyloxycarbonylamino-3-methylbutanoic acid by the procedure described in Example 56 to give the title compound.

$^1$H NMR (200 MHz, CD$_3$OD): 1.29 (s, 2H), 1.30 (s, 3H), 1.39 (s, 3H), 1.45–1.68 (m, 3H), 1.75 (dt, 13, 4 Hz, 1/2H), 1.88 (dt, 13, 4 Hz, ½H), 2.09 (m, 2H), 3.13–3.4 (m, 3H), 3.69 (m, 2H), 4.02 (t, 14 Hz, 1H), 4.48–4.59 (m, 3H), 5.0 (t, 5 Hz, 1H), 6.77 (d, 8 Hz, ½H), 7.06–7.18 (m, 4H), 7.29–7.4 (m, 4.5H). FAB-MS calculated for C$_{28}$H$_{38}$N$_4$O$_3$ 478; found 479.8 (M+H).

EXAMPLE 58

N-[1(R)-[(2,3-dihydrospiro[1H-indene-1,4'-piperidin]-1'-yl)carbonyl]-2-(phenylmethyloxy)ethyl]-N'-(1,1-dimethyl-2-amino)ethyl urea trifluoroacetate A solution 60 mg of the intermediate obtained from Example 63, Step A in 2 ml 1:1 TFA/CH$_2$Cl$_2$ was stirred for 1 hour then stripped and azeotroped from toluene. The residue was dissolved in 1 ml CH$_2$Cl$_2$ and 18 μl triethylamine and then added to an acylating solution that was prepared by stirring 25 mg of 1-N-t-butyloxy-carbonylamino-2-amino-2-methylpropane (*EUR. J. Biochem.* 1985, 146, 9) and 21.5 mg of carbonyldiimidazole in 2 ml CH$_2$Cl$_2$ for 1 hour. The solution was stirred 16 hours and then poured into 100 ml of ether and washed sequentially with 1N NaHSO$_4$ (aq.), water, saturated aqueous NaHCO$_3$ and brine. The organic phase was washed with MgSO$_4$, filtered and concentrated. The material was purified by MPLC (20×150 mm, silica gel, 0–7.5% methanol in CH$_2$Cl$_2$, linear gradient over 500 ml). A solution of this material in 5 ml 1:1 TFA/CH$_2$Cl$_2$ was stirred for ½ hour and then concentrated and azeotroped from toluene to give 11.2 mg of the title compound.

$^1$H NMR (400 MHz, CD$_3$OD): 1.25–1.41 (m, 6H), 1.45–168 (m, 3H), 1.76 (dt, 12, 4 Hz, ½H), 1.89 (dt, 12, 4 Hz, ½H), 2.1 (m, 2H), 2.9 (m, 3H), 3.07 (dd, 13, 4 Hz, 1H), 3.16–3.35 (m, 2H), 3.62–3.71 (m, 2H), 4.0 (t, 13 Hz, 1H), 4.48–4.59 (m, 3H), 4.95 (m, 1H), 6.77 (d, 8 Hz, ½H), 7.06–7.2 (m, 4H), 7.3–7.4 (m, 4.5H). FAB MS calculated for C$_{28}$H$_{38}$N$_4$O$_3$ 478; found 479.9 (M+H).

EXAMPLE 59

N-[1(R)-[(2,3-dihydro-3-oxospiro[1H-indene-1,4'-piperidin]-1'yl)-carbonyl]-3-cyclohexylpropyl]-2-amino-2-methylpropanamide trifluoroacetate Step A:

[1(R)-[(2,3-dihydro-3-oxospiro[1H-indene-1,4'-piperidin]-1'-yl)carbonyl]-3-cyclohexylpropyl]carbamic acid 1,1-dimethylethyl ester A solution of 701 mg of intermediates obtained from Example 4, Step A in 10 ml 1:1 TFA/CH$_2$Cl$_2$ was stirred for 1 hour then stripped and azeotroped from toluene. This residue and 673 mg of the intermediate obtained from Example 38, Step A were used in the coupling procedure described in Example 20, Step A to afford 514 mg (46%) of the title compound.

$^1$H NMR (300 MHz, CDCl$_3$): 0.75–0.98 (m, 2H), 1.05–1.3 (m, 6H), 1.4 (s, 4H), 1.44 (s, 5H), 1.5–1.78 (m, 8H), 1.8–2.13 (m, 3H), 2.16–2.75 (m, 1H), 2.66 (s, 2H), 3.2 (dd, 22, 12 Hz, 1H), 4.03 (bd, 12 Hz, 1H), 4.62 (m, 1H), 4.73 (bd, 12 Hz, 1H), 5.42 (bd, 6 Hz, 1H), 7.37–7.46 (m, 2H), 7.63 (t, 7 Hz, 1H), 7.73 (m, 1H). FAB-MS calculated for C$_{28}$H$_{40}$N$_2$O$_4$ 468; found 469.6 (M+H).

Step B:

N-[1(R)-[(2,3-dihydro-3-oxospiro[1H-indene-1,4'-piperidin]-1'-yl)-carbonyl]-3-cyclohexylpropyl]-2-amino-2-methylpropanamide trifluoroacetate The title compound (277 mg, 99.9%) was prepared from 274 mg of the intermediate obtained from this Example, Step A according to the procedure described in Example 55, Step B with the exception that a 1:1 TFA/CH$_2$Cl$_2$ mixture was used instead of a 1:1 methanol/concentrated HCl (aq.) to remove the t-butyloxycarbonyl group.

$^1$H NMR (300 MHz, CD$_3$OD): 1.0 (m, 2H), 1.2–1.4 (m, 6H), 1.44 (s, 1H), 1.6–2.15 (m, 15H), 2.3 (m, 1H), 2.82 (s, 1H), 2.84 (s, 1H), 2.9 (m, 1H), 4.19 (d, 13 Hz, 1H), 4.69 (d, 13 Hz, 0.1H), 4.90 (m, 1H), 7.5 (m, 1H), 7.67 (d, 7 Hz, 1H), 7.7–7.8 (m, 1H). FAB-MS calculated for C$_{27}$H$_{39}$N$_3$O$_3$ 453; found 454.5 (M+H).

EXAMPLE 60

N-[1(R)-[(2,3-dihydro-3(R,S)-hydroxyspiro[1H-indene-1,4'-piperidin]-1'-yl)carbonyl]-3-cyclohexylpropyl]-2-amino-2-methylpropanamide trifluoroacetate Sodium borohydride (14.5 mg) was added to a room temperature solution of 110.5 mg of the compound prepared in Example 59, Step B in 2 ml of methanol. After 3 hours, the solution was concentrated and the material was purified by flash chromatography (silica gel, methanol, NH$_4$OH (aq.), CH$_2$Cl$_2$) to afford 44.7 mg of the intermediate. A 0° C. solution of this material in 1 ml CH$_2$Cl$_2$ was treated with 7.6 gl of TFA and then concentrated to give 45 mg (41%) of the title compound.

$^1$H NMR (400 MHz, CD$_3$OD): 0.92 (m, 2H), 1.25–1.35 (m, 5H), 1.39 (s, 3H), 1.5 (m, 1H), 1.6–1.99 (m, 15H), 2.14 (dt, 12, 4 Hz, ½H), 2.6 (m, 1H), 2.91 (m, 1H), 3.38 (dd, 10, 12 Hz, 1H), 4.05 (m, 1H), 4.5 (m, 1H), 4.86 (m, 1H), 5.24 (t, 6 Hz, 1H), 7.18 (m, 1H), 7.26 (m, 2H), 7.38 (m, 1H). FAB-MS calculated for C$_{27}$H$_{41}$N$_3$O$_3$ 455; found 456.5 (M+H).

EXAMPLE 61

N-[1(S)-[(2,3-dihydrospiro[1H-indene-1,4'-piperidin]-1'-yl)carbonyl]-2-[(1-methylethylthio)ethyl]-2-amino-2-methylpropanamide trifluoroacetate Step A:

N-[1(S)-[(2,3-dihydrospiro[1H-indene-1,4'-piperidin]-1'yl)carbonyl]-2-[(1-methylethylthio)ethyl]carbamic acid 1,1-dimethylethyl ester To a solution of 2 g of d-cysteine in 200 ml of 3:1 THF/water was added 2.73 g t-butyldicarbonate and 2.9 g NaHCO$_3$. After stirring overnight, the THF was stripped off, the mixture was acidified with 1N NaHSO$_4$ (aq.), and then extracted with 250 ml ethyl acetate. The organic phase was dried over MgSO$_4$, filtered and s concentrated. This residue (417 mg) was dissolved in 5 ml THF and treated with 133 mg of 60% suspension of NaH in oil. Isopropyl iodide (151 μl) and 2 ml DMF were added and the solution was stirred 48 hours. The solution was poured into 150 ml ether and then washed 5 times with water. The organic phase was dried over MgSO$_4$, filtered and concentrated. Purification by flash chromatography (silica gel, ethyl acetate/hexanes/acetic acid=1/1/0.02) afforded 235 mg (60%) of the desired intermediate. All of this material was subjected to the procedure described in Example 20, Step A to afford 172 mg (44%) of the title compound.

$^1$H NMR (200 MHz, CDCl$_3$): 1.2–1.35 (m, 6H), 1.44 (s, 4.5H), 1.45 (s, 4.5H), 1.55–2.0 (m, 5H), 2.11 (t, 7 Hz, 2H), 2.75–3.0 (m, 5H), 3.33 (m, 1H), 4.05 (m, 1H), 4.6 (m, 1H), 4.85 (m, 1H), 5.5 (m, 1H), 7.1–7.3 (m, 4H). FAB-MS calculated for C$_{24}$H$_{36}$N$_2$O$_3$S 432; found 433 (M+H).

Step B:

N-[1(S)-[(2,3-dihydrospiro[1H-indene-1,4'-piperidin]-1'-yl)carbonyl]-2-[(1-methylethylthio)ethyl]-2-amino-2-methylpropanamide trifluoroacetate The title compound was prepared from 172 mg of the intermediate obtained in Step A and 121 mg of BOC-α-methylalanine according to the procedure described in Example 55, Step B, with the exception that 2 ml 1:1 TFA/CH$_2$Cl$_2$ was used instead of methanol/HCl (aq.) was used to remove the t-butyloxycarbonyl group. This afforded 12.4 mg of the title compound.

$^1$H NMR (400 MHz, CD$_3$OD): 1.25 (m, 6H), 1.6 (s, 8H), 1.66–2.0 (m, 2H), 2.14 (q, 8 Hz, 2H), 2.78–3.05 (m, 6H), 3.38 (m, 1H), 4.05 (m, 1H), 4.5 (m, 1H), 5.05 (t, 7 Hz, 1H), 7.05–7.2 (m, 4H). FAB-MS calculated for C$_{23}$H$_{35}$N$_3$O$_2$S 417; found 418.3 (M+H).

EXAMPLE 62

N-[1(S)-[(2,3-dihydrospiro[1H-indene-1,4'-piperidin]-1'-yl)carbonyl]-2-[(ethylthio)ethyl]-2-amino-2-methylpropanamide trifluoroacetate Step A:

N-[1(S)-[(2,3-dihydrospiro[1H-indene-1,4'-piperidin]-1-yl)carbonyl]-2-[(ethylthio)ethyl]carbamic acid 1,1'-dimethylethyl ester The title compound was prepared from d-cysteine according to the procedure given in Example 61, Step A with the exception that iodoethane was used instead of 2-iodopropane.

$^1$H NMR (200 MHz, CDCl$_3$, 1:1 mixture of conformers): 1.2–1.35 (m, 6H), 1.44 (s, 4.5H), 1.45 (s, 4.5H), 1.5–1.95 (m, 4H), 2.11 (t, 7 Hz, 2H), 2.61 (t, 7 Hz, 1H), 2.7–3.0 (m, 5H), 3.33 (m, 1H), 4.05 (m, 1H), 4.61 (m, 1H), 4.87 (m, 1H), 5.51 (m, 1H), 7.06–7.26 (m, 4H). FAB-MS calculated for C$_{23}$H$_{34}$N$_2$O$_2$S 418; found 419.2 (M+H).

Step B:

N-[1(S)-[(2,3-dihydrospiro[1H-indene-1,4'-piperidin]-1'-yl)carbonyl]-2-[(ethylthio)ethyl]-2-amino-2-methylpropanamide trifluoroacetate The title compound was prepared from the intermediate obtained in this Example, Step A and 95 mg of BOC-α-methylalanine according to the procedure described in Example 55, Step B.

$^1$H NMR (400 MHz, CD$_3$OD): 1.26 (m, 6H), 1.5–1.95 (m, 10H), 2.14 (q, 7 Hz, 2H), 2.75–3.05 (m, 5H), 3.38 (m, 1H), 4.05 (m, 1H), 4.5 (m, 1H), 5.07 (t, 6 Hz, 1H), 7.05–7.2 (m, 4H). FAB-MS calculated for C$_{22}$H$_{33}$N$_3$O$_2$S 403; found 403.1 (M+H).

EXAMPLE 63

Preparation of
N-[1(R)-[(2,3-dihydrospiro[1H-indene-1,4'-piperidin]-1'-yl)carbonyl]-2-(phenylmethyloxy)ethyl]-2-amino-2-methylpropanamide hydrochloride Step A:

N-[1(R)-[(2,3-dihydrospiro[1H-indene-1,4'-piperidin]-1'-yl)carbonyl]-2-(phenylmethyloxy)ethyl]carbamic acid 1,1-dimethylethyl ester A mixture of commercial N-t-Boc-O-benzyl-D-serine (160 mg; 0.54 mmoles), 1,3-dicycloheylcarbodiimide (118 mg; 0.57 mmoles), 1-hydroxybenzotriazole (77 mg; 0.57 mmoles), triethylamine (80λ; 58 mg; 0.58 mmole), 2,3-dihydrospiro(1H-indene-1,4'-piperidine) hydrochloride (Example 1, Step A; 128 mg; 0.57 mmoles), and 3 mL chloroform was stirred over night under a nitrogen atmosphere. After filtration, the entire reaction mixture was applied to four 20×20cm×1,000μ silica gel GF plates and developed with 2:3 hexane:ethyl acetate. After isolation of the desired band, extraction with ethyl acetate afforded 224 mg (89%) of the title compound. Calc. for C$_{28}$H$_{36}$N$_2$O$_4$:MW=464.6; found m/e=(m+1) 465.6.

Step B:

1'-[[2(R)-amino-1-oxo-3-(phenylmethyloxy)]propyl]-2,3-dihydrospiro[1H-indene-1,4'-piperidine]

The compound from Step A above (203 mg; 0.44 mmoles) was dissolved in ca. 1 mL trifluoroacetic acid. After standing for 30 minutes, the reaction mixture was concentrated to an oil under reduced pressure, and partitioned between chloroform and 1M K$_2$HPO$_4$, adjusting the pH to above nine as needed with dilute NaOH. The mix was extracted three times with chloroform, the combined extracts dried with MgSO$_4$, and filtered. Evaporation of the solvent under reduced pressure gave the title compound, as 180 mg of clear gum suitable for the next reaction. Calc. for C$_{23}$H$_{28}$N$_2$O$_2$:MW=364.5; found m/e=(m+1) 365.1.

Step C:

N-[1(R)-[(2,3-dihydrospiro[1H-indene-1,4'-piperidin]-1'-yl)carbonyl]-2-(phenylmethyloxy)ethyl]2-[[1,1-dimethylethloxy)carbonyl]amino]-2-methylpropanamide A solution of 230 mg of the compound from Step B above (0.63 mmoles), 363 mg of BOP (0.82 mmoles), 141 mg of N-t-Boc-α-methylalanine (0.69 mmoles), and 181λ of triethylamine (13 1 mg; 1.30 mmoles) in 2 mL of methylene chloride was stirred for about three hours. It was then diluted with 7 mL hexane and 14 mL of ethyl acetate, washed twice with 5% citric acid solution, then twice with 5% NaHCO$_3$ solution and dried over MgSO$_4$. The combined aqueous washes were extracted three times with chloroform, the combined extracts washed once with 5% NaHCO$_3$ solution and, after drying with MgSO$_4$, added to the original organic layer. After filtration, evaporation of the solvent under reduced pressure afforded 383 mg of crude product, which was purified by preparative TLC on three 20×20 cm×1,000μ silica gel GF plates, developed with 2:3 hexane:ethyl acetate. The product appeared as a broad diffuse band ca. R$_f$ 0.7. Extraction of the isolated band with ethyl acetate afforded the title compound 304 mg. Calc. for C$_{32}$H$_{43}$N$_3$O$_5$:MW=549.7; found m/e=(m+1) 550.8.

Step D:

N-[1(R)-[(2,3-dihydrospiro[1H-indene-1,4'-piperidin]-
1'-yl)carbonyl]-2-(phenylmethyloxy)ethyl]-2-
amino-2-methylpropanamide A solution of 585 mg of the compound from Step C above in ca. 3 mL of trifluoroacetic acid was allowed to stand for 30 minutes, then concentrated to a thick oil on the aspirator. It was then worked up as in Step B to give 401 mg of the title compound, as a thick gum. Calc. for $C_{27}H_{35}N_3O_3$: MW=449.6; found m/e (m+1) 450.4. PMR (in δ from TMS; CDCl$_3$): 8.2–8.35 (m), 7.28–7.38 (bs), 7.28–2.04 (m), (6.9) 6.86–6.7 (m), 5.05–5.24 (m), 4.7–4.44 (m), 4.55 (s), 4.02 (bt, J=15 Hz), 3.74–3.58 (m), 3.17 (b quart, J=15 Hz), 3.0–2.7 (m), 2.14–1.96 (m), 1.96–1.66 (m). 1.66–1.45 (m), 1.45–1.29 (bs).
Step E:

N-[1(R)-[2,3-dihydrospiro[1H-indene-1,4'-piperidin]-
1'-yl)carbonyl]-2-(phenylmethyloxy)ethyl]-2-
amino-2-methylpropanamide hydrochloride A sample of the compound from Step D above was dissolved in ca. 10-fold acetic acid, and treated with 1–2 equivalents of conc. HCl. Upon lyophillization, the title material, was obtained.

EXAMPLE 64

Preparation of N-[1
(S)-[(2,3-dihydrospiro[1H-indene-1,4'-piperidin]-1'-
yl)carbonyl]-2-(phenylmethylthio)ethyl]-2-amino-2-
methylpropanamide hydrochloride Step A:

N-[1
(S)-[(2,3-dihydrospiro[1H-indene-1,4'-piperidin]-1'-
yl)carbonyl]-2-(phenylmethylthio)ethyl]carbamic
acid 1,1-dimethylethyl ester Substituting N-t- Boc-S-benzyl-D-serine for N-t-Boc-O-benzyl-D-cysteine in Step A, Example 63, the title compound (8) was obtained. Calc. for $C_{28}H_{36}N_2O_3S$:MW= 480.7; found m/e=(m+1) 481.6.
Step B:

1'-[[2(S)-amino-1-oxo-3-(phenylmethylthio)]propyl]-
2,3-dihydrospiro[1H-indene-1,4'-piperidine]

Substituting [1 (S)-[(2,3-dihydrospiro[1H-indene-1,4'-piperidin]-1'-yl)carbonyl]-2-(phenylmethylthio)ethyl]carbamic acid 1,1-dimethylethyl ester for the product of Example 63, Step A in Step B, Example 63, the title compound was obtained. Calc. for $C_{23}H_{28}N_2OS$:MW= 380.6; found m/e=(m+1) 381.1.
Step C:

N-[1(S)-[(2,3-dihydrospiro[1H-indene-1,4'-piperidin]-
1'-yl)carbonyl]-2-(phenylmethylthio)ethyl]2-[[1,1-
dimethylethyloxy)carbonyl]amino]-2-methyl-
propanamide Substituting the compound from Step B above for the compound from Example 63, Step B in Step C, Example 63, the title compound was obtained. Calc. for $C_{32}H_{43}N_3O_4S$: MW=565.8; found m/e=(m+1) 566.9.
Step D:

N-[1
(S)-[(2,3-dihydrospiro[1H-indene-1,4'-piperidin]-1'-
yl)carbonyl]-2-(phenylmethylthio)ethyl]-2-amino-
2-methylpropanamide Substituting the compound from Step C above for compound from Example 63, Step C in Step D, Example 78, the title compound was obtained. Calc. for $C_{27}H_{35}N_3O_4S$: MW=465.7; found m/e=(m+1) 466.6. PMR (in δ from TMS; CD$_3$OD): 7.5–7.0 (m), 5.1–4.95 (m), 4.62 (bs), 4.5 (bd, J=14 Hz), 3.8 (bd, J=8 Hz), 3.3–3.1 (m), 2.8–3.0 (m), 2.4–2.8 (m), 2.08–2.16 (t, J=8 Hz), 1.9–1.6 (bm), 1.4–1.6 (bm), 1.4–1.28 (bs), 1.1–0.7 (vbm).
Step E:

N-[1(S)-[(2,3-dihydrospiro[1H-indene-1,4'-piperidin]-
1'-yl)carbonyl]-2-(phenylmethylthio)ethyl]-2-
amino-2-methylpropanamide hydrochloride Substituting the compound from Step D above for compound from Example 63 Step D in Step E, Example 63, the title compound was obtained.

EXAMPLE 65

Preparation of
N-[1(S)-[(2,3-dihydrospiro[1H-indene-1,4'-piperidin]-
1'-yl)carbonyl]-2-(phenylmethylsulfonyl)ethyl]-
2-amino-2-methylpropanamide hydrochloride The crude TFA—salt obtained in Step D of Example 64 (vide supra) was NOT partitioned between CHCl$_3$ and 1M K$_2$HPO$_4$, but was instead taken up again in TFA and treated at 0° C. with 30% H$_2$O$_2$ for several hours, followed by concentration to an oil at aspirator pressure. After partitioning between CHCl$_3$ and 1M K$_2$HPO$_4$, the pH was adjusted to ca. 9, the mix extracted with CHCl$_3$, the extract dried over MgSO$_4$ and concentrated to an oil. Preparative TLC using 20×20 cm×1000 g silica gel GF plates, developed with 0.5:5:95 conc. NH$_4$OH:MeOH:CHCl$_3$, afforded, along with the two more polar sulfoxide diastereomers, the free base of the title compound. Calc. for $C_{27}H_{35}N_3O_4S$: MW=497.7; found m/e=(m+1) 498.7. PMR (in δ from TMS;CDCl$_3$): 8.38 (dd, J=9, 16), 7.52–7.46 (m), 7.41–7.30 (m), 7.23–7.04 (m), 5.6–5.36 (m), 4,6–4.32 (m), 3.98–3.78 (bd, J=14), 3.6–3.3 (m), 3.3–3.0 (m), 3.0–2.7 (m), 2.2–1.98 (m), 1.9–1.65 (m), 1.65–1.4 (bs). Substituting this material for the compound from Step D, Example 63 in Step E, Example 63, the title compound was obtained.

For the more polar sulfoxides N-[1(S)-[(2,3-dihydrospiro-[1H-indene-1,4'-piperidin]-1'yl)carbonyl]-2-(phenylmethylsulfinyl)-ethyl]-2-amino-2-methylpropanamide. Calc. for $C_{27}H_{35}N_3O_3S$: MW=481.7; found m/e=(m+1) 482.6. PMR (in a from TMS;CDCl$_3$): 8.48–8.3 (bt, J=8 Hz), 7.4–7.3 (m), 7.25–7.15 (m), 7.15–7.02 (m), 5.46–5.3 (bm), 4.6–4.4 (bm), 4.4 (s), 4.14 (s), 4.08 (s), 4.04 (s), 3.97 (s), 4.05–3.8 (bm), 3.3–3.05 (bm), 3.0–2.96 (m), 2.82 (bd, J=3 Hz), 2.76 (m), 2.12–1.98 (m), 1.9–1.68 (m), 1.6 (bs), 1.52 (bs), 1.42 (bs).

For the less polar sulfoxides N-[1 (S)-[(2,3-dihydrospiro [1H-indene-1,4'-piperidin]-1'-yl)carbonyl]-2-(phenylmethylsulfinyl)ethyl]-2-amino-2-methylpropanamide. Calc. for $C_{27}H_{35}N_3O_3S$: MW=481.7; found m/e=(m+1) 482.6. PMR (in δ from TMS;CDCl$_3$): 8.48 (bt, J=7 Hz), 7.44–7.3 (m), 7.25–7.16 (m), 7.16–7.04 (m), 5.38–5.2 (m), 4.56 (bd, J=12 Hz), 4.21 (dd, J=6,12 Hz), 4.09 (dd, J=2,12 Hz), 3.87 (bd, J=12 Hz), 3.3–3.1 (m), 3.1–3.0 (m), 2.97(s), 2.93 (s), 2.89 (s), 2.86 (bs), 2.8 (bs), 2.26 (bt, J=6 Hz), 1.79 (bdt, J=3,12 Hz), 1.6 (bs), 1.55 (bs), 1.42 (bs).

EXAMPLE 66

Preparation of
N-[1(R)-[(2,3-dihydro-3-oxospiro[1H-indene-1,4'-piperidin]-1'-yl)carbonyl]-2-(phenylmethyloxy)ethyl]-2-amino-2-methylpropanamide hydrochloride Step A:

N-[1(R)-[(2,3-dihydro-3-oxospiro[1H-indene-1,4'-piperidin]-1'yl)carbonyl]-2-(phenylmethyloxy)ethyl]carbamic acid 1,1-dimethylethyl ester Substituting 2,3-dihydro-3-oxospiro(1H-indene-1,4'-piperidine) trifluoroacetate (Example 4, Step B) for 2,3-dihydrospiro-(1H-indene-1,4'-piperidine) hydrochloride in Step A, Example 63, the title compound was obtained. Calc. for $C_{28}H_{34}N_2O_5$:MW=478.6; found m/e=(m+1) 479.7.

Step B:

1'-[[2(R)-amino-1-oxo-3-(phenylmethyloxy)]propyl]-2,3-dihydro-3-oxospiro[1H-indene-1,4'-piperidine]

Substituting the compound from Step A above for the product of Example 63 Step A in Step B, Example 63, the title compound was obtained. Calc. for $C_{23}H_{26}N_2O_3$:MW=378.5; found m/e=(m+1) 379.1.

Step C:

N-[1(R)-[(2,3-dihydro-3-oxospiro[1H-indene-1,4'-piperidin]-1'yl)carbonyl]-2-(phenylmethyloxy)ethyl 2-[1,1-dimethylethyloxy)carbonyl]amino]-2-methylpropanamide Substituting the compound from Step B above for the product of Example 63, Step B in Step C, Example 63, the title compound was obtained. Calc. for $C_{32}H_{41}N_3O_6$:MW=563.7; found m/e=(m+1) 564.8.

Step D:

N-[1(R)-[(2,3-dihydro-3-oxospiro[1H-indene-1,4'-piperidin]-1'yl)carbonyl]-2-phenylmethyloxyethyl]2-amino-2-methylpropanamide Substituting the compound from Step C above for the compound from Example 63, Step C in Step D, Example 63, the title compound was obtained. Calc. for $C_{27}H_{33}N_3O_4$:MW=463.6; found m/e=(m+1) 464.6. PMR (in δ from TMS; CDCl$_3$): 8.31 (dd, J=8, 18 Hz), 7.76–7.56 (m), 7.56–7.24 (m), 6.93 (d, J=8 Hz), 5.24–5.06 (m), 4.77 (bd, J=12 Hz), 4.62–4.4 (m), 4.14 (bdd, J=12, 23 Hz), 3.78–3.55 (m), 3.09 (bquin, J=10 Hz), 2.86–2.5 (m), 2.60 (bs), 2.1–1.64 (m), 1.72 (bs), 1.64–1.22 (m), 1.36 (bs).

Step E:

N-[1(R)-[(2,3-dihydro-3-oxospiro[1H-indene-1,4'-piperidin]-1'yl)carbonyl]-2-(phenylmethyloxy)ethyl]-2-amino-2-methylpropanamide hydrochloride A sample of the product from Step D above was dissolved in ca. 10-fold acetic acid, and treated with 1–2 equivalents of conc. HCl. Upon lyophillization, the title material, was obtained.

EXAMPLE 67

Preparation of
N-[1-[(2,3-dihydrospiro[1H-indene-1,4'-piperidin]-1'-yl)carbonyl]-3-phenoxypropyl]-2-amino-2-methylpropanamide hydrochloride Step A:

N-Boc-O-phenyl-(R,S)-homoserine (24).

A mixture of O-phenyl-(R,S)-homoserine (A. W. Coulter, J. B. Lombardini, Paul Talalay, *Mol. Pharmacology*, 10, 305 (1974)), 0.9 g (4.5 mmoles), 6.3 g t-butyl carbonic anhydride (29 mmoles), 1.6 g NaHCO$_3$ (19 mmoles), 25 mL water and 75 mL THF was stirred for two days, concentrated to a paste at aspirator pressure, and partitioned between hexane and water, adjusting to pH 9 with dilute NaOH. The mix was extracted five times with hexane, brought to pH 4 with a mixture of KH$_2$PO$_4$ and 2.5N HCl, and extracted several times with ether. After drying over MgSO$_4$, the combined ether extracts were concentrated under reduced pressure to give crude title compound which was used directly in the next step. Calc. for $C_{28}H_{36}N_2O_4$:MW=464.6; found m/e=(m+1) 465.6.

Step B:

N-[1-[(2,3-dihydrospiro[1H-indene-1,4'-piperidin]-1'-yl)carbonyl]-3-phenoxypropyl]carbamic acid 1,1-dimethylethyl ester Substituting the compound from Step A above for N-t-BOC-O-benzyl-D-serine in Step A, Example 63, the title compound was obtained. Calc. for $C_{28}H_{36}N_2O_4$:MW=464.6; found m/e=(m+1) 465.6.

Step C:

1'-[2-amino-1-oxo-4-phenoxybutyl]-2,3-dihydrospiro-[1H-indene-1,4'-piperidine]

Substituting the compound from Step B above for the compound from Example 63, Step A in Step B, Example 78, the title compound was obtained. Calc. for $C_{23}H_{28}N_2O_2$:MW=364.5; found m/e 32 (m+1) 365.2.

Step D:

N-[1-[(2,3-dihydrospiro[1H-indene-1,4'-piperidin]-1'-yl)carbonyl]-3-phenoxypropyl]-2-[1,1-dimethylethyloxy)carbonyl]amino]-2-methylpropanamide Substituting the compound from Step C above for the product from* Example 63, Step B in Step C, Example 63, the title compound was obtained. Calc. for $C_{32}H_{43}N_3O_5$:MW=549.7; found m/e=(m+1) 550.9.

Step E:

N-[1-[(2,3-dihydrospiro[1H-indene-1,4'-piperidin]-1'-yl)carbonyl]-3-phenoxypropyl]-2-amino-2-methylpropanamide Substituting the compound from Step D above for the compound from Example 63, Step C in Step D, Example 63, the title compound was obtained. PMR (in δ from TMS; CDCl$_3$): 8.36 (dd, J=8,20 Hz), 7.32–7.1 (m), 7.0–6.82 (m), 6.78 (d, J=7 Hz), 5.28–5.08 (quin, J=8 Hz), 4.61 (bd, J=12 Hz), 4.2–3.9 (m), 3.36–3.16 (bquar, J=8 Hz), 3.0–2.78 (m), 2.2–2.2 (m), 2.2–1.97 (m), 1.97–1.6 (m), 1.56 (bs), 1.35 (bs).

Step F:

N-[1-(2,3-dihydrospiro[1H-indene-1,4'-piperidin]-1'-yl)carbonyl]-3-phenoxypropyl]-2-amino-2-methylpropanamide hydrochloride A sample of the product from Step D above was dissolved in ca. 10-fold acetic acid, and treated with 1–2 equivalents of conc. HCl. Upon lyophillization, the title material, was obtained. Calc. for $C_{27}H_{35}N_3O_3 \cdot HCl:MW=449.6+HCl$; found m/e=(m+1) 450.5.

EXAMPLE 68

Preparation of
N-[1(R)-[(2,3-dihydrospiro[1H-indene-1,4'-piperidin]-1'-yl)carbonyl]-2-(phenylmethyloxy)ethyl]-2-(2-(R)-hydroxypropyl)amino-2-methylpropanamide hydrochloride Step A:

N-[1(R)-[(2,3-dihydrospiro[1H-indene-1,4'-piperidin]-1'-yl)carbonyl]-2-(phenylmethyloxy)ethyl]-2-(2-(R)-(2-tetrahydropyranloxy)propyl)amino-2-methylpropanamide To 260 mg (1.5 mmoles) of methyl O-2-tetrahydropyranyl-(R)-lactate, made by the procedure of J. B. Martin and E. S. Lutton, *J. Am. Oil Chemists' Soc.*, 427, 529 (1965), in 5 mL of ether was added, under a nitrogen atmosphere, at −78° C., with vigorous stirring, over ca. one minute, 1.0 mL of 1.0M DIBAL (in hexane). The clear solution as held at −78° C. for one hour, then cannulated into 10 mL of 1M $KH_2PO_4$, while stirring vigorously under a nitrogen atmosphere at 0° C. The gelatinous aqueous phase was extracted several times with ether (with centrifugation to aid phase separation), the extracts dried over $MgSO_4$, and the ether removed under reduced pressure. The crude aldehyde was then combined with 75 mg of N-[1(R)-[(2,3-dihydrospiro[1H-indene-1,4'-piperidin]-1'yl)carbonyl]-2-(phenylmethyloxy)ethyl]-2-amino-2-methylpropanamide (0.17 mmole), 73 mg of anhydrous sodium acetate (0.89 mmoles), 0.5 mL of MeOH, and stirred under a nitrogen atmosphere for three hours. After adding 70 mg of solid sodium cyanoborohydride (1.1 mmoles), stirring was continued over night. The mixture was then concentrated to a paste under nitrogen and the residue partitioned between chloroform and water, extracted several times with chloroform, the extracts dried with $MgSO_4$, and the solvent removed under a nitrogen stream. Preparative TLC on one 20×20 cm×1000µ silica gel GF plate with ethyl acetate afforded 50 mg of the title compound Calc. for $C_{35}H_{49}N_3O_5:MW=591.8$; found m/e=(m+1) 592.7.

Step B:

N-[1(R)-[(2,3-dihydrospiro[1H-indene-1,4'-piperidin]-1'-yl)carbonyl]-2-(phenylmethyloxy)ethyl]-2-(2-(R)-hydroxypropyl)amino-2-methylpropanamide To 50 mg of the compound from Step A above in 1.0 mL of MeOH was added dropwise, with stirring, 1.0 mL of 9N HCl, and the clear solution left standing over night. The solution was concentrated to dryness, and partitioned between chloroform and 1M $K_2HPO_4$, adjusting the pH to ca. 9 with 2.5M NaOH. The mixture was extracted several times with chloroform, the extracts dried with $MgSO_4$ and taken to dryness. Preparative TLC on one 20×20 cm×250µ silica gel GF plate with ethyl acetate afforded 20 mg of the title compound. Calc. for $C_{30}H_{41}N_3O_4:MW=507.7$; found m/e=(m+1) 508.9. PMR (in δ from TMS; $CDCl_3$) :8.24 (d, J=8 Hz), 7.4–7.3 (m), 7.25–7.1 (m), 6.77 (d, J=6 Hz), 5.21 (bquar, J=8 Hz), 4.65–4.5 (m), 4.1–3,85 (m), 3.67 (t, J=6 Hz), 3.21 (quin, J=12 Hz), 2.91 (t, J=8 Hz), 2.85–2.75 (m), 2.75–2.59 (m), 2.53 (d, J=6 Hz), 2.48 (d, J=6 Hz), 2.15–1.9 (m), 1.9–1.5 (m), 1.35 (bs), 1.18 (d, J=7 Hz).

Step C:

N-[1(R)-[(2,3-dihydrospiro[1H-indene-1,4'-piperidin]-1'-yl)carbonyl]-2-(phenylmethyloxy)ethyl]-2-(2-(R)-hydroxypropyl)amino-2-methylpropanamide hydrochloride To a solution of 20 mg of N-[1(R)-[(2,3-dihydrospiro[1H-indene-1,4'-piperidin]-1'-yl)carbonyl]-2-(phenylmethyloxy)ethyl]-2-(2-(R)-hydroxypropyl)amino-2-methylpropanamide (0.04 mmoles) in 1 mL of HOAc was added 0.01 mL of conc. HCl (0.12 mmoles), and the solution lyophyllized over night to give the title compound. Calc. for $C_{30}H_{41}N_3O_4+HCl:MW=507.7+HCl$; found m/e=(m+1) 509.4.

EXAMPLE 69

Preparation of
N-[1(R)-[(2,3-dihydrospiro[1H-indene-1,4'-piperidin]-1'-yl)carbonyl]-2-(phenylmethyloxy)ethyl]-3-(2-(R)-hydroxypropyl)amino-3-methylbutanamide hydrochloride Step A:

N-[1(R)-[(2,3-dihydrospiro[1H-indene-1,4'-piperidin]-1'-yl)carbonyl]-2-(phenylmethyloxy)ethyl]3-[[1,1-dimethylethyloxy)carbonyl]amino]-3-methylbutanamide Following the procedure described in Example 63, Step C, but substituting N-t-Boc-β,β-dimethyl-β-alanine for N-t-Boc-α-methylalanine, the title compound was obtained. Calc. for $C_{33}H_{45}N_3O_5:MW=563.7$; found m/e=(m+1) 564.9.

Step B:

N-[1(R)-[(2,3-dihydrospiro[1H-indene-1,4'-piperidin]-1'-yl)carbonyl]-2-(phenylmethyloxy)ethyl]-3-amino-3-methylbutanamide Following the procedure described in Example 63, Step D, but substituting the compound from Step A above for the compound from Example 63, Step C the title compound was obtained. Calc. for $C_{28}H_{37}N_3O_3:MW=463.6$; found m/e=(m+1) 464.7.

Step C:

N-[1(R)-[(2,3-dihydrospiro[1H-indene-1,4'-piperidin]-1'-yl)carbonyl]-2-(phenylmethyloxy)ethyl]-3-(2-(R)-(2-tetrahydropyranyloxy)propyl)amino-3-methylpropanamide Following the procedure described in Example 68, Step A, but substituting the compound from Step B above for compound from Example 63, Step D the title compound was obtained. Calc. for $C_{36}H_{51}N_3O_5:MW+605.8$; found m/e=(m+1) 606.6.

Step D:

N-[1(R)-[(2,3-dihydrospiro[1H-indene-1,4'-piperidin]-
1'-yl)carbonyl]-2-(phenylmethyloxy)ethyl]-3-(2-
(R)-hydroxypropyl)amino-3-methylbutanamide Following the procedure described in Example 68, Step B, but substituting the compound from Step C above for the compound from Example 68, Step A the title compound was obtained. Calc. for $C_{31}H_{43}N_3O_4$:MW+521.7; found m/e= (m+1) 522.8. PMR (in δ from TMS; CDCl$_3$):9.44 (bt, J=8 Hz), 7.22 (bs), 7.24–7.08 (bm), 5.32–5.18 (m), 4.7–4.1 (m), 4.54 (bs), 4.1–3.05 (bm), 4.6–4.8 (m), 3.18 (bquart, J=12 Hz), 2.98–2.86 (m), 2.81 (bs), 2.75 (bs), 2.58–2.46 (m), 2.42 (d, J=12 Hz), 2.32 (d, J=8 Hz), 2.25 (d, J=12 Hz), 2.15–1.95 (m), 1.85–1.4 (m), 1.3–1.1 (m).

Step E:

N-[1(R)-[(2,3-dihydrospiro[1H-indene-1,4'-piperidin]-
1'-yl)carbonyl]-2-(phenylmethyloxy)ethyl]-3-(2-
(R)-hydroxypropyl)amino-3-methylproanamide
hydrochloride Following the procedure described in Example 68, Step C, but substituting the compound from Step D above for the compound from Example 68, Step B the title compound was obtained.

EXAMPLE 70

Preparation of
N-[1(R)-[(2,3-dihydrospiro[1H-indene-1,4'-piperidin]-
1'-yl)carbonyl]-2-(phenylmethyloxy-
carbonyl)ethyl]-2-amino-2-methylpropanamide
hydrochloride Step A:

N-[1(R)-[(2,3-dihydrospiro[1H-indene-1,4'-piperidin]-
1'-yl)carbonyl]-2-(phenylmethyloxy-carbonyl)ethyl]-2-
[[1,1-dimethylethyloxy)carbonyl]amino]-2-
methylpropanamide Following the procedure described in Example 63, Step A through Step C, but substituting N-BOC-D-glutamic acid-α-benzyl ester for N-BOC-O-benzyl-D-serine in Step A, the title compound was obtained. Calc. for $C_{33}H_{43}N_3O_6$:MW= 577.7; found m/e=(m+1) 578.

Step B:

N-[1(R)-[(2,3-dihydrospiro[1H-indene-1,4'-piperidin]-
1'-yl)carbonyl]-2-(phenylmethyloxy-
carbonyl)ethyl]-2-amino-2-methylpropanamide Following the procedure described in Example 63, Step D, but substituting the compound from Step A above for the compound from Example 63, Step C the title compound is obtained. Calc. for $C_{28}H_{35}N_3O_4$:477.6; found m/e=(m+1), 478.7. PMR (in δ from TMS; CDCl$_3$): 8.4 (dd, J=8,6 Hz), 7.25–7.1 (m), 7.1–7.02 (m), 5.35–5.2 (m), 5.2–5.1 (m), 4.57 (bd, J=12 Hz), 4.05 (bd, J=12 Hz), 3.23 (dd, J=20,12 Hz), 3.0–2.8 (m), 2.69 (dr, J=16,5 Hz), 2.08 (t, J=6 Hz), 1.9–1.5 (m), 1.35 (bs).

Step C:

N-[1(R)-[(2,3-dihydrospiro[1H-indene-1,4'-piperidin]-
1'-yl)carbonyl]-2-(phenylmethyloxy
carbonyl)ethyl]-2-amino-2-methylpropanamide
hydrochloride Following the procedure described in Example 63, Step E, but substituting the compound from Step B, above for the compound from Step D, Example 63, the title compound was obtained.

EXAMPLE 71

Preparation of
N-1(R)-[(2,3-dihydrospiro[1H-indene-1,4'-piperidin]-
1'-yl)carbonyl]-2-
(4'-phenylmethyloxyphenyl)ethyl]-2-amino-2-methyl-
propanamide hydrochloride Step A:

N-[1(R)-(2,3-dihydrospiro[1H-indene-1,4'-piperidin]-
1'-yl)carbonyl]-2-(4'-phenylmethyloxy-
phenyl)ethyl]-2-[[1,1-dimethylethyl-
oxy)carbonyl]amino]-2-methylpropanamide Following the procedure described in Example 63, Step A to Step C, but substituting N-BOC-O-phenyl-D-tyrosine for N-BOC-O-benzyl-D-serine, the title compound was obtained. Calc. for $C_{38}H_{47}N_3O_5$:MW=625.8; found m/e= (m+1) 626.5.

Step B:

N-1(R)-[(2,3-dihydrospiro[1H-indene-1,4'-piperidin]-
1'-yl)carbonyl]-2-(4'-phenylmethyloxy-
phenyl)ethyl]-2-amino-2-methylpropanamide Following the procedure described in Example 63, Step D, but substituting the compound from Step A above for the compound from Example 63, Step C, the title compound was obtained. Calc. for $C_{33}H_{39}N_3O_3$:MW=525.7; found m/e=(m+1) 526.9. PMR (in δ from TMS; CDCl$_3$):8.23 (t, J=8 Hz), 7.45–7.3 (m), 7.3–7.0 (m), 7.0–6.85 (m), 5.2–5.08 (m), 5.02–5.0 (m), 4.98 (bd, J=12 Hz), 3.79 (bt, J=12 Hz), 3.2–2.6 (m), 2.05–1.9 (m), 1.8–1.65 (bm, 1.6–1.4 (m), 1.34 (s), 1.32 (s), 1.29 (s), 0.8 (dt, J=13,5 Hz).

Step C:

N-1(R)-[(2,3-dihydrospiro[1H-indene-1,4'-piperidin]-
1'-yl)carbonyl]-2-(4'-phenylmethyloxy-
phenyl)ethyl]-2-amino-2-methylpropanamide
hydrochloride Following the procedure described in Example 63, Step E, but substituting the compound from Step B, above for the compound from Example 63, Step D, the title compound was obtained.

EXAMPLE 72

Preparation of
N-1(R)-[(2,3-dihydrospiro[1H-indene-1,4'-piperidin]-
1'-yl)carbonyl]-2-(4'-hydroxyphenyl)ethyl]-2-
amino-2-methylpropanamide hydrochloride Step A:

N-[1(R)-[(2,3-dihydrospiro[1H-indene-1,4'-piperidin]-
1'-yl)carbonyl]-2-(4'-hydroxyphenyl)ethyl]-2-
[[1,1-dimethylethyloxy)carbonyl]amino]-2-
ethylpropanamide A solution of 104 mg of N-[1(R)-[(2,3-dihydrospiro[1H-indene-1,4'-piperidin]-1'-yl)carbonyl]-2-(4'benzyloxyphenyl)ethyl]-2-[[1,1-dimethylethyloxy)carbonyl]amino]-2-methylpropanamide in 1 mL of MeOH was vigorously stirred for 18 hrs with 9 mg of 20% Pd(OH)$_2$ on carbon in a hydrogen atmosphere. After removal of the catalyst and evaporation of the solvent, crude title compound was obtained which was sufficiently pure for further reacion. Calc. for $C_{31}H_{41}N_3O_5$:MW=535.7; found m/e=(m+1) 536.

Step B:

N-1(R)-[(2,3-dihydrospiro[1H-indene-1,4'-piperidin]-1'-yl)carbonyl]-2-(4'-hydroxyphenyl)ethyl]-2-amino-2-methylpropanamide Following the procedure described in Example 63, Step D, but substituting the compound from Step A above for the compound from Example 63, Step C, the title compound was obtained. Calc. for $C_{26}H_{33}N_3O_3$:MW=435.6; found m/e=(m+1) 436.4. PMR (in δ from TMS; CDCl$_3$): 8.22 (t, J=8 Hz), 7.25–7.15 (m), 7.1 (d, J=9 Hz), 7.01 (d, J=9 Hz), 6.77 (d, J=9 Hz), 6.72 (d, J=9 Hz), 5.14 (dd, J=16,10 Hz) 4.55 (bd, J=12 Hz), 3.95 (bd, J=12 Hz), 3.15 (t, J=10 Hz), 3.02–2.7 (m), 2.1–1.9 (m), 1.77 (dt, J=13,5 Hz), 1.6–1.45 (m), 1.34 (s), 1.30 (s), 1.28 (s), 1.05 (dr, J=12,4).

Step C:

N-1(R)-[(2,3-dihydrospiro[1H-indene-1,4'-piperidin]-1'-yl)carbonyl]-2-(4'-hydroxyphenyl)ethyl]-2-amino-2-methylpropanamide hydrochloride Following the procedure described in Example 1, Step E, but substituting the compound from Step B above for the compound from Example 63 Step D, the title compound was obtained.

EXAMPLE 73

N-[1(R)-[(2,3-Dihydro-spiro[1H-indene-1,4'-piperdin]-1'-yl)carbonyl]-4-phenylbutyl]-2-amino-2-methylpropanamide hydrochloride Step A:

(2R)-2-amino-5-phenyl-pentanoic acid

To a stirred solution of N-[(1,1-dimethylethoxy)carbonyl] amino-(2S,3R)-(+)-6-oxo-2,3-diphenyl-4-morpholinecarboxylate, (1.0 g, 2.8 mmol) and cinnamyl bromide (2.78 g, 14 mmol) in dry THF (70 mL) at −78° C., was added dropwise sodium hexamethyldisilazide (5.6 mL; 1.0M solution in hexane). The reaction mixture was stirred for 30 minutes, then poured into ethyl acetate (150 mL) and washed with brine, dried over anhydrous magnesium sulfate, filtered and evaporated. The crude product was first washed with warm hexane and then with an ether:hexane (1:1) mixture. The solid material was the desired product. A solution of this intermediate (1.0 g, 2.1 mmol) in CH$_2$Cl$_2$ (2 mL) and TFA (2 mL) was stirred at room temperature for 1 h. The solvents were removed under reduced pressure and the residue was dissolved in saturated aqueous sodium bicarbonate solution and extracted with CHCl$_3$. The organic layer was washed with brine, dried over potassium carbonate, filtered and evaporated to give the amine as a foam which was used without purification. Approximately 0.6 g (1.62 mmol) of this material was dissolved in 40 mL of (2:1) EtOH:THF and hydrogenated under 40 psi using PdCl$_2$/C for 24 h. The catalyst was filtered off through celite pad and the solvent was evaporated to give the title compound as a colorless solid.

$^1$H NMR (400MHz, CD$_3$OD) δ7.2 (m, 5H), 3.77 (t, 1H), 2.6 (t, 2H), 1.9 (m, 4H).

Step B:

(2R)-2-[(1,1-dimethylethoxy)carbonyl]amino-5-phenylpentanoic acid

Prepared from the intermediate of step A using the BOCON procedure as described in Example 77, Step B. The crude product was purified by preparative TLC using 10% MeOH in CH$_2$Cl$_2$.

$^1$H NMR (400MHz, CDCl$_3$) δ7.25 (m, 5H), 5.1 (m, 1H), 4.4 (m, 1H), 2.6 (m, 2H), 1.7 (m, 4H), 1.4 (s, 9H).

Step C:

N-[1(R)-[(2,3-Dihydro-spiro[1H-indene-1,4'-piperdin]-1'-yl)carbonyl]-4-phenylbutyl]-2-[(1,1-dimethylethoxy)carbonyl]amino-2-methylpropanamide hydrochloride To a solution of 85 mg (0.29 mmol) of the intermediate from Step B in 5 mL of chloroform was added 77 mg (0.35 mmol) of (2,3-dihydro-spiro[1H-indene-1,4'-piperdine]hydrochloride, 0.15 mL (0.70 mmol) of N-methyl morpholine, 55 mg (0.42 mmol) of HOBT, and 84 mg (0.42 mmol) of EDC and stirred at RT for 16 h. The reaction mixture was diluted with ether (10 mL) and washed with 10 mL of 10%-aqueous citric acid, with 10 mL of saturated sodium bicarbonate solution, dried over anhydrous magnesium sulfate, filtered, and concentrated to yield a yellow oily product.

To a solution of the above oily product in 3 mL of dichloromethane was added trifluoroacetic acid (3 mL) and stirred at RT for 1 h. The reaction mixture was concentrated, basified with 10 mL of 5% aqueous sodium carbonate solution, and extracted with dichloromethane (3×5 mL). The combined organics were dried over anhydrous carbonate, filtered, and concentrated to give the product as a brown oil. To a solution of this material in 5 mL of chloroform was added 80 mg (0.35 mmol) of 2-(tert-butoxycarbonyl)amino-2-methylpropanoic acid, 55 mg (0.42 mmol) of HOBT, and 84 mg (0.42 mmol) of EDC and stirred at RT for 4 h. The reaction mixture was diluted with ether (10 mL) and washed with 10 mL of 10% aqueous citric acid, with 10 mL of saturated sodium bicarbonate solution, dried over anhydrous magnesium sulfate, filtered, and concentrated to yield a yellow oily product. Flash chromatography (10 g SiO$_2$; CH$_2$Cl$_2$-Acetone 98:2) gave 79 mg of the product as a colorless oil.

$^1$H NMR (400MHz, CDCl$_3$) δ7.24–7.00 (m, 9H), 6.98 (m, 1H), 5.00 (bs, 1H), 4.95–4.90 (m, 1H), 4.55 (bd, 1H), 3.90–3.72 (m, 1H), 3.20–3.00 (m, 2H), 2.95 (t, 2H), 2.85–2.55 (m, 4H), 2.10 (t, 2H), 1.90–1.65 (m, 6H), 1.52 (s, 2H), 1.50 (s, 2H), 1.49 (s, 1H), 1.48 (s, 1H), 1.40 (s, 9H)

Step D:

N-[1(R)-[(2,3-Dihydro-spiro[1H-indene-1,4'-piperdin]-1'-yl)carbonyl]-4-phenylbutyl]-2-amino-2-methylpropanamide hydrochloride To 79 mg of the intermediate from Step C in 4 mL of dioxane was added 1.0 mL of 4M hydrochloric acid in dioxane and stirred at RT for 1 h. The reaction mixture was evaporated to dryness to yield 64 mg of the title compound as a white solid.

$^1$H NMR(CD$_3$OD, 400MHz) δ7.30–7.10 (m, 9H), 7.08 (m, 1H), 4.88 (ddd, 1H), 4.50–4.40 (m, 1H), 3.68–3.60 (bd, 1H), 3.52–3.45 (bd, 1H), 3.30–3.10 (m, 2H), 2.90 (t, 2H), 2.85–2.75 (m, 4H), 2.20–2.00 (m, 4H), 1.85 (dt, 1H), 1.70 (dt, 1H), 1.65 (s, 4H), 1.61 (s, 1H), 1.55 (dt, 1H), 1.48 (dt, 1H)

EXAMPLE 74

N-[1(R)-[(2,3-Dihydro-3-oxo-spiro[1H-indene-1,4'-piperdin]-1'-yl)carbonyl]-4-phenylbutyl]-2-amino-2-methylpropanamide hydrochloride Step A:

N-[1(R)-[(2,3-Dihydro-3-oxo-spiro[1H-indene-1,4'-piperdin]-1'-yl)carbonyl]-4-phenylbutyl]-2-[(1,1-dimethylethoxy)carbonyl]amino-2-methylpropanamide The title compound was prepared using the procedure described in Example 73, Step C but spiro[1H-indene-1,4'-piperdin]-3(2H)-one was used in place of 2,3-dihydro-spiro [1H-indene-1,4'-piperidine].

$^1$H NMR (CDCl$_3$, 200 MHz) δ7.75 (d, 1H), 7.62 (t, 1H), 7.55 (t, 1H), 7.40 (dt, 1H), 7.30–7.05 (m, 5H), 5.00 (bs, 1H), 4.98–4.90 (m, 1H), 4.70 (bd, 1H0, 3.93 (bt, 1H), 3.20–2.90 (m, 1H0, 2.78–2.60 (m, 2H), 2.60 (s, 2H), 1.90–1.55 (m, 7H), 1.53 (s, 3H), 1.45 (s, 3H), 1.43 (s, 9H)

Step B:

N-[1(R)-[(2,3-Dihydro-3-oxo-spiro[1H-indene-1,4'-piperdin]-1'-yl)carbonyl]-4-phenylbutyl]-2-amino-2-methylpropanamide trifluoroactate To the product obtained from Step A in 2 mL of dichloromethane was added 2 mL of trifluoroacetic acid and stirred at RT for 1 h. The reaction mixture was concentrated under reduced pressure to yield the title compound as a colorless solid.

$^1$H NMR (CDCl$_3$, 200 MHz) δ7.78 (d, 1H), 7.64 (t, 1H), 7.59 (t, 1H), 7.38 (dt, 1H), 7.30–7.05 (m, 5H), 4.98–4.90 (m, 1H), 4.70 (bd, 1H), 3.93 (bt, 1H), 3.20–2.90 (m, 1H), 2..78–2.60 (m, 2H), 2.60 (s, 2H), 1.90–1.55 (m, 7H), 1.53 (s, 3H), 1.45 (s, 3H)

EXAMPLE 75

N-[1(R)-[(2,3-Dihydro-3(RS)-hydroxyspiro[1H-indene-1,4'-piperdin]-1'-yl)carbonyl]-4-phenylbutyl]-2-amino-2-methylpropanamide To a solution of 74 mg of N-[1(R)-[(2,3-Dihydro-3-oxo-spiro[1H-indene-1,4'-piperdin]-1'-yl)carbonyl]-4-phenylbutyl]-2-amino-2-methylpropanamide trifluoroactate (prepared as described in Example 74) in 10 mL of methanol 0° C. was added 37 mg of sodium borohydride and stirred for 1 h. The reaction was poured into 5 mL of saturated aqueous sodium bicarbonate solution and extracted with chloroform (3×10 mL). The combined organics were washed with brine (5 mL), dried over anhydrous potassium carbonate, filtered, and concentrated to give a colorless foam.

This material is a diastereomeric mixture. $^1$H NMR (CDCl$_3$, 400 MHz) δ8.25 (dd, 1H), 7.40 (bt, 1H), 7.32–7.20 (m, 5H), 7.18–7.10 (m, 3H), 7.00 (t, 1H), 5.23 (dt, 1H), 4.93–4.82 (m, 1H), 4.55 (bt, 1H), 3.80 (bt, 1H), 3.20–3.10 (m, 1H), 3.75 (dr, 1H), 3.70–3.62 (m, 1H), 3.62–3.55 (m, 1H), 2.95 (ddd, 1H), 1.95–1.50 (m, 6H), 1.45 (bd, 1H), 1.35 (s, 3H), 1.32 (S, 3H)

EXAMPLE 76

N-[1(R)-[(2,3-Dihydro-spiro[1H-indene-1,4'-piperdin]-1'-yl)carbonyl]-2-(1-methyl-indol-3-yl)]-2-amino-2-methylpropanamide hydrochloride Step A:

N-[1(R)-[(2,3-Dihydro-spiro[1H-indene-1,4'-piperdin]-1'-yl)carbonyl]-2-(1-methyl-indol-3-yl)]-2-[(1,1-dimethylethoxy)carbonyl]amino-2-methylpropanamide hydrochloride To 0.506 g(1.60 mmol) of (2RS)-NtBOC-1-methyltryptophan in 15 mL of chloroform was added 0.35 g (1.58 mmol) of 2,3-dihydro-spiro[1H-indene-1,4'-piperidine]hydrochloride, 1.30 mL(3.20 mmol) of N-methyl morpholine, 0.241 g (1.58 mmol) of HOBT, and 0.48 g (2.40 mmol) of EDC and stirred at RT for 16 h. The reaction mixture was diluted with 15 mL of ether washed with 15 mL of 10% aqueous citric acid, 15 mL of saturated sodium bicarbonate solution, dried over anhydrous magnesium sulfate, filtered, and concentrated to give a crude material as a pale yellow oil which was used without purification. To this material in 5 mL of methanol was added 5 mL of conc. HCl and stirred at RT for 2 h. The reaction mixture was concentrated and azeotroped with toluene (2×10 mL). This residue was used without purification.

To 0.23 g (0.58 mmol) of the above HCl salt in 10 mL of CHCl$_3$ was added 0.16 g (0.69 mmol) of the N-tBOC a-methyl alanine, 97 μL of triethylamine, 89 mg (0.58 mmol) of HOBT, and 0.14 g (0.69 mmol) of EDC and stirred at RT for 16 h. The reaction mixture was diluted with 15 mL of ether washed with 15 mL of 10% aqueous citric acid, 15 mL of saturated sodium bicarbonate solution, dried over anhydrous magnesium sulfate, filtered, and concentrated to give a crude material as a pale yellow oil. Flash chromatography (10 g SiO$_2$; hexane-ethyl acetate 1:1) gave 0.193 g of the desired product as a colorless oil. To a solution of this material in 3.0 mL of ethanol was added 0.10 g of 10% Pd/C and hydrogenated with a H$_2$ balloon overnight. The catalyst was filtered off through a pad of celite and the o filtrate was concentrated to yield 0.176 g of the compound as a pinkish solid.

The compound exists as a 3:2 mixture of conformers. $^1$H NMR(CDCl$_3$, 400 MHz) δ8.30 (t, 1H), 7.75 (d, ⅔H), 7.60 (d, ⅓H), 7.30–6.90 (m, 7H), 6.60 (bd, 1H), 5.30–5.10 (m, 1H), 4.45 (d, 1H), 5.00 (bs, 1H), 3.73 (s, 1H), 3.71 (s, 2H), 3.70–3.55 (m, 1H), 3.20 (bt, 2H), 2.90 (t, ⅔H), 2.89–2.78 (m, 2H), 2.65 (t, 1H), 2.50 (t, ⅓H), 1.80–2.00 (m, 2H), 1.70–1.40 (m, 2H), 1.37 (s, 3H), 1.35 (s, 3H), 1.30 (s, 9H), 1.18 (dt, ⅔H), 0.95 (d, ⅓H), 0.34 (dt, ⅓H)

Step B:

N-[1(R)-[(2,3-Dihydro-spiro[1H-indene-1,4'-piperdin]-1'-yl)carbonyl]-2-(1-methyl-indol-3-yl)]-2-amino-2-methylpropanamide hydrochloride To 0.176 g of the intermediate from Step A in 2 mL of dichloromethane was added 2.0 mL of trifluoroacetic acid and stirred at RT for 1 h. The residue was basified with 5 mL of 10% aqueous sodium carbonate solution, and extracted with chloroform (3×5 mL). The combined organics were washed with brine (10 mL), dried over potassium carbonate, filtered, and concentrated to yield a thick oil. The compound exists as a 3:2 mixture of conformers.

$^1$H NMR(CDCl$_3$, 400 MHz) δ8.30 (t, 1H), 7.75 (d, ⅔H), 7.60 (d, ⅓H), 7.30–6.90 (m, 7H), 6.60 (bd, 1H), 5.30–5.10 (m, 1H), 4.45 (d, 1H), 5.00 (bs, 1H), 3.73 (s, 1H), 3.71 (s, 2H), 3.70–3.55 (m, 1H), 3.20 (bt, 2H), 2.90 (t, ⅔H), 2.89–2.78 (m, 2H), 2.65 (t, 1H), 2.50 (t, ⅓H), 1.80–2.00 (m, 2H), 1.70–1.40 (m, 2H), 1.37 (s, 3H), 1.35 (s, 3H), 1.30 (s, 9H), 1.18 (dt, ⅔H), 0.95 (d, ⅓H), 0.34 (dt, ⅓H)

EXAMPLE 77

N-[1(R)-[2,3-Dihydro[1H-indene-1,4'-piperidin]-1'-yl)carbonyl]-3-(4-hydroxyphenyl)propyl]-2-amino-2-methylpropanamide hydrochloride Step A:

(2R)-4-(4-hydroxyphenyl)-2-amino-butanoic acid hydrobromide

A solution of (2R)-2-[(methoxycarbonyl)amino]-4-(4-methoxyphenyl)-butanoic acid (5.0 g, 18.7 mmol) in 5 mL of 30% HBr in acetic acid was heated at 60° C. overnight. The reaction mixture was cooled to room temperature and the solvent was removed under reduced pressure to give the title compound as an orange solid.

$^1$H NMR (400 MHz, CD$_3$OD) δ7.1 (d, J=8.44 Hz, 2H), 6.7 (d, J=8.49 Hz, 2H), 4.0 (m, 1H), 2.7 (m, 2H), 2.1 (m, 2H).

Step B:

(2R)-4-(4-hydroxyphenyl)-2-(t-butoxycarbonyl)amino-butanoic acid

To a stirred solution of (2R)-4-(4-hydroxyphenyl)-2-amino-butanoic acid hydrobromide (5.0 g, 18.18 mmol) and triethylamine (5.25 mL, 2 eq) in dioxane (50 mL) and water (50 mL) at 0° C. was added a solution of 2-(tert-butoxycarbonyloxyimino)-2-phenylacetonitile (BOCON) (4.9 g) in dioxane (10 mL). The reaction mixture was allowed to warm up to room temperature and stirred for five hours when it became homogeneous: The reaction mixture was diluted with ethyl acetate (EtOAc) and the organic was seperated. The aqueous layer was acidified with citric acid (20%) and extracted with EtOAc. The combined organics were washed with brine, dried over magnesium sulfate, filtered and evaporated to give the desired material.

$^1$H NMR (400 MHz, CDCl$_3$) δ7.0 (d, J=8.4 Hz, 2H), 6.7(d, J=8.4 Hz, 2H), 5.1 (d, J=8.14 Hz, 1H), 4.3(m, 1H), 2.6 (t, 2H), 2.0 (m, 2H), 1.5 (s, 9H).

Step C:

N-[1(R)-[(2,3-Dihydro-spiro[1H-indene-1,4'-piperdin]-1'-yl)carbonyl]-3-(4-hydroxyphenyl)propyl]-2-[(1,1-dimethylethoxy)carbonyl]amino-2-methylpropanamide To a solution of (2R)-4-(4-hydroxyphenyl)-2-(tert-butoxycarbonyl)amino-butanoic acid(1 g, 3.3 mmol) and 2,3-dihydro-spiro[1H-indene-1,4'-piperdine]hydrochloride (0.75 g), N-methyl-morpholine (0.76 mL) and HOBT (0.5 g) in CHCl$_3$ (20 mL) was added EDC (0.97 g) and stirred at room temperature. The reaction mixture was poured into ice-water and extracted with chloroform. The organic phase was washed with brine, dried over magnesium sulfate, filtered and evaporated. This material was purified on silica gel using 10% methanol in chloroform. To a solution of the above compound in MeOH (1.0 mL) was added concentrated hydrochloric acid (0.5 mL) at room temperature and stirred under a nitrogen atmosphere. The reaction mixture was stirred for 1.5 hr and then the solvent was evaporated under reduced pressure to give the product as a yellow solid. To a solution of this material (0.1 g, 0.29 mmol) and 2-(tert-butoxycarbonyl)amino-2-methyl-propanoic acid (0.072 g, 1.2 eq) and HOBT (0.048 g, 1.2 eq) in CHCl$_3$ (2 mL) was added EDC (0.08 g, 1.5 eq) and stirred overnight. The reaction mixture was poured into aqueous sodium bicarbonate solution and extracted with CHCl$_3$, washed with brine, dried over magnesium sulfate, filtered and evaporated. The crude product was purified on silica gel using 5% MeOH in CHCl$_3$ to give the title compound.

$^1$H NMR (400 MHz, CDCl$_3$) δ7.2 (m, 6H), 6.8 (d, J=8.4 Hz, 2H), 5.0 (m, 1H), 4.5 (m, 1H), 3.5 (m, 2H), 2.9 (t, 2H), 2.8 (m, 4H), 2.2 (t, 2H) 2.0 (m, 2H), 1.8 (m, 4H), 1.6 (s, 6H), 1.4 (s, 9H).

Step D:

N-[1(R)-[(2,3-Dihydro-spiro[1H-indene-1,4'-piperdin]-1'-yl)carbonyl]-3-(4-hydroxyphenyl)propyl]-2-amino-2-methylpropanamide A solution of the intermediate from Step C in MeOH (1 mL) and concentrated HCl (0.5 mL) was stirred at room temperature under nitrogen atmosphere for 1 h. Evaporation of the reaction mixture gave the title compound.

$^1$H NMR (400 MHz, CD$_3$OD) δ7.2 (m, 6H), 6.8 (d, J=8.4 Hz, 2H), 4.5(m, 1H), 3.5 (m, 2H) 2.9 (t, 2H), 2.8 (m 4H), 2.2 (t, 2H), 2.0 (m, 2H), 1.8 (m, 4H), 1.6 (s, 6H).

EXAMPLE 78

N-[1(R)-[(2,3-Dihydro-spiro[1H-indene-1,4'-piperdin]-1'-yl)carbonyl]-3-(4-methoxyphenyl)propyl]-2-amino-2-methylpropanamide Step A:

N-[1(R)-[(2,3-Dihydro-spiro[1H-indene-1,4'-piperdin]-1'-yl) carbonyl]-3-(4-methoxyphenyl)propyl]-2-[(1,1-dimethylethoxy)carbonyl]amino-2-methylpropanamide To a solution of (2R)-2-[(methoxycarbonyl)amino]-4-(4-methoxyphenyl)-butanoic acid (2 g, 0.75 mmol), 2,3-dihydro-spiro[1H-indene-1,4'-piperdine]hydrochloride (0.16 g, 0.75 mmol ), HOBT 0.12 g, 0.89 mmol), and N-methylmorpholine (0.16 mL, 1.5 mmol) in chloroform was added EDC (0.21 g, 1.5 eq) and stirred at RT. The work-up and isolation is the same as Step C, Example 77. A solution of this crude product in 5 mL of 30% HBr in acetic acid was heated at 60° C. for 30 min. The reaction mixture was cooled to room temperature and the solvent was removed under reduced pressure to give the title compound as an orange solid. A solution of this material in chloroform was treated with 2-(t-butoxycarbonyl)amino-2-methyl-propanoic acid, N-methyl morpholine, HOBT (0.048 g, and EDC (0.08 g, 1.5 eq) and stirred overnight. The reaction mixture was poured into aqueous sodium bicarbonate solution and extracted with CHCl$_3$, washed with brine, dried over magnesium sulfate, filtered and evaporated. The crude product was purified on silica gel using 5% MeOH in CHCl$_3$ to give the title compound;

$^1$H NMR (400 MHz, CDCl$_3$) δ7.2 (m, 6H), 6.8 (d, J=8.6 Hz, 2H), 5.0 (m, 1H), 4.5 (m, 1H), 3.7 (s, 3H), 3.5 (m, 2H), 2.9 (t 2H), 2.8 (m, 4H), 2.2 (t, 2H), 2.0 (m, 2H), 1.8 (m, 4H), 1.6 (s, 6H), 1.4 (s, 9H).

Step B:

N-[1(R)-[(2,3-Dihydro-spiro[1H-indene-1,4'-piperdin]-1'-yl)carbonyl]-3-(4-methoxyphenyl)propyl]-2-amino-2-methylpropanamide hydrochloride Prepared from the intermediate from Step A as described in Example 77, Step D. Purified by preperative TLC using 5% MeOH in CHCl$_3$.

¹H NMR (400 MHz, CDCl₃) δ7.2 (m, 6H), 6.8 (d, J=8.6 Hz, 2H), 4.5 (m, 1H), 3.7 (s, 3H), 3.5 (m, 2H), 2.9 (t, 2H), 2.8 (m, 4H), 2.2 (t, 2H) 2.0 (m, 2H), 1.8 (m, 4H), 1.6 (s, 6H).

EXAMPLE 79

N-[1(R)-[(2,3-Dihydro-spiro[1H-indene-1,4'-piperdin]-1'-yl)carbonyl]-3-phenylpropyl]-2-amino-2-methylpropanamide hydrochloride Step A:

N-[1(R)-[(2,3-Dihydro-spiro[1H-indene-1,4'-piperdin]-1'-yl)carbonyl]-3-phenylpropyl]-2-[(1,1-dimethylethoxy)carbonyl]amino-2-methylpropanamide To a solution of (2R)-2-[(tert-butoxycarbonyl)amino]-4-phenyl-butanoic acid (0.1 g, 0.37 mmol), 2,3-dihydro-spiro[1H-indene-1,4'-piperdine]hydrochloride (0.10 g, 0.45 mmol), N-methyl-morpholine (0.1 mL, 2 eq), and HOBT (1 eq) in 3mL of chloroform was added and EDC (0.14 g, 0.73 mmol) and stirred at RT overnight. The work-up and isolation is the same as Example 77, Step C. The crude product was purified on silica gel using 20% ethyl acetate in hexane. This material (0.25 g, 0.56 mmol) was hydrogenated in ethyl alcohol using catalytic amount of 10% Pd/C and a hydrogen balloon at room temperature overnight. The catalyst was filtered off and washed with MeOH. Upon evaporation of the solvent the reduced material was obtained. This material was deprotected as described in Example 77, Step C. This intermediate was coupled to 2-(tert-butoxycarbonyl)amino-2-methyl-propanoic acid as illustrated in Example 77, Step C. The title compound was obtained by purification of the residue on silica gel using 5% MeOH in CHCl₃.

¹H NMR (400 MHz, CDCl₃) δ7.2 (m, 9H), 5.0 (m, 1H), 4.5 (m, 1H), 3.5 (m, 2H), 2.9 (t, 2H), 2.8 (m, 4H), 2.2 (t, 2H), 2.0 (m, 2H), 1.8 (m, 4H), 1.6 (s, 6H), 1.4 (s, 9H).

Step B:

N-[1(R)-[(2,3-Dihydro-spiro[1H-indene-1,4'-piperdin]-1'-yl)carbonyl]-3-phenylpropyl]-2-amino-2-methyl-propanamide hydrochloride The title compound prepared from the intermediate from Step A as described in Example 77, Step D.

¹H NMR (400 MHz, CD₃OD) δ7.2 (m, 9H), 4.5 (m, 1H), 3.5 (m, 2H), 2.9 (t, 2H), 2.8 (m, 4H), 2.2 (m, 4H), 1.6 (m, 4H), 1.4 (s, 6H).

EXAMPLE 80

1'-[2-[(2-amino-2-methyl-1-oxopropyl)amino]-1-oxo-3-(phenylmethoxy)propyl]spiro[1,H-indene-1,4'-piperidine]-3-carboxylic acid methylester hydrochloride Step A:

3-[[Trifluoromethyl)sulfonyl]oxy]spiro[1H-indene-1,4'-piperidine]-1'-carboxylic acid-1,1-dimethylethylester To a solution of 420 mg (1.46 mmol) of the intermediate obtained from Example 4 (Step A) in 3.2 ml of THF at 0° C. was added 3.2 ml (1.60 mmol 0.5M in hexane) of potassium bis(trimethylsilyl)amide. The reaction mixture was stirred for one hour and then 571 mg (1.60 mmol) of N-phenyltrifluromethane sulfonamide was added. After 4 hours the reaction was quenched with water and extracted with ethyl acetate. The organic layer was dried over sodium sulfate and concentrated. Purification by flash chromatography (silica gel, hexane/ethyl acetate 3:1) provided 483 mg (1.15 mmol) of the title compound as a white solid.

¹HNMR (200 MHz, CDCl₃): 7.65–7.14 (m, 4H), 6.66 (s, 1H), 4.30–4.15 (m, 2H), 3.24–2.96 (m, 2H), 2.06 (dt, 2H), 1.50 (s, 9H), 1.49–1.38 (m, 2H).

Step B:

Spiro[1H-indene-1,4'-piperidine]-3,1'-dicarboxylic acid-1'-(1,1 dimethylethyl)-3-methyl ester A solution of 434 mg (1.0 mmol) of the intermediate from Step A, 0.28 ml (2.0 mmol) of triethylamine, 16 mg (0.06 mmol) of triphenylphosphine, and 6.0 mg (0.03 mmol) of palladium acetate in 1.8 ml of methanol and 4.0 ml of DMF was purged for 5 minutes with carbon monoxide and then stirred under a carbon monoxide atmosphere for 5 hours. The reaction mixture was diluted with water and extracted repeatedly with ethyl acetate. The ethyl acetate layer was dried over sodium sulfate and concentrated. Purification by flash chromatography (silica gel, hexane/ethyl acetate 6:1) provided 187 mg (0.54 mmol) of the title compound as a colorless oil.

¹HNMR (200 MHz, CDCl₃): 7.99–7.94 (m, 1H), 7.71 (s, 1H), 7.34–7.26 (m, 3H), 4.24–4.18 (m, 2H), 3.91 (s, 3H), 3.13 (dr, 2H), 2.03 (dt, 2H), 1.51 (s, 9H), 1.46–1.25 (m, 2H).

Step C:

2(R)-[[-2-[1,1-dimethylethoxy)carbonyl]amino]-2,2-dimethyl-1-oxoethyl]amino-2-(phenylmethoxy)ethyl)-1-propanoic acid allyl ester The title compound was prepared from commerically available BOC-O-BEN-D-Serine and allyl alcohol, followed by TFA treatment and coupling to Boc-α-methylalanine following the procedure described in Example 4, Step C.

Step D:

(2R)-[[-2-(1,1-dimethylethoxy)carbonyl]amino]-2,2-dimethyl-1-oxoethyl]amino-2-(phenylmethyloxy)ethyl)-1-propanoic acid To a stirred solution of the crude intermediate obtained in Step A (6.7 g, 15.9 mmol), tetrakis (triphenylphosphine)palladium (1.8 g, 0.1 eq) and, triphenyl phosphine (1.25 g, 0.3 eq) was added a solution of potassium-2-ethyl hexanoate (35 mL, 0.5M solution in EtOAc). The reaction mixture was stirred at room temperature under nitrogen atmosphere for 1 h and then diluted with ether (100 mL) and poured into ice-water. The organic layer was separated and the aqueous fraction was acidified with citric acid (20%), then extracted with EtOAc. The EtOAc extracts were washed with brine, dried over magnesium sulfate, filtered and evaporated to give the title compound as a solid.

¹H NMR (400 Hz, CD₃OD) δ7.3 (s, 5H), 4.7 (m, 1H), 4.5 (s, 2H), 4.0 (m, 1H), 3.6 (m, 1H), 1.4 (d, 6H), 1.3 (s, 9H).

Step E:

1'-[2-[[(1,1-dimethylethyloxycarbonyl)-2-amino-2-methyl-1-oxopropyl)amino]-1-oxo-3-(phenylmethoxy)propyl]spiro-[1H-indene-1,4'-piperidine]-3-carboxylic acid methyl ester The title compound (88 mg, 0.132 mmol) was prepared from the intermediate obtained in Step B (180 mg, 0.524 mmol) and the intermediate prepared in Step D (212 mg, 0.576 mmol) according to the procedure described in Example 1 Step B.
Step F:

1'-[2-[(2-amino-2-methyl-1-oxopropyl)amino]-1-oxo-3-(phenylmethoxy)propyl]spiro[1H-indene-1,4'-piperidine]-3-carboxylic acid methyl ester hydrochloride The title compound (88 mg, 0.132 mmol)was prepared from the intermediate obtained in Step E (117 mg, 0.193 mmol) according to the procedure described in Example 1 Step C.

$^1$HNMR (400 MHz, CD$_3$OD 1:1 mixture of conformers): 7.92–7.84 (m, 1H), 7.86 (d, 1H), 7.40–7.18 (m, 7½H), 6.98 (d, 1H), 5.22–5.15 (m, 1H), 4.61–4.52 (m, 3H), 4.18 (d, 1H), 3.90+3.88 (s, 3H total), 3.81–3.73 (m, 2H), 3.55–3.42 (m, 1H), 3.15–3.08 (m, 1H), 2.20–2.06 (m, ½H), 2.03–1.92 (m, 1½H),1.57+1.54+1.53+1.52 (s, 6H total), 1.38–1.27 (m, 2H).

EXAMPLE 81

1'-[2-[(2-amino-2-methyl-1-oxapropyl)amino]-1-oxo-3-(phenylmethoxypropyl]spiro[1H-indene-1,4'-piperidine]-3-carboxylic acid hydrochloride To a solution of the title compound from Example 80 (Step F) in methanol was added 0.054 ml of 1N potassium hydroxide. After 12 hours of stirring at room temperature TLC analysis showed that there was still starting material present so 0.025 ml of 50% potassium hydroxide was added. TLC analysis after 1 hour showed that the starting material was gone. The reaction mixture was acidified with 1N HCL and then concentrated. The residue was suspended in methanol and filtered through a cotton plug. Purification by MPLC (Sephadex LH-20, methanol) provided 15.8 mg (0.032 mmol) of the title compound.

$^1$HNMR (400 MHz, CD$_3$OD 1:1 mixture of conformers): 7.92–7.90 (m, 1H), 7.50 (d, 1H), 7.40–7.12 (m, 7½H), 6.98 (d, ½H), 5.22–5.16 (m, 1H), 4.60–4.51 (m, 3H), 4.16–4.12 (m, 1H), 3.83–3.73 (m, 2H), 3.49–3.33 (m, 1H), 3.15–3.09 (m, 1H), 2.17–2.14 (m, 1/2H), 2.01–1.90 (m, 1½H), 1.61+1.57+1.55 (s, 6H total), 1.37–1.28 (m, 2H).

EXAMPLE 82

N-[1(R)-[[3-(hydroxymethyl)-2,3-dihydrospiro[1H-indene-1,4'-piperidin]-1'-yl]carbonyl]-2-(phenylmethoxy)ethyl]-2-amino-2-methylpropananmide hydrochloride Step A:

1'-[2-[[(1,1-dimethylethyloxycarbonyl)-2-amino-2-methyl-1-oxopropyl)amino]-1-oxo-3-(phenylmethoxy)propyl]-2,3-dihydrospiro[1H-indene-1,4'-piperidine]-3-carboxylic acid methyl ester To a suspention of Tellurium (52.6 mg, 0.412 mmol) in ethanol (2.0 ml ) was added sodiumborohydride (36.6 mg, 0.99 mmol) and the mixture was refluxed for 10 minutes. A solution of the title compound from Example 79, Step E (100 mg, 0.165 mg) in ethanol (1.0 ml ) was cannulated into the reaction mixture at room temperature. The reaction mixture was then stirred over night, filtered and concentrated. The residue was dissolved in ethyl acetate and 1N KOH was added. The aqueous layer was then extracted with ethyl acetate (3×1 vol). The organic layers were dried over anhydrous sodium sulfate, filtered and concentrated. Flash chromatography (silica gel, methylene chloride/ethyl acetate 2:1) gave the title compound (91 mg, 0.15 mmol) as a clear glass.

Step B:

N-[(R)-[[3-(hydroxymethyl)-2,3-dihydrospiro[1H-indene-1,4'-piperidin]-1'-yl]carbonyl]-2-(phenylmethoxy)ethyl]-2-[[(1,1-dimethylethoxycarbonyl]amino-2-methylpropanamide A portion of the intermediate from Step A (42.1 mg, 0.069 mmol) was dissolved in methylene chloride and cooled to −10° C. DIBALH (0.172 ml, 0.172 mmol) was added and the reaction mixture was stirred until the starting material was consumed. The reaction was quenched with 3 drops of water and then a spatula of KF on alumina was added. The mixture was stirrred for 3 h, filtered and then stripped. The residue was purified by flash chromatography (silica gel, s methylene chloride/acetone 4:1) to give the title compound (22.6 mg, 0.039 mmol).

Step C:

N-[1(R)-[[3-(hydroxymethyl)-2,3-dihydrospiro[1H-indene-1,4'-piperidin]-1'-yl]carbonyl]-2-(phenylmethoxy)ethyl]-2-amino-2-methylpropananmide trifluroacetamide A solution of the intermediate prepared in Step B (12.1 mg, 0.21 mol) in a 1:1 mixture of methylene chloride and TFA was stirred at room temperature for 3 h. The solution was concentrated and the residue was azeotroped from toluene. MPLC (LH$_{20}$ column, methanol ) gave the title compound (4.8 mg, 0.008 mmol).

$^1$HNMR (400 MHz, CD$_3$OD 1:1 mixture of diastereomers and a 1:1 mixture of conformers): 7.40–7.09 (m, 8.5H), 6.87–6.68 (m, 0.5H), 5.20–5.14 (m, 1H), 4.62–4.45 (m, 3H), 4.09–3.95 (m, I H), 3.88–3.81 (m, 1H), 3.78–3.61 (m 3H), 2.95–2.86 (m, I H), 2.48–2.39 (m, 1H), 2.13–2.09 (m, 0.5H), 1.95–1.71 (m, 2.5H), 1.59–1.48 (m, 8H).

EXAMPLE 83A

N-[[1(R)-[[3-[(dimethylamino)carbonyl]-2,3-dihydrospiro[1H-indene-1,4'-piperidine]]-1'-yl]carbonyl]-2-(phenylmethoxy)ethyl]-2-amino-2-methylpropanamide hydrochloride Step A:

1'-[2-[[(1,1-dimethylethoxycarbonyl)-2-amino-methyl-1-oxopropylamino]-1-oxo-3-(phenylmethoxy)propyl]-2,3-dihydrospiro[1H-indene-1,4'-piperidinel-3-carboxylic acid A portion of the intermediate from Example 82A, Step A (312 mg, 0.502 mmol) was dissloved in methanol (3.0 ml)/H$_2$O (1.0 ml) and lithium hydroxide was added (14.4 mg, 0.602 mmol) and the solution was stirred overnight. The solution was concentrated to dryness and the residue was dissolved in ethylacetate/1N HCL. Extraction with ethyl acetate followed by drying and concentration gave the title compound (289 mg, 0.47 mmol).

Step B:

N-[[1(R)-[[3-[(dimethylamino)carbonyl]-2,3-dihydro-spiro-[1H-indene-1,4'-piperidine]-1-yl]carbonyl]-2-(phenylmethoxy)ethyl]-2-[[(2,2-dimethyl-ethoxylcarbonyl]amino]-2-methylpropanamide The intermediate from Step A (17.5 mg, 0.028 mmol) was reacted with EDC (8.2 mg, 0.043 mmol), HOBT (5.8 mg, 0.043), NMM (4.5 mM, 0.043 mmol) and dimethyl amine hydrochloride (3.4 mg, 0.043 mmol) according to the procedure described in Example 1, Step A. Flash chromatography (silica gel, methylene chloride acetone 2:1) provided the title compound (15.2 mg, 0.023).

Step C:

N-[[1(R)-[[3-[(dimethylamino)carbonyl]-2,3-dihydrospiro-[1H-indene-1,4'-piperidin]-1'-yl]carbonyl-2-(phenylmethoxy)ethyl]-2-amino-2-methylpropanamide hydrochloride The intermediate from Step B was stirred in a mixture of methanol, con HCL, and water. The solution was concentrated and azeotroped from toluene and finally dried under vacuum to give the title compound (12.1 mg, 0.021 mmol).

EXAMPLE 83B

Resolution of 1'[(1,1-dimethylethoxy)carbonyl]-2,3-dihydrospiro(1H-indene-1,4'-piperidine]-3-carboxylic acid ethyl ester Method A Enantiomer 1

Step A:

1'-[1,1-(dimethylethoxy)carboxyl]-[1H-indene-1,4'-piperidine]-3-carboxylic acid ethyl ester The title compound was prepared following the procedure described in Example 80, Step B except that ethanol was used instead of methanol.

$^1$HNMR (200 MHz, CDCl$_3$): 8.0–7.9 (m, 1H), 7.7 (s, 1H), 7.4–7.2 (m, 3H), 4.39 (q, 2H) 4.3–4.2 (m, 2H), 3.13 (dt, 2H), 2.03 (dt, 2H), 1.51 (s, 9H), 1.46–1.25 (m, 2H), 1.44 (t,3H).

Step B:

1'-(1,1-dimethylethyloxy)carbonyl]-2,3-dihydro-spiro[1H-indene-1,4'-piperidine]-3-carboxylic acid To a solution of the title compound from Step A (4.0 g, 11.2 mmol) in methanol (30 ml) at 0° C. was added 2 N KOH (16.8 ml, 33.6 mmol). The reaction was warmed to room temperature and stirred for 3 h at which time TLC analysis showed that the starting material had been consumed. The methanol was removed under vacuum and the residue was dissloved in ethyl acetate. 1N HCl was added and the layers were separated and the aqueous layer was extracted with ethyl acetate (3×1 vol). The combined organic layers were washed with saturated aqueous NaCl, dried over anhydrous sodium sulfate, filtered and concentrated to provide the title compound (3.28 g, 9.9 mmol) as a white solid.

$^1$HNMR (200 MHz, CDCl$_3$): 8.06–7.80 (m, 1H), 7.86 (s, 1H), 7.4–7.3 (m, 3H), 4.32–4.18 (m, 2H), 3.18 (dt, 2H), 2.06 (dt, 2H), 1.51 (s, 9H), 1.46–1.25 (m, 2H), H).

Step C:

1'[(1,1-dimethylethoxy)carbonyl]-2,3-dihydrospiro(1H-indene-1,4'-piperidine]-3-carboxylic acid To a suspension of Pd/C (300 mg) in methanol (20 ml) and ethyl acetate (10 ml) was added the title compound (1.2 g, 3.6 mmol) from Step B. The reaction mixture was purged with hydrogen and then stirred under a hydrogen balloon for 1 h. The mixture was filtered through celite and concentrated to give the title compound (1.1 g, 33 mmol).

$^1$HNMR (200 MHz, CDCl$_3$): 7.50–7.42 (m, 1H), 7.34–7.12 (m, 3H), 4.22–4.04 (m, 3H), 3.06–2.84 (m, 2H), 2.40 (d, 2H), 1.88–1.6 (m, 4H), 1.50 (s, 9H).

Step D:

2,3-dihydrospiro[1H-indene-1,4'-piperidine]-3,1'-dicarboxylic acid 1'-(1,1-dimethylethyl) 3-(1-[(ethoxy)carbonyl]ethyl)diester To a solution of the intermediate from Step C in toluene at 0° C. was added sodium hydride (99 mg, 80%, 3.3 mmol). The reaction mixture was stirred for 15 minutes and then DMF (0.050 ml) and oxalyl chloride (3.0 ml 2N in methylene chloride) were added. The reaction mixture was stirred for 1 h and then concentrated. The residue was redissolved in toluene and cooled to −10° C. S-Ethyllactate (0.413 mmol, 3.6 mmol) was added followed immediately by N-methyl pyrrolididne (1.1 ml, 10.5 mmol). The reaction was stirred for three minutes and then quenched with an excess of dimethylamino propyl amine. The toluene layer was diluted with ethyl acetate and washed with 1N HCl and saturated aqueous sodium chloride. The organic layer was dried over anhydrous magnesium sulfate, filtered and concentrated. Flash Chromatography (silica gel, hexane/ethyl acetate 4:1) gave a 5:1 mixture of diastereomers (725 mg ). The mixture could be enriched to almost 10:1 by MPLC (silica gel, hexane/ethyl acetate 10:1).

$^1$HNMR (200 MHz, CDCl$_3$): 7.58–7.49 (m, 1H), 7.32–7.12 (m, 3H), 5.15 (q, 4H), 4.35–4.04 (m, 4H), 3.08–2.85 (m, 2H), 2.45–2.36 (m, 2H), 1.94–1.60 (m, 4H), 1.54 (d, 3H), 1.50 (s, 9H), 1.22 (t, 3H).

Step E:

1'[(1,1-dimethylethoxy)carbonyl]-2,3-dihydrospiro(1H-indene-1,4'-piperidine]-3-carboxylic acid ethyl ester Enantiomer 1

To a solution of the title compound from Step D (400 mg, 0.928 mmol) in ethanol (10 ml) was added titanium isopropoxide (0.303 ml,1.02 mmol). The reaction mixture was heated to reflux until TLC analysis showed that the starting material had been consumed. The solvent was removed under vacuum and the residue was purified by flash chromatography (silica gel, hexane/ethyl acetate 6:1) to give the title compound (313 mg, 0.87 mmol)

EXAMPLE 83C

Resolution of 1'[(1,1-dimethylethoxy)carbonyl]-2,3-dihydrospiro(1H-indene-1,4'-piperidine]-3-carboxylic acid ethyl ester Method A Enantiomer 2

Step A:

2,3-dihydrospiro[1H-indene-1,4'-piperidine]3,1'-dicarboxylic acid 1'-(1,1-dimethylethyl) 3-(2-oxo-4,4-dimethyltetrahydrofuran-3-yl) diester The title compound (437 mg, 0.98 mmol) was prepared from the intermediate prepared in Example 83 B Step C (512 mg, 1.55 mmol), following the procedure used in Example 83 B Step D, except that R-Pantolactone (242 mg, 1.86 mmol) was used instead of S-ethyllactate.

$^1$HNMR (200 MHz, CDCl$_3$): 7.58–7.48 (m, 1H), 7.32–7.15 (m, 3H), 5.42 (s, 1H), 4.35–4.05 (m, 5H), 3.05–2.85 (m, 2H), 2.55–2.30 (m, 2H), 2.0–1.60 (m, 2H), 1.50 (s, 9H), 1.32–1.18 (m, 2H), 1.20 (s, 3H), 1.08 (s, 3H).

Step B:

1'[(1,1-dimethylethoxy)carbonyl]-2,3-dihydrospiro(1H-indene-1,4'-piperidine]-3-carboxylic acid ethyl ester Enantiomer 2

The title compound (302 mg, 0.84 mmol) was prepared from the intermediate prepared in Step A (413 mg, 0.94 mmol) following the procedure used in Example 83 B,Step E.

EXAMPLE 83D

Resolution of 1'[(1,1-dimethylethoxy)carbonyl]-2,3-dihydrospiro(1H-indene-1,4'-piperidine]-3-carboxylic acid ethyl ester Method B Enantiomer 1

Step A:

1'-(1,1-dimethylethyloxycarbonyl]-2,3-dihydrospiro[1H-indene-1,4'-piperidine]-3-carboxylic acid Enantiomer 1

To a solution of the title compound from Example 83B, Step C (2.5 g, 7.5 mmol) in toluene (10 ml) was added R-methyl benzylamine. The reaction mixture was warmed until a clear solution was obtained and then cooled to room temperature. A seed crystal (obtained from a similar experiment on a smaller scale) was added and the solution was stored for 18 h at room temperature and then for 1 h at 0° C. The crystals were recovered by filtration and then dissloved in 1N HCl. The acid solution was extracted with ethyl acetate (3×1 Vol). The organic layer was washed with 1N HCl (1×vol), saturated aqueous sodium chloride, dried over anydrous magnesium sulfate, filtered and concentrated to provide the title compound (800 mg, 2.4 mmol) as a white solid.

To a solution of the title compound from Step A (800 mg, 2.4 mmol) in methylene chloride/ethanol 5:1 at 0° C. was added DMAP (30 mg, 0.245 mmol) and EDC (605 mg, 3.16 mmol). The reaction mixture was stirred for 1 h and then concentrated to one half of it's original volume and loaded onto a flash column. Flash chromatography (silica gel, hexane/ethyl acetate 4:1) gave the title compound (800 mg, 2.2 mmol). HPLC analysis (chiralcel OD, 98.5% hexane/ 1.5% isopropanol, 35° C., 1 ml/min. E$_1$ retention time 11.5 min; E$_2$ retention time 15.8 min) showed it to be approximately a 30:1 mixture of enantiomers.

EXAMPLE 83E

Resolution of 1'[(1,1-dimethylethoxy)carbonyl]-2,3-dihydrospiro(1H-indene-1,4'-piperidine]-3-carboxylic acid ethyl ester Method B Enantiomer 2

Step A:

1'-(1,1-dimethylethyloxy)carbonyl]-2,3-dihydrospiro[1H-indene-1,4'-piperidine]-3-carboxylic acid Enantiomer 2

The title compound from Example 83 B, Step C (2.63 g, 7.9 mmol) was resolved using the procedure described in Example 83 DStep A except that S- methyl benzylamine (1.02 ml, 7.9 mmol) was used. The title compound (798 mg, 2.4 mmol) was obtained as a white solid.

Step B:

1'[(1,1-dimethylethoxy)carbonyl]-2,3-dihydrospiro(1H-indene-1,4'-piperidine]-3-carboxylic acid ethyl ester Enantiomer 2

The title compound (623 mg,1.73 mmol) was prepared from the title compound of Step A (601 mg,1.81 mmol) and EDC (571 mg, 2.98 mmol) in a 5:1 mixture of methylene chloride and ethanol. HPLC analysis (chiralcel OD,[4.6 mm, 250 mm] 98.5% hexane/1.5% isopropanol, 35° C., 1 ml/min. E$_1$ retention time 11.5 min; E$_2$ retention time 15.8 min) showed it to be approximately a 35:1 mixture of enantiomers.

EXAMPLE 84

1'-[2[[(2-amino-2-methyl-1-oxo propyl)amino]5-(phenyl-1-1-oxopentyl]2,3-dihydrospiro[1H-indene-1,4'-piperidine]-3-carboxylic acid ethyl ester hydrochloride Diastereomer 2

Step A:

1'-[2[[1,1-dimethylethoxy)carbonyl]amino-5-phenyl-1-oxopentyl]-2,3-dihydrospiro[1H-indene-1,4'-piperidine]-3-carboxylic acid ethyl ester Enantiomer 2

The title compound from Example 83 C, Step B (289 mg, 0.80 mmol) was stirred for 1 h in a mixture of methylene chloride and TFA (1:1). The solution was then concentrated and azeotroped from toluene (3×10 ml). A portion of the residue (268.5 mg, 0.72 mmol) was reacted with the intermediate prepared in Example 73, Step B, (285.7 mg, 756 mmol), EDC (178.7 mg, 0.936 mmol), HOBT (126.6 mg,0.936 mmol), and NMM (0.079 ml, 0.72 mmol) in methylene chloride according to the procedure used for Example 1, Step A to provide the title compound (196.2 mg, 0.36 mmol).

Step B:

1'[2-[[2-[[(1,1-dimethylethoxy)carbonyl]amino]-2-methyl-1-oxopropyl]amino]-5-phenyl-1-oxopentyl]-2,3-dihydrospiro-[1H-indene-1,4'-piperidine]-3-carboxylic acid ethyl ester The title compound from Step A (155 mg, 0.29 mmol) was treated with TFA as in Step A and the residue was reacted with BOC-α-methyl alanine (73.5 mg, 0.377 mmol), EDC (72.0 mg, 0.377 mmol), HOBT (53 mg, 0.377 mmol), NMM (0.032 ml, 0.290 mmol) according to the procedure used for Example 1, Step A. Flash chromatography provided the title compound (112 mg, 0.18 mmol).

Step C:

1'-[2[[(2-amino-2-methyl-1-oxopropyl)amino]5-(phenyl-1-oxopentyl]-2,3-dihydrospiro[1H-indene-1,4'-piperidine]-3-carboxylic acid ethyl ester hydrochloride Diastereomer 2

The title compound from Step B (100 mg, 0.16 mmol) was stirred in 4N HCl/dioxane for 1.5 h. The solution was concentrated and azeotroped from toluene. After drying under high vacuum the title compound (84.6 mg, 0.159 mmol) was obtained as a white solid.

$^1$HNMR (400 MHz, CD$_3$OD): 7.36 (dd, 1H), 7.28–7.02 (m, 8H), 4.89–4.80 (m, 1H), 4.49–4.45 (m, 1H), 4.24–4.01 (m, 3H), 3.93–3.81 (m, 1H), 3.26–3.22 (m, 1H), 2.91–2.85 (m, 1H), 2.71–2.63 (m, 2H), 2.46–2.38 (m, 2H), 2.02 (dt, 1H), 1.82–1.64 (m, 5H), 1.62+1.60 (s, 6H total), 1.55–1.48 (m, 2H), 1.30 (t, 3H).

EXAMPLE 85

1'-[2-[[(2-amino-2-methyl-1-oxopropyl)amino]-5-(phenyl-1-oxopentyl]-2,3-dihydrospiro[1H-indene-1,4'-piperidine]-3-carboxylic acid ethyl ester hydrochloride Diastereomer 1

Step A:

2,3-dihydrospiro[1H-indene-1,4'-piperidine]-3-carboxylic acid ethyl ester hydrochloride The intermediate obtained in Example 83D, Step B (780 mg, 2.17 mmol) was stirred in 4N HCl/dioxane until TLC analysis showed that the starting material was consumed. The solution was concentrated and the residue was azeotroped from toluene to give a white solid (561.2 mg, 2.15 mmol).

Step B:

1'-[2[[1,1-dimethylethoxy)carbonyl]amino-5-phenyl-1-oxopentyl]-2,3-dihydrospiro[1H-indene-1,4'-piperidine]-3-carboxylic acid ethyl ester A portion of the intermediate obtained in Step A (222 mg, 0.752 mmol) was reacted with (2R)-2-[(1,1-dimethylethoxy)carbonyl]- amino-5-phenyl-pentanoic acid (Example 73, Step B) (312 mg, 0.827 mmol), EDC (215 mg, 1.1 mmol), HOBT (159 mg, 1.1mmol) and NMM (0.082 ml, 0.752 mmol) according to the procedure used in Example 1, Step A. The title compound (217 mg, 0.399 mmol) was obtained as a white foamy solid after flash chromatography.

Step C:

1'[2-[[2-[[(1,1-dimethylethoxy)carbonyl]amino]-2-methyl-1-oxopropyl]amino]-5-phenyl-1-oxopentyl]-2,3-dihydrospiro-[1H-indene-1,4'-piperidine]-3-carboxylic acid ethyl ester The title compound (200 mg, 0.374) from Step B was treated with 4N HCl/dioxane as in Step A. The residue was then reacted with BOC-α-methylalanine (95 mg, 0.468 mmol), EDC (107 mg, 0.56 1 mmol), HOBT (76 mg, 0.561 mmol) and NMM (0.41 ml, 0.374 mmol) according to the procedure described for Example 1, Step A. The title compound (174 mg, 0.281 mmol) was obtained after flash chromatography.

Step D:

1'-[2-[[(2-amino-2-methyl-1-oxopropyl)amino]5-(phenyl-1-oxopentyl]-2,3-dihydrospiro[1H-indene-1,4'-piperidine]-3-carboxylic acid ethyl ester hydrochloride Diastereomer 1

The title compound (167 mg, 0.269 mmol) from Step C was reacted as in Example 84, Step C to give the title compound (146.3 mg, 0.263 mmol) as a white solid.

$^1$HNMR (400 MHz, CD$_3$OD): 7.35 (d, 1H), 7.27–7.10 (m, 7.5H), 7.01 (d, 0.5H), 4.52–4.48 (m, 1H), 4.32–4.11 (m, 3H), 3.88–3.84 (m, 1H), 3.26–3.23 (m, 1H), 2.90–2.84 (m, 1H), 2.75–2.60 (m, 2H), 2.45–2.38 (m, 2H), 1.88–1.48 (m, 8H), 1.61+1.59 (s, 6 H total), 1.31–1.27 (m, 3H). FAB-MS: 520 (M+1).

EXAMPLE 86

1'-[2-(R)-[(2-amino-2-methyl-1-oxopropyl)amino]-3-(indol-3-yl)-1-oxopropyl]-2,3-dihydrospiro[1H-indene-1,4'-piperidine]-3-carboxylic acid ethyl ester hydrochloride Diastereomer 1

Step A:

1'[2-[[(1,1-dimethylethoxy)carbonyl]amino]-3-indol-3-yl)-1-oxopropyl]-2,3-dihydrospiro[1H-indene-1,4'-piperidine]-3-carboxylic acid ethyl ester The intermediate prepared in Example 85, Step A (235 mg, 0.796 mmol) was reacted with Boc-D-Trp (290 mg, 0.955 mmol), EDC (228 mg, 1.20 mmol), HOBT (162 mg, 1.20 mmol), and NMM (0.87 ml, 0 796 mmol) in methylene chloride according to the procedure described in Example 1, Step A. Flash chromatography (silica gel, hexane/ethyl acetate 1:1) gave the title compound (287 mg, 0.525 mmol).

Step B:

1'-[2(R)-[[2-[[(1,1-dimethylethoxy)carbonyl]amino]-2-methyl-1-oxopropyl]amino-3-indole-3-yl-1-oxopropyl]-2,3-dihydrospiro[1H-indene-1,4'-piperidine]-3-carboxylic acid ethyl ester The title compound (198 mg, 0.31 mmol) was prepared from the intermediate obtained in Step A (280 mg, 0.5 13 mmol) and BOC-α-methylalanine (130 mg, 0.641 mmol) according to the procedure described in Example 85, Step C.

Step C:

1'-[2-(R)-[(2-amino-2-methyl-1-oxopropyl)amino]-3-(indol-3-yl)-1-oxopropyl}]-2,3-dihydrospiro[1H-indene-1,4'-piperidine]-3-carboxylic acid ethyl ester hydrochloride Diastereomer 1

The title compound (146 mg, 0.231 mmol) from Step B was reacted as in Example 84, Step C to give the title compound (121.7. mg, 0.215 mmol) as a white solid. FAB-MS: 531 (m+1).

EXAMPLE 87

1'-[2-[[(2-amino-2-methyl-1-oxopropyl)amino]-5-(phenyl-1-oxopentyl]-2,3-dihydrospiro[1H-indene-1,4'-piperidine]-3-carboxylic acid ethyl ester hydrochloride Diastereomer 2

Step A:

2,3-dihydrospiro[1H-indene-1,4'-piperidine]-3-
carboxylic acid ethyl ester hydrochloride The intermediate obtained in Example 83E, Step B (623 mg, 1.73 mmol) was stirred in 4N HCl/dioxane until TLC analysis showed that the starting material was consumed. The solution was concentrated and the residue was azeotroped from toluene to give a white solid (481 mg, 1.63 mmol).
Step B:

1'[2-[[(1,1-dimethylethoxy)carbonyl]amino]-3-indol-
3-yl]-1-oxopropyl]-2,3-dihydrospiro[1H-indene-
1,4'-piperidine]-3-carboxylic acid ethyl ester A portion of the intermediate obtained in Step A (240.4 mg, 0.815 mmol) was reacted with Boc-D-Trp (297 mg, 0.978 mmol), EDC (233 mg, 1.22 mmol), HOBT (177 mg, 1.22 mmol), and NMM (089 ml, 0,815 mmol) according to the procedure described in Example 1 Step A. The title compound (268 mg, 0.425 mmol) was obtained after flash chromatography.
Step C:

1'-[2(R)-[[2-[[(1,1-dimethylethoxy)carbonyl]amino]-2-
methyl-1-oxopropyl]amino-3-indole-3-yl-1-
oxopropyl]-2,3-dihydrospiro[1H-indene-1,4'-
piperidine]-3-carboxylic acid ethyl ester The intermediate from Step B (250 mg, 0.458 mmol) was treated with 4N HCl as in Example 85, Step A. The residue was reacted with BOC-α-methylalanine (116.2 mg, 0.572 nmol), EDC (131 mg. 0.68 mmol), HOBT (99 mg, 0.68 mmol) and NMM (050 ml, 0.57 mmol) according to the procedure described for Example 1, Step A. The title compound (217 mg, 0.34 mmol) was obtained as a white solid after flash chromatography.
Step D:

1'-[2-[[2-amino-2-methyl-1-oxopropyl)amino]-5-
(phenyl-1-oxopentyl]-2,3-dihydrospiro[1H-indene-1,4'-
piperidine]-3-carboxylic acid ethyl ester
hydrochloride Diastereomer 2

The intermediate obtained from Step C (207 mg, 0.32 mmol) was reacted as in Example 84, Step C to give the title compound (173 mg, 0.30 mmol) as a white solid.
¹HNMR (400 MHz, CD₃OD, 2:1 mixture of conformers): 7.61 (d, ⅔H), 7.54 (d, ⅓H), 7.40–7.01 (m, 7⅓H), 6.65 (d, ⅔H), 5.28–5.22 (m,1H), 4.39–4.32 (m, 1H), 4.18–4.13 (m,2H), 4.06 (t, ⅓H), 3.95 (t, ⅔H), 3.78–3.70 (m, 1H), 3.20–3.17 (m, 4/3H), 3.03 (dt, ⅔H), 2.66–2.55 (m, 1H), 2.22–2.10 (m, 2H), 1.85 (dt, ⅓H), 1.61+1.60+1.50 (s, 6 H total), 1.45–1.38 (m, 5/3H), 1.28–1.22 (m, 3H), 1.05 (dt, ⅔H), 0.85 (dd, ⅔H), 0.1 (dt, ⅔H).

EXAMPLE 88

1'[2-(R)-[(2-amino-2-methyl-1-oxopropyl)amino]-3-
(phenylmethoxy)-1-oxopropyl]-2,3-dihydrospiro[1H-
indene-1,4'-piperidine]-3-carboxylic acid ethyl ester
hydrochloride Diastereomer 1

Step A:

1'-[2-[[(1,1-dimethylethoxy)carbonyl]amino-3-
(phenylmethoxy)-1-oxopropyl]-2,3-dihydrospiro[1H-
indene-1,4'-piperidine]-3-carboxylic acid ethyl ester A portion of the intermediate prepared in Example 85, Step A (16 1.9 mg, 0.549 mmol) was reacted with Boc-D-O-BenSer (202 mg, 0.0.686 mmol), EDC (157 mg, 0.823 mmol), HOBT (119 mg, 0.82 mmol), and NMM (0.60 ml, 0.549 mmol) in methylene chloride according to the procedure described in Example 1, Step A. Flash chromatography (silica gel, hexane/ethyl acetate 2:1) gave the title compound (168.6 mg, 0.316 mmol).
Step B:

1'[2(R)-[[2-[-[1,1
dimethylethoxy)carbonyl]amino)-2-methyl-1-
oxopropyl)amino]-2-phenylmethoxyethyl]-2,3-
dihydrospiro[1H-indene-1,4'-piperidine]-3-carboxylic
acid ethyl ester The intermediate from Step A (161 mg, 0.30 mmol) was treated with 4N HCl as in Example 85, Step A. The residue was reacted with BOC-α-methylalanine (76 mg, 0.375 mmol), EDC (85.9 mg. 0.45 mmol), HOBT (60.7 mg, 0.45 mmol) and NMM (00.033 ml, 0.30 mmol) according to the procedure described for Example 1, Step A. The title compound (123 mg, 0.20 mmol) was obtained as a white solid after flash chromatography.
Step C:

1'[2-(R)-[(2-amino-2-methyl-1-oxopropyl)amino]-3-
(phenylmethoxy)-1-oxopropyl]-2,3-dihydrospiro[1H-
indene-1,4'-piperidine]-3-carboxylic acid ethyl ester
hydrochloride Diastereomer 1

The intermediate obtained from Step B (108 mg, 0.178 mmol) was reacted as in Example 84, Step C to give the title compound (89.7 mg, 0.165 mmol) as a white solid.
¹HNMR (400 MHz, CD₃OD): 7.40–7.12 (m, 8.5H), 6.85–6.80 (m, 0.5H), 5.25–5.13 (m, 1H), 4.61–4.48 (m, 2.5H), 4.26–4.03 (m, 3.5H), 3.82–3.70 (2H), 3.42–3.25 (m 1H), 2.95–2.80 (m, 1H), 2.48–2.36 (m, 2H), 1.90–1.50 (m, 10H), 1.30 (t, 3H).

EXAMPLE 89

1'-[2-(R)-[(2-amino-2-methyl-1-oxopropyl)amino]-3-
(phenylmethoxy)-1-oxopropyl]-2,3-
dihydrospiro[1H-indene-1,4'-piperidine]-3-carboxylic
acid ethyl ester hydrochloride Diastereomer
2

Step A:

1'-[2-[[(1,1-dimethylethoxy)carbonyl]amino-3-
(phenylmethoxy)-1-oxopropyl]-2,3-dihydrospiro[1H-
indene-1,4'-piperidine]-3-carboxylic acid ethyl ester A portion of the intermediate obtained in Example 87, Step A, (240.4 mg, 0.815 mmol) was reacted with Boc-D-O-BenSer (240 mg, 1.0 mmol), EDC (233 mg, 1.22 mmol), HOBT (177 mg, 1.22 mmol), and NMM (089 ml, 0,815 mmol) according to the procedure described in Example 1 Step A. The title compound (335 mg, 0.62 mmol) was obtained after flash chromatography.
Step B:

117

1'-[2(R)-[[2-[-[1,1-dimethylethoxy)carbonyl]amino)-2-methyl-1-oxopropyl)amino]-2-phenylmethoxyethyl]-2,3-dihydrospiro[1H-indene-1,4'-piperidine]-3-carboxylic acid ethyl ester The intermediate from Step A (297 mg, 0.55 mmol) was treated with 4N HCl as in Example 85, Step A. The residue was reacted with BOC-α-methylalanine (141 mg, 0.69 mmol), EDC (159 mg. 0.833 mmol), HOBT (120 mg, 0.833 mmol) and NMM (0.60 ml, 0.55 mmol) according to the procedure described for Example 1, Step A. The title compound (272.8 mg, 0.449 mmol) was obtained as a white solid after flash chromatography (silica gel, methylene chloride/ethyl acetate 4:1).
Step C:

1'-[2-(R)-[(2-amino-2-methyl-1-oxopropyl)amino]-3-(phenylmethoxy)-1-oxopropyl]-2,3-dihydrospiro[1H-indene-1,4'-piperidine]-3-carboxylic acid ethyl ester hydrochloride Diastereomer 2

The intermediate obtained from Step B (206 mg, 0.339 mmol) was reacted as in Example 84, Step C to give the title compound (176.7 mg, 0.325 mmol) as a white solid.
$^1$HNMR (400 MHz, CD$_3$OD): 7.40–7.10 (m, 8H), 6.88–6.84 (m, ½H), 5.17 (t, 1H), 4.57–4.47 (m, 2H), 3.78–3.71 (m, 2H), 2.95–2.85 (m, 1H), 2.51–2.40 (m, 2H), 2.09 (dt, ½H), 1.80–1.45 (m,⅝H), 1.62+1.58+1.52 (s, 6H total), 1.31–1.26 (m, 3H). FAB-MS 522 M+1).

EXAMPLE 90

1'-[2-[[2-amino-2-methyl-1-oxopropyl]amino]5-phenyl-1-oxopentyl]-2,3-dihydrospiro[1H-indene 1,4'-piperidine-3-carboxylic benzyl ester hdyrochloride Diastereomer 1

Step A:

1'-[(1,1-dimethylethoxy)carbonyl]-2,3-dihydrospiro[1H-indene-1,4'-piperidine1-3-carboxylic acid benzyl ester The title compound from Example83 D, Step A, (945 mg, 2.83 mmol) was coupled to benzyl alcohol (0.45 ml, 4.25 mmol) in methylene chloride according to the procedure described in Example 83D, Step B. The title compound (993 mg, 2.34 mmol) was obtained after flash chromatography (silica gel, hexane/ethyl acetate 7:1).
Step B:

1'-[2-[[(1,1-dimethylethoxylcarbonyl]amino]-5-phenyl-1-oxopentyl]-2,3-dihydrospiro[1H-indene-1,4'-piperidine]-3-carboxylic acid benzyl ester The intermediate obtained from Step A (380 mg, 0.899 mmol) was reacted with the compound prepared in Example 73, Step B, (338 mg, 0.899 mmol), EDC (255 mg, 1.34 mmol), HOBT (189 mg, 1.34 mmol) and NMM (0.98 ml, 0.899 mmol) according to the procedure used in Example 1, Step A. Flash chromatography (silica gel, hexane/ethyl acetate 4:1) gave the title compound (319 mg, 0.535 mmol).
Step C:

118

1'-[2-[[2-[[(1,1-dimethylethoxy)carbonyl]amino]-2-methyl-1-oxopropyl]amino]-5-phenyl-1-oxopentyl]-2,3-dihydro-[[1H-indene-1,4'-piperidine]-3-carboxylic acid benzyl ester The intermediate from Step B (321 mg, 0.54 mmol) was treated with 4N HCl as in Example 85, Step A. The residue was reacted with BOC-α-methylalanine (137 mg, 0.67 mmol), EDC (154 mg. 0.81 mmol), HOBT (114 mg, 0.81 mmol) and NMM (0.60 ml, 0.54 mmol) according to the procedure described for Example 1, Step A. The title compound (315 mg, 0.46 mmol) was obtained as a white solid after flash chromatography (silica gel, methylene chloride/ethyl acetate 4:1).
Step D:

1'-[2-[[2-amino-2-methyl-1-oxopropyl]amino]5-phenyl-1-oxopentyl]-2,3-dihydrospiro[1H-indene 1,4'-piperidine-3-carboxylic benzyl ester hdyrochloride Diastereomer 1

The intermediate obtained from Step C (241 mg, 0.35 mmol) was reacted as in Example 84, Step C to give the title compound (201 mg, 0.328 mmol) as a white solid.
$^1$HNMR (400 MHz, CDCL$_3$): 9.0–8.8 (m, 2H), 7.85–7.78 (m, ½H), 7.60–7.50 (m, ½H), 7.40–7.08 (m, 13½H), 6.92 (d, ½H), 5.15 (dd, 2H), 4.95–4.85 (m, 1H), 4.57–4.40 (m, 1H), 4.11–4.07 (m, 1H), 3.77–3.67 (m, 1H), 3.25–2.90 (m, 2H), 2.80–2.55 (m, 2H), 2.48–2.25 (m, 2H), 1.90–1.40 (m, 10H).

EXAMPLE 91

1'-[-2-[[-2-amino-2-methyl-1-oxopropyl]amino]-5-phenyl-1-oxopentyl]-2,3-dihydrospiro[1H-indene-1,4'-piperidine]-3-carboxylic acid hydrochloride Diastereomer 1

To a suspension of Pd/C (25 mg, 10 %) in ethanol (3.0 ml ) was added the title compound from Example 90, Step D (147 mg, 0.24 mmol) the reaction mixture was purged with hydrogen and then stirred under a hydrogen filled balloon for 2 h. The mixture was filtered through celite and concentrated to give the title compound (119 mg, 0.22 mmol) as a white solid.
$^1$HNMR (400 MHz, CD$_3$OD): 7.40 (d, 1H), 7.28–7.10 (m, 7½H), 7.02 (d, ⅔H), 4.53–4.45 (m, 1H), 4.12 (m 1H), 3.85 (m, 1H), 3.30–3.25 (m, 1H), 2.94–2.82 (m, 1H), 2.75–2.65 (m, 2H), 2.45–2.35 (m, 2H), 1.90–1.52 (m, 14H).

EXAMPLE 92

1'-[2-[[2-amino-2-methyl-1-oxopropyl]amino]5-phenyl-1-oxopentyl]-2,3-dihydrospiro[1H-indene 1,4'-piperidine-3-carboxylic benzyl ester hydrochloride Diastereomer 2

Step A:

1'-[(1,1-dimethylethoxy)carbonyl]-2,3-dihydrospiro[1H-indene-1,4'-piperidine]-3-carboxylic acid benzyl ester The title compound from Example 83 E, Step B (935 mg, 2.8 mmol) was coupled to benzyl alcohol (0.60 ml, 5.6 mmol) in methylene chloride according to the procedure described in Example 83 D, Step B. The title compound (1.0 g, 2.4 mmol) was obtained after flash chromatography (silica gel, hexane/ethyl acetate 7:1).
Step B:

1'-[2-[[(1,1-dimethylethoxylcarbonyl]amino]-5-phenyl-1-oxopentyl]-2,3-dihydrospiro[1H-indene-1,4'-piperidine]-3-carboxylic acid benzyl ester The intermediate from Step A (368 mg, 0.87 mmol) was treated with 4N HCl as in Example 85, Step A. The residue was reacted with the compound prepared in Example 73, Step B (327.6 mg, 0.869 mmol), EDC (248.9 mg. 1.3 mmol), HOBT (183.3 mg, 1.3 mmol) and NMM (0.95 ml, 0.87 mmol) according to the procedure described for Example 1, Step A. The title compound (323 mg, 0.54 mmol) was obtained as a white solid after flash chromatography.
Step C:

1'-[2-[[2-[[(1,1-dimethylethoxy)carbonyl]amino]-2-methyl-1-oxo
propyl]amino]-5-phenyl-1-oxopentyl]-2,3-dihydro[1H-indene-1,4'-piperidine]-3-carboxylic acid benzyl ester The intermediate from Step B (311 mg, 0.521 mmol) was treated with 4N HCl as in Example 85, Step A. The residue was reacted with BOC-α-methylalanine (132 mg, 0.65 mmol), EDC (149 mg, 782 mmol), HOBT (110 mg, 0.78 mmol) and NMM (0.57 ml, 0.52 mmol) according to the procedure described for Example 1, Step A. The title compound (239 mg, 0.35 mmol) was obtained as a white solid after flash chromatography.
Step D:

1'[2-[[2-amino-2-methyl-1-oxopropyl]amino]-5-phenyl-1-oxopentyl]-2,3-dihydrospiro[1H-indene 1,4'-piperidine-3-carboxylic benzyl ester hydrochloride Diastereomer 2

The intermediate obtained from Step C (201 mg, 0.297 mmol) was reacted as in Example 84, Step C to give the title compound (162 mg, 0.265 mmol) as a white solid.

$^1$HNMR (400 MHz, CDCL$_3$): 8.9–8.80 (m, 2H), 7.75–7.70 (m, ½H), 7.60–7.55 (m, 1/2H), 7.38–7.05 (m, 13½H), 6.93 (d, ½H), 5.20–5.14 (m, 2H), 4.4.93–4.84 (m, 1H), 4.51–4.41 (m, 1H), 4.15–4.00 (m, 1H), 3.80–3.65 (m, 1H), 3.20–2.99 (m, 1H), 2.75–2.55 (m, 2H), 2.45–2.25 (m, 1H), 2.35–2.21 (m, 1H), 2.0–1.60 (m, 12 1/2H), 1.50–1.35 (m, 3/2).

EXAMPLE 93

1'-[-2-[[-2-amino-2-methyl-1-oxopropyl]amino]-5-phenyl-1-oxopentyl]-2,3-dihydrospiro[1H-indene-1,4'-piperidine]-3-carboxylic acid hydrochloride Diastereomer 2

To a suspension of Pd/C (25 mg, 10%) in ethanol (3.0 ml) was added the title compound from Example 92, Step D (138 mg, 0.225 mmol) the reaction mixture was purged with hydrogen and then stirred under a hydrogen filled balloon for 2 h. The mixture was filtered through celite and concentrated to give the title compound (110.6 mg, 0.21 mmol) as a white solid.

$^1$HNMR (400 MHz, CD$_3$OD): 7.40–7.39 (m, 1H), 7.28–7.01 (m,8H), 4.49–4.45 (m,1H), 4.13–4.07 (m, 1H), 3.92–3.80 (m, 1H), 3.33–3.21 (m, 1H), 3.01–2.83 (m, ⅔H), 2.75–2.60 (m, ⅗H), 2.49–2.38 (m, ⅔H), 2.02 (dt, ⅓H), 1.76–1.30 (m, 15H).

EXAMPLE 94

1'-[2(R)-[[(2-amino-2-methyl-1-oxopropyl)amino]-3-(indole-3-yl)-1-oxopropyl]-2,3-dihydrospiro[1H-indene-1,4'-piperidine]-3,3-dicarboxylic acid diethyl ester hydrochloride Step A:

1-'[(1,1-dimethylethoxy)carbonyl]-2,3-dihydrospiro[1H-indene-1,4'-piperidine]-3,3-dicarboxylic acid diethyl ester A sample of the title compound from Example 83B, Step A, was hydrogenated over Pd/C in EtOH. The catalyst was removed and the solvent was evaporated.

To a solution of the residue (750 mg, 2.08 mmol) in THF at 0° C. was added a solution of potassium bis(trimethylsilyl)amide (4.5 ml,2.28 mmol) and the reaction mixture was stirred for 1.5 h. Ethyl chloroformate (2.28 mmol) was added and the mixture was strirred for 3 h. The reaction was quenched with 1N HCL and extracted with ethyl acetate (3×1 vol). The combined organic layers were washed with saturated sodium chloride and dried over magnesium sulfate. Filteration followed by concentration provided the title compound (789 mg, 1.83 mmol).
Step B:

1'-[2(R)-[[2-[[(1,1-dimethylethoxy)carbonyl]amino]-2-methyl-1-oxopropyl]-2,3-dihydrospiro[1H-indene-1,4'-piperidine]-3,3-dicarboxylic acid diethyl ester The intermediate from Step A (130 mg, 0.301 mmol) was treated with 4N HCl as in Example 85, Step A. The residue was reacted with the intermediate from Example 4, Step D (128.7 mg, 0.45 mmol), EDC (86 mg. 0.451 mmol), HOBT (65 mg, 0.451 mmol) and NMM (0.036 ml, 0.331 mmol) according to the procedure described for Example 1, Step A. The title compound (114 mg, 0.162 mmol) was obtained as a white solid after flash chromatography.
Step C:

1'-[2(R)-[[(1,1-dimethylethoxy)carbonyl]amino]-2-methyl-1-oxopropyl]amino]-3-indole-3-yl)-1-oxopropyl]-2,3-dihydrospiro[1H-indene-1,4'-piperidine]-3,3-dicarboxylic acid diethyl ester hydrochloride The intermediate obtained from Step B (101 mg, 0.143 mmol) was reacted as in Example 84, Step C to give the title compound (84.8 mg, 0.132 mmol) as a white solid.

$^1$HNMR (400 MHz, CD$_3$OD mixture of conformers): 7.62 (d, ⅔H), 7.54 (d, ⅓H), 7.45–7.01 (m, 7 ⅓H), 6.63 (d, ⅔H), 5.26–5.22 (m,⅔H), 5.20–5.16 (m, ⅓H), 4.38–4.37 (m, 1H), 4.20–4.10 (m, 3H), 3.77–3.73 (m, 1H), 3.30–3.15 (m), 3.05–3.00 (m), 2.69–2.50 (m), 1.62+1.50 (s, 6H total), 1.30–1.15 (m, 6H), 1.00–0.87 (m,), 0.12 (dt, ⅔H). FAB-MS 603 M+1).

EXAMPLE 95

N-[1(R)[[3-(pyridin-2-yl)spiro[1H-indene-1,4'-piperidine]-1'-yl]carbonyl-4-phenylbytyl]-2-amino-2-methylpropanamide hydrochloride Step A:

3-(pyridin-2-yl)spiro[1H-indene-1,4'-piperidine]-1'-carboxylic acid 1,1-dimethylethyl ester To a solution of the intermediate obtained from Example 80, Step A (502 mg, 1.15 mmol) and 2-trimethyl stannyl pyridine (332 mg, 1.38 mmol) in toluene (10 ml) was added triphenylphosphine (30.3 mg, 0.115 mmol) and tetrakis(triphenylphosphine)palladium (132 mg, 0.114 mmol). The reaction was refluxed for 12 h, cooled to room temperature and diluted with ethyl acetate and water. The aqueous layer was extracted with ethyl acetate and the combined organic layers were dried over anhydrous sodium sulfate, filtered and concentrated. Flash chromatography of the residue (silica gel, hexane/ethyl acetate 4:1) gave the title compound (128 mg, 0.353 mmol).
Step B:

[1-[[3-(pyridin-2-yl)spiro[1H-indene-1,4'-piperidine]-1'-yl]carbonyl]-4-phenylbutyl]carbamic acid 1,1-dimethylethyl ester The intermediate from Step A (120 mg, 0.33 1 mmol) was treated with 4N HCl as in Example 85, Step A. The residue was reacted with the compound prepared in Example 73, Step B (97 mg, 0.33 mmol), EDC (94.7 mg. 0.496 mmol), HOBT (67 mg, 0.49 mmol) and NMM (0.076 ml, 0.66 mmol) according to the procedure described for Example 1, Step A. The title compound (123 mg, 0.23 mmol) was obtained as a white solid after flash chromatography.
Step C:

N-[(R)-[[3-pyridin-2-yl)spiro[1H-indene-1,4'-piperidin]-1'-yl]carbonyl]-4-phenylbytyl-2-[[(1,1-dimethylethoxy)carbonyl]amino]-2-methylpropanamide The intermediate from Step B (120 mg, 0.223 mmol) was treated with 4N HCl as in Example 82, Step A. The residue was reacted with Boc-α-methylalanine (54 mg, 0.267 mmol), EDC (64 mg. 0.335 mmol), HOBT (47 mg, 0.335 mmol) and NMM (0.51 ml, 0.467 mmol) according to the procedure described for Example 1, Step A. The title compound (108 mg, 0.17 mmol) was obtained as a white solid after flash chromatography.
Step D:

N-[1(R)[[3-(pyridin-2-yl)spiro[1H-indene-1,4'-piperidine]-1'-yl]carbonyl-4-phenylbytyl]-2-amino-2-methylpropanamide hydrochloride The intermediate obtained from Step C (103 mg, 0.16 mmol) was reacted as in Example 84, Step C to give the title compound (83.1 mg, 0.15 mmol) as a white solid. $^1$HNMR (400 MHz, CD$_3$OD): 8.99–8.91 (m, 1H), 8.77–8.73 (m, 1H), 8.41 (d, 1H), 8.13–8.10 (m, 1H), 7.86(d, 1H), 7.61–7.10 (m, 9H), 4.65–4.60 (m, I H), 4.14–4.02 (m, 1H), 3.73–3.52 (m, 2H), 3.22–3.15 (m, 1H), 2.75–2.62 (m, 2H), 2.45–2.36 (m, 1H), 2.22–1.44 (m, 13H). FAB-MS 523 (M+1).

EXAMPLE 96

N-[1(R)-[[1,2,3,5,6,7,2',3'-octahydrospiro[4H-azepine-4,1'-[1H]inden]-1-yl]carbonyl]-2-(indole-3-yl)ethyl]-2-[[1,1-dimethylethoxy)carbonyl]-amino-2-methylpropanamide Step A:

2',3'-dihydro-4,4-ethylenedioxyspiro[cyclohexane-1,1'-[1H]indene]

To a solution of indene (0.84 g, 7.3 mmol) in THF at 0° C. was added lithium bis(trimethylsilyl)amide (14.6 ml, 14.6 mmol). After 30 minutes of stirring the anion was cannulated into a solution of 1,5-diiodo-3-ethylenedioxypentane (2.79 g, 7.3 mmol) prepared as described in *J. Am. Chem. Soc.* 1990, 9001–9003). The reaction mixture was stirred for 1 h and then warmed to room temperature over night. The reaction mixture was concentrated and purified by flash chromatography (silica gel, hexane/ethyl acetate 10:1) to give the title compound (1.2 g, 4.9 mmol).
Step B:

2',3'-dihydro-4-oxospiro[cyclohexane-1,1'-[1H]indene

The title compound (1.2 g, 4.95 mmol) was dissolved in acetone (22 ml) and water (1 ml) and PPTS (0.37 g, 1.49 mmol were added. The mixture was heated to reflux until most of the starting material had been consumed by TLC. The mixture was cooled, concentrated, and 10% sodium carbonate was added. The aqueous layer was extracted with ether. The ether extracts were dried over sodium sulfate, filtered, and concentrated. Flash chromatography (silica gel, hexanes/ether 5:1) gave the title compound (0.95 g, 4.8 mmol).
Step C:

1,2,3,5,6,7,2',3'-octahydrospiro[4H-azepine-4,1'-[1H]-indene]-1-carboxylic acid phenylmethyl ester The intermediate obtained in Step B (100 mg, 0.5 mmol) was hydrogenated over Pd/C in methanol. The residue was then dissolved in chloroform and a solution of hydrazic acid (2.5 eq) was added followed by concentrated H$_2$SO$_4$. After stirring overnight the mixture was made basic with 50% NaOH and the aqueous layer was extracted with ethyl acetate. The organic layer was was dried over magnesium sulfate, filtered, and concentrated. The crude product (56.3 mg, 0.26 mmol) was dissolved in THF and treated with LAH (0.497 ml, 1M THF, 0.497 mmol). After stirring over night TLC analysis showed some starting material remained so the mixture was heated to reflux. After 3 h there was still starting material present so another equivalent of LAH was added. After another hour the reaction was cooled and then quenched with 1N KOH. The aqeous layer was extracted with ethyl acetate. The combined organic layers were dried over anhydrous sodium sulfate, filtered and concentrated to give a complex mixture of products (49.6 mg). Purification was not possible so the amine was protected by treatment with excess CBZCL and triethylamine in methylene chloride. Flash chromatograpy (silica gel, hexanes:ethyl acetate 3:1) gave the title compound (25.3 mg, 0.075 mmol).
Step D:

N-[1(R)-[[1,2,3,5,6,7,2',3'-octahydrospiro[4H-azepine-4,1'-[1H-inden]-1-yl]carbonyl]-2-(indole-3-yl)ethyl]-2-[[(1,1-dimethylethoxy)carbonyl]amino-2-methylpropanamide The intermediate obtained in Step C (21.3 mg, 0.063 mmol) was hydrogenated in ethanol over Pd/C. The residue obtained after filtration and concentration was reacted with the compound prepared in Example 4 Step D (20.6. mg, 0.053 mmol), EDC (13.9 mg, 0.073 mmol), and HOBT (9.8 mg, 0.073 mmol) according to the procedure described in Example 1, Step A. Flash chromatography (silica gel, methylene chloride:ethyl acetate 3:1) gave the title compound (18.2 mg, 0.31 mmol).

Step E:

N-[(R)-[[1,2,3,5,6,7,2'-3'octahydrospiro[4H-azepine-4,1'-[1H]indene]-1 yl]carbonyl-2-(indole-3-yl)ethyl-2-amino-2-methylpropanamide hdyrochloride The intermediate obtained in Step D (15.3 mg, 0.026 mmol) was treated with 4N HCL/dioxane according to the procedure described in Example 84, Step C. The title compound (11.9 mg, 0.023 mmol) was obtained as a white solid. FAB-MS 473 (M+1).

EXAMPLE 97

N-[1(R)-[[3-[[(methanesulfonyl)amino]carbonyl]-2,3-dihydrospiro[1H-indene-1,4'-piperidin]-1'-yl]carbonyl]-2-(indole-3-yl)ethyl]-2-amino-2-methylpropanamide trifluoroacetic acid salt Step A:

3-[[(methanesulfonyl)amino]carbonyl]-2,3-dihydrospiro[1H-indene-1,4'-piperidine]-1'-carboxylic acid 1,1-dimethyl-ethyl ester To a solution of the title compound from Example 83B, Step B (335 mg, 1.02 mmol), in THF (4 ml) and DMF (0.05 ml) at 0° C. was added sodium hydride (33.6 mg, 1.12 mmol) and the mixture was stirred for 30 minutes. Oxalyl chloride (0.75 ml of 2N, 150 mmol) was added to the mixture and stirred for 1 hour. The mixture was concentrated and the residue was suspended in THF. To a solution of methanesulfonamide (194 mg, 1.12 mmol) in THF was added n-butyl lithium (0.63 ml, 1.27 mmol) the mixture was stirred for 10 minutes. The acid chloride/THF suspension was then cannulated into the sulfonamide anion and the mixture was stirred over night. The reaction was quenched with 1N HCl and extracted with ethyl acetate (3×1 vol). The ethyl acetate layer was washed with saturated sodium chloride, dried over anhydrous magnesium sulfate, filtered and concentrated. Purification by MPLC (LH$_{20}$ column, methanol) provided the title compound (242 mg, 0.586 mmol).

Step B:

3-[[methanesulfonyl)amino]carbonyl]-[1H-indene-1,4'-piperidine]1'-carboxylic acid 1,1-dimethylethyl ester The title compound from Step A (238 mg, 058 mmol) was added to a suspension of Pd/C (40 mg), purged with hydrogen and stirred under a hydrogen balloon for 3 h. The mixture was filtered through celite and concentrated to give the title compound (231 mg, 0.586 mol).

Step C:

N-[1(R)-[[3-[[(methanesulfonyl)amino]carbonyl]-2,3-dihydrospiro[1H-indene-1,4'-piperidin]-1'-yl]carbonyl]-2-(indole-3-yl)ethyl]-2-[[(1,1-dimethyl-ethoxy)carbonyl]amino]-2-methylpropanamide A portion of the title compound from Step B (87 mg, 0.213 mmol) was stirred in a 1:1 mixture of TFA/methylene chloride for 1 h and then concentrated and azeotoped from toluene (3×5 ml). The residue was dissolved in methylene chloride and treated with EDC (162 mg, 0.85 mmol), HOBT (114 mg, 0.85 mmol), NMM (0.62 ml, mmol) and the compound prepared in Example 4, Step D (220 mg, 0.56 mmol), according to the procedure described for Example 1, Step A except that the reaction was worked up with 1N HCl instead of with saturated sodium bicarbonate. Purification by MPLC (LH$_{20}$ column, methanol) gave the title compound (119 mg, 0.17 mmol).

Step D:

N-[1(R)-[[3-[[(methanesulfonyl)amino]carbonyl]-2,3-dihydrospiro[1H-indene-1,4'-piperidin]-1'-yl]carbonyl]-2-(indole-3-yl)ethyl]-2-amino-2-methylpropananmide trifluoroacetic acid salt The title compound from Step C (51.5 mg, 0.075 mmol) was dissolved in a 1:1 mixture of TFA and methylene chloride and stirred for 1.5 hours. The solution was concentrated and the residue was azeotroped from toluene. Purification by MPLC (LH$_{20}$ column, methanol) gave the title compound (37.3 mg, 0.053 mol).

$^1$HNMR (400 MHz, CD$_3$OD 2:1 conformers; 1:1 mixture of diastereomers): 7.64–7.61 (m), 7.54 (d), 7.44 (d,), 7.39–7.35 (m), 7.28–7.00 (m), 6.69–6.63 (m), 5.27–5.22 (m), 5.21–5.17 (m), 4.45–4.30 (m), 4.05–3.94 (m), 3.85–3.70 (m),3.24 (s), 3.21 (s),3.06–2.97 (m), 2.66–2.57 (m), FAB-MS 580 (M+1).

EXAMPLE 98

1'-[2(R)-[(2-amino-2-methyl-1-oxopropyl)amino]-5-phenyl-1-oxopentyl]-2,3-dihydrospiro[1H-indene-1,4'-piperidine]-3-acetic acid ethyl ester hydrochloride
Diastereomer 2

Step A:

3-[[(ethoxy)carbonyl]methylene]-2,3-dihydrospiro[1H-indene-1,4'-piperidine]-1'-carboxylic acid 1,1-dimethylethylester To a solution of triethyl phosphonoacetate (41.9 mmol, 9.39 g) in THF (100 ml) at 0° C., was added potassium bis(trimethylsilyl) amide (50.2 mmol, 0.5M solution). The mixture was stirred at 0° C. for 45 min. A solution of the intermediate from Example 4 Step A (10.51 g, 34.9 mmol) in THF (200 ml) was added. The whole was stirred at 0° C. for an hour and at room temperature for 70 hr. Saturated aqueous ammonium chloride (50 ml) was added and the THF was removed. The aqueous layer was extracted with ethyl acetate (3×150 ml). The combined ethyl actate layers were washed with brine, and dried over sodium sulfate. The title compound was obtained as a colorless oil by evaporation and purification by flash chromatography (EtOAc:hexane=2:8) (5.74 g, 44%).

$^1$H NMR (CDCl$_3$, 400 MH): δ1.28 (t, 3H), 1.46 (m, 2H), 1.49 (s, 9H), 1.82 (m, 2H), 2.85 (s, 0.8H), 2.93 (m, 2H), 3.24 (s, 1.2H), 4.14 (m, 2H), 4.20 (q, 2H), 5.96 (m, 0.4H), 6.31 (m, 0.6H), 7.27 (m, 2H), 7.39 (m, 1H), 7.59 (d, 0.6H), 8.78 (d, 0.4H).

Step B:

1'-[(1,1-dimethylethoxy)carbonyl]-2,3-dihydrospiro[1H-indene-1,4'-piperidinel-3-acetic acid A mixture of the title compound (4.54 g, 12.2 mmol) from Step A and palladium on carbon (0.50 g) in MeOH/EtOAc (100 ml) was hydrogenated under a hydrogen balloon for 2 hr. The mixture was then filtered and evaporated. The residue and NaOH (0.98 g, 24.4 mmol) were dissolved in a mixture of MeOH (40 ml) and water (20 ml), and the solution was stirred at room temperature for 20 hr. Methanol was removed and the aqueous solution was diluted with water (50 ml). The solution was acidified with 1N HCl to pH-3. The resulting cloudy solution was extracted with EtOAc (3×150 ml). The combined EtOAc layers were washed with brine, and dried over sodium sulfate. A white solid was obtained after evaporation (3.73 g, 89%).

$^1$H NMR (CDCl$_3$, 400 MH): δ1.49 (s, 9H), 1.55 (m, 4H), 2.04 (m, 1H), 2.47 (dd, 1H), 2.61 (dd, 1H), 2.92 (m, 2H), 2.98 (dd, 1H), 3.63 (m, 1H), 4.08 (m, 2H), 7.18 (4H).

Step C:

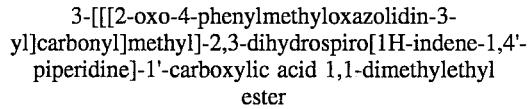

To a well stirred solution of the title compound from Step B (1.00 g, 2.90 mmol) in THF (20 ml) at −78° C. for 5 min, were added triethyl amine (0.49 ml, 3.4 mmol) and trimethylacetyl chloride (0.39 ml, 3.19 mmol). The resulting slurry was stirred at −78° C. for 5 min and 0° C. for 1 hr. Meanwhile, a separate solution of (R)-(+)-4-benzyl-2-oxazolidinone (0.57 g, 3.19 mmol) in THF (10 ml) was cooled to −78° C., followed by addition of n-BuLi (3.84 mmol, 2.39 ml, 1.6M solution), and was stirred at −78° C. for 10 min. The solution was added to the slurry at −78° C. and the whole was stirred at −78° C. for 40 min and 0° C. for 30 min. Saturated aqueous ammonium chloride (10 ml) was added and the THF was removed. The aqueous was extracted with EtOAc (3×50 ml). The combined EtOAc layers were washed with brine and dried over sodium sulfate. Two pure diastereomers were obtained by MPLC (EtOAc/hexane 2:8) (0.29 g of diastereomer 1 and 0.436 g of diastereomer 2).

HPLC ((Rainin Microsorb Si 80-125-C5,1 mL/min, hexane/isopropanol gradient 3% to 5% 0–10 min;5%–50% 10–15min;50 % 15–20 min; 50%–3% 20–25min. D$_1$ retention time 12.6 min; D$_2$ retention time 14.1 min.

Diastereomer 1 $^1$H NMR (CDCl$_3$, 400 MH): δ7.25 (m, 9H), 4.72 (m, 1H), 4.22 (m, 2H), 4.10 (m, 2H), 3.70 (m, 1H), 3.52 (dd, 1H), 3.33 (dd, 1H), 3.11 (dd, 1H), 2.95 (m, 2H), 2.79 (dd, 1H), 2.62 (dd, 1H), 2.01 (m, 1H), 1.59 (m, 4H), 1.47 (s, 9H).

Diastereomer 2 $^1$H NMR (CDCl$_3$, 400 MH): δ1.47 (s, 9H), 1.55 (m, 5H), 2.02 (m, 1H), 2.63 (dd, 1H), 2.79 (dd, 1H), 2.90 (m, 2H), 3.03 (dd, 1H), 3.36 (dd, 1H), 3.58 (dd, 1H), 3.75 (m, 1H), 4.10 (m, 2H), 4.20 (m, 2H), 4.71 (m, 1H), 7.25 (m, 9H).

Step D:

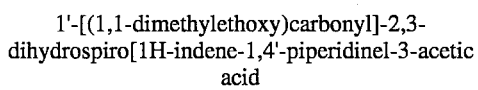

To a solution of benzyl alcohol (1.24 ml, 11.9 mmol) in THF (50 ml) at 0° C., was added n-BuLi (8.96 mmol, 5.6 ml, 1.6M). The mixture was stirred at 0° C. for 15 min. A solution of the title compound (3.00 g, 6.0 mmol) from Step C in THF (50 ml) was added and the whole was stirred at 0° C. for 3 hr. Saturated aqueous ammonium chloride (20 ml) was added and THF was removed. The organic was extracted with EtOAc (3×150 ml). The combined EtOAc layers were washed with brine, and dried over sodium sulfate. A colorless oil was obtained by flash chromatography (EtOAc:hexane=1:9); [α]$_D$=+7.07° (c=1.06, CH$_2$Cl$_2$). The oil was dissolved in EtOH (100 ml) and charged with Pd/C (0.52 g) and hydrogen (balloon). The mixture was stirred at room temperature for 1 hr. The titled compound was obtained by filtration and evaporation in 97% yield (2.00 g) as a white solid.

$^1$H NMR (CDCl$_3$, 400 MH): δ1.47 (s, 9H), 1.57 (m, 4H), 2.04 (m, 1H), 2.47 (dd, 1H), 2.61 (dd, 1H), 2.93 (m, 2H), 3.00 (m, 1H), 3.64 (m, 1H), 4.07 (m, 2H), 7.20 (m, 4H).

Step E:

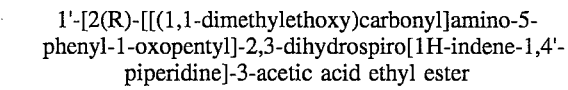

A solution of the title compound (2.00 g, 5.79 mmol) from Step D in EtOH (50 ml) and thionyl chloride (5 ml, 57.9 mmol) was stirred at room temerature for 20 hr. The solution was concentrated by vacuum and azeotroped from toluene (2×2 ml). To a mixture of the residue, (HOBT) (1.57 g, 11.59 mmol), (2R)-N-boc-2-amino-5-phenylpentanoic acid (Example 73, Step B) (1.70 g, 5.79 mmol), 4-methylmorpholine (0.76 ml, 6.96 mmol) in methylene chloride (100 ml) at 0° C., 1- and EDC (2.22 g, 11.59 mmol) was added. The mixture was stirred at room temperature for 2 hr and then diluted with methylene chloride (100 ml). The solution was washed with water (50 ml), brine, and dried over sodium sulfate. The titled compound was purified by flash chromatography (EtOAc:hexane=3:7) as a colorless thick oil (72%, 2.28 g).

$^1$H NMR (CDCl$_3$, 400 MH): δ1.25 (m, 3H), 1.43 (m, 9H), 1.52 (m, 5H), 1.65 (m, 4H), 1.89 (m, 0.5H), 2.06 (m, 0.5H), 2.40 (m, 1H), 2.60 (m, 2H), 2.76 (m, 1H), 2.88 (m, 1H), 3.05 (t, 0.5H), 3.22 (t, 0.5H), 3.61 (m, 1H), 3.73 (d, 0.5H), 3.81 (d, 0.5H), 4.20 (m, 2H), 4.60 (m, 2H), 5.48 (m, 1H), 7.18 (m, 9H).

Step F:

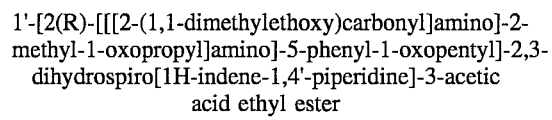

A mixture of the title compound (2.28 g, 4.15 mmol) from Step E and hydrogen chloride (10 ml, 4M in dioxane) in EtOH (5 ml) was stirred at room temperature for 3 hr. The solvent was removed. To a mixture of the residue, BOC-α-methylalanine (0.84 g, 4.15 mmol), HOBT (0.84 g, 6.2 mmol), 4-methylmorpholine in methylene chloride (50 ml) at 0° C., and EDC (1.19 g, 6.20 mmol) was added. The whole was stirred at room temperature for 20 hr. The mixture was washed with water, brine and dried over sodium sulfate. The title compound was purified by flash column (EtOAc:hexane=1:1) to give a white solid (80%, 2.10 g).

$^1$H NMR (CDCl$_3$, 400MH): δ1.25 (m, 3H), 1.40 (s, 9H), 1.52 (m, 14H), 1.72 (m, 2H), 1.88 (m, 0.5H), 2.05 (m, 0.5H), 2.40 (m, 1H), 2.58 (m, 2H), 2.70 (m, 1H), 2.89 (m, 1H), 3.04 (t, 0.5H), 3.21 (t, 0.5H), 3.62 (m, 1H), 3.75 (d, 0.5H), 3.85 (d, 0.5H), 4.18 (m, 2H), 4.52 (t, 1H), 4.95 (m, 2H), 7.18 (m, 9H).

Step G:

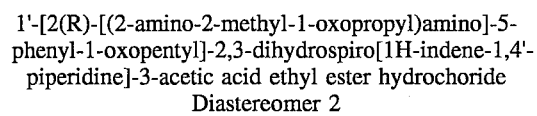

A solution of the compound (1.60 g, 2.20 mmol) from Step F and HCl in dioxane (20 ml) was stirred at room temperature for 1 hr. The solvent was removed to afford a white solid (100%, 1.44 g). [α]$_D$=+7.8° (c=0.90, CH$_3$OH).

$^1$H NMR (CD$_3$OD, 400 MH): δ1.28 (m, 3H), 1.52 (m, 4H), 1.58 (m, 6H), 1.75 (m, 4H), 1.90 (m, 0.5H), 2.18 (m, 0.5H), 2.47 (m, 1H), 2.68 (m, 3H), 2.83 (m, 1H), 2.92 (m, 1H), 3.20 (t, 0.5H), 3.30 (t, 0.5H), 3.61 (m, 1H), 3.81 (d, 0.5H), 3.90 (d, 0.5H), 4.17 (m, 2H), 4.45 (t, 1H), 4.88 (m, 1H), 7.20 (m, 9H). FAB-MS: 534 (M+1)

EXAMPLE 99

1'-[2(R)-[(2-amino-2-methyl-1-oxopropyl)amino]-5-phenyl-1-oxopentyl]-2,3-dihydrospiro[1H-indene-1,4'-piperidine]-3-acetic acid ethyl ester hydrochloride Diastereomer 1

Step A:

1'-[(1,1-dimethylethoxy)carbonyl]-2,3-dihydrospiro[1H-indene-1,4'-piperidine]-3-acetic acid The benzyl ester of the title compound was obtained from diastereomer 1 of Example 98 Step C:[α]$_D$=−7.00° (c=2.53, CH$_2$Cl$_2$). The title compound was obtained from the benzyl ester as described in Example 98, Step D.

$^1$H NMR (CDCl$_3$, 400 MH): δ7.20 (m, 4H), 4.10 (m 2H), 3.62 (m, 1H), 2.94 (dd, 1H), 2.90 (m, 2H), 2.62 (dd, 1H), 2.45 (dd, 1H), 2.01 (m, 1H), 1.55 (m, 4H), 1.47 (s, 9H).

Step B:

1'-[2(R)-[[(1,1-dimethylethoxy)carbonyl]amino-5-phenyl-1-oxopentyl]-2,3-dihydrospiro[1H-indene-1,4'-piperidine]-3-acetic acid ethyl ester The title compound was obtained in 78% yield from Step A using the procedure described in Example 98, Step E.

$^1$H NMR (CDCl$_3$, 400 MH): δ7.20 (m, 8H), 7.10 (m, 0.5H), 6.92 (m, 0.5H), 5.49 (m, 1H), 4.58 (m, 2H), 4.20 (m, 2H), 3.76 (m, 1H), 3.61 (m, 1H), 3.12 (m, 1H), 2.89 (m, 1H), 2.78 (m, 1H), 2.68 (m, 1H), 2.58 (m, 1H), 2.39 (m, 1H), 1.70 (m, 4H), 1.55 (m, 6H), 1.42 (s, 9H), 1.25 (m, 3H).

Step C:

1'-[2(R)-[[[2-(1,1-dimethylethoxy)carbonyl]amino]-2-methyl-1-oxopropyl]amino]-5-phenyl-1-oxopentyl]-2,3-dihydrospiro[1H-indene-1,4'-piperidine]-3-acetic acid ethyl ester The title compound was obtained in 87% yield from Step B using the procedure described in Example 98, Step F.

$^1$H NMR (CDCl$_3$, 400 MH): δ7.20 (m, 8.5H), 6.92 (m, 0.5H), 4.98 (m, 2H), 4.50 (m, 1H), 4.20 (m, 2H), 3.79 (m, 1H), 3.61 (m 1H), 3.12 (m, 1H), 2.90 (m, 1H), 2.78 (m, 1H), 2.67 (m, 1H), 2.57 (m, 1H), 2.39 (m, 1H), 1.98 (m, 0.5H), 1.75 (m, 4.5H), 1.50 (m, 12H), 1.42 (s, 9H), 1.28 (m, 3H).

Step D:

1'-[2(R)-[(2-amino-2-methyl-1-oxopropyl)amino]-5-phenyl-1-oxopentyl]-2,3-dihydrospiro[1H-indene-1,4'-piperidine]-3-acetic acid ethyl ester hydrochoride Diastereomer 1

The title compound was obtained in 94% yield from Step C using the procedure described in Example 98, Step G.

$^1$H NMR (CD$_3$OD, 400 MH): δ7.23 (m, 8H), 7.11 (m, 0.5H), 6.97 (m, 0.5H), 4.85 (m, 2H), 4.47 (m, 1H), 4.19 (m, 2H), 3.88 (m, 1H), 3.62 (m, 1H), 3.25 (m, 1H), 2.88 (m, 2H), 2.75 (m, 3H), 2.48 (m, 1H), 1.99 (m, 0.5H), 1.77 (m, 4.5H), 1.52 (m, 12H), 1.28 (m, 3H). FAB-MS: 534 (M+1)

EXAMPLE 100

1'-[2(R)-[(2-amino-2-methyl-1-oxopropyl)amino]-5-phenyl-1-oxopentyl]-2,3-dihydrospiro[1H-indene-1,4'-piperidine]-3-acetic acid hydrochloride Diastereomer 1

A solution of the intermediate 12 (0.010 g, 0.015 mmol) from Example 99, Step C and NaOH (0.19 g, 4.75 mmol) in H20/EtOH (10 ml) was stirred at room temperature for 20 hr. The EtOH was removed and the aqueous was adjusted pH-3 with 1N HCl. The cloudy solution was extracted with EtOAc (3×15 ml). The combined EtOAc layers were washed with brine, dried over sodium sulfate. The solvent was evaporated and the residue was treated with HCl (1 ml, 4M in dioxane) for 20 hr. A white solid was obtained after evaporation.

$^1$H NMR (CD$_3$OD, 400 MH): a 7.21 (m, 8H), 7.10 (m, 0.5H), 6.96 (m, 0.5H), 4.45 (m, 1H), 3.89 (m, 1H), 3.65 (m, 1H), 3.30 (m, 1H), 2.90 (m, 2H), 2.68 (m, 3H), 2.40 (m, 1H), 2.00 (m, 0.5H), 1.75 (m, 4.5H), 1.60 (m, 12H).

EXAMPLE 101

1'-[2(R)-[2-amino-2-methyl-1-oxopropyl)amino]-5-phenyl-1-oxopentyl]-2,3-dihydrospiro[1H-indene-1,4'-piperidine]-3-acetic acid benzyl ester hydrochloride Diastereomer 2

Step A:

1'-[(1,1-dimethylethoxy)carbonyl]-2,3-dihydrospiro[1H-indene-1,4'-piperidinel-3-acetic acid benzyl ester The title compound was obtained in 65% yield from diastereomer 2 obtained in Example 98 Step C using the procedure described in the first half part of Example 98, Step D.

$^1$H NMR (CDCl$_3$, 400 MH): δ7.34 (m, 5H), 7.15 (m, 4H), 5.17 (d, 2H), 4.06 (m, 2H), 3.64 (m, 1H), 2.95 (dd, 1H), 2.88 (m, 2H), 2.00 (dt, 1H), 1.50 (m, 4H), 1.46 (s, 9H).

Step B:

1'-[2(R)-[[(1,1-dimethylethoxy)carbonyl]amino]-5-phenyl-1-oxopentyl]-2,3-dihydrospiro[1H-indene-1,4'-piperidine]-3-acetic acid benzyl ester The intermediate obtained in Step A was stirred in 4N HCl/dioxane for 1 hr. and concentrated and azeotroped from toluene. The residue was coupled to (D)-N-BOC-2-amino-5-phenyl-pentanoic acid using HOBT, NMM and EDC in methylenechloride to give the title compound.

$^1$H NMR (CDCl$_3$, 400 MH): δ7.18 (m, 14H), 5.47 (m, 1H), 5.18 (m, 2H), 4.65 (m, 1H), 4.52 (m, 1H), 3.80 (m, 0.5H), 3.70 (m, 0.5H), 3.61 (m, 1H), 3.18 (m, 0.5H), 2.95 (m, 1.5H), 2.55 (m, 3H), 2.05 (m, 0.5H), 1.86 (m, 0.5H), 1.70 (m, 2H), 1.54 (m, 8H), 1.46 (d, 9H).

Step C:

1'-[2-[[2-[[(1,1-dimethylethoxy)carbonyl]amino]-1-oxopropyl]amino]-5-phenyl-1-oxopentyl]-2,3-dihydrospiro[1H-indene-1,4'-piperidine-3-acetic acid benzyl ester The title compound was obtained in 84% yield from the intermediate prepared in Step B using the procedure described in Example 98, Step F.

$^1$H NMR (CDCl$_3$, 400 MH): δ7.20 (m, 14H), 5.19 (m, 2H), 5.00 (s, 1H), 4.92 (m, 1H), 4.50 (t, 1H), 3.82 (d, 0.5H), 3.74 (d, 0.5H), 3.61 (m, 1H), 3.15 (t, 0.5H), 2.95 (m, 1.5H), 2.60 (m, 4H), 2.05 (m, 0.5H), 2.88 (m, 0.5H), 2.72 (m, 2H), 0.1.50 (m, 14H), 1.40 (s, 9H).

Step D:

1'-[2(R)-[2-amino-2-methyl-1-oxopropyl)amino]-5-phenyl-1-oxopentyl]-2,3-dihydrospiro[1H-indene-1,4'-piperidine]-3-acetic acid benzyl ester hydrochloride The title compound was obtained from the intermediate prepared in Step C using the procedure described in Example 98, Step G.

$^1$H NMR (CD$_3$OD, 400 MH): δ7.20 (m, 14H), 5.20 (m, 2H), 4.42 (m, 1H), 3.88 (m, 0.5H), 3.80 (m, 0.5H), 3.61 (m, 1H), 3.25 (m, 0.5H), 3.12 (m, 0.5H), 2.99 (m, 1H), 2.70 (m, 2H), 2.56 (m, 2H), 2.18 (m, 0.5H), 1.90 (m, 0.5H), 1.78 (m, 4H), 1.60 (m, 6H), 1.50 (m, 6H).

EXAMPLE 102

1'-[2(R)-[(2-amino-2-methyl-1-oxopropyl)amino]-5-phenyl-1-oxopentyl]-2,3-dihydrospiro[1H-indene-1,4'-piperidine]-3-acetic acid hydrochloride Diastereomer 2

A solution of the title compound from Example 101, Step C (0.155 g, 0.23 mmol) and HCl in dioxane (4M, 2 ml) was stirred at room temperature for 20 hr. The solvent was removed. To a solution of the residue in MeOH (10 ml), was added Pd/C (0.05 g). The mixture was charged with hydrogen (balloon) for 1 hr. A white solid was obtained in 79% yield (0.966 g) after evaporation of the solvent. $[\alpha]_D$+6.9° (c=1.02, CH$_3$OH).

$^1$H NMR (CD$_3$OD, 400 MH): δ7.15 (m, 9H), 4.46 (t, 1H), 3.90 (d, 0.5H), 3.80 (d, 0.5H), 3.61 (m, 1H), 3.25 (m, 1H), 2.89 (m, 2H), 2.68 (m, 3H), 2.39 (m, 1H), 2.18 (m, 0.5H), 1.90 (m, 0.5H), 1.75 (m, 4H), 1.60 (m, 13H).

EXAMPLE 103

1'-[2(R)-[(2-amino-2-methyl-1-oxopropyl)amino]-3-(indole-3-yl)-1-oxopropyl]-2,3-dihydrospiro[1H-indene-1,4'-piperidine]-3-acetic acid ethyl ester hydrochloride Diastereomer 1

Step A:

1'-[2-[[2-[[(1,1-dimethylethoxy)carbonyl]amino]-1-oxopropyyl]amino]-2-(indol-3-yl)ethyl]-2,3-dihydrospiro[1H-indene-1,4'-piperidine-3-acetic acid ethyl ester A solution of the intermediate from from Example 99, Step A (0.069 g, 0.20 mmol) in EtOH (10 ml) was mixed with thionyl chloride and the mixture was stirred for 48 hr. The solvent was removed and the residue was reacted with the intermediate prepared in Example 4, Step D according to the procedure described in Example 98, Step E. The title compound was obtained in 57% yield (0.079 g).

$^1$H NMR (CDCl$_3$, 400 MH, 1:2 conformers): a 8.39 (s, ⅔H), 8.30 (s, ⅓H), 7.76 (d, ⅔H), 7.60 (d, ⅓H), 7.40 (d, ⅔H), 7.33 (d, ⅓H), 7.15 (m, 6H), 6.50 (m, 1H), 5.31 (m, ⅔H), 5.20 (m, ⅓H), 5.00 (m, 1H), 4.40 (m, 1H), 4.12 (m, 2H), 3.48 (m, 2H), 3.18 (m, 2H), 2.82 (m, 2H), 2.61 (m, ⅔H), 2.47 (m, ⅓H), 2.30 (m, 3H), 1.40 (m, 17H), 1.22 (m, 3H), 0.87 (m, 2H), 0.40 (t, 1H).

Step B:

1'-[2(R)-[(2-amino-2-methyl-1-oxopropyl)amino]-3-(indole-3-yl)-1-oxopropyl]-2,3-dihydrospiro[1H-indene-1,4'-piperidine]-3-acetic acid ethyl ester hydrochloride The intermediate from Step A (0.079 g, 0.114 mmol), trifluoroacetic acid (2 ml), anisole (2 ml) and methylene chloride (2 ml) were stirred at room temperature for 20 hr. The solvent was removed and a flash column was carded out (CH$_2$Cl$_2$:MeOH:NH$_4$OH=90:10:1) to give a colorless oil. The oil was treated with HCl (1 ml, 4M in dioxane) and dried to afford a pink solid in 100% yield.

$^1$H NMR (CD$_3$OD, 400 MH, conformers 1:2): a 8.31 (d, ⅔H), 8.23 (d, ⅓H), 7.64 (d, ⅔H), 7.54 (d, ⅓H), 7.47 (d, ⅔H), 7.37 (d, ⅓H).

The title compound was obtained in 76% yield from diastereomer 2 of Example 98, Step D using the procedure described in Example 103, Step A.

$^1$H NMR (CDCl$_3$, 400 MH, rotamer 1:2): δ8.40 (br s, 1H), 7.72 (d, ⅔H), 7.61 (d, ⅓H), 7.17 (m, 6H), 6.54 (m, 1H), 5.22 (m, 1H), 5.04 (br s, 1H), 4.39 (m, 1H), 4.10 (m, 2H), 3.48 (m, 2H), 3.18 (m, 2H), 2.81 (m, 2H), 2.55 (m, 1H), 2.29 (m, 2H), 1.90 (m, ⅓H), 1.40 (m, 16H), 1.25 (m, 6H), 0.88 (m, 1H), 0.00 (m, ⅔H).

Step B:

1'-[2(R)-[(2-amino-2-methyl-1-oxopropyl)amino]-3-(indole-3-yl)-1-oxopropyl]-2,3-dihydrospiro[1H-indene-1,4'-piperidine]-3-acetic acid ethyl ester hydrochloride The title compound was obtained in 100% yield from the intermediate obtained in Step A using the procedure described in Example 103, Step B. $[\alpha]_D$–40° (c=0.15, CH$_3$OH).

$^1$H NMR (CD$_3$OD, 400 MH, rotamer 1:2): δ7.60 (d, ⅔H), 7.55 (d, ⅓H), 7.35 (d, 1H), 7.12 (m, 6H), 6.64 (d, 1H), 5.21 (m, 1H), 4.38 (m, 1H), 4.15 (m, 2H), 3.72 (m, 1H), 3.40 (m, 1H), 3.22 (m, 2H), 3.06 (m, 1H), 2.80 (m, 1H), 2.69 (m, ⅓H), 2.58 (m, ⅔H), 2.35 (m, 2H), 2.02 (td, ⅓H), 1.62 (m, 6H), 1.38 (m, 2H), 1.20 (m, 5H), 0.90 (d, 1H), 0.00 (td, ⅔H). FAB-MS: 545 (M+1).

EXAMPLE 105

1'-[2(R)-[(2-amino-2-methyl-1-oxopropyl)amino]-3-(indole-3-yl)-1-oxopropyl]-2,3-dihydrospiro[1H-indene-1,4'-piperidine]-3-acetic acid hydrochloride Diastereomer 2

The title compound was obtained in 56% (0.030 g) by hydrolyzing the intermediate prepared in Example 104, Step B(0.0564 g, 0.097 mmol) from Example 7, Step B with NaOH in EtOH/H$_2$0, followed by acidification with HCl and MPLC purification. $[\alpha]_D$–32.6° (c=0.95, CH$_3$OH).

$^1$H NMR (CD$_3$OD, 400 MH, rotamer 1:2): δ8.29 (d, ⅔H), 8.23 (d, ⅓H), 7.60 (d, ⅔H), 7.55 (d, ⅓H), 7.35 (d, 1H), 7.15 (m, 6H), 6.65 (d, 1H), 5.31 (m, 1H), 4.31 (m, 1H), 3.71 (m, 1H), 3.40 (m, 1H), 3.20 (m, 2H), 3.07 (t, 1H), 2.80 (m, 1H), 2.70 (m, ⅓H), 2.60 (m, ⅔H), 2.35 (m, 2H), 2.01 (m, ⅓H), 1.62 (m, 6H), 1.40 (m, 2H), 1.22 (m, 2H), 0.90 (m, 1H), 0.00 (m, ⅔H). FAB-MS: 517 M+1)

EXAMPLE 106

1'-[2(R)-[(2-amino-2-methyl-1-oxopropyl)amino]-3-(phenylmethoxy)-1-oxopropyl]-2,3-dihydrospiro[1H-indene-1,4'-piperidine]-3-acetic acid ethyl ester hydrochloride Diastereomer 2

Step A:

1'-[2(R)-[[(1,1-dimethylethoxy)carbonyl]amino]-2-(phenylmethoxy)ethyl]2,3-dihydrospiro[1H-indene-1,4'-piperidine]-3-acetic acid ethyl ester The title compound from Example 98, Step D (160 mg, 0.367 mmol) was treated with ethanol and thionyl chloride according to the procedure used in Example 98, Step E. The resulting product was coupled to N-Boc-O-ben-D-Serine (127 mg, 0.458 mmol) with EDC (105 mg, 0.551 mmol), HOBT (74 mg, 0.551 mmol), and NMM (0.040 ml, 0.367 mmol) following the procedure described in Example 1 (163,917). Flash chromatography (silica gel, hexane/ethyl acetate 2:1) gave the title compound (19 1 mg, 0.34 mmol).
Step B:

1'-[2(R)-[[[2-[(1,1-dimethylethoxy)carbonyl]amino]-2-methyl-1-oxopropyl]amino]amino]-2-phenyl-methoxy)ethyl]2,3-dihydrospiro[1H-indene-1,4'-piperidine]-3-acetic acid ethyl ester The intermediate from Step A (180 mg, 0.327 mmol) was treated with 4N HCl as in Example 85 Step A. The residue was reacted with Boc-α-methylalanine (83 mg, 0.41 mmol), EDC (94 mg. 0.49 mmol), HOBT (66 mg, 0.49 mmol) and NMM (0.36 ml, 0.327 mmol) according to the procedure described for Example 1 Step A. The title compound (157 mg, 0.249 mmol) was obtained as a white solid after flash chromatography.
Step C:

1'[2(R)-[(2-amino-2-methyl-1-oxopropyl)amino]-3-(phenylmethoxy)-1-oxopropyl]-2,3-dihydrospiro[1H-indene-1,4'-piperidine]-3-acetic acid ethyl ester hydrochloride Diastereomer 2

The intermediate from Step B (68 mg, 0.11 mmol) was stirred in 4N HCl/dioxane for 2 h. The solution was concentrated and azeotroped from toluene. After drying under high vacuum the title compound (56.7 mg, 0.10 mmol) was obtained as a white solid.

$^1$HNMR (400 MHz, CD$_3$OD 1:1 mixture of conformers): 7.40–7.28 (m, 5H), 7.22–7.10 (m, ½H), 6.92–6.88 (m, ½H), 5.18–5.15 (m, 1H), 4.60–4.45 (m, 3H), 4.25–4.18 (m, 2H), 4.08–3.96 (m, 1H), 3.85–3.70 (m, 2H), 3.68–3.55 (m, 1H), 3.88–3.18 (m, 1H), 2.90–2.80 (m, 2H), 2.65–2.59 (m, 1H), 2.51–2.40 (m, 1H), 2.18 (dt, ½H), 1.95 (dt, ½H), 1.65–1.50 (m, 10H), 1.32–0.128 (m, 3H).

EXAMPLE 107

1'-[2(R)-[(2-amino-2-methyl-1-oxopropyl)amino]-3-phenylmethoxy)-1-oxopropyl]-2,3-dihydrospiro[1H-indene-1,4'-piperidine]-3-acetic acid hydrochloride Diastereomer 2

Step A:

1'-[2(R)-[[[2-[(1,1-dimethylethoxy)carbonyl]amino]-2-methyl-1-oxopropyl]amino]-2-(phenylmethoxy)ethyl]-2,3-dihydrospiro[1H-indene-1,4'-piperidine]-3-acetic acid Lithium hydroxide monohydrate (7.2 mg, 0.17 mmol) was added to the intermediate prepared in Example 106 Step B (73 mg, 0.11 mmol) in a mixture of acetonitrile and water. The reaction mixture was stirred for 16 h and then made acidic with 1N HCL. The aqueous layer was extracted with ethyl acetate (3×1 vol). The organic layer was washed with brine, dried over magnesium sulfate, filtered and concentrated to give the title compound (55.8 mg, 0.09 mmol).
Step B:

1'-[2(R)-[(2-amino-2-methyl-1-oxopropyl)amino]-3-phenylmethoxy)-1-oxopropyl]-2,3-dihydrospiro[1H-indene-1,4'-piperidine]-3-acetic acid hydrochloride Diastereomer 2

The intermediate from Step A (47.8 mg, 0.079 mmol) was stirred in 4N HCl/dioxane for 2 h. The solution was concentrated and azeotoped from toluene. After drying under high vacuum the title compound (38.8 mg, 0.72 mmol) was obtained as a white solid.

$^1$HNMR (400 MHz, CD$_3$OD 1:1 mixture of conformers): 7.34–7.25 (m, 4H), 7.22–7.10 (m, 9⁄2H), 6.92–6.88 (m, ½H), 5.20–5.15 (m, 1H), 4.60–4.45 (m, 3H), 4.05–3.98 (m, 1H), 3.79–3.70 (m, 2H), 3.65–3.55 (m, 1H), 3.40–3.18 (m, 1H), 2.95–2.80 (m, 2H), 2.68–2.62 (m, 1H), 2.44–2.38 (m, 1H), 2.15 (dt, 1/2H), 1.94 (dt, ½H), 1.62–1.48 (m, 10H).

EXAMPLE 108

1'-[2(R)-[(2-amino-2-methyl-1-oxopropyl)amino]-5-phenyl-1-oxopentyl]-2,3-dihydrospiro[1H-indene-1,4'-piperidine]-3-acetic acid ethyl ester hydrochoride Diastereomer 1 & Diastereomer 2

Step A:

1'-[(1,1-dimethylethoxy)carbonyl]-2,3-dihydrospiro[1H-indene-1,4'-piperidine]-3-acetic acid ethyl ester The title compound was obtained in 78% yield (0.67 g) from the title compound (0.86 g, 2.31 mmol) in Example 98, Step A, by hydrogenation with Pd/C under a hydrogen filled balloon.

$^1$H NMR (CDCl$_3$, 400 MH): δ7.20 (m, 4H), 4.18 (q, 2H), 4.07 (m, 2H), 3.61 (m, 1H), 2.90 (m, 2H), 2.88 (dd, 1H), 2.57 (dd, 1H), 2.40 (dd, 1H), 2.00 (td, 1H), 1.50 (m, 4H), 1.46 (s, 9H), 1.29 (t, 3H).
Step B:

1'-[2(R)-[[(1,1-dimethylethoxy)carbonyl]amino]-5-phenyl-1-oxopentyl]-2,3-dihydrospiro[1H-indene-1,4'-piperidine]-3-acetic acid ethyl ester The title compound was obtained in 80% yield (0.40 g) as a colorless oil by treatment of the title compound (0.34 g, 0.91 mmol) from Step A with HCl in EtOH, followed by coupling to the compound prepared in Example 73, Step B using the procedure described in Example 98, Step E.

$^1$H NMR (CDCl$_3$, 400 MH): δ7.18 (m, 7H), 7.10 (m, 1H), 6.99 (m, 0.5H), 6.91 (m, 0.5H), 5.48 (m, 1H), 4.60 (m, 2H), 4.19 (m, 2H), 3.75 (m, 1H), 3.60 (m, 1H), 3.12 (m, 1H), 2.88

(m, 1H), 2.78 (m, 1H), 2.68 (m, 1H), 2.58 (m, 1H), 2.40 (m, 1H), 1.70 (m, 4H), 1.50 (m, 6H), 1.40 (m, 9H), 1.25 (m, 3H).
Step C:

1'-[2(R)-[[[2-(1,1-dimethylethoxy)carbonyl]amino]-2-methyl-1-oxopropyl]amino]-5-phenyl-1-oxopentyl]-2,3-dihydrospiro[1H-indene-1,4'-piperidine]-3-acetic acid ethyl ester The title compound was obtained in 70% yield (0.32 g) from the title compound (0.40 g, 0.73 mmol) from Step B using the procedure described in Example 98, Step F.

$^1$H NMR (CDCl$_3$, 400 MH): δ7.18 (m, 8H), 6.99 (m, 0.5H), 6.92 (m, 0.5H), 4.91 (m, 2H), 4.51 (m, 1H), 4.18 (m, 2H), 3.75 (m, 2H), 3.60 (m, 1H), 3.10 (m, 1H), 2.89 (m, 1H), 2.67 (m, 1H), 2.57 (m, 1H), 2.40 (m, 1H), 1.72 (m, 2H), 1.50 (m, 12H), 1.40 (s, 9H), 1.22 (m, 6H).
Step D:

1'-[2(R)-[(2-amino-2-methyl-1-oxopropyl)amino]-5-phenyl-1-1-oxopentyl]-2,3-dihydrospiro[1H-indene-1,4'-piperidine[-3-acetic acid ethyl ester hydrochoride Diastereomer 1 & Diastereomer 2

The title compound was obtained in 100% yield (0.126 g) from the title compound (0.14 g, 0.22 mmol) from Step C using the procedure described in Example 98, Step G.

$^1$H NMR (CD3OD, 400 MH): δ8.12 (m, 1H), 7.20 (m, 8H), 7.04 (m, 0.5H), 6.98 (m, 0.5H), 4.45 (m, 1H), 4.19 (m, 2H), 3.89 (m, 1H), 3.61 (m, 1H), 3.25 (m, 1H), 2.88 (m, 2H), 2.67 (m, 3H), 2.45 (m, 1H), 2.20 (m, 0.5H), 2.00 (m, 0.5H), 1.78 (m, 4H), 1.60 (m, 11H), 1.29 (m, 3H). FAB-MS: 534 (M+1).

EXAMPLE 109

1'-[2(R)-[(2-amino-2-methyl-1-oxopropyl)amino]-5-phenyl-1-oxopentyl]-2,3-dihydrospiro[1H-indene-1,4'-piperidine]-3-acetic acid hydrochloride Diastereomers 1 and 2

The title compound was obtained from the title compound in Example 108, Step C using the procedure described in Example 100, Step A.

$^1$H NMR (CD$_3$OD, 400 MH): δ8.12 (m, 1H), 7.20 (m, 8H), 7.04 (m, 0.5H), 6.98 (m, 0.5H), 4.45 (m, 1H), 3.89 (m, 1H), 3.61 (m, 1H), 3.25 (m, 1H), 2.88 (m, 2H), 2.67 (m, 3H), 2.45 (m, 1H), 2.20 (m, 0.5H), 1.99 (m, 0.5H), 1.78 (m, 4H), 1.60 (m, 11H).

EXAMPLE 110

N-dimethyl-1'-[2(R)-[(2-amino-2-methyl-1-oxopropyl)amino]-5-phenyl-1-oxopentyl]2,3-dihydrospiro[1H-indene-1,4'-piperidine]-3-acetamide hydrochloride Step A:

N-dimethyl-1'-[2(R)-[[[2-(1,1-dimethylethoxy)carbonyl]amino]-2-methyl-1-oxopropyl)amino]-5-phenyl-1-oxopentyl]2,3-dihydrospiro[1H-indene-1,4'-piperidine]-3-acetamide hydrochloride A mixture of the title compound from Example 108, Step C, and NaOH in EtOH/H$_2$O was stirred at room temperature for 20 hr. The EtOH was removed and the aqueous was acidified with HCl. The cloudy solution was extracted with EtOAc (3×20 ml). The combined EtOAc layers were washed with brine, and dried over sodium sulfate. After evaporating the sovent, the residue was mixed with dimethylamine hydrochloride and coupling reagents using the procedure described in Example 98, Step F to afford the title compound.

$^1$H NMR (CDCl$_3$, 400 MH): δ7.18 (m, 8H), 6.99 (m, 0.5H), 6.92 (m, 0.5H), 4.91 (m, 2H), 4.50 (m, 1H), 3.71 (m, 2H), 3.15 (m, 1H), 3.00 (s, 6H), 2.90 (m, 1H), 2.80 (m, 1H), 3.68 (m, 3H), 2.40 (m, 1H), 2.00 (m, 0.5H), 1.88 (m, 0.5H), 1.70 (m, 4H), 1.47 (m, 20H).
Step B:

N-dimethyl-1'-[2(R)-[(2-amino-2-methyl-1-oxopropyl)-amino]-5-phenyl-1-oxopentyl]2,3-dihydrospiro[1H-indene-1,4'-piperidine]-3-acetamide hydrochloride The title compound from Step A was treated with HCl (4M in dioxane) at room temperature for 2 hr to afford the title compound.

$^1$H NMR (CD$_3$OD, 400 MH): δ8.13 (m, 1H), 7.18 (m, 8H), 7.03 (m, 0.5H), 6.98 (m, 0.5H), 4.48 (m, 1H), 3.85 (m, 1H), 3.65 (m, 1H), 3.28 (m, 1H), 3.08 (t, 3H), 3.01 (d, 3H), 2.88 (m, 1H), 2.68 (m, 2H), 2.50 (m, 1H), 2.20 (m, 0.5H), 1.95 (m, 0.5H), 1.76 (m, 4H), 1.54 (m, 12H). FAB-MS: 533 (m+1).

EXAMPLE 111

N-ethyl-1'-[2(R)-[(2-amino-2-methyl-1-oxopropyl)amino]-5-phenyl-1-oxopentyl]2,3-dihydrospiro[1H-indene-1,4'-piperidine]-3-acetamide hydrochloride Step A:

N-ethyl-1'-[2(R)-[[[2-(1,1-dimethylethoxy)carbonyl]amino]-2-methyl-1-oxopropyl)amino]-5-phenyl-1-oxopentyl]2,3-dihydrospiro[1H-indene-1,4'-piperidine]-3-acetamide hydrochloride The title compound was obtained from the intermediate obtained in Example 106, Step C using the procedure described in Example 110, Step A, except the diethylamine hydrochloride was used.

$^1$H NMR (CDCl$_3$, 400 MH): δ7.15 (m, 8H), 6.99 (m, 0.5H), 6.91 (m, 0.5H), 5.48 (m, 1H), 4.90 (m, 2H), 4.50 (m, 1H), 3.70 (m, 2H), 3.32 (m, 2H), 3.11 (m, 1H), 2.65 (m, 4H), 2.21 (m, 1H), 1.98 (m, 0.5H), 1.88 (m, 0.5H), 1.70 (m, 4H), 1.46 (m, 21H), 1.12 (m, 3H).
Step B:

N-ethyl-1'-[2(R)-[(2-amino-2-methyl-1-oxopropyl)amino]-5-phenyl-1-oxopentyl]-2,3-dihydrospiro[1H-indene-1,4'-piperidine]3-acetamide hydrochloride The title compound was obtained from the intermediate obtained in Step A using the procedure described in Example 110, Step B.

$^1$H NMR (CD$_3$OD, 400 MH): δ8.17 (m, 1H), 7.20 (m, 8H), 7.02 (m, 0.5H), 6.98 (m, 0.5H), 4.48 (m, 1H), 3.90 (m, 1H), 3.65 (m, 1H), 3.27 (m, 3H), 2.72 (m, 4H), 2.29 (m, 1H), 2.20 (m, 0.5H), 1.98 (m, 0.5H), 1.73 (m, 4H), 1.55 (m, 12H), 1.18 (m, 3H). FAB-MS: 533

EXAMPLE 112

1'-[2(R)-[(2-amino-2-methyl-1-oxopropyl)amino]-5-phenyl-1-oxopentyl]-2,3-dihydrospiro[1H-indene-1,4-piperidine]-3-propionic acid ethyl ester hydrochloride Step. A:

1'-[(1,1-dimethylethoxycarbonyl]-2,3-dihydrospiro[1H-indene-1,4'-piperidine]-3-propionic acid ethyl ester A mixture of the title compound (1.0388 g, 2.8 mmol) from Example 98, Step A, and Pd/C (0.28 g) in EtOH/EtOAc (80 ml) was hydrogenated with a balloon for 30 min. The mixture was filtered and the solvent was evaporated. To a solution of the residue and dibromomethane (0.43 ml, 6.16 mmol) in THF (20 ml) at −78° C. for 10 min, was added dropwise a freshly prepared solution of lithium tetramethylpiperidine (6.16 mmol) in THF (10 ml) at 0° C. over 10 min. The mixture was stirred at −78° C. for 10 min. A newly prepared lithium hexamethyldisilazane (5.6 mmol) in THF (10 ml) at 0° C. was added dropwise in 5 min to the mixture at −78° C. The mixture was then slowly warmed to 0° C. in an ice-bath for 30 min. n-BuLi (10.5 ml, 16.8 mmol, 1.6M) was added slowly over 10 min. The mixture was stirred at 0° C. for 5 min and warmed to room temperature for 45 min. The color of the solution changed from yellow to brown. The mixture was then cooled to −78° C. and quenched into a stirred solution of acidic ethanol (30 ml) dropwise at 0° C. over 30 min. The solution was diluted with EtOAc (200 ml) and washed with 1N HCl (30 ml). The aqueous was extracted with EtOAc (2×30 ml). The combined EtOAc layers were washed with brine, and dried over sodium sulfate. The title compound was obtained in 48% yield (0.522 g) as a colorless oil by flash column (EtOAc:hexane= 1:9).

$^1$H NMR (CDCl$_3$, 400 MH, 1:1 mixture): δ7.20 (m, 4H), 4.12 (m, 4H), 3.18 (m, 1H), 2.90 (m, 2H), 2.44 (m, 2H), 2.34 (m, 1H), 2.02 (m, 1H), 1.73 (m, 1H), 1.60 (m, 4H), 1.47 (m, 10H), 1.28 (m, 3H).

Step B:

1'-[2(R)-[[(1,1-dimethylethoxy)carbonyl]amino]-5-phenyl-1-oxopentyl]-2,3-dihydrospiro[1H-indene-1,4'-piperidine]-3-propionic acid ethyl ester The title compound was obtained as a colorless oil in 71% is yield (0.542 g) from the title compound (0.522 g, 1.34 mmol) from Step A using the procedure described in Example 108, Step B.

$^1$H NMR (CDCl$_3$, 400 MH, 1:1 mixture): δ7.20 (m, 7H), 7.10 (m, 1H), 6.99 (m, 0.5H), 6.91 (m, 0.5H), 5.49 (m, 1H), 4.58 (m, 2H), 4.12 (m, 2H), 3.75 (m, 1H), 3.17 (m, 2H), 2.68 (m, 3H), 2.41 (m, 2H), 2.31 (m, 1H), 2.02 (m, 0.5H), 1.89 (m, 0.5H), 1.70 (m, 4H), 1.52 (m, 6H), 1.49 (m, 9H), 1.27 (m, 3H).

Step C:

1'-[2(R)-[[[2-[(1,1-dimethylethoxy)carbonyl]amino]-2-methyl-1-oxopropyl]amino]-5-phenyl-1-oxopentyl]-2,3-dihydrospiro[1H-indene-1,4'-piperidine-3-propionic acid ethyl ester The title compound was obtained as a colorless oil in 90% yield (0.556 g) from the title compound (0.542 g, 0.96 mmol) from Step B using the procedure described in Example 108, Step C.

$^1$H NMR (CDCl$_3$, 400 MH, 1:1 mixture): δ7.18 (m, 8H), 6.99 (m, 0.5H), 6.91 (m, 0.5H), 4.95 (m, 2H), 4.50 (m, 1H), 4.12 (m, 2H), 3.78 (m, 1H), 3.18 (m, 2H), 3.06 (m, 1H), 2.67 (m, 3H), 2.40 (m, 2H), 2.32 (m, 1H), 2.00 (m, 0.5H), 1.80 (m, 0.5H), 1.70 (m, 4H), 1.50 (m, 21H), 1.22 (m, 3H).

Step D:

1'-[2(R)-[(2-amino-2-methyl-1-oxopropyl)amino]-5-phenyl-1-oxopentyl]-2,3-dihydrospiro[1H-indene-1,4-piperidine]-3-propionic acid ethyl ester hydrochloride The title compound was obtained as a white solid in 100% yield (0.086 g) from the title compound (0.0955 g, 0.15 mmol) from Step C using the procedure described in Example 108, Step D.

$^1$H NMR (CD$_3$OD, 400 MH, 1:1 mixture): δ7.18 (m, 7H), 7.10 (m, 1H), 7.02 (m, 0.5H), 6.98 (m, 0.5H), 4.45 (m, 1H), 4.12 (m, 2H), 3.85 (m, 1H), 3.20 (m, 2H), 2.89 (m, 1H), 2.68 (m, 2H), 2.55 (m, 1H), 2.47 (m, 2H), 2.32 (m, 1H), 2.19 (m, 0.5H), 1.95 (m, 0.5H), 1.72 (m, 4H), 1.50 (m, 12H), 1.25 (m, 3H). FAB-MS: 548 (M+1).

EXAMPLE 113

1'-[2(R)-[(2-amino-2-methyl-1-oxopropyl)amino]-5-phenyl-1-oxopentyl]-2,3-dihydrospiro[1H-indene-1,4'-piperdine]-3-propionic acid hydrochloride The title compound was obtained from the title compound of Example 112 as a white solid using the procedure described in Example 109, Step A.

$^1$H NMR (CD$_3$OD, 400 MH, 1:1 mixture): δ7.18 (m, 8H), 7.02 (m, 0.5H), 6.98 (m, 0.5H), 4.45 (m, 1H), 3.88 (m, 1H), 3.25 (m, 2H), 2.89 (m, 1H), 2.69 (m, 2H), 2.55 (m, 1H), 2.43 (m, 2H), 2.35 (m, 1H), 2.20 (m, 0.5H), 1.98 (m, 0.5H), 1.75 (m, 4H), 1.60 (m, 12H). FAB-MS: 520 (M+1).

EXAMPLE 114

N-[1(R)-[[3-(methylthio)-2,3-dihydrospiro[1H-indene-1,4'-piperidin]-1'-yl]carbonyl]-2-indole-3-yl)ethyl]-2-amino-2-methylpropanamide hydrochloride Step A:

1'-[(1,1-dimethylethyloxy)carbonyl]-3,4-dihydro-3-(R)(S)hydroxypspiro[1H-indene-1,4'-piperdine To a solution of the intermediate prepared in Example 4, Step A (1.50 g, 5.00 mmol) in anhydrous MeOH (60 ml) at 0° C., was added NaBH4 (0.23 g, 5.98 mmol). The whole was stirred at room temperature for 2 hr. The MeOH was removed and 1N NaOH (50 ml) was added. The aqueous was extracted with EtOAc (3×150 ml). The combined EtOAc layers were washed with brine and dried over sodium sulfate. The title compound was obtained in 100 % yield (1.52 g) as a white solid upon removal of the solvent. The compound was used for the next step without purification.

$^1$H NMR (CDCl$_3$, 200 MH): δ7.20 (m, 4H), 5.29 (m, 1H), 4.11 (m, 2H), 2.95 (m, 2H), 2.50 (dd, 1H), 1.50 (m, 13H).

Step B:

3-methylthio-2,3-dihydrospiro[1H-indene-1,4'-piperidine]-1'-carboxylic acid 1,1-dimethyl ester To a solution of the title compound (1.50 g, 4.95 mmol) from Step A in methylene chloride (50 ml), were added TsCl (1.06 g, 5.4 mmol), Et3N (0.76 ml, 5.4 mmol) and catalytic amount of dimethylaminopyridine. The mixture was stirred at room temperature for 20 hr. Water was added and the mixture was extracted with EtOAc (3×50 ml). The combined EtOAc layers were washed with brine, and dried over sodium sulfate. A white solid was obtained upon removal of the solvent. A mixture of the white solid and sodium thiomethoxide s (0.42 g, 5.94 mmol) in DMF (20 ml) was stirred at 50°–60° C. for 24 hr. Water was added and the mixture was extracted with EtOAc (3×100 ml). The combined EtOAc layers were washed with water, brine, and dried over sodium sulfate. The title compound was obtained in 54% yield (0.89 g) as a colorless oil after flash chromatography (EtOAc:hexane=1:9).

$^1$H NMR (CDCl$_3$, 200 MH): δ7.28 (m, 4H), 4.30 (t, 1H), 4.10 (m, 2H), 2.98 (t, 2H), 3.58 (dd, 1H), 2.08 (m, 3H), 1.98 (m, 2H), 1.65 (m, 2H), 1.50 (s, 9H), 1.28 (t, 1H).

Step C:

N-{1(R)-[[3-(methylthio)-2,3-dihydrospiro[1H-indene-1,4'-piperidine]-1'yl]carboyl]-2-[[(1,1-dimethylethoxycarbonyl]amino]-2-methyl propanamide A mixture of the compound obtained in Step B (0.86 g, 2.58 mmol), concentrated HCl (6 ml), MeOH (10 ml), and water (3 ml) was stirred at room temperature for 2 hr. The solvent was removed and the residue was dried under high vacuum. The residue was coupled to the intermediate obtained in Example 4, Step D (0.97 g, 2.58 mmol) under the conditions described in Example 1, Step A. The title compound was obtained in 78 % yield (1.22 g) as a thick oil after flash chromatography (EtOAc:hexane=1:1).

$^1$H NMR (CDCl$_3$, 400 MH, 1:1 mixture, 1:2 conformers): δ8.14 (s, ⅓H), 8.08 (s, ⅔H), 7.76 (d, ⅔H), 7.60 (m, ⅓H), 7.20 (m, 7H), 7.07 (m, ⅓H), 6.50 (m, ⅔H), 5.29 (m, ⅔H), 5.20 (m, ⅓H), 4.99 (m, 1H), 4.42 (m, 1H), 4.14 (m, 1H), 3.56 (m, 1H), 3.18 (m, ⅔H), 2.91 (m, ⅓H), 2.59 (m, ⅔H), 2.50 (m, ⅓H), 2.28 (m, 1H), 1.98 (m, 3H), 1.79 (1H), 1.57 (s, 4H), 1.46 (m, 14H), 1.00 (m, 2H), 0.31 (m, ⅔H), 0.10 (m, ⅓H).

Step D:

N-[1(R)-[[3-(methylthio)-2,3-dihydrospiro[1H-indene-1,4'-piperidin]-1'-yl]carbonyl]-2-indole-3-yl)ethyl]-2-amino-2-methylpropanamide hydrochloride The title compound was obtained from the intermediate prepared in Step C as a pink solid using the procedure described in Example 103, Step B.

$^1$H NMR (CD$_3$OD, 400 MH, 1:2 conformers): δ7.62 (m, ⅔H), 7.55 (d, ⅓H), 7.43 (d, ⅓H), 7.39 (m, ⅔H), 7.30 (m, ⅓H), 7.17 (m, 6H), 6.64 (m, ⅔H), 5.25 (m, ⅔H), 5.19 (m, ⅓H), 4.36 (m, 1H), 4.22 (m, ⅓H), 4.18 (m, ⅔H), 3.76 (m, 1H), 3.34 (m, ⅓H), 3.20 (m, 1H), 3.03 (m, ⅔H), 2.61 (m, 1H), 2.40 (m, 1H), 2.00 (d, 1H), 2.92 (d, 2H), 1.86 (m, 1H), 1.61 (s, 5H), 1.51 (d, 1H), 1.40 (m, 1H), 1.25 (m, 1H), 1.10 (m, 1H), 0.30 (m, ⅔H), 0.09 (m, ⅓H). FAB-MS: 505 (M+1).

EXAMPLE 115

N-[1(R)-[[3-(methylsulfonyl)-2,3-dihydrospiro[1H-indene-1,4'-piperidin]-1'-yl)-carbonyl]-2-(indole-3-yl]ethyl]-2-amino-2-methylpropanamide hydrochloride Step A:

N-[1(R)-[[3-(methylsulfonyl)-2,3-dihydrospiro[1H-indene-1,4'-piperidine]-1'-yl]carbonyl-2-[[(1,1-dimethylethoxy)-carbonyl]amino]-2-methylpropanamide The title compound was obtained by oxidation of the compound prepared in Example 114, Step C with mCPBA in methylene chloride at –78° C. and subsequent flash column purification.

$^1$H NMR (CDCl$_3$, 400 MH, 1:1 mixture, 1:3 conformers): δ8.38 (d, ⅔H), 8.30 (s, ⅓H), 7.72 (m, ⅔H), 7.55 (m, ⅓H), 7.20 (m, 6H), 7.08 (m, ⅓H), 6.52 (d, ⅓H), 6.45 (d, ⅓H), 5.25 (m, 1H), 4.99 (br s, 1H), 4.50 (m, 2H), 3.57 (m, 1H), 3.18 (m, 2H), 2.80 (m, 1H), 2.70 (m, 3H), 2.50 (m, 1H), 2.37 (m, 1H), 2.18 (m, 1H), 1.72 (m, 2H), 1.49 (m, 15H), 1.15 (m, 1H), 0.90 (m, 1H), 0.20 (m, ⅔H), 0.02 (m, ⅓H).

Step B:

N-[1(R)-[[3-(methylsulfonyl)-2,3-dihydrospiro[1H-indene-1,4'-piperidin]-1'-yl)-carbonyl]-2-(indole-3-yl]ethyl]-2-amino-2-methylpropanamide hydrochloride The title compound was obtained from the compound prepared in Step A using the procedure described in Example 103, Step B.

$^1$H NMR (CD$_3$OD, 400 MH, 1:1 mixture, 1:2 conformers): δ8.32 (m, ⅔H), 8.25 (m, ⅓H), 7.30 (m, 8H), 6.70 (m, 1H), 5.29 (m, ⅔H), 5.20 (m, ⅓H), 4.81 (m, 2H), 4.40 (m, 1H), 3.80 (m, 1H), 3.30 (m, 2H), 3.08 (m, 1H), 2.95 (s, 1H), 2.89 (s, 2H), 2.63 (m, 1H), 2.45 (m, 1H), 2.30 (m, 1H), 1.84 (m, 1H), 1.65 (s, 5H), 1.50 (s, 1H), 1.23 (m, 1H), 0.89 (m, 1H), 0.22 (m, ⅔H), 0.08 (m, ⅓H). FAB-MS: 537 (M+1).

EXAMPLE 116

N-[1-[[3-methoxy)carbonyl]pyridin-2-yl]spiro[1H-indene-1,4'-piperidin]-1'-yl]carbonyl]-4-phenylbutyl]-2-amino-2-methylpropanamide hydrochloride Step A:

3-(trimethylstannyl)spiro[1H-indene-1,4'-piperidine]-1'-carboxylic acid 1,1-dimethylethyl ester A mixture of the intermediate prepared in Example 80, Step A (2.00 g, 4.6 mmol), LiCl (1.27 g, 30 mmol), hexamethylditin (1.51 g, 4.6 mmol) and 10% mole of tetrakis(triphenylphosphine)palladium (0.53 g, 0.46 mmol) in THF was stirred at 60° C. for 24 hr under nitrogen. Water (20 ml) was added and the aqueous was extracted with EtOAc (3×40 ml). The combined EtOAc layers were s washed with brine, and dried over sodium sulfate. The title compound was obtained as a colorless oil in 60% yield (1.24 g) after flash chromatography (EtOAc:hexane=2:8).

$^1$H MNR (CDCl$_3$, 400 MH): δ7.22 (m, 4H), 6.90 (s, 1H), 4.12 (m, 2H), 3.12 (m, 2H), 1.92 (m, 2H), 1.52 (s, 6H), 1.47 (s, 9H), 1.30 (m, 2H), 0.30 (s, 3H).

Step B:

N-[1-[[3-[[2-)methoxycarbonyl]pyridyl]spiro[1H-indene-1,4'-piperidine]-1-carboxylic acid-1,1-dimethylethylester A mixture of the title compound (0.25 g, 0.56 mmol) from Step A, methyl 2-bromopyridium-3-carboxylate (0.121 g, 0.56 mmol) and 10% mole of tetrakis(triphenylphosphine)palladium (64.7 mg) in toluene (20 ml) was heated to reflux for 24 hr. The solution was diluted with methylene chloride (50 ml) and washed with water, brine, and dried over sodium sulfate. The title compound was obtained in 36% yield (85mg) as a solid after flash chromatography (EtOAc:hexane=3:7).

$^1$H NMR (CDCl$_3$, 400 MH): δ8.81 (d, 1H), 8.15 (d, 1H), 7.38 (m, 2H), 7.20 (m, 3H), 6.99 (s, 1H), 4.21 (m, 2H), 3.52 (s, 3H), 3.14 (m, 2H), 2.08 (m, 2H), 1.47 (m, 11H).

Step C:

[1-[[3-[[(3-methoxy)carbonyl]pyridin-2-yl]spiro[1H-indene-1,4'-piperidin]-1'-yl]carbonyl]-4-phenylbutyl]-carbamic acid 1,1-dimethylethyl ester The title compound was obtained in 78% yield (0.106 g) from the title compound in Step B (0.096 g) under the coupling conditions described in Example 98, Step E.

$^1$H NMR (CDCl$_3$, 400 MH): δ8.82 (m, 1H), 8.18 (m, 1H), 7.40 (m, 1H), 7.22 (m, 9H), 6.95 (d, 1H), 5.49 (m, 1H), 4.67 (m, 2H), 3.96 (d, 0.5H), 3.88 (d, 0.5H), 3.52 (s, 3H), 3.38 (t, 0.5H), 3.29 (t, 0.5H), 3.00 (m, 1H), 2.65 (m, 2H), 2.10 (m, 0.5H), 1.98 (m, 0.5H), 1.75 (m, 4H), 1.54 (m, 3H), 1.47 (d, 9H).

Step D:

N-[1-[[3-[[(3-methoxy)carbonyl]pyridin-2-yl]spiro[1H-indene-1,4'-piperidin]-1'-yl]carbonyl]-4-phenylbutyl]-2-[[(1,1-dimethylethoxy)carbonyl]amino]-2-methylpropanamide The title compound was obtained in 84% yield (0.101 g) from the title compound in Step C (0.106 g) under the coupling conditions described in Example 1, Step F.

$^1$H NMR (CDCl$_3$, 400 MH): δ8.80 (m, 1H), 8.18 (m, 1H), 7.39 (m, 1H), 7.18 (m, 9H), 6.92 (d, 1H), 4.98 (m, 2H), 4.60 (m, 1H), 3.98 (d, 0.5H), 3.89 (d, 0.5H), 3.52 (s, 3H), 3.35 (t, 0.5H), 3.23 (t, 0.5H), 2.98 (t, 1H), 2.62 (m, 2H), 2.10 (m, 0.5H), 1.98 (m, 0.5H), 1.75 (m, 4H), 1.62 (m, 3H), 1.48 (m, 15H).

Step E:

N-[1-[[3-methoxy)carbonyl]pyridin-2-yl]spiro[1H-indene-1,4'-piperidin]-1'-yl]carbonyl]-4-phenylbutyl]-2-amino-2-methyl-propanamide hydrochloride The title compound was obtained in 100% yield from the title compound in Step D using the procedure described in Example 98, Step G.

$^1$H NMR (CD$_3$OD, 400 MH): δ9.00 (m, 1H), 8.18 (m, 1H), 7.47 (m, 1H), 7.20 (m, 10H), 4.60 (m, 1H), 4.12 (d, 0.5H), 4.00 (d, 0.5H), 3.65 (s, 3H), 3.60 (m, 1H), 3.12 (m, 1H), 2.68 (m, 2H), 2.35 (m, 0.5H), 2.10 (m, 0.5H), 1.72 (m, 4H), 1.62 (m, 6H), 1.50 (m, 4H).

EXAMPLE 117

N-[1-[[3-[[(3-carboxylic acid]pyridin-2-yl]spiro[1H-indene-1,4'-piperidine]-1'-yl]carbonyl]-4-phenylbutyl]-amino-2-methyl-propanamide hydrochloride The title compound was obtained by hydrolysis of the title compound from Example 116, Step D with LiOH in MeOH/H$_2$O at room temperature for 20 hr and followed by deprotection with HCl/dioxane for 2 hr.

$^1$H NMR (CD$_3$OD, 400 MH): δ8.98 (m, 0.5H), 8.22 (m, 0.5H), 8.10 (m, 0.5H), 7.45 (m, 1H), 7.20 (m, 10H), 4.60 (m, 1H), 4.10 (m, 0.5H), 4.00 (m, 0.5H), 3.50 (m, 3H), 3.10 (m, 1H), 2.68 (m, 2H), 2.35 (m, 0.5H), 2.10 (m, 0.5H), 1.80 (m, 4H), 1.56 (m, 10H). FAB-MS: 567 (m+1).

EXAMPLE 118

N-[1-[[3-[2-ethoxycarbonyl]phenyl]-2,3-dihydrospiro[1H-indene-1,4'-piperidine-1'-yl]carbonyl]-4-phenylbutyl]-2-amino-2-methyl-propanamide hydrochloride Step A:

3-[2-[(ethoxy)carbonyl]phenyl]spiro[1H-indene-1,4'-piperidine]-1'-carboxylic acid 1,1-dimethylethyl ester The title compound was obtained in 47% yield (0.181 g) from the title compound from Example 16, Step H (0.40 g, 0.89 mmol) and ethyl 2-bromobenzoate (0.225 g, 0.98 mmol) using the procedure described in Example 114, Step B.

$^1$H NMR (CDCl$_3$, 400 MH): δ7.94 (d, 1H), 7.52 (m , 1H), 7.43 (m, 2H), 7.38 (d, 1H), 7.32 (m, 2H), 7.00 (d, 1H), 6.74 (s, 1H), 4.21 (m, 2H), 4.09 (q, 2H), 3.10 (m, 2H), 2.08 (m, 2H), 1.47 (m, 11H), 0.83 (t, 3H).

Step B:

[1-[[3-[[(2-ethoxy)carbonyl]phenyl]-spiro[1H-indene-1,4'-piperidin]-1'-yl]carbonyl]-4-phenylbutyl]-carbamic acid 1,1-dimethylethyl ester The title compound was obtained in 84% yield (0.208 g) from the title compound of Step A (0.176 g, 0.41 mmol) using the procedure described in Example 101, Step B.

$^1$H NMR (CDCl$_3$, 400 MH): δ7.95 (d, 1H), 7.55 (m, 1H), 7.46 (m, 1H), 7.39 (d, 1H), 7.29 (m, 1H), 7.27 (m, 2H), 7.19 (m, 5H), 6.99 (m, 1H), 6.69 (d, 1H), 5.49 (m, 1H), 4.67 (m, 2H), 3.92 (m, 3H), 3.38 (t, 0.5H), 3.28 (t, 0.5H), 3.00 (m, 1H), 2.62 (m, 2H), 2.10 (m, 0.5H), 1.97 (m, 0.5H), 1,74 (m, 4H), 1.47 (m, 12H), 0.84 (m, 3H).

Step C:

N-[1-[[3-[[2-ethoxycarbonyl]phenyl]spiro[1H-indene-1,4'-piperidin]-1'-yl]carbonyl]-4-phenylbutyl]-2-[[1,1-dimethylethoxy)carbonyl]amino]-2-methylpropanamide The title compound was obtained in 93% yield (0.22 g) from the title compound of Step B (0.208 g, 0.34 mmol) using the procedure described in Example 98, Step F.

$^1$H NMR (CDCl$_3$, 400 MH): δ7.95 (d, 1H), 7.55 (m, 1H), 7.44 (m, 1H), 7.39 (m, 1H), 7.18 (m, 8H), 6.99 (m,, 1H), 6.69 (d, 1H), 5.07 (d, 1H), 4.97 (m, 1H), 4.66 (m, 1H), 3.94 (m, 3H), 3.37 (t, 0.5H), 3.25 (t, 0.5H), 2.99 (t, 1H), 2.64 (m, 2H), 2.03 (m, 1H), 1.78 (m, 4H), 1.50 (m, 19H), 0.83 (t, 3H).

Step D:

N-[1-[[3-[2-ethoxycarbonyl]phenyl]-spiro[1H-indene-1,4'-piperidine-1'-yl]carbonyl]-4-phenylbutyl]-2-amino-2-methylpropanamide hydrochloride The title compound was obtained as a white solid from the title compound of Step C using the procedure described in Example 98, Step G.

$^1$H NMR (CD$_3$OD, 400 MH): δ7.93 (m, 1H), 7.64 (m, 1H), 7.48 (m, 2H), 7.38 (m, 1H), 7.19 (m, 8H), 6.90 (d, 1H), 4.95 (m, 1H), 4.58 (m, 1H), 4.00 (m, 3H), 3.50 (m, 1H), 3.12 (m, 1H), 2.70 (m, 2H), 2.05 (m, 1H), 1.80 (m, 6H), 1.62 (m, 6H), 1.47 (m, 2H), 0.89 (m, 3H). FAB-MS: 594 (m+1).

EXAMPLE 119

N-[1-[[3-[[(2-ethoxy)carbonyl]phenyl]2,3'-dihydrospiro[1H-indene-1,4'-piperidin]-1'-yl]carbonyl-4-phenylbutyl]-2-amino-2-methylpropanamide hydrochloride Step A:

N-[1-[[3-[[(2-ethoxy)carbonyl]phenyl]2,3-dihydrospiro[1H-indene-1,4'-piperidin]-1'-yl]carbonyl-4-phenylbutyl]-2-[[(1,1-dimethylethoxy)carbonyl]amino]-2-methylpropanamide The title compound was obtained from the intermediate obtained in Example 116, Step C in 90% yield (0.086 g) by hydrogenation with Pd/C in EtOH under a hydrogen filled balloon.

$^1$H NMR (CDCl$_3$, 400 MH, 1:1 mixture): δ7.87 (m, 1H), 7.38 (m, 1H), 7.15 (m, 10H), 6.90 (d, 1H), 5.25 (m, 1H), 5.08 (m, 0.5H), 4.93 (m, 0.5H), 4.57 (m, 1H), 4.37 (m, 2H), 3.80 (m, 1H), 3.17 (m, 1H), 2.90 (m, 2H), 2.60 (m, 2H), 2.00 (m, 1H), 1.77 (m, 2H), 1.60 (m, 2H), 1.42 (m, 24H).

Step B:

N-[1-[[3-[[(2-ethoxy)carbonyl]phenyl]2,3'-dihydro-[1H-indene-1,4'-piperidin]-1'-yl]carbonyl-4-phenylbutyl]-2-amino-2-methylpropanamide hydrochloride The title compound was obtained from the compound prepared in Step A as a white solid using the procedure described in Example 98, Step G.

$^1$H NMR (CD$_3$OD, 400 MH): δ7.83 (m, 1H), 7.42 (m, 1H), 7.18 (m, 10H), 6.85 (d, 1H), 5.21 (m, 1H), 4.49 (m, 1H), 4.35 (m, 2H), 3.86 (m, 1H), 2.96 (m, 2H), 2.69 (m, 4H), 2.27 (m, 0.5H), 2.00 (m, 0.5H), 1.76 (m, 5H), 1.62 (m, 6H), 1.39 (m, 3H).

EXAMPLE 120

N-ethyl-1'-[2(R)-[(2-amino-2-methyl-1-oxopropyl)amino]-5-phenyl-1-oxopentyl]-2,3-dihydrospiro[1H-indene-1,4'-piperidine]-3-acetamide hydrochloride Diastereomer 2

Step A:

N-ethyl-1'-[2(R)-[[[2-(11,-dimethylethoxy)carbonyl]amino]-2-methyl-1-oxopropyl)amino]-5-phenyl-1-oxopentyl]2,3-dihydrospiro[1H-indene-1,4'-piperidine]-3-acetamide hydrochloride The title compound from Example 101 Step C (0.12 g) was s hydrogenated and the resulting acid was coupled to ethylamine according to the procedure described in Example 110, Step A.

$^1$H NMR (CDCl$_3$, 400 MH): δ7.20 (m, 9H), 5.40 (m, 1H), 4.92 (m, 2H), 4.50 (m, 1H), 3.75 (m, 2H), 3.32 (m, 2H), 3.20 (m, 0.5H), 3.05 (m, 0.5H), 2.65 (m, 4H), 2.22 (m, 1H), 2.05 (m, 0.5H), 1.88 (m, 0.5H), 1.73 (m, 2H), 1.47 (m, 23H), 1.13 (m, 3H).

Step B:

N-ethyl-1'-[2(R)-[(2-amino-2-methyl-1-oxopropyl)amino]-5-phenyl-1-oxopentyl]-2,3-dihydrospiro[1H-indene-1,4'-piperidine]-3-acetamide hydrochloride The title compound was obtained from the title compound in Step A using the procedure described in Example 110, Step B.

$^1$H NMR (CD$_3$OD, 400 MH): δ8.15 (t, 1H), 7.18 (m, 9H), 4.46 (t, 1H), 3.91 (d, 0.5H), 3.81 (d, 0.5H), 3.61 (m, 1H), 3.30 (m, 2H), 2.70 (m, 5H), 2.25 (m, 1.5H), 1.90 (m, 0.5H), 1.78 (m, 4H), 1.60 (m, 13H), 1.18 (m, 3H). FAB-MS: 533 (M+1).

EXAMPLE 121

N-[1(R)-[(2,3 dihydrospiro[1H-indene-1,4'-piperidin]-1'-yl)carbonyl]-2-(3',5'-[dimethoxyphenyl]methyloxy)ethyl]-2-amino-2-methylpropanamide hydrochloride Prepared from 3,5-dimethoxybenzyl chloride (559 mg, 3.0 mmole) by the procedure described in Example 40, Step A, and then Example 40, Step B to give 80 mg of the title compound.

$^1$H NMR (400 MHz, CD$_3$OD mixture of conformers): 7.18–7.08 (m,3½H), 6.80 (d, 7 Hz, ½H), 6.53 (s, 1H), 6.49 (s, 1H), 6.42 (s, ½H), 6.39 (s, ½H), 5.16 (t, 5 Hz, 1H), 4.50 (m, 3H), 4.04 (m, 1H), 3.79 (s, 3H), 3.72 (s, 3H), 3.75 (m, 2H), 3.27 (m, 1H), 2.90 ( m, 3H), 2.11 (m, 2H), 1.90–1.52 (m, 4H), 1.63 (s, ⅗H), 1.60 (s, 9/2H). FAB-MS: 510.8 (M+1).

EXAMPLE 122

N-[1(R)-[(2,3 dihydrospiro[1H-indene-1,4'-piperidin]-1'-yl)carbonyl]-2-(3',5'-bis [trifluoromethyl]phenylmethyloxy)ethyl]-2-amino-2-methyl-propanamide hydrochloride Prepared from 3,5-bis(trifluoromethyl)benzyl chloride (787 mg, 3.0 mmole) by the procedure described in Example 40, Step A, and then Example 40, Step B to give 106 mg of the title compound.

$^1$H NMR (400 MHz, CD$_3$OD mixture of conformers): 7.99 (s, 1H), 7.95 (s, 1H), 7.91 (s, 1H), 7.20–7.03 (m, 3½H), 6.74 (d, 7 Hz, ½H), 5.25 (t, 7 Hz, 1H), 4.78 (s, 1H), 4.73 (s, 1H), 4.50 (m, 1H), 4.11 (m, 1H), 3.84 (m, 2H), 3.33 (m, 1H), 2.92 (m, 3H), 2.12 (m, 2H), 1.95–1.50 (m, 4H), 1.64 (s, ½H), 1.60 (s, ½H), 1.59 (s, ½H), 1.58 (s, ½H). FAB-MS: 586.7 (M+1).

EXAMPLE 123

N-[1(R,S)-[(2,3 dihydrospiro[1H-indene-1,4'-piperidin]-1'-yl)carbonyl]-2-[(2'-pyridothio)ethyl]-2-amino-2-methylpropanamide trifluoroacetate Step A:

N-acetyl-S-(2-pyridyl)-(D,L)-cysteine methyl ester

To a solution of 2-mercaptopyridine (244 mg, 2.2 mmole) in 3 ml of acetonitrile was added methyl acetamidoacrylate (286 mg, 2.0 mmole) and potassium carbonate (552 mg, 4.0 mmole) at room temperature. The solution was heated to 50° C. for 16 hours and then poured into water. The mixture was extracted with methylene chloride. The organic layers were dried over sodium sulfate and concentrated. Purification by chromatatron (silica gel, methylene chloride/methanol=15/1) gave 250 mg (50%) of title compound.

¹H NMR (200 MHz, CDCl₃ mixture of conformers): 8.42 (d, 5 Hz, 1H), 7.82 (m, 1H), 7.52 (td, 7, 2 Hz, 1H), 7.25 (d, 7 Hz), 7.06 (td, 5, 2 Hz), 4.77 (m, 1H), 3.73 (s, 3H), 3.62 (d, 8 Hz, 1H), 3.58 (d, 8 Hz, 1H), 1.95 (s, 3H).

Step B:

N-[1(R,S)-[(2,3 dihydrospiro[1H-indene-1,4'-piperidin]-1'-yl)carbonyl]-2-[(2'-pyridothio)ethyl]carbamic acid 1,1-dimethylethyl ester To a solution of the intermediate obtained in this Example, Step A (250 mg, 0.98 mmole) in 1 ml methanol and 1 ml 12N hydrochloric acid was refluxed for 16 hours, and then concentrated. The residue in 1 ml 1N aqueous sodium hydroxide was added di-t-butyldicarbonate in 1 ml 1,4-dioxane at room temperate. After 24 hours, the mixture was diluted with ethyl acetate and acidified with 0.5N hydrochloric acid to pH=2.0. The organic layer was dried over s sodium sulfate, filtered and concentrated. The residue in 10 ml methylene chloride was added spiro[1H-indane-1,4'-piperidine]hydrochloride (233 mg, 1.0 mmole), EDC, HOBt, and triethylamine (140 ml, 1.0 mmole). The reaction was stirred for four hours and poured into water. The mixture was extracted with ethyl acetate and the organic extract was dried (Na₂SO₄) and then evaporated. The residue was purified by chromatatron (silica gel) to give 160 mg (34%) of the title compound.

¹H NMR (200 MHz, CDCl₃, mixture of diastereomers and conformers): 8.36 (m, 1H), 7.48 (m, 1H), 7.22–6.93 (m, 6H), 5.55 (m, 1H), 5.08 (m, 1H), 4.65–4.14 (m, 2H), 3.75–3.22 (m, 3H), 2.95 (t, 7 Hz, 2H), 2.86 (m, 1H), 2.10 (t, 7 Hz, 2H), 1.95–1.70 (m, 4H), 1.42 (s, 9H).

Step C:

N-[1(R,S)-[(2,3 dihydrospiro[1H-indene-1,4'-piperidin]-1'-yl)carbonyl]-2-[(2'-pyridothio)ethyl]-2-amino-2-methylpropanamide trifluoroacetate Prepared from the intermediate obtained from this Example, Step B (160 mg, 0.34 mmole), by the procedure described in Example 38, Step C to give 112 mg (57%) of the title compound.

¹H NMR (200 MHz, CD₃OD, mixture of diastereomers and conformers): 8.41 (m, 1H), 7.61 (m, 1H), 7.33–7.10 (m, 6H), 5.28 (m, 1H), 4.43 (m, 2H), 3.78 (m, 1H), 3.50–3.20 (m, 2H), 2.94 (t, 7 Hz, 2H), 2.91 (m, 1H), 2.16 (m, 2H), 2.03–1.55 (m, 4H), 1.63 (s, ½H), 1.60 (s, ½H), 1.59 (s, ½H), 1.58 (s, ½H). FAB-MS: 453.5 (M+1).

EXAMPLE 124

N-[1(R,S)-[(2,3 dihydrospiro[1H-indene-1,4'-piperidin]-1'-yl)carbonyl]-2(R,S)-[(2'-pyridosulfinyl)ethyl]-2-amino-2-methyl-propanamide hydrochloride and N-[1(R,S)-[(2,3 dihydrospiro[1H-indene-1,4'-piperidin]-1'-yl)carbonyl]-2-(R,S)-[(2'-pyridosulfonyl)ethyl]-2-amino-2-methyl-propanamide hydrochloride A solution of N-[1(R,S)-[(2,3 dihydrospiro[1H-indene-1,4'-piperidin]-1'-yl)carbonyl]-2-[(2'-pyridothio)ethyl]-2-amino-2-methylpropanamide trifluoroacetate (81 mg, 0.143 mmole) in 0.5 ml TFA was slowly added 30% hydrogen peroxide (20.4 ml) at 0° C. After stirring overnight, the reaction mixture was concentrated and purified by Pre-TLC (silica gel, CH₂Cl₂/MeOH/NH₄OH=15/1/0.1). Three compounds were isolated. All of these three compounds were acidified by HCl in ether to give hydrochloride salt.

¹H NMR (400 MHz, CD₃OD, more polar sulfoxide mixture of diastereomers and conformers): 8.70 (m, 1½H), 8.12 (t, 7 Hz, 1H), 8.00 (m, 1H), 7.58 (m, 1H), 7.19–7.07 (m, 3½H), 5.49 (m, 1H), 4.42 (d, 13 Hz, 1H), 4.00 (m, 1H), 3.57 (m, 1H), 3.36 (m, 2H), 2.93 (t, 7 Hz, 2H), 2.86 (m, 1H), 2.13 (m, 2H), 1.90–1.54 (m, 10H). FAB-MS: 469.5 (M+1).

¹H NMR (400 MHz, CD₃OD, less polar sulfoxide mixture of diastereomers and conformers): 8.69 (m, 1H), 8.54 (m, ½H), 8.09 (t, 7 Hz, 1H), 7.96 (t, 8 Hz, 1H), 7.56 (m, 1H), 7.20–7.07 (m, 3½H), 5.54 (m, 1H), 4.46 (dd, 12, 1 Hz, 1H), 4.00 (m, 1H), 3.74 (m, 1H), 3.36(dd, 13, 8 Hz, 2H), 2.94 (t, 7 Hz, 2H), 2.91 (m, 1H), 2.13 (m, 2H), 2.00–1.60 (m, 4H) 1.56 (s, ⅔H), 1.55 (s, ½H), 1.43 (s, ⅔H), 1.40 (s,⅔H). FAB-MS: 469.5 (M+1).

¹H NMR (400 MHz, CD₃OD, sulfone, mixture of diastereomers and conformers): 8.77 (m, 1H), 8.70 (m, ½H), 8.13 (m, 2H), 7.73 (m, 1H), 7.20–7.05 (m, 3½H), 5.51 (m, 1H), 4.39 (m, 1H), 4.12–3.97 (m, 2H), 3.83 (m, 1H), 3.35 (m, 1H), 2.93 (t, 7 Hz, 2H), 2.87 (m, 1H), 2.14 (m, 2H), 2.00–1.60 (m, 4H) 1.60 (s, ⅔H), 1.57 (s, ⅔H), 1.55 (s, 3H). FAB-MS: 485.6 (M+1).

EXAMPLE 125

N-[1 (S)-[(2,3 dihydrospiro[1H-indene-1,4'-piperidin]-1'-yl)carbonyl]-2-[(cyclopropylmethylthio)ethyl]-2-amino-2-methylpropanamide trifluoroacetate Step A:

N-[1(R,S)-[(2,3 dihydrospiro[1H-indene-1,4'-piperidin]-1'-yl)carbonyl]-2-[(cyclopropylmethylthio)ethyl]carbamic acid 1,1-dimethylethyl ester The title compound (166 mg) was prepared from d-cysteine according to the procedure given in Example 61, step A with the exception that bromomethyl cyclopropane was used instead of 2-iodopropane.

¹H NMR (200 MHz, CDCl₃, 1:1 mixture of conformers): 0.24(m, 2H), 57 (m, 2H), 1.0 (m, 1H), 1.44 (s, 4.5H), 1.45 (s, 4.5H), 1.5–2.0 (m, 5H), 2.11 (t, 7 Hz, 2H), 2.53 (t, 7 Hz, 2H), 2.8–3.05 (m, 4H), 3.33 (m, 1H), 4.05 (m, 1H), 4.62 (m, 1H), 4.88 (m, 1H), 5.5 (m, 1H), 7.1–7.3 (m, 4H), FAB MS calculated for C₂₅H₃₆N₂O₃S 444; found 445 (M+H).

Step B:

N-[1 (S)-[(2,3 dihydrospiro[1H-indene-1,4'-piperidin]-1'-yl)carbonyl]-2-[(cyclopropylmethylthio)ethyl]-2-amino-2-methylpropanamide trifluoroacetate The title compound was prepared from 166 mg of the intermediate obtained in step A and 91 mg of BOC-α-methyl alanine according to the procedure described in Example 61, step B.

¹H NMR (200 MHz, CD₃OD): 0.2 (m, 2H), 0.55 (m, 2H), 0.95(m, 1H), 1.5–2.0 (m, 10H), 2.13 (m, 2H), 2.5 (m, 2H), 2.75–3.1 (m, 5H), 3.3–3.5 (m, 1H), 4.07 (m, 1H), 4.50 (m, 1H), 0.09 (m, 1H), 7.05–7.25 (m, 4H). FAB MS calculated for C₂₄H₃₅N₃O₂S 429; found 430 (M+H).

EXAMPLE 126

N-[1(S)-[(2,3 dihydrospiro[1H-indene-1,4'-piperidin]-1'-yl)carbonyl]-2-[(cyclopropylmethylsulfinyl)ethyl]-2-amino-2-methylpropanamide trifluoroacetate A solution of the intermediate obtained in Example 125, step A in 5 ml 1:1 TFA/CH$_2$Cl$_2$ was stirred for 1 hour. The solution was concentrated under vacuum and azeotroped 2 times from toluene. The residue was dissolved in 10 ml CH$_2$Cl$_2$ and cooled to 0° C. EDC, HOBt, NMM and a-methyl alanine were added and the solution was stirred for 16 hours while gradually warming to room temperature. The solution was poured into ethyl acetate and washed sequentially with 1N NaHSO$_4$(aq.), water, saturated NaHCO$_3$(aq.) and brine. The organic phase was dried over anhydrous MgSO$_4$, filtered and concentrated. The material was purified by flash chromatography (25×150 mm, silica gel, 60% ethyl acetate in hexanes). A solution of 26.5 mg of this material in 2 ml methanol was treated with a solution of 22 mg NaIO$_4$ in 1 ml water and stirred for 1 hour. The mixture was poured into ethyl acetate and washed sequentially with 1N NaHSO$_4$(aq.), water, saturated NaHCO$_3$(aq.) and brine. The organic phase was dried over anhydrous MgSO$_4$, filtered and concentrated. The material was purified by flash chromatography (25×150 mm, silica gel, 0–5% methanol in CH$_2$Cl$_2$) to provide 22 mg (81%) of the desired intermediate. A solution of this material in 1 ml CH$_2$Cl$_2$ and 1 ml TFA was stirred for 1 hour and then concentrated to afford 25 mg of the title compound.

$^1$H NMR (200 MHz, CD$_3$OD): 0.43 (m, 2H), 0.7 (m, 2H), 1.3 (m, 1H), 1.5–2.2 (m, 12H), 2.7–3.5 (m, 8H), 4.0 (m, 1H), 4.5 (m, 1H), 5.44 (m, 1H), 6.64 (d, 7 Hz, ½H), 7.05–7.25 (m, 4H). FAB MS calculated for C$_{24}$H$_{35}$N$_3$O$_3$S 445; found 446 (M+H).

EXAMPLE 127

N-[1(S)-[(2,3 dihydrospiro[1H-indene-1,4'-piperidin]-1'-yl)carbonyl]-2-[(cyclopropylmethylsulfonyl)ethyl]-2-amino-2-methylpropanamide trifluoroacetate The title compound (22 mg) was prepared from the intermediate obtained in Example 125, step A according to the procedure given in Example 126, with the exception that 115 mg of OXONE were used instead of NaIO$_4$.

$^1$H NMR (200 MHz, CD$_3$OD): 0.46 (m, 2H), 0.72 (m, 2H), 1.19 (m, 1H), 1.5–2.2 (m, 12H), 2.8–3.0 (m, 1H), 2.94 (t, 6 Hz, 2H), 3.12 (t, 6 Hz, 2H), 3.3–3.83 (m, 3H), 4.07 (m, 1H), 4.47 (m, 1H), 5.56 (m, 1H), 7.05–7.20 (m, 4H). FAB MS calculated for C$_{24}$H$_{35}$N$_3$O$_4$S 461; found 462 (M+H).

EXAMPLE 128

N-[1(S)-[(2,3 dihydrospiro[1H-indene-1,4'-piperidin]-1'-yl)carbonyl]-2-[(2-methyl-1-propenylthio)ethyl]-2-amino-2-methylpropanamide trifluoroacetate Step A:

N-[1(R,S)-[(2,3 dihydrospiro[1H-indene-1,4'-piperidin]-1'-yl)carbonyl]-2-[(2-methyl-1-propenylthio)ethyl]carbamic acid 1,1-dimethylethyl ester The title compound (438 mg) was prepared from d-cysteine according to the procedure given in Example 61, step A with the exception that 3-bromo-2-methyl propene was used instead of 2-iodopropane.

$^1$H NMR (200 MHz, CDCl$_3$, 1:1 mixture of conformers): 1.45(s, 4.5H), 1.46(s, 4.5H), 1.62(s, 3H), 1.7–1.9(m, 4H), 2.1(m, 2H), 2.6–3.4(m, 10H), 4.0(m, 1H), 4.51 (m, 1H), 4.88(s, 2H), 5.5(m, 1H), 7.1–7.26(m, 4H). FAB MS calculated for C$_{25}$H$_{36}$N$_2$OS 444; found 445 (M+H).

Step B:

N-[1(S)-[(2,3 dihydrospiro[1H-indene-1,4'-piperidin]-1'-yl)carbonyl]-2-[(2-methyl-1-propenylthio)ethyl-]-2-amino-2-methylpropanamide trifluoroacetate The title compound (17.2 mg) was prepared from 438 mg of the intermediate obtained in step A and 240 mg of BOC-α-methyl alanine according to the procedure described in Example 61, Step B.

$^1$H NMR (200 MHz, CD$_3$OD): 1.5–1.9 (m, 9H), 1.62 (s, 3H), 2.14 (m, 3H), 2.65–3.43 (m, 10H), 4.07 (m, 1H), 4.49 (m, 1H), 4.88 (m, 2H), 5.07 (m, 1H), 7.05–7.1 (m, 4H). FAB MS calculated for C$_{24}$H$_{35}$N$_3$O$_2$S 429; found 430 (M+H).

EXAMPLE 129

N-[1(S)-[(2,3 dihydrospiro[1H-indene-1,4'-piperidin]-1'-yl)carbonyl]-2-[(2-methyl-1-propenylsulfinyl)ethyl]-2-amino-2-methylpropanamide trifluoroacetate The title compound (42.7 mg) was prepared from the intermediate obtained in Example 128, step A according to the procedure given in Example 126.

$^1$H NMR (400 MHz, CD$_3$OD): 1.55–165 (m, 8H), 1.70–2.0 (m, 5H), 2.1–2.17 (m, 2H), 2.9–3.0 (m, 3H), 3.07–3.67 (m, 5H), 3.98–4.03 (m, 1H), 4.49 (m, 1H), 4.47–5.08 (m, 1H), 5.08–5.14 (m, 2H), 5.42–5.46 (m, 1H), 7.05–7.18 (m, 4H). FAB MS calculated for C$_{24}$H$_{35}$N$_3$O$_3$S 445; found 446 (M+H).

EXAMPLE 130

N-[1(S)-[(2,3 dihydrospiro[1H-indene-1,4'-piperidin]-1'-yl)carbonyl]-2-[(2-methyl-1-propenylsulfonyl)ethyl]-2-amino-2-methylpropanamide trifluoroacetate The title compound was prepared from the intermediate obtained in Example 128, step A according to the procedure given in Example 129, with the exception that 86 mg of OXONE were used instead of NaIO$_4$.

$^1$H NMR (200 MHz, CD$_3$OD): 1.49–2.19(m, 12H), 1.96(s, 3H), 2.87–3.0(m, 3H), 3.25–4.1(m, 6H), 4.44–4.5(m, 1H), 5.18–5.25(m, 2H), 5.48–5.60(m, 1H), 7.07–7.15(m, 4H). FAB MS calculated for C$_{24}$H$_{35}$N$_3$O$_4$S 461; found 462 (M+H).

EXAMPLE 131

N-[1(S)-[(2,3 dihydrospiro[1H-indene-1,4'-piperidin]-1'-yl)carbonyl]-2-[(2-methylpropylthio)ethyl]-2-amino-2-methylpropanamide trifluoroacetate About 50 mg of 10% Pd on carbon was added to a solution of the product obtained in Example 128, step B in 2 ml methanol. This mixture was stirred for 16 hours under 1 atom. of hydrogen and then filtered through Celite and concentrated to provide 6.9 mg of the title compound.

$^1$H NMR (400 MHz, CD$_3$OD): 0.97–1.01 (m, 4H), 1.1–1.43 (m, 2H), 1.56–1.96 (m, 11H), 2.12–2.17 (m, 2H), 2.43–2.5 (m, 2H), 2.75–3.03 (m, 4H), 3.29–3.43 (m, 4H), 4.04–4.08 (m, 1H), 4.48–4.51 (m, 1H), 5.06 (t, 6 Hz, 1H), 5.08–5.14 (m, 2H), 7.05–7.20 (m, 4H). FAB MS calculated for C$_{24}$H$_{37}$N$_3$O$_2$S 431; found 432 (M+H).

EXAMPLE 132

N-[1(S)-[(2,3 dihydrospiro[1H-indene-1,4'-piperidin]-1'-yl)carbonyl]-2-[(2-methylpropylsulfonyl)ethyl]-2-amino-2-methylpropanamide trifluoroacetate The title compound was prepared from the product obtained in Example 130 according to the procedure given in Example 131.

$^1$H NMR (400 MHz, CD$_3$OD): 1.21 (m, 5H), 1.43–1.45 (m, 1H), 1.57–1.64 (m, 7H), 1.7–2.17 (m, 5H), 2.34 (m, 1H), 2.92–2.97 (m, 2.5H), 3.1 (m, 1.5H), 3.3–3.75 (m, 4H), 4.03–4.07 (m, 1H), 4.45 (m, 1H), 5.53 (m, 1H), 7.05–7.2 (m, 4H). FAB MS calculated for C$_{24}$H$_{37}$N$_3$O$_4$S 463; found 464 (M+H).

EXAMPLE 133

N-[1(R,S)-[(2,3 dihydrospiro[1H-indene-1,4'-piperidin]-1'-yl)carbonyl]-2-[(phenylthio)ethyl]-2-amino-2-methylpropanamide trifluoroacetate Step A:

The title compound was prepared from 1.29 g of N-acetyl-S-phenyl-d,l-cysteine and 1.28 g of the spiroindane hydrochloride according to the procedure given in Example 38, Step B.

$^1$H NMR (200 MHz, CD$_3$OD): 1.35–2.12 (m, 9H), 2.7–2.95 (m, 3H), 3.1–3.35 (m, 3H), 3.7 (m, 1H), 4.44 (m, 1H), 5.07 (m, 1H), 7.05–7.48 (m, 9H). FAB MS calculated for C$_{24}$H$_{28}$N$_2$O$_2$S 408; found 409 (M+H).

Step B:

N-[1(R,S)-[(2,3 dihydrospiro[1H-indene-1,4'-piperidin]-1'-yl)carbonyl]-2-[(phenylthio)ethyl]-2-amino-2-methylpropanamide trifluoroacetate A solution of the intermediate obtained in step A in 100 ml methanol and 100 ml of concentrated aqueous HCl was refluxed for 16 hours. The solution was concentrated and azeotroped 2 times from benzene. To a solution of this salt in 50 ml CH$_2$Cl$_2$ was added 1.0 g BOC-α-methyl alanine, NMM, EDC and HOBt. This solution was stirred for 16 hours and then poured into 700 ml ethyl acetate and washed with 1N NaHSO$_4$ (aq.), H$_2$O and saturated aqueous NaHCO$_3$. The organic layer was dried over MgSO$_4$, filtered and concentrated. The material was purified by MPLC(40% EtOAc/hexane, silica gel) to provide. 633 mg of the BOC-protected intermediate. The BOC protecting group was removed from 77.6 mg of this intermediate by stirring in 1 ml CH$_2$Cl$_2$ and 1 ml TFA for 1 hour and then concentrating to afford the title compound.

$^1$H NMR (200 MHz, CD$_3$OD): 1.39–1.75 (m, 10H), 2.03–2.2 (m, 2H), 2.75–2.93 (m, 3H), 3.13–3.4 (m, 4H), 3.62 (m, 1H), 4.41 (m, 1H), 7.05–7.5 (m, 9H). FAB MS calculated for C$_{26}$H$_{33}$N$_3$O$_2$S 451; found 452 (M+H).

EXAMPLE 134

N-[1(R,S)-[(2,3 dihydrospiro[1H-indene-1,4'-piperidin]-1'-yl)carbonyl]-2-[(phenylsulfinyl)ethyl]-2-amino-2-methylpropanamide trifluoroacetate A solution of 84 mg of the BOC-protected intermediate synthesized in Example 133, step B in 2 ml of methanol was treated with a solution of 67 mg NaIO$_4$ in 1 ml water. After 1 hour the solution was poured into 200 ml of ethyl acetate and washed with water. The organic layer was dried over MgSO$_4$, filtered and concentrated. The material was purified by flash chromatography(60% EtOAc/hexane) to afford 14.9 mg (17%) of the desired intermediate. A solution of this material in 2 ml of 1:1 TFA:CH$_2$Cl$_2$ was stirred for 1 hour and then concentrated to provide the title compound(16 mg, about 100%).

$^1$H NMR (200 MHz, CD$_3$OD): 1.3–1.9 (m, 10H), 2.03–2.2 (m, 2H), 2.89–2.95 (m, 3H), 3.15–3.4 (m, 3H), 3.7–3.97 (m, 1H), 4.43 (m, 1H), 5.26–5.45 (m, 1H), 7.1–7.2 (m, 4H), 7.6–7.78 (m, 5H). FAB MS calculated for C$_{26}$H$_{33}$N$_3$O$_3$S 467; found 468 (M+H).

EXAMPLE 135

N-[1(R)-[[2,3-dihydro-3[[(methylamino)carbonyl]amino]spiro[1H-indene-1,4'-piperidin]-1'-yl]carbonyl]-2-(indol-3-yl)ethyl-2-amino-2-methylpropanamide hydrochloride Step A:

3-amino-2,3-dihydrospiro[1H-indene-1,4'-piperidine]-1'-carboxylic acid 1,1-dimethylethyl ester To a mixture of the intermediate obtained in Example 4 Step A (850 mg, 2.80 mmol) and hydroxylamine hydrochloride (2.1 g, 29.5 mmol in ethanol (8 ml) and water (8 ml) was added 10% sodium hydroxide and the mixture was stirred overnight. The pH was adjusted to 12 with sodium hydroxide and the mixture was extracted with ethyl acetate (5×1 vol). The organic layers were dried over sodium sulfate, filtered, and concentrated to provide the oxime. The crude product (700 mg, 2.20 mmol) was added to a suspension of palladium hydroxide (350 mg) in acetic acid (3.0 ml). The mixture was purged with hydrogen and stirred under a hydrogen atmosphere for 14 hours. The mixture was filtered through celite, concentrated and azeotroped from toluene to yield the title compound (623 mg, 2.09 mmol).

Step B:

2,3-dihydro-3-[[(methyl-amino)carbonyl]amino]spiro[1H-indene-1,4'-piperidine]-1'-carboxylic acid 1,1-dimethylethyl ester To a mixture of the intermediate obtained in Step A (263 mg, 0.865 mmol) and triethylamine (0.145 ml, 1.03 mmol) in methylene chloride was added methylisocyanate (0.061 ml, 1.03 mmol). The reaction mixture was stirred overnight and then applied to a flash chromatography column. Flash chromatography (silica gel, methylene chloride/ethyl acetate 1:1) provided the title compound (206 mg, 0.57 mmol).

Step C:

N-[1(R)-[[2,3-dihydro-3[[(methyl-amino)carbonyl]amino]spiro[1H-indene-1,4'-piperidin]-1'-yl]carbonyl]-2-(indol-3-yl)ethyl]-2-[[(1,1-dimethylethoxy)carbonyl]amino]-2-methylpropanamide hydrochloride The title compound from Step B (125 mg, 0.348 mmol) was stirred for 1 h in a mixture of methylene chloride and TFA (1:1). The solution was then concentrated and azeotroped from toluene (3×10 ml). The residue was reacted with the compound prepared in Example 4, Step D (145 mg, 0.38 mmol), EDC (86.4 mg, 0.45 mmol), HOBT (61.0 mg, 0.45 mmol), and NMM (0.42 ml, 0.383 mmol) in methylene chloride according to the procedure used for Example 1, Step A, to provide the title compound (78 mg, 0.125 mmol).

Step D:

N-[1(R)-[[2,3-dihydro-3[[(methyl-amino)carbonyl]amino]spiro[1H-indene-1,4'-piperidin]-1'-yl]carbonyl]-2-(indol-3-yl)ethyl-2-amino-2-methylpropanamide hydrochloride The title compound (49.1 mg, 0.88 mmol) was prepared from the immediate obtained in Step C (68 mg, 0.10 mmol) according to the procedure described in Example 4, Step F.

$^1$HNMR (400 MHz, CD$_3$OD 1:1 mixture of diastereomers): 7.40–7.13 (m), 6.93–6.92 (m), 6.80–6.78 (m) 5.29–5.13 (M), 4.62–4.45 (m), 4.15–4.02 (m), 3.80–3.65 (m), 2.96–2.70 (m), 2.25–2.15 (m), 2.05–1.90 (m), 1.75–1.45 (m) FAB-MS: 522 (M+1).

EXAMPLE 136

Preparation of N-[1(R)-[[3-[(methylsulfonyl)amino]-2,3-dihydrospiro[1H-indene-1,4'-piperidin]-1'-yl]carbonyl]-2-(phenylmethoxy)ethyl]-2-amino-2-methylpropanamide hydrochloride Step A:

1'-(1,1-Dimethylethyloxycarbonyl)-3-(methylsulfonyl)amino-2,3-dihydrospiro(1H-indene-1,4'-piperidine)

A sample of 1'-(1,1-Dimethylethyloxycarbonyl)-3-amino-2,3-dihydrospiro(1H-indene-1,4'-piperidine), prepared by hydrogenation of 500 mg of oxime (1.58 mmole) as in Example 135 Step A, in 3.5 mL methylene chloride containing 475 mg of DMAP (2.46×1.58 mmole), and 550λ of triethylamine (2.51×1.58 mmole), was stirred under nitrogen in an ice bath while adding a solution of 270λ of methanesulfonyl chloride (2.2×1.58 mmole) in 3 mL methylene chloride dropwise over 2–3 minutes. The suspension was stored over night in the refrigerator. It was then washed twice with water, dried with magnesium sulfate and concentrated under reduced pressure to a gum. Preparative TLC on four 8"×8"×1,000 g GF silica gel plates using 1:2 ethyl acetate: hexane afforded the title compound, which crystallized on standing. Yield: 322 mg (54%)

Calc. for C$_{19}$H$_{28}$N$_2$O$_4$S: MW=380.51; found m/e=(m+1) 381.1.

Step B:

3-(Methylsulfonyl)amino-2,3-dihydrospiro(1H-indene-1,4'-piperidine)

The product from the previous example was taken up with cooling in an ice bath in ca. 3 mL of TFA. When the dissolution was complete, the bath was removed, and the reaction allowed to stand for 30 minutes. It was then concentrated to a gum under reduced pressure, taken up in chloroform, and shaken with 1M dipotassium hydrogen phosphate to which sufficient sodium hydroxide solution had been added to bring the pH to >10. The organic phase was removed and the extraction repeated with three more portions of chloroform. After drying with magnesium sulfate, the combined chloroform solutions were concentrated and the resultant crude product purified by preparative tlc on three 8"×8"×1,000μ silica gel GF plates developed with 0.5:5:95 conc. ammonium hydroxide:methanol:chloroform. Extraction of the isolated band with 3:30:70 conc. ammonium hydroxide:methanol:chloroform, and evaporation afforded the title compound.

Calc. for C$_{14}$H$_{19}$N$_2$O$_2$S: MW=279.38; found m/e=(m+1) 280.9.

PMR (200 MHz; CDCl$_3$): 7.44–7.24 (m, 4H), 5.03 (t, J=8 Hz, 1H), 4.65 (bs, 1H), 3.12 (s, 3H), 3.11–3.02 (m, 1H), 2.95–2.72 (m, 3H), 2.09 (dr, J=4, 12 Hz, 1H), 1.9–1.7 (m, 3H), 1.7–1.4 (m, 3H).

Step C:

N-[1(R)-[[3-[(Methylsulfonyl)amino]-2,3-dihydrospiro[1H-indene-1,4'-piperidin]-1'-yl]carbonyl]-2-phenylmethyloxy)-ethyl]carbamic acid 1,1-dimethylethyl ester Substituting the product from the above step in Step A, Example 63, for 2,3-dihydrospiro(1H-indene-1,4'-piperidine)hydrochloride, and EDC for DCC, the title compound is obtained.

Calc. for C$_{29}$H$_{39}$N$_3$O$_6$S: MW=557.71; found m/e=(m+1) 558.9

Step D:

1'-[[2(R)-Amino-1-oxo-3-(phenylmethyloxy)]propyl]-3-[(methylsulfonyl)amino]-2,3-dihydrospiro[1H-indene-1,4'-piperidine]

Substituting the product from the above step in Step B, Example 63, for 2,3-dihydrospiro(1H-indene-1,4'-piperidine)hydrochloride, the title compound is obtained.

Calc. for C$_{24}$H$_{31}$N$_3$O$_4$S: MW=457.59; found m/e=(m+1) 458.5.

Step E:

N-[[1(R)-3-[(Methylsulfonyl)amino]-2,3-dihydrospiro[1H-indene-1,4'-piperidine]]-1'-yl)carbonyl]-2-(phenylmethyloxy)ethyl]2-[(1,1-dimethylethyloxy)carbonyl]amino]-2-methylpropanamide Substituting the product from the above step in Step C, Example 63, for the product from Step B, Example 63, the title compound is obtained.

Step F:

N-[1(R)-[[3-[(Methylsulfonyl)amino]-2,3-dihydrospiro[1H-indene-1,4'-piperidin]-1'-yl]carbonyl]-2-(phenylmethoxy)ethyl]-2-amino-2-methylpropanamide Substituting the product from the above step in Step D, Example 63, for the product from Step C, Example 63, the title compound is obtained.

Calc. for $C_{28}H_{38}N_4O_5S$: MW=542.7; found m/e=(m+1) 543.8

PMR (200 MHz; $CDCl_3$): 8.31("quart", J=8 Hz), 7.45–7.19 (m), 6.9–6.8 (m), 6.73–6.63 (m), 5.25–4.9 (m), 4.7–4.4 (m), 4.60 (s), 4.57 (s), 4.07 (bt, J=1 4 Hz), 3.81–3.51 (m), 3.32–2.98 (m), 3.08 (s), 2.98–2.65 (m), 2.13–1.70 (m), 1.70–1.25 (m), 1.34 (s).

Step G:

N-[1(R)-[[3-[(Methylsulfonyl)amino]-2,3-dihydrospiro[1H-indene-1,4'-piperidin]-1'-yl]carbonyl]-2-(phenylmethoxy)ethyl]-2-amino-2-methylpropanamide hydrochloride Substituting the product from the above step in Step E, Example 63, for the product from Step D, Example 63, the title compound is obtained.

EXAMPLE 137

Preparation of N-[1(R)-[[3-[[(phenylmethoxy)carbonyl]amino]-2,3-dihydrospiro[1H-indene-1,4'-piperidin]-1'-yl]carbonyl]-2-(phenylmethoxy)ethyl]-2-amino-2-methylpropanamide hydrochloride Step A:

1'-(1,1-Dimethylethyloxycarbonyl)-3-[(phenylmethoxy)-carbonyl]amino-2,3-dihydrospiro(1H-indene-1,4'-piperidine A sample of ca. 0.55g 1'-(1,1-dimethylethyloxycarbonyl)-3-amino-2,3-dihydrospiro(1H-indene-1,4'-piperidine)(1.82 mmole), in 5 mL methylene chloride containing 243 mg of DMAP (1.1×1.82 mmole), and 277λ, of triethylamine (1.1×1.82 mmole), was stirred under nitrogen in an ice bath while adding a solution of 317λ of benzyloxycarbonyl chloride (1.2×1.82 mmole) in 2 mL methylene chloride dropwise over 2–3 minutes. The suspension was stored over night in the refrigerator. It was then washed with water, 5% citric acid, dried with magnesium sulfate and concentrated under reduced pressure to a gum. Preparative TLC on eight 8"×8"×1,000μ silica gel GF plates using 1:1 ether:hexane afforded 250 mg of the title compound. Calc. for $C_{27}H_{36}N_4O_6S_2$: MW=576.7; found m/e=(m+1) 577.5.

Step B:

3-[(Phenylmethoxy)carbonyl]amino-2,3-dihydrospiro(1H-indene-1,4'-piperidine

The product from the previous example was taken up in ca. 2 mL anisole, cooled in an ice bath, and treated with ca. 2mL of TFA. The bath was removed, and the reacion allowed to stand for 30 minutes. It was then concentrated to a gum under reduced pressure, taken up in chloroform, and shaken with 1M dipotassium hydrogen phosphate to which sufficient sodium hydroxide solution had been added to bring the pH to >10. The organic phase was removed and the extraction repeated with three more portions of chloroform. After drying with magnesium sulfate, the combined chloroform solutions were concentrated and the resultant Crude product purified by preparative tlc on three 8"×8"×1,000 m GF silica plates developed with 1:10:90 conc. ammonium hydroxide:methanol:chloroform. Extraction of the isolated band with 3:30:70 conc. ammonium hydroxide:methanol:chloroform, and evaporation afforded the title compound.

Calc. for $C_{21}H_{24}N_2O_2$: MW=336.44; found m/e=(m+1) 337.0.

PMR (200 MHz; $CDCl_3$): 7.45–7.33 (m, 4H), 7.33–7.2 (m, 5H), 5.36–5.2 (m), 5.16 (s, 2H), 5.1–4.94 (m), 4.13 (bs), 3.25–3.2 (m), 3.14 (s, 3H), 3.0–2.7 (m), 2.19 (dt, J=4, 12 Hz), 1.88–1.45 (m).

Step C:

N-[1(R)-3-[(Phenylmethoxy)carbonyl]amino]-2,3-dihydrospiro[1H-indene-1,4'-piperidin]-1'-yl]carbonyl]-2-phenylmethyloxy)ethyl]carbamic acid 1,1-dimethylethyl ester Substituting the product from the above step in Step A, Example 63, for 2,3-dihydrospiro(1H-indene-1,4'-piperidine)hydrochloride, and EDC for DCC, the title compound is obtained.

Step D:

1'-[[2(R)-Amino-1-oxo-3-(phenylmethyloxy)]propyl]-3-[(phenylmethoxy)carbonyl]amino-2,3-dihydrospiro[1H-indene-1,4'-piperidine]

Substituting the product from the above step in Step B, Example 63, for 2,3-dihydrospiro(1H-indene-1,4'-piperidine)hydrochloride, the title compound is obtained.

Step E:

N-[1(R)-[[3-[(Phenylmethoxy)carbonyl]amino-2,3-dihydrospiro[1H-indene-1,4'-piperidin]-1'-yl]carbonyl]-2-(phenylmethyloxy)ethyl]-2-[(1,1-dimethylethyloxy)carbonyl]-amino-2-methylpropanamide Substituting the product from the above step in Step C, Example 63, for the product from Step B, Example 63, the title compound is obtained.

Calc. for $C_{40}H_{50}N_4O_7$: MW=698.87; found m/e=(m+1) 699.7.

Step F:

N-[1(R)-[[3-[(Phenylmethoxy)carbonyl]amino-2,3-dihydrospiro[1H-indene-1,4'-piperidin]-1'-yl]carbonyl]-2-(phenylmethyloxy)ethyl]-2-amino-2-methylpropanamide Substituting the product from the above step in Step D, is Example 63, for the product from Step C, Example 63, the title compound is obtained.

Calc. for $C_{35}H_{42}N_4O_5$: MW=598.75; found m/e=(m+1) 599.8.

PMR (200 mHz; CDCl$_3$): 8.28 (dd, J=10,14 Hz), 7.44–7.1 (m), 6.75–6.84 (m), 6.65 (bd, J=6 Hz), 5.35–5.07 (m), 5.14 (bs), 4.7–4.4 (m), 4.18–3.87 (bm), 3.75–3.5 (m), 3.14 (bquin, J=12 Hz), 2.95–2.6 (m), 2.1–1.8 (m), 1.85 (bs), 1.8–1.45 (m), 1.35 (bs), Step G:

N-[1(R)-[[3-[[(Phenylmethoxy)carbonyl]amino]-2,3-dihydrospiro[1H-indene-1,4'-piperidin]-1'-yl]carbonyl]-2-(phenylmethoxy)ethyl]-2-amino-2-methylpropanamide hydrochloride Substituting the product from the above step in Step E, Example 63, for the product from Step D, Example 63, the title compound is obtained.

EXAMPLE 138

Preparation of N-[1(R)-[[3-[[[[methoxycarbonyl]methyl]sulfonyl]amino]-2,3-dihydrospiro[1H-indene-1,4'-piperidin]-1'-yl]carbonyl]-2-(indole-3-yl)ethyl]-2-amino-2-methyl-propanamide hydrochloride Step A:

1'-(1,1-Dimethylethyloxycarbonyl)-3-[[[methoxycarbonyl]-methyl]sulfonyl]amino-2,3-dihydrospiro(1H-indene-1,4'-piperidine)

A sample of 1'-(1,1-dimethylethyloxycarbonyl)-3-amino-2,3-dihydrospiro(1H-indene-1,4'-piperidine), prepared by hydrogenation of 500 mg of oxime (1.58 mmole) as in Example 135, in 2 mL methylene chloride containing 475 mg of DMAP (2.46×1.58 mmole), and 550λ of triethylamine (2.51×1.58 mmole), was stirred under nitrogen in an ice bath while adding a solution of 400λ of 8.4M methyl chlorosulfonylacetate (2.13×1.58 mmole) in 2 mL methylene chloride dropwise over 2–3 minutes. The suspension was stored overnight in the refrigerator. It was then washed twice with water, then with 5% citric acid. Atypically, solid material was still present in suspension; this was s removed by filtration, the filtrate dried with magnesium sulfate and concentrated under reduced pressure. Again, solid formed and was removed by filtration. Finally, preparative TLC on four 8"×8"×1,000μ GF silica gel plates using 2:1 ethyl acetate:hexane afforded 389 mg of the title compound Calc. for $C_{21}H_{30}N_2O_6S$: MW=438.54; found m/e=(m+1) 439.1.

Step B:

3-[[(Methoxycarbonyl)methyl]sulfonyl]amino-2,3-dihydrospiro(1H-indene-1,4'-piperidine)

Substituting the product of the above step in Example 137, Step B, for the product from Example 137, Step A, the title compound is obtained.

Calc. for $C_{16}H_{21}N_2O_4S$: MW=337.42; found m/e=(m+1) 339.0.

PMR (200 MHz; CDCl$_3$): 7.47 (dd, J=2, 8 Hz, 1H), 7.40–7.22 (m, 3H), 5.03 (t, J=8 Hz, 1H), 4.21 (d, J=16 Hz, 1H), 4.10 (d, J=16 Hz, 1H), 3.96 (bs), 3.83 (s, 3H), 2.28–2.1 (m, 2H), 2.91 (bquar, J=10 Hz, 2H), 2.75 (dd, J=8, 14 Hz, 1H), 2.18 (dt, J=4, 12 Hz, 1H), 1.95 (dd, J=8, 14 Hz, 1H), 1.79 (bdd, J=4, 14 Hz, 1H), 1:58 (bdd, J=14, 28 Hz, 2H).

Step C

N-[1(R)-[[3-[[[(Methoxycarbonyl)methyl]sulfonyl]amino]-2,3-dihydrospiro[1H-indene-1,4'-piperidin]-1'-yl]carbonyl]-2-(indole-3-yl)ethyl]-2-[(1,1-dimethylethyloxy)carbonyl]-amino-2-methylpropanamide Substituting the product of the above step in Example 63, Step C for the product from Example 63, Step B, and the product from Example 4, Step D for N-t-Boc-α-methylalanine, the title compound is obtained.

Calc. for $C_{36}H_{46}N_5O_8S$: MW=708.86; found m/e=(m+1) 710.3.

Step D:

N-[1(R)-[[3-[[[(Methoxycarbonyl)methyl]sulfonyl]amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for $C_{31}H_{38}N_5O_6S$: MW=608.74; found m/e=(m+1) 610.2.

PMR (200 MHz; in δ from TMS; CDCl$_3$): 8.65 (s), 8.55 (s), 8.32 (t, J=8 Hz), 7.72 (d, J=6 Hz), 7.61 (d, J=8 Hz), 7.45–7.29 (m), 7.29–7.2 (m), 7.2–7.02 (m), 6.06 (t, J=8 Hz), 5.35–5.08 (vbs), 4.98–4.77 (m), 4.21 (bd, J=12 Hz), 4.2–3.95 (m), 3.81 (s), 3.61 (bd, J=14 Hz), 3.28–3.04 (m), 2.99–2.76 (m), 2.72–2.25 (m), 2.0–1.4 (m), 1.34 (s), 1.28–1.1 (m), 1.05–0.7 (m), 0.54–0.3 (m).

Step E:

N-[1(R)-[[3-[[[(Methoxycarbonyl)methyl]sulfonyl]amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 139

Preparation of N-[1(R)-[[3-[(Methylsulfonyl)amino]-2,3-dihydrospiro-[1H-indene-1,4'-piperidin]-1'-yl]carbonyl]-2-(indole-3-yl)ethyl]-2-amino-2-methylpropanamide hydrochloride Step A:

N-[[1(R)-3-[(Methylsulfonyl)amino]-2,3-dihydrospiro[1H-indene-1,4'-piperidin]]-1'-yl)carbonyl]-2-(indole-3-yl)ethyl]2-{{1,1-dimethylethyloxy)carbonyl]amino]-2-methylpropanamide Substituting the product of Example 136, Step B in Example 63, Step C for the product from Example 63, Step B, and the product from Example 63, Step C for N-t-Boc-α-methylalanine, the title compound is obtained.

Calc. for $C_{34}H_{45}N_5O_6S$: MW=650.82; found m/e=(m+1) 651.9.

Step B:

N-[1(R)-[[3-[(Methylsulfonyl)amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained Calc. for $C_{29}H_{36}N_5O_4S$: MW=550.7; found m/e=(m+1) 552.6.

PMR (200 MHz; in δ from TMS; CDCl$_3$): 8.59 (s), 8.54–8.26 (m), 7.76 (d, J=8 Hz), 7.66 (d, J=8 Hz), 7.3–7.04 (m), 6.64 (t, J=8 Hz), 5.36–5.1 (m), 4.97–4.76 (m), 4.46 (bd, J=12 Hz), 3.66 (bd, J=12), 3.22 (t, J=6 Hz), 3.1 (s), 3.06 (s), 3.1–2.8 (m), 2.8–2.3 (m), 2.1–1.75 (m), 1.1 (bs), 1.65–1.45 (m), 1.39 (s), 1.35 (s), 1.30–1.05 (m), 1.05–0.8 (m), 0.6–0.4 (m).

Step C:

N-[1(R)-[[3-[(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 140

Preparation of N-[1(R)-[[3-[[[phenylmethoxy]carbonyl]amino]-2,3-dihydrospiro[1H-indene-1,4'-piperidin]-1'-yl]carbonyl]-2-(indole-3-yl)ethyl]-2-amino-2-methylpropanamide hydrochloride Step A:

N-[1(R)-3-[[Phenylmethoxy]carbonyl]amino-2,3-dihydrospiro[1H-indene-1,4'-piperidin]]-1'-yl)carbonyl]-2-(indole-3-yl)ethyl]2-{{1,1-dimethylethyl-oxy)carbonyl]-amino]-2-methylpropanamide Substituting the product of Example 136, Step B in Example 63, Step C for the product from Example 63, Step B, and the product from Example 4, Step D for N-t-Boc-α-methylalanine, the title compound is obtained.

Calc. for $C_{41}H_{49}N_5O_6$: MW=707.88; found m/e=(m+1) A MESS.

Step B:

N-[1(R)-[[3-[[[Phenylmethoxy]carbonyl]amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained Calc. for $C_{36}H_{41}N_5O_4$: MW=607.76; found m/e=(m+1) 608.3.

PMR (200 MHz; in δ from TMS; CDCl$_3$): 8.44–8.24 (m), 7.75 (t, J=6 Hz), 7.64 (d, J=8 Hz), 7.45–7.3 (m), 7.3–7.19 (m), 7.19–7.0 (m), 6.65–6.53 (m), 5.35–5.05 (m), 5.16 (s), 5.12 (s), 4.93 (t, J=8 Hz), 4.47 (bd, J=14 Hz), 3.7–3.5 (bm), 3.2 (t, J=6 Hz), 3.07–277 (m), 2.77–2.3 (m), 2.1–1.75 (m), 1.1 (bs), 1.65–1.45 (m), 1.39 (s), 1.35 (s), 1.30–1.05 (m), 1.05–0.8 (m), 0.6–0.4 (m).

Step C:

N-[1(R)-[[3-[[[Phenylmethoxy]carbonyl]amino]-2,3-dihydrospiro[1H-indene-1,4'-piperidin]-1'-yl]carbonyl]-2-(indole-3-yl)ethyl]-2-amino-2-methylpropanamide hydrochloride Subtituting the product from the above step in Step E, Example 63, for the product from Step D, Example 63, the title compound is obtained.

EXAMPLE 141

Preparation of N-[1(R)-[[3-[(phenylsulfonyl)amino]-2,3-dihydrospiro-[1H-indene-1,4'-piperidin]-1'-yl]carbonyl]-2-(phenylmethoxy)ethyl]-2-amino-2-methylpropanamide hydrochloride Step A:

N-[1(R)-[[3-Amino-2,3-dihydrospiro[1H-indene-1,4'-piperidin]-1'-yl]carbonyl]-2-(phenylmethoxy)ethyl]-2-[(1,1-dimethylethyloxy)carbonyl]amino-2-methylpropanamide A solution of N-[[1(R)-3-[(phenylmethoxy)carbonyl]amino]-2,3-dihydrospiro[1H-indene-1,4'-piperidine]]-1'-yl)carbonyl]-2-(phenylmethyloxy)ethyl]2-[(1,1-dimethyl-ethyloxy)carbonyl]amino]-2-methylpropanamide (Example 137, Step E), 43 mg, in 1 mL methanol containing 10 mg of 20% Pd(OH)$_2$/C, was shaken for 18 hrs under a 35 psi atmosphere of hydrogen. After filtration to remove the catalyst, the solvent was removed under reduced pressure, and the crude product was subjected to preparative TLC on one 8"×8"×250μ GF silica gel plate with 0.2:2:98 Conc. NH$_4$OH:MeOH:CHC$_{13}$ to give ca. 27 mg of the title compound Calc. for $C_{32}H_{44}N_4O_5$: MW=564.73; found m/e -(m+1) 566.0.

Step B:

N-[1(R)-[[3-[(Phenylsulfonyl)amino]-2,3-dihydrospiro[1H-indene-1,4'-piperidin]-1'-yl]carbonyl]-2-(phenylmethoxy)ethyl]-2-[(1,1-dimethylethyloxy)carbonyl]amino-2-methyl-propanamide The product from the above step, 39 mg, in 0.5 ml methylene chloride, containing 135λ of triethyl amine and 12 mg DMAP, was stirred in an ice bath under a nitrogen atmosphere, while a solution of 10λ benzoyl chloride in 0.2 ml of methylene chloride was added dropwise over a five minute period. The reaction was allowed to stir for 2 hrs, after which it was stored over night in the refrigerator.

After washing with water and drying with magnesium sulfate, the crude product was subjected to preparative TLC on one 8"×8"×1,000μ GF silica gel plate with 3:1 ethyl acetate:hexane to give the title compound.

Calc. for $C_{38}H_{48}N_4O_7S$: MW=704.89; found m/e=(m+1) 705.6.

Step C:

N-[1(R)-[[3-[(Phenylsulfonyl)amino]-2,3-dihydrospiro[1H-indene-1,4'-piperidin]-1'-yl]carbonyl]-2-(phenylmethoxy)ethyl]-2-amino-2-methylpropanamide.

Substituting the product from the above step in Step D, Example 63, for the product from Step C, Example 63, the title compound is obtained.

Calc. for $C_{33}H_{40}N_4O_5S$: MW=604.77; found m/e=(m+1) 605.9.

PMR (200 MHZ; in δ from TMS; $CDCl_3$): 8.25 (dd, J=8,14 Hz), 7.96 (d, J=8 Hz), 7.66–7.48 (m), 7.24–7.04 (m), 7.04–6.88 (m), 6.77–6.66 (m), 6.64–6.54 (m), 5.2–5.0 (m), 5.0–5.75 (m), 4.6–4.4 (m), 4.52 (s), 4.50 (s), 3.98 (bt, J=12 Hz), 3.72–3.52 (m), 3.16–2.85 (m), 2.85–2.54 (m), 2.54–2.30 (m), 2.15 (vbs), 2.05–1.8 (m), 1.8–1.64 (m), 1.64–1.4 (m), 1.35 (bs).

Step D:

N-[1(R)-[[3-[(Phenylsulfonyl)amino]-2,3-dihydrospiro[1H-indene-1,4'-piperidin]-1'-yl]carbonyl]-2-(phenylmethoxy)ethyl]-2-amino-2-methylpropanamide hydrochloride Substituting the product from the above step in Step E, Example 63, for the product from Step D, Example 63, the title compound is obtained.

EXAMPLE 142

Preparation of N-[1(R)-[[3-[(phenylsulfonyl)amino]-2,3-dihydrospiro-[1H-indene-1,4'-piperidin]-1'-yl]carbonyl]-2-(indole-3-yl)ethyl]-2-amino-2-methyl-propanamide hydrochloride Step A:

N-[1(R)-[[3-Amino-2,3-dihydrospiro[1H-indene-1,4'-piperidin]-1'-yl]carbonyl]-2-(indole-3-yl)ethyl]-2-[(1,1-dimethylethyloxy)carbonyl]amino-2-methylpropanamide If N-[[1(R)-3-[(phenylmethoxy)carbonyl]amino]-2,3-dihydrospiro[1H-indene-1,4'-piperidine]]-1'-yl)carbonyl]-2-(indole-3-yl)ethyl]2-[(1,1-dimethylethyloxy)carbonyl]amino]-2-methylpropanamide (Example 140, Step E) is substituted in Example 141, Step A, for the product of Example 137, Step E, the title compound is obtained.

Step B:

N-[1(R)-[[3-(Phenylsulfonyl)amino-2,3-dihydrospiro[1H-indene-1,4'-piperidin]-1'-yl]carbonyl]-2-(indole-3-yl)ethyl]-2-[(1,1-dimethylethyl-oxy)carbonyl]amino-2-methyl-propanamide If the product from the above step is substituted in Example 142, Step B, for the product of Example 142, Step A, the title compound is obtained.

Calc. for $C_{39}H_{46}N_5O_6S$: MW=712.89; found m/e=(m+1) 714.2.

Step C:

N-[1(R)-[[3-[(Phenylsulfonyl)amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for $C_{34}H_{38}N_5O_4S$: MW=612.77; found m/e=(m+1) 614.3.

PMR (200 MHz; in δ from TMS; $CDCl_3$): 8.34 (t, J=8 Hz), 8.25–8.1 (m), 7.94 (t, J=8 Hz), 7.74 (d, J=8 Hz), 7.7–7.28 (m), 7.37 (d,t J=8,4 Hz), 7.32–6.9 (m), 6.85 (d, J=8 Hz), 6.56 (t, J=6 Hz), 5.32–5.1 (m), 4.74 (bd, J=8 Hz), 4.41 (bd, J=14 Hz), 3.61 (bd, J=16 Hz), 3.3–3.1 (m), 2.96–2.66 (m), 2.65–2.37 (m), 2.37–2.15 (m), 1.95–1.66 (m), 1.66–1.42 (m), 1.56 (bs), 1.42–1.31 (m), 1.31–1.2 (m), 0.97–0.72 (m), 0.54–0.33 (m).

Step D:

N-[1(R)-[[3-[(Phenylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 143

Preparation of N-[1(R)-[[3-[(benzoyl)amino]-2,3-dihydrospiro[1H-indene-1,4'-piperidin]-1'-yl]carbonyl]-2-(indole-3-yl)ethyl]-2-amino-2-methylpropanamide hydrochloride Step A:

N-[1(R)-[[3-[(Benzoyl)amino]-2,3-dihydrospiro[1H-indene-1,4'-piperidin]-1'-yl]carbonyl]-2-(indole-3-yl)ethyl]-2-[(1,1-dimethylethyloxy)carbonyl]amino-2-methylpropanamide If in the reaction of Example 142 Step B, benzoyl chloride is substituted for benzenesulfonyl chloride, the title compound is obtained.

Calc. for $C_{40}H_{46}N_5O_5$: MW=676.84; found m/e=(m+1) 678.0.

Step B:

N-[1(R)-[[3-[(Benzoyl)amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for $C_{35}H_{38}N_5O_3$: MW=576.72; found m/e=(m+I) 578.5.

PMR (200 MHz; in δ from TMS; $CDCl_3$): 8.82 (s), 8.72 (s), 8.63 (s), 8.37–8.2 (m), 7.8–7.64 (m), 7.64–7.54 (m), 7.54–7.31 (m), 7.31–7.16 (m), 7.16–6.97 (m), 6.68–6.55 (m), 6.5–6.35 (m), 5.67–5.43 (m), 5.34–5.07 (m), 4,42 (bd, J=12 Hz), 3.7–3.48 (m), 3.3–3.08 (m), 3.02–2.72 (m), 2.72–2.3 (m), 2.3–2.0 (vbs), 2.04–1.71 (m), 1.71–1.4 (m), 1.36 (s), 1.34–1.05 (m), 1.05–0.8 (m), 0.6–0.4 (m).

Step C:

N-[1(R)-[[3-[(benzoyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 144

Preparation of
N-[1(R)-[[3-[[[cyclohexyl]carbonyl]amino]-2,3-dihydrospiro[1H-indene-1,4'-piperidin]-1'-yl]carbonyl]-2-(indole-3-yl)ethyl]-2-amino-2-methylpropanamide hydrochloride Step A:

N-[1(R)-[[3-[[[Cyclohexyl]carbonyl]amino]-2,3-dihydrospiro[1H-indene-1,4'-piperidin]-1'-yl]carbonyl]-2-(indole-3-yl)ethyl]-2-[(1,1-dimethylethyloxy)carbonyl]amino-2-methylpropanamide If in the reaction of Example 142, Step B, cyclohexylcarbonyl chloride is substituted for benzenesulfonyl chloride, the title compound is obtained Calc. for $C_{40}H_{52}N_5O_5$: MW=682.89; found m/e=(m+1) 684.3.

Step B:

N-[1(R)-[[3-[[[cyclohexyl]carbonyl]amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for $C_{35}H_{44}N_5O_3$: MW=582.77; found m/e=(m+1) 584.7.

PMR (200 MHz; in δ from TMS; CDCl$_3$): 8.91 (bd, J=20 Hz), 8.89 (bd, J=12 Hz), 8.35–8.15 (m), 7.69 (t, J=6 Hz), 7.59 (t, J=6 Hz), 7.4 (d, J=8 Hz), 7.27–6.96 (m), 6.67–6.53 (m), 5.84–5.65 (m), 5.48–5.08 (m), 4.50–4.26 (m), 3.7–3.45 (m), 3.3–3.12 (bs), 3.0–2.65 (m), 2.65–2.2 (m), 2.2–2.0 (m), 2.0–1.72 (bs), 1.6–1.1 (bs), 1.0–0.85 (m), 0.6–0.4 (m).

Step C:

N-[1(R)-[[3-[[[cyclohexyl]carbonyl]amino]-2,3-dihydrospiro[1H-indene-1,4'-piperidin]-1'-yl]carbonyl]-2-(indole-3-yl)ethyl]-2-amino-2-methylpropanamide hydrochloride Subtituting the product from the above step in Step E, Example 63, for the product from Step D, Example 63, the title compound is obtained.

EXAMPLE 145

Preparation of
N-[1(R)-[[3-[(acetyl)amino]-2,3-dihydrospiro[1H-indene-1,4'-piperidin]-1'-yl]carbonyl]-2-(indole-3-yl)ethyl]-2-amino-2-methylpropanamide hydrochloride Step A:

N-[1(R)-[[3-[(Acetyl)]amino]-2,3-dihydrospiro[1H-indene-1,4'-piperidin]-1'-yl]carbonyl]-2-(indole-3-yl)ethyl]-2-[(1,1-dimethylethyloxy)carbonyl]amino-2-methylpropanamide The product obtained from Example 142, Step A, is taken up in ca. ten fold (v/w) pyridine, and treated with an equal volume of acetic anhydride. The mixture is warmed on a steam bath for fifteen minutes, then treated dropwise with swirling with an equal volume of water. When the initial exothermic reaction is over, the mixture is warmed again on the steam bath for five minutes to complete the hydrolysis of excess anhydride, and concentrated to a small volume under reduced pressure. The residue is diluted with 5% aqueous citric acid and extracted several times with chloroform. The combined extracts are washed with 1M dipotassium hydrogen phosphate, dried with magnesium sulfate, and the solvent removed under reduced pressure. The residue is subjected to preparative TLC as in Example 142, Step B to afford the title compound.

Calc. for $C_{35}H_{44}N_5O_5$: MW=614.77; found m/e=(m+1) 616.1.

Step B:

N-[1(R)-[[3-[(Acetyl)amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for $C_{30}H_{36}N_5O_3$: MW=514.65; found m/e=(m+1) 516.6.

PMR (200 MHz; in δ from TMS; CDCl$_3$): 8.9–8.74 (m), 8.74–8.54 (m), 8.48–8.28 (m), 7.74 (t, J=6 Hz), 7.64 (t, J=4 Hz), 7.44–7.0 (m), 6.66–6.54 (m), 5.95–5.77 (m), 5.5–5.1 (m), 4.44 (bd, J=1 2 Hz), 3.67–3.46 (m), 3.3–3.1 (m), 3.02–2.71 (m), 2.71–2.28 (m), 2.03 (s), 2.01 (s), 1.95–1.8 (m), 1.7 (bs), 1.55–1.4 (m), 1.36 (bs), 1.32 (bs), 1.28–0.98 (m), 0.98–0.75 (m), 0.58–0.34 (m).

Step C:

N-[1(R)-[[3-[(Acetyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 146

Preparation of
N-[1(R)-[[3-[(N-methyl-N-methylsulfonyl)amino]-2,3-dihydrospiro[1H-indene-1,4'-piperidin]-1'-yl]carbonyl]-2-(phenylmethoxy)ethyl]-2-amino-2-methylpropanamide hydrochloride Step A:

1'-(1,1-Dimethylethyloxycarbonyl)-3-(N-methyl-N-methylsulfonyl)amino-2,3-dihydrospiro(1H-indene-1,4'-piperidine)

A solution of 467 mg (1.15 mmole) of 1'-(1,1-dimethylethyloxycarbonyl)-3-(methylsulfonyl)amino-2,3-dihydrospiro(1H-indene-1,4'-piperidine)(prepared as in Example 136, Step A) in 5 mL of DMF, was stirred under a nitrogen atmosphere in an ice bath. To it was added 74 mg (1.6×1.15 mmoles) of 60% NaH in oil, and stirring was continued for 1–2 hours, at which time frothing had stopped, and a relatively clear solution was in hand. To this was added, with stirring, 115λ (1.6×1.15 mmoles)of methyl iodide. The ice bath was then removed and the reaction was stirred at ambient temperature over night. Removal of the bulk of the DMF under high vacuum left a residue which was partitioned between chloroform and 1M potassium x s dihydrogen phosphate. The chloroform was removed and the aqueous phase further extracted several times with chloroform. The combined chloroform phases were dried with magnesium sulfate, filtered, and the filtrate concentrated under reduced pressure. The residue was subjected to preparative TLC on three 8"×8"×1,000 μ slica gel GF plates, using 1:2 ethyl acetate:hexane, affording 379 mg of the title compound.

Calc. for $C_{20}H_{30}N_2O_4S$: MW=394.53; found m/e=(m+1) 394.8.

Step B:

3-(N-Methyl-N-methylsulfonyl)amino-2,3-dihydrospiro-(1H-indene-1,4'-piperidine)

The product from the previous example was taken up with cooling in an ice bath in ca. 3 mL of TFA. When the dissolution was complete, the bath was removed, and the reacion allowed to stand for 30 minutes. It was then concentrated to a gum under reduced pressure, taken up in chloroform, and shaken with 1M dipotassium hydrogen phosphate to which sufficient sodium hydroxide solution had been added to bring the pH to >10. The organic phase was removed and the extraction repeated with three more portions of chloroform. After drying with magnesium sulfate, the combined chloroform solutions were concentrated and the resultant crude product purified by preparative tic on three 8"×8"×1,000 μ silica gel GF plates developed with 0.5:5:95 conc. ammonium hydroxide:methanol:chloroform. Extraction of the isolated band with 3:30:70 conc. ammonium hydroxide:methanol:chloroform, and evaporation afforded the title compound.

Calc. for $C_{15}H_{22}N_2O_2S$: MW=294.41; found m/e=(m+1) 295.0.

PMR (200 MHz; in d from TMS; $CDCl_3$): 7.4–7.2 (m, 5H), 5.59 (t, J=8 Hz, 1H), 3.2–3.05 (m, 2H), 3.01 (s, 3H), 2.98–2.7 (m, 2H), 2.63 (s, 3H), 2.59 (dd, J=8, 14 Hz, 1H), 2.15 (dt, J=4, 12 Hz, 1H), 1.79 (dd, J=8, 12 Hz, 1H), 1.69–1.4 (m, 3H).

Step C:

N-[1(R)-[[3-[(N-Methyl-N-methylsulfonyl)amino]-2,3-dihydrospiro[1H-indene-1,4'-piperidin]-1'-yl]carbonyl]-2-phenylmethyloxy)ethyl]carbamic acid 1,1-dimethylethyl ester Substituting the product from the above step in Step A, Example 63, for 2,3-dihydrospiro(1H-indene-1,4'-piperidine)hydrochloride, and EDC for DCC, the title compound is obtained.

Calc. for $C_{30}H_{41}N_3O_6S$: MW=571.74; found m/e=(m+1) 572.6.

Step D:

1'-[[2(R)-Amino-1-oxo-3-(phenylmethyloxy)]propyl]-3-[(N-methyl-N-methylsulfonyl)amino]-2,3-dihydrospiro[1H-indene-1,4'-piperidine]

Substituting the product from the above step in Step B, Example 63, for the product from Step A, Example 63, the title compound is obtained.

Step E:

N-[[1(R)-3-[(N-Methyl-N-methylsulfonyl)amino]-2,3-dihydrospiro[1H-indene-1,4'-piperidin]]-1'-yl)carbonyl]-2-(phenylmethyloxy)ethyl]2-[(1,1-dimethylethyloxy)carbonyl]amino]-2-methylpropanamide Substituting the product from the above step in Step C, Example 63, for the product from Step B, Example 63, the title compound is obtained.

Calc. for $C_{34}H_{48}N_4O_7S$: MW=656.84; found m/e=(m+1) 656.9.

Step F:

N-[1(R)-[[3-[(N-Methyl-N-methylsulfonyl)amino]-2,3-dihydrospiro[1H-indene-1,4'-piperidin]-1'-yl]carbonyl]-2-(phenylmethoxy)ethyl]-2-amino-2-methylpropanamide Substituting the product from the above step in Step D, Example 63, for the product from Step C, Example 63, the title compound is obtained.

Calc. for $C_{29}H_{40}N_4O_5S$: MW=556.73; found m/e=(m+1) 557.7

PMR (200 mHz; in δ from TMS; $CDCl_3$): 8.4–8.2 (m), 7.4–7.1 (m), 6.9–6.8 (m), 6.7–6.6 (m), 5.58 (t, J=8 Hz), 5.28–5.06 (m), 4.8–4.58 (m), 4.53 (s), 4.25–3.9 (bm), 3.8–3.54 (m), 3.4–3.05 (m), 3.1 (s), 2.95–2.7 (m), 2.62 (s), 2.6–2.45 (m), 2.2–1.9 (m), 1.9–1.7 (m), 1.65 (s), 1.6–1.46 (m), 1.39 (bs).

Step G:

N-[1(R)-[[3-[(N-Methyl-N-methylsulfonyl)amino]-2,3-dihydrospiro[1H-indene-1,4'-piperidin]-1'-yl]carbonyl]-2-(phenylmethoxy)ethyl]-2-amino-2-methylpropanamide hydrochloride Substituting the product from the above step in Step E, Example 63, for the product from Step D, Example 63, the title compound is obtained.

EXAMPLE 147

Preparation of N-[1(R)-[[3-[[N-Methyl-N-methylsulfonyl]amino]-2,3-dihydrospiro[1H-indene-1,4'-piperidin]-1'-yl]carbonyl]-2-(indole-3-yl)ethyl]-2-amino-2-methylpropanamide hydrochloride Step A:

N-[[1(R)-3-[(N-Methyl-N-methylsulfonyl)amino]-2,3-dihydrospiro[1H-indene-1,4'-piperidin]]-1'-yl)carbonyl]-2-(indole-3-yl)ethyl]2-[(1,1-dimethylethyloxy)carbonyl]-amino]-2-methylpropanamide Substituting the product of Example 146, Step B in Example 139, Step A for the product from Example 136, Step B, the title compound is obtained.

Calc. for $C_{35}H_{36}N_5O_6S$: MW=665.88; found m/e=(m+1) 666.2.

Step B:

N-[1(R)-[[3-[(N-Methyl-N-methylsulfonyl)amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for $C_{30}H_{39}N_5O_4S$; MW=565.74; found m/e=(m+1) 566.7

PMR (200 MHZ; in δ from TMS; $CDCl_3$): 8.49 (bt, J=10 Hz), 8.37–8.22 (m), 7.72 (t, J=8 Hz), 7.6 (t, J=6 Hz), 7.40 (t, J=8 Hz), 7.34–7.0 (m), 6.64–6.54(m), 5.54–5.32 (m), 5.32–5.06 (m), 4.58–4.38 (bin), 3.64 (bt, J=14 Hz), 3.29–3.12 (m), 2.98 (s), 2.93 (s), 2.56 (s), 2.54 (s), 2.52 (s), 2.50 (s), 2.24–2.2 (m), 2.15 (bs), 1.7–1.25 (m), 1.38 (bs), 1.35–1.2 (m), 1.0–0.9 (bin), 0.65–0.45 (bm).

Step C:

N-[1(R)-[[3-[N-Methyl-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 148

Preparation of
N-[1(R)-[[3-[[N-benzyl-N-methylsulfonyl]amino]-2,3-dihydrospiro[1H-indene-1,4'-piperidin]-1'-yl]carbonyl]-2-(indole-3-yl)ethyl]-2-amino-2-methylpropanamide hydrochloride Step A:

1'-(1,1-Dimethylethyloxycarbonyl)-3-(N-benzyl-N-methylsulfonyl)amino-2,3-dihydrospiro(1H-indene-1,4'-piperidine)

Substituting benzyl bromide in Example 146, Step A, for methyl iodide, the title compound is obtained.

Calc. for $C_{26}H_{34}N_2O_4S$: MW=470.63; found m/e=(m+1) 471.5.

Step B:

3-(N-Benzyl-N-methylsulfonyl)amino-2,3-dihydrospiro-(1H-indene-1,4'-piperidine)

Substituting the product of the previous step in Example 146, Step B, for the product obtained in Example 146, Step A, the title compound is obtained.

Calc. for $C_{26}H_{34}N_2O_4S$: MW=370.51; found m/e=(m+1) 371.0.

PMR (200 MHz; in d from TMS; $CDCl_3$): 7.34–7.14 (m, 10H), 5.64 (t, J=6 Hz, 1H), 4.40 (d, J=16 Hz, 1H), 4.12 (d, J=16 Hz, 1H), 3.1–2.94 (m, 2H), 2.87 (s, 3H), 2.86–2.73 (m, 1H), 2.73–2.51 (m, 2H), 2.04 (dr, J=4, 12 Hz, 1H), 1.74 (dd, J=8, 12 Hz, 1H), 1.58 (bdt, J=4, 12 Hz, 1H), 1.37 (bdt, J=2, 16 Hz, 2H).

Step C:

N-[[1(R)-3-[(N-Benzyl-N-methylsulfonyl)amino]-2,3-dihydrospiro[1H-indene-1,4'-piperidin]]-1'-yl)carbonyl]-2-(indole-3-yl)ethyl]2-[(1,1-dimethylethyl-oxy)carbonyl]-amino-2-methylpropanamide Substituting the product obtained in the step above for the product from Example 146, Step B in Example 147, Step A, the title compound is obtained.

Calc. for $C_{41}H_{51}N_5O_6S$: MW=741.95; found m/e=(m+1) 742.7.

Step D:

N-[1(R)-[[3-[(N-Benzyl-N-methylsulfonyl)amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for $C_{36}H_{43}N_5O_4S$: MW=0.641.84; found m/e=(m+1) 642.1.

PMR (200 MHZ; in δ from TMS; $CDCl_3$): 8.64 (s), 8.6–8.5 (m), 7.71 (t, J=6 Hz), 7.61 (t, J=8 Hz), 7.42 (t, J=8 Hz), 7.36–7.0 (m), 6.65–6.53 (m), 5.6–5.4 (m), 5.35–5.06 (m), 4.9–4.28 (m), 4.15–3.9 (m), 3.65–3.45 (m), 3.3–3.1 (m), 2.9 (s), 2.85 (s), 2.8–2.48 (m), 2.48–2.3 (m), 2.22 (s), 1.9–1.45 (m), 1.39 (bs), 1.34–1.22 (m), 1.22–1.03 (bm), 1.0–0.75 (bm), 0.72–0.55 (bm), 0.55–0.36 (m).

Step E:

N-[1(R)-[[3-[N-Benzyl-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 149

Preparation of
N-[1(R)-[[3-[N-[[[phenylmethoxy]carbonyl]methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Step A:

1'-(1,1-Dimethylethyloxycarbonyl)-3-(N-[[[phenyl-methoxy]carbonyl]methyl]-N-(methylsulfonyl)amino-2,3-dihydrospiro(1H-indene-1,4'-piperidine)

Substituting benzyl bromoacetate (prepared from commercial bromoacetic acid and phenyldiazomethane (Syn. Commun., 8,569 (1978))) in Example 146, Step A, for methyl iodide, the title compound is obtained.

Calc. for $C_{28}H_{36}N_2O_6S$: MW=528.67; found m/e=(m+1) 529.7.

Step B:

3-(N-[[[Phenylmethoxy]carbonyl]methyl]-N-(methylsulfonyl)amino-2,3-dihydrospiro(1H-indene-1,4'-piperidine)

Substituting the product of the previous step in Example 146, Step B, for the product obtained in Example 146, Step A, the title compound is obtained.

Calc. for $C_{23}H_{28}N_2O_4S$: MW=428.55; found m/e=(m+1) 429.1.

PMR (200 MHz; in d from TMS; $CDCl_3$): 7.36–7.14 (m, 9H), 5.47 (t, J=8 Hz, 1H), 5.16 (d, J=14 Hz, 1H), 5.06 (d, J=14 Hz, 1H), 4.05 (d, J=20 Hz, 1H), 3.69 (d, J=20 Hz, 1H), 3.26 (s, 3H), 3.2–3.0 (m, 2H),3.0–2.58 (m), 2.15 (dt, J=4, 12 Hz, 1H), 1.72 (bdd, J=4, 12 Hz, 1H), 1.59 (dd, J=8, 12 Hz, 1H), 1.44 (bt, J=12 Hz, 2H).

Step C:

N-[[1(R)-3-[(N-N-[[[Phenylmethoxy]carbonyl]methyl]-N-methylsulfonyl)amino]-2,3-dihydrospiro[1H-indene-1,4'-piperidin]-1'-yl]carbonyl]-2-(indole-3-yl)ethyl]2-[(1,1-dimethylethyloxy)carbonyl]amino]-2-methylpropanamide Substituting the product obtained in the step above for the product from Example 146, Step B, in Example 147, Step A, the title compound is obtained.

Calc. for $C_{43}H_{53}N_5O_8S$: MW=799.99; found m/e - (m+1) 800.8.

Step D:

N-[1(R)-[[3-[(N-[[[Phenylmethoxy]carbonyl]methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for $C_{38}H_{45}N_5O_6S$: MW=699.87; found m/e=(m+1) 700.4.

PMR (200 mHz; in a from TMS; $CDCl_3$): 8.65 (s), 8.6–8.5 (m), 8.4–8.25 (m), 7.71 (t, J=8 Hz), 7.61 (t, J=6 Hz), 7.5–6.95 (m), 6.62–6.5 (m), 5.4–4.95 (m), 4.42 (bd, J=14 Hz), 3.99 (t, J=6 Hz), 3.90 (t, J=6 Hz), 3.7–3.4 (m), 3.2 2(s), 3.16 (s), 3.0–2.8 (bm), 2.8–2.55 (bm), 2.55–2.2 (m), 2.2–2.17 (vbs), 1.34 (bs), 1.3–1.2 (m), 1.2–1.0 (m), 1.0–0.6 (m), 0.55–0.45 (m).

Step E:

N-[1(R)-[[3-[N-[[[Phenylmethoxy]carbonyl]methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 150

Preparation of
N-[1(R)-[[3-[N-(Carboxymethyl)-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Step A:

N-[1(R)-[[3-[N-(Carboxymethyl)-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide A solution of ca. 25 mg of N-[1(R)-[[3-[N-[[[phenylmethoxy]carbonyl]methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide from Example 149, Step D, in 0.5 mL of methanol containing 25 mg of 10% Pd/C, is shaken under a 50 psi atmosphere of hydrogen over night. After filtration and taking the filtrate to dryness under reduced pressure, the title compound is obtained.

Calc. for $C_{31}H_{39}N_5O_6S$: MW=609.75; found m/e=(m+1) 610.4.

PMR (200 mHz; in δ from TMS; $CD_3OD$): 8.3–8.05 (m), 7.55–7.3 (m), 7.3–6.9 (m), 6.3 (t, J=6 Hz), 5.5–4.95 (m), 4.35–4.1 (bin), 3.9–3.25 (m), 3.23 (s), 3.15 (s), 3.09 (s), 3.0–2.3 (m), 1265–1.4 (m), 1.52 (s), 1.2–1.05 (m), 0.84–0.55 (m).

Step B:

N-[1(R)-[[3-[N-(Carboxymethyl)-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 151

Preparation of
N-[1(R)-[[3-[N-[[ethoxycarbonyl]methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Step A:

1'-(1,1-Dimethylethyloxycarbonyl)-3-(N-[[ethoxycarbonyl]methyl]-N-(methylsulfonyl)amino-2,3-dihydrospiro(1H-indene-1,4'-piperidine)

Substituting ethyl bromoacetate in Example 146, Step A, for methyl iodide, the title compound is obtained.

Calc. for $C_{23}H_{34}N_2O_6S$: MW=466.60; found m/e=(m+1) 467.1.

Step B:

3-(N-[[Ethoxycarbonyl]methyl]-N-(methylsulfonyl)amino-2,3-dihydrospiro(1H-indene-1,4'-piperidine Substituting the product of the previous step in Example 146, Step B, for the product obtained in Example 146, Step A, the title compound is obtained.

Calc. for $C_{18}H_{26}N_2O_4S$: MW=366.48; found m/e=(m+1) 367.0.

PMR (200 MHz; $CDCl_3$): 7.35–7.15 (m, 4H), 5.46 (t, J=8 Hz, 1H), 4.11 (quar J=7 Hz, 2H), 3.95 (d, J=18 Hz, 1H), 3.65 (d, J=18 Hz, 1H), 3.26 (s, 3H), 3.12–2.95 (m, 2H), 2.95–2.6 (m, 4H), 2.08 (dt, J=4, 12 Hz, 1H), 1.72–1.35 (m, 3H), 1.19 (t, J=7 Hz, 3H).

Step C:

N-[[1(R)-3-[(N-[[Ethoxycarbonyl]methyl]-N-methylsulfonyl)amino]-2,3-dihydrospiro[1H-indene-1,4'-piperidine]]-1'-yl)carbonyl]-2-(indole-3-yl)ethyl]2-[(1,1-dimethylethyloxy)carbonyl]amino]-2-methylpropanamide Substituting the product obtained in the step above for the product from Example 146, Step B in Example 147, Step A, the title compound is obtained.

Calc. for $C_{38}H_{51}N_5O_8S$: MW=737.92; found m/e=(m+1) 738.1.

Step D:

N-[1(R)-[[3-[(N-[[Ethoxycarbonyl]methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for $C_{33}H_{43}N_5O_6S$: MW=637.80; found m/e=(m+1) 638.1.

PMR (200 mHz; CDCl₃): 8.34 (t, J=8 Hz), 7.75 (t, J=6 Hz), 7.62 (t, J=8 Hz), 7.40 (t, J=8 Hz), 7.35–7.2 (m), 7.2–7.01 (m), 6.62–6.51 (m), 5.49 (t, J=8 Hz), 5.4–5.1 (m), 4.69 (bd, J=12 Hz), 4.46 (bd, J=12 Hz), 4.10 (dquin, J=2,6 Hz), 3.97–3.88 (m), 3.88–3.75 (m), 3.74–3.5 (m), 3.46 (d, J=6 Hz), 3.24 (d, J=4 Hz), 3.28 (s), 3.27–2.82 (m), 2.82–2.62 (m),2.62–2.22 (m), 2.16–1.89 (m), 1.71 (s), 1.62–1.38 (m), 1.46 (s), 1.33 (s), 1.28 (d, J=4 Hz), 1.26–1.11 (m), 1.10.95 (m), 0.86 (bd, J=16 Hz), 0.51 (dt, J=4,12 Hz).

Step E:

N-[1(R)-[[3-[N-[[Ethoxycarbonyl]methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 152

Preparation of N-[1(R)-[[3-[N-[[[4-phenylmethoxy]carbonyl]phenyl]-methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Step A:

1'-(1,1-Dimethylethyloxycarbonyl)-3-[N-[[[4-phenylmethoxy]carbonyl]phenyl]methyl]-N-(methylsulfonyl)-amino-2,3-dihydrospiro(1H-indene-1,4'-piperidine)

Substituting benzyl α-bromo-p-toluate, (prepared from commercial α-bromo-p-toluic acid and phenyldiazomethane (Syn. Commun., 8,569 (1978))) in Example 146, Step A, for methyl iodide, the title compound is obtained.

Calc. for C₃₄H₄₀N₂O₆S: MW=604.77; found m/e=(m+1) 605.

Step B:

3-(N-[[[Phenylmethoxy]carbonyl]methyl]-N-(methylsulfonyl)amino-2,3-dihydrospiro(1H-indene-1,4'-piperidine)

Substituting the product of the previous step in Example 146, Step B, for the product obtained in Example 146, Step A, the title compound is obtained.

Calc. for C₂₉H₃₂N₂O₄S: MW=504.65; found m/e=(m+1) 505

PMR (200 MHz; CDCl₃): 7.35–7.15 (m, 4H), 5.46 (t, J=8 Hz, 1H), 4.11 (quar J=7 Hz, 2H), 3.95 (d, J=18 Hz, 1H), 3.65 (d, J=18 Hz, 1H), 3.26 (s, 3H), 3.12–2.95 (m, 2H), 2.95–2.6 (m, 4H), 2.08 (dt, J=4, 12 Hz, 1H), 1.72–1.35 (m, 3H), 1.19 (t, J=7 Hz, 3H).

Step C:

N-[[1(R)-3-[N-[[[4-Phenylmethoxy]carbonyl]phenyl]-methyl]-N-(methylsulfonyl)amino]-2,3-dihydrospiro[1H-indene-1,4'-piperidine]]-1'-yl)carbonyl]-2-(indole-3-yl)ethyl]2-[(1,1-dimethylethyloxy)carbonyl]amino]-2-methylpropanamide Substituting the product obtained in the step above for the product from Example 146, Step B in Example 147, Step A, the title compound is obtained.

Calc. for C₄₉H₅₅N₅O₈S: MW=874.07; found m/e=(m+1) 876.2.

Step D:

N-[1(R)-[[3-[N-[[[4-Phenylmethoxy]carbonyl]phenyl]-methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide Substituting the product from the above step in Step D, Example 63, for the product from Step C, Example 63, the title compound is obtained.

Calc. for C₄₄H₄₇N₅O₆S: MW=773.96; found m/e=(m+1) 776.1.

PMR (200 mHz; in δ from TMS; CDCl₃): 8.4–8.2(m), 8.18 (bs), 8.09 (d, J=8 Hz), 7.95 (t, J=8 Hz), 6.77 (d, J=8 Hz), 7.67–7.5 (m), 7.5–7.32 (m), 7.32–7.0 (m), 6.55 (dd, J=1 6,6 Hz), 5.58–5.44 (m), 5.44–5.3 (m), 5.35 (s), 5.3–5.0 (m), 4.55–4.2 (m), 4.2–3.95 (m), 3.85–3.75 (m), 3.6 (bd, J=14 Hz), 3.3–3.1 (m), 3.0–2.85 (m), 2.87 (s), 2.85–2.56 (m), 2.56–2.0 (m), 2.0–1.4 (m), 1.35 (bs),1.0–0.75 (m), 0.75–0.58 (m), 0.58–0.3 (m).

Step E:

N-[1(R)-[[3-[N-[[[4-Phenylmethoxy]carbonyl]phenyl]-methyl]-N-(methylsulfonyl)amino]-2,3-dihydrospiro[1H-indene-1,4'-piperidin]-1'-yl]carbonyl]-2-(indole-3-yl)ethyl]-2-amino-2-methylpropanamide hydrochloride Substituting the product from the above step in Step E, Example 63, for the product from Step D, Example 63, the title compound is obtained.

EXAMPLE 153

N-[1(R)[[3-(1H-tetrazol-5-yl)spiro[1H-indene-1,4'-piperidine]-1'-yl]carbonyl]-2-(indol-3-yl)ethyl]-2-amino-2-methylpropanamide hydrochloride Step A:

3-cyanspiro[1H-indene-1,4'-piperidine]-1'-carboxylic acid 1,1-dimethylethyl ester To a solution of the intermediate prepared in Example 80 Step A (834 mg, 1.92 mmol) and triethylamine (0.405 ml, 2.89 mmol) in toluene (5 ml) was added trimethylsilyl cyanide (0.384 ml, 2.89 mmol) and tetrakis triphenylphosphine (110.9 mg, 0.096 mmol). The reaction mixture was stirred overnight and then quenched with 1N HCL. The aqueous layer was extracted with ethyl acetate (3×1 vol). The organic layer was washed with brine, dried over magnesium sulfate, filtered and concentrated. Flash chromatography (silica gel hexane/ethyl acetate 6:1) gave the title compound (328 mg, 1.05 mmol).

Step B:

3(1H-tetrazol-5-yl)-spiro[1H-indene-1,4'-piperidine]-1'-carboxylic acid 1,1-dimethylethyl ester To a solution of the title compound from Step A (298 mg, 0.96 mmol) in toluene was added trimethylstannyl azide (787 mg, 3.84 mmol). The mixture was refluxed for 18 hours and then cooled and 1N HCL was added. The aqueous layer was extracted with ethyl acetate (3×1 vol) and the organic layer was washed with water, brine, dried over magnesium sulfate and concentrated. Purification by MPLC (LH₂₀ col-

Step C:

N-[1-[[3-(1H-tetrazol-5-yl)spiro[1H-indene-1,4'-piperidin]-1'-yl]carbonyl]-2-(indol-3-yl)ethyl]-2-[[(1,1-dimethylethoxy)carbonyl]amino]-2-methyl-propanamide The intermediate prepared in Step B (134 mg, 0.379 mmol) was dissolved in a mixture of methanol (1.6 ml), concentrated HCL (0.9 ml), and water (0.20 ml) and stirred for 18 hours. The material was o concentrated under vacuum and the residue was azeotroped from toluene. The residue was then dissolved in methylene choride/DMF and the compound prepared in Example 4, Step D (162 mg, 0.417 mmol), NMM (0.083 ml, 0.76 mmol), HOBT (77 mg, 0.57 mmol), and finally EDC (108 mg, 0.57 mmol) were added. The reaction mixture s was stirred for 18 hours and then poured into ethyl acetate (100 ml). The organic layer was washed with 1N HCL, brine, dried over magnesium sulfate, filtered and concentrated. MPLC ($LH_{20}$ column methanol) gave slightly impure material futher purification was carried out by flash chromatography (silica gel, methylene chloride/methanol 9:1) to give the title compound (68 mg, 0.10 mmol).

Step D:

N-[1(R)[[3-(1H-tetrazol-5-yl)spiro[1H-indene-1,4'-piperidine]-1'-yl]carbonyl]-2-(indol-3-yl)ethyl]-2-amino-2-methylpropanamide hydrochloride The compound prepared in Step C (60 mg, 0.096 mmol) was dissolved in a mixture of methanol (1.6 ml), concentrated HCL (0.9 ml), and water (0.2 ml). The reaction mixture was stirred over night and then concentrated and azeotroped from methanol. After drying under high vacuum the title compound was obtained as a white solid (52.2 mg, 0.093 mmol).

$^1$HNMR ($CD_3OD$, 400 MHz~2:1 mixture of conformers): 8.05–7.97(m, 1H), 7.70–6.91 (m, 9H), 5.39–5.20 (m, 1H), 4.52–4.44(m, 1H), 4.02–3.89 (m,1H), 3.4–3.3 (m, 1H hidden), 3.05–2.95 (m, 1H), 2.87 (dt, 1H), 2.18–2.10 (m, ⅓H), 2.0–1.85 (m, ⅓H),1.64+1.63+1.55+1.52 (s, 6H total), 1.38–1.25 (m, 2H), 1.19–1.05 (m, 1H), 0.08–0.074 (m, ⅔H), 0.048 (dt, ⅔H).

What is claimed is:

1. A compound of the formula:

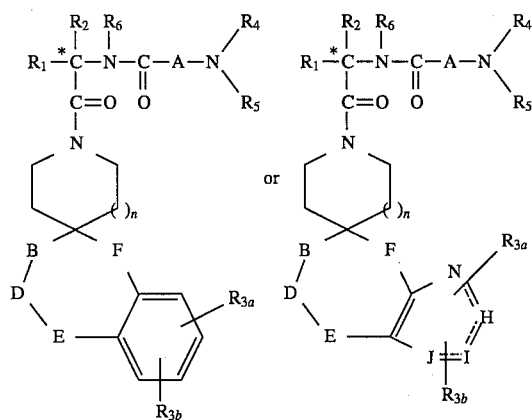

wherein:

$R_1$ is selected from:
$C_1$–$C_{10}$ alkyl, aryl, heteroaryl, aryl ($C_1$–$C_6$ alkyl), heteroaryl ($C_1$–$C_6$ alkyl), $C_3$–$C_7$ cycloalkyl($C_1$–$C_6$alkyl), $C_1$–$C_5$alkyl-K-$C_1$–$C_5$ alkyl, aryl($C_0$–$C_5$alkyl)-K-($C_1$–$C_5$ alkyl), heteroaryl($C_0$–$C_5$alkyl)-K-($C_1$–$C_5$ alkyl), and $C_3$–$C_7$ cycloalkyl($C_0$–$C_5$ alkyl)-K-($C_1$–$C_5$ alkyl), where K is selected from: O, $S(O)_m$, $N(R_2)C(O)$, $C(O)N(R_2)$, OC(O), C(O)O, —$CR_2$=$CR_2$— and —C≡C— where $R_2$ and the alkyl groups may be futher substituted by 1 to 5 halogen, $S(O)mR_{2a}$, 1 to 3 of $OR_{2a}$ or $C(O)OR_{2a}$ and the aryl and heteroaryl may be further substituted by phenyl, phenoxy, halophenyl, 1 to 3 of $C_1$–$C_6$ alkyl, 1 to 3 of halogen, 1 to 2 of $OR_2$, methylenedioxy, $S(O)_mR_2$, 1 to 2 of $CF_3$, $OCF_3$, nitro, $N(R_2)(R_2)$, $N(R_2)C(O)(R_2)$, $C(O)OR_2$, $C(O)N(R_2)(R_2)$, $SO_2N(R_2)(R_2)$, $N(R_2)SO_2$ aryl, $N(R_2)SO_2$ heteroaryl or $N(R_2)SO_2R_2$ $R_2$ is selected from:
hydrogen, $C_1$–$C_6$ alkyl, and $C_3$–$C_7$ cycloalkyl, and where two $C_1$–$C_6$ alkyl groups are present on one atom, they may be optionally joined to form a $C_3$–$C_8$ cyclic ring optionally including oxygen, sulfur or $NR_{2a}$;

$R_{2a}$ is hydrogen or $C_1$–$C_6$ alkyl;

$R_{3a}$ and $R_{3b}$ are independently selected from:
hydrogen, halogen, $C_1$–$C_6$ alkyl, $OR_2$, cyano, $OCF_3$, methylenedioxy, nitro, $S(O)_mR$, $CF_3$ or $C(O)OR_2$, and when $R_{3a}$ and $R_{3b}$ are in an ortho arrangement they maybe joined to form a $C_5$ to $C_8$ aliphatic or aromatic ring optionally including 1 or 2 heteroatoms selected from oxygen, sulfer, or nitrogen;

$R_4$ and $R_5$ are independently selected from:
hydrogen, $C_1$–$C_6$ alkyl, and substituted $C_1$–$C_6$ alkyl where the substituents may be 1 to 5 halo, 1 to 3 hydroxy, 1 to 3 $C_1$–$C_{10}$ alkanoyloxy, 1 to 3 $C_1$–$C_6$ alkoxy, phenyl, phenoxy, 2-furyl, $C_1$–$C_6$ alkoxycarbonyl, $S(O)_m(C_1$–$C_6$ alkyl); or $R_4$ and $R_5$ can be taken together to form —$(CH_2)_rL_a(CH_2)_s$— where $L_a$ is $C(R_2)_2$, O, $S(O)_m$ or $N(R_2)$, r and s are independently 1 to 3 and $R_2$ is as defined above;

$R_6$ is hydrogen or $C_1$–$C_6$ alkyl;

A is:

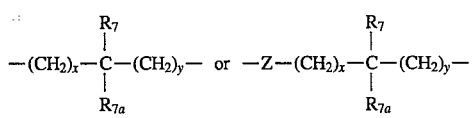

where x and y are independently 0–3;

Z is N—$R_2$ or O;

$R_7$ and $R_{7a}$ are independently selected from:
hydrogen, $C_1$–$C_6$ alkyl, trifluoromethyl, phenyl, and substituted $C_1$–$C_6$ alkyl where the substituents are selected from: imidazolyl, phenyl, indolyl, p-hydroxyphenyl, $OR_2$, $S(O)_mR_2$, $C(O)OR_2$, $C_3$–$C_7$ cycloalkyl, $N(R_2)(R_2)$, and $C(O)N(R_2)(R_2)$; or $R_7$ and $R_{7a}$ can independently be joined to one or both of $R_4$ and $R_5$ groups to form an alkylene bridge between the terminal nitrogen and the alkyl portion of the $R_7$ or $R_{7a}$ groups, wherein the bridge contains 1 to 5 carbons atoms;

B, D, E, and F are independently $C(R_8)(R_{10})$, or C=O, such that one or two of B, D, E, or F may be optionally missing to provide a 5, 6, or 7 membered ring; or B and D or D and E taken together may be $CR_8$=$CR_{10}$, where $CR_8$=$CR_{10}$ may include a benzofusion in which $R_8$ and $R_{10}$ ethylene units are linked to form a phenyl ring;

$R_8$ and $R_{10}$ are independently selected from:
hydrogen, $R_2$, $(CH_2)_q$aryl, $(CH_2)_q$heteroaryl, $(CH_2)_qO(R_2)$,
$(CH_2)_qO(CH_2)_t$aryl, $(CH_2)_qO(CH_2)_t$heteroaryl,
$(CH_2)_qOC(O)R_2$,
$(CH_2)_qOC(O)(CH_2)_t$aryl,
$(CH_2)_qOC(O)(CH_2)_t$heteroaryl,
$(CH_2)_qOC(O)N(R_2)(R_2)$,
$(CH_2)_qOC(O)N(R_2)(CH_2)_t$aryl,
$(CH_2)_qOC(O)N(R_2)(CH_2)_t$heteroaryl, $(CH_2)_qC(O)R_2$,
$(CH_2)_qC(O)(CH_2)_t$aryl, $(CH_2)_qC(O)(CH_2)_t$heteroaryl,
$(CH_2)_qC(O)OR_2$,
$(CH_2)_qC(O)O(CH_2)_t$aryl,
$(CH_2)_qC(O)O(CH_2)_t$heteroaryl,
$(CH_2)_qC(O)N(R_2)(R_2)$, $(CH_2)_qC(O)N(R_2)(CH_2)_t$aryl,
$(CH_2)_qC(O)N(R_2)(CH_2)_t$heteroaryl,$(CH_2)_qN(R_2)(R_2)$,
$(CH_2)_qN(R_2)(R_9)$, $(CH_2)_qS(O)_mR_2$,
$(CH_2)_qS(O)_m(CH_2)_t$aryl,
$(CH_2)_qS(O)_m(CH_2)_t$heteroaryl, $(CH_2)_qSO_2N(R_2)(R_2)$,
$(CH_2)_qSO_2N(R_2)(CH_2)_t$aryl,
$(CH_2)_qSO_2N(R_2)(CH_2)_t$heteroaryl,
$(CH_2)_q$(1H-tetrazol-5-yl, $(CH_2)_qC(O)NHSO_2R_2$,
$(CH_2)_qC(O)NHSO_2(CH_2)_t$aryl,
$(CH_2)_qC(O)NHSO_2(CH_2)_t$heteroaryl,
$(CH_2)_qSO_2NHC(O)R_2$, $(CH_2)_qSO_2NHC(O)(CH_2)_t$aryl,
$(CH_2)_qSO_2NHC(O)(CH_2)_t$heteroaryl,
$(CH_2)_qSO_2NH(CH_2)_t$aryl,
$(CH_2)_qSO_2NH(CH_2)_t$heteroaryl, and
$(CH_2)_qSO_2N(R_2)$—C≡N and the $(CH_2)_t$ may be substituted by 1 to 2 $C_{1-4}$ alkyl and the $R_2$, $(CH_2)_q$ and aryl groups may optionally be substituted by 1 to 5 halogen, 1 to 3 $OR_{2a}$, $C(O)OR_{2a}$, $C(O)O(CH_2)_t$aryl, 1 to 3 $C_1-C_4$ alkyl, $C(O)N(R_{2a})(R_{2a})$, $SO_2N(R_{2a})(R_{2a})$, $S(O)_mR_{2a}$, $N(R_{2a})(R_{2a})$, 1 to 2 $CF_3$, or 1H-tetrazol-5-yl;

$R_9$ is selected from:
$R_2$, $(CH_2)_q$aryl, $(CH_2)_q$heteroaryl, $C(O)R_2$, $C(O)(CH_2)_t$aryl, $C(O)(CH_2)_t$heteroaryl, $C(O)N(R_2)(R_2)$, $C(O)N(R_2)(CH_2)_t$aryl, $C(O)N(R_2)(CH_2)_t$heteroaryl, $C(O)OR_2$, $C(O)O(CH_2)_t$aryl, $C(O)O(CH_2)_t$heteroaryl, $S(O)_2N(R_2)(R_2)$, $SO_2N(R_2)(CH_2)_t$aryl, $SO_2N(R_2)(CH_2)_t$heteroaryl, $SO_2R_2$, $SO_2(CH_2)_t$aryl, and $SO_2(CH_2)_t$ heteroaryl and the $(CH_2)_t$ may be substituted by 1 to 2 $C_1-C_4$ alkyl and the $R_2$, $(CH_2)_q$ and aryl and heteroaryl may be substituted by 1 to 5 halogen, 1 to 3 $OR_{2a}$, $C(O)OR_{2a}$, $C(O)O(CH_2)_t$aryl, 1 to 3 $C_1-C_4$ alkyl, $C(O)N(R_{2a})(R_{2a})$, $SO_2N(R_{2a})(R_{2a})$, $S(O)_mR_{2a}$, $N(R_{2a})(R_{2a})$ or 1 to 2 $CF_3$;

m is 0 to 2;
n is 1 or 2;
q is 0 to 3;
t is 0 to 3;
aryl is independently selected from: phenyl and napthyl, and heteroaryl is independently selected from: pyridyl, thiophenyl, thienyl, furanyl, benzothiophenyl, tetrazolyl, indolyl, N-methyl indolyl, dihydroindolyl, indazolyl, N-formylindolyl, benzimidazolyl, thiazolyl, pyrimidinyl and thiadiazloyl;
G, H, I and J are independently a carbon, nitrogen, sulfur or oxygen atom, such that at least one of G, H, I and J is a heteroatom, only one or two of G, H, I and J may be sulfur or oxygen, and one of G, H, I or J may be optionally missing to afford a 5 or 6 membered heterocyclic aromatic ring;

and pharmaceutically acceptable salts and individual diastereomers thereof.

2. The compound of claim 1 of the formula:

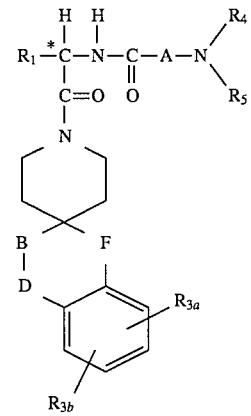

wherein:
$R_1$ is selected from:
$C_1-C_{10}$ alkyl, aryl ($C_1-C_4$ alkyl), heteroaryl ($C_1-C_4$ alkyl), $C_3-C_6$ cycloalkyl ($C_1-C_4$ alkyl), ($C_1-C_4$ alkyl)-K-($C_1-C_4$ alkyl), aryl($C_0-C_5$alkyl)-K-($C_1-C_4$ alkyl), heteroaryl($C_0-C_5$alkyl)-K-($C_1-C_4$ alkyl), ($C_3-C_7$cycloalkyl)($C_0-C_5$ alkyl)-K-($C_1-C_4$alkyl) where K is selected from O, $S(O)_m$, —$CR_2$=$CR_2$—, —C≡C— and $N(R_2)C(O)$, where $R_2$ and the alkyl groups may be further substituted by 1 to 7 halogen, $S(O)_mC_1-C_4$alkyl, 1 to 2 $OR_2$ or $C(O)OR_{2a}$ and the aryl and heteroaryl may be further substituted by 1 to 2 $C_1-C_4$ alkyl, 1 to 2 halogen, $OR_2$, $CF_3$, $OCF_3$, methylenedioxy, $S(O)_mR_{2a}$, $SO_2N(R_{2a})(R_{2a})$ or $N(R_{2a})SO_2R_{2a}$;

$R_2$ is selected from:
hydrogen, $C_1-C_6$ alkyl, $C_3-C_7$cycloalkyl, and, if two $C_1-C_6$ alkyl groups are present on one atom, they may be optionally joined to form a $C_4-C_6$ cyclic ring optionally including oxygen, sulfur or $NR_{2a}$;

$R_{2a}$ is hydrogen or $C_1-C_6$ alkyl;

$R_{3a}$ and $R_{3b}$ are independently selected from:
hydrogen, halogen, $C_1-C_4$ alkyl, $OR_2$, methylenedioxy, nitro, $S(O)_mC_1-C_4$alkyl, $CF_3$ and $C(O)OR_2$;

$R_4$ and $R_5$ are independently selected from:
hydrogen, $C_1-C_6$ alkyl, substituted $C_1-C_6$ alkyl where the substituents may be 1 to 5 halo, 1 to 2 hydroxy, 1 to 2 $C_1-C_6$ alkanoyloxy, 1 to 2 $C_1-C_6$ alkyloxy or $S(O)_m(C_1-C_4$ alkyl);

A is:

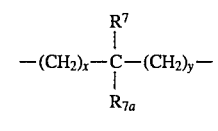

or

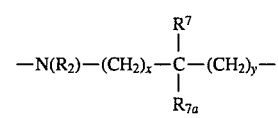

where x and y are independently 0–3;
$R_7$ and $R_{7a}$ are independently selected from:
hydrogen, $C_1-C_4$ alkyl, substituted $C_1-C_4$ alkyl where the substituents are from 1 to 3 fluoro or imidazolyl, phenyl, indolyl, $S(O)_mC_1-C_4$alkyl, $C(O)OR_2$ or $R_7$ and $R_{7a}$ can independently be joined to one or both of the $R_4$ and $R_5$ groups to form an alkylene bridge between the terminal nitrogen and the alkyl portion of the $R_7$ or $R_{7a}$ groups, wherein the bridge contains 1 to 3 carbon atoms; B, D and F are independently $C(R_8)(R_{10})$ or C=O, such that one of B, D or F may be optionally missing to provide a 5 or 6 membered ring; or B and D taken together may be $CR_8=CR_{10}$ and $CR_8=CR_{10}$ may include a benzofusion in which $R_8$ and $R_{10}$ ethylene units are linked to form a phenyl ring;

$R_8$ and $R_{10}$ are independently selected from:
hydrogen, $R_2$, $(CH_2)_q$aryl, $(CH_2)_q$aryl, $(CH_2)_qOR_2$, $(CH_2)_qO(CH_2)_t$aryl $(CH_2)_qOC(O)R_2$, $(CH_2)_qO(CH_2)_t$aryl $(CH_2)_qOC(O)R_2$, $(CH_2)_qC(O)OR_2$, $(CH_2)_qC(O)O(CH_2)_t$aryl, $(CH_2)_qC(O)O(CH_2)_t$heteroaryl, $(CH_2)_qC(O)N(R_2)(R_2)$, $(CH_2)_qC(O)N(R_2)(CH_2)_t$aryl, $(CH_2)_qC(O)N(R_2)(CH_2)_t$heteroaryl, $(CH_2)_qN(R_2)C(O)R_2$, $(CH_2)_qN(R_2)C(O)(CH_2)_t$aryl, $(CH_2)_qN(R_2)C(O)(CH_2)_t$heteroaryl, $(CH_2)_qN(R_2)C(O)N(R_2)(R_2)$, $(CH_2)_qN(R_2)C(O)N(R_2)(CH_2)_t$aryl, $(CH_2)_qN(R_2)C(O)N(R_2)(CH_2)_t$heteroaryl, $(CH_2)_qN(R_2)SO_2R_2$, $(CH_2)_qN(R_2)SO_2(CH_2)_t$aryl, $(CH_2)_qN(R_2)SO_2(CH_2)_t$heteroaryl, $(CH_2)_qS(O)_mR_2$, $(CH_2)_qS(O)_m(CH_2)_t$aryl, $(CH_2)_qS(O)_m(CH_2)_t$heteroaryl, $(CH_2)_qS(O)_mNHCN$, $(CH_2)_qS(O)_mN(R_2)CN$, $(CH_2)_q$(1H-tetrazol-5-yl), $(CH_2)_qC(O)NHSO_2R_2$, $(CH_2)_qC(O)NHSO_2(CH_2)_t$aryl, $(CH_2)_qC(O)NHSO_2(CH_2)_t$heteroaryl, $(CH_2)_qSO_2NH(CH_2)_t$aryl, $(CH_2)_qSO_2NH(CH_2)_t$heteroaryl, $(CH_2)_qSO_2NHC(O)R_2$, $(CH_2)_qSO_2NHC(O)(CH_2)_t$aryl, and $(CH_2)_qSO_2NHC(O)(CH_2)_t$heteroaryl, and where the $(CH_2)_t$ and $(CH_2)_q$ may be substituted by 1 to 2 $C_1-C_2$ alkyl and the $C_1-C_6$ alkyl, $R_2$ and the aryl and heteroaryl may be substituted by 1 to 2 halogens, $OR_{2a}$, $C(O)OR_a$, $C(O)O(CH_2)_t$aryl, $S(O)_mC_1-C_4$ alkyl, 1 to 2 $C_1-C_3$ alkyl or 1H-tetrazol-5-yl;

m is 0 to 2;

q is 0 to 3;

t is 0 to 3;

aryl is independently selected from: phenyl and napthyl, and heteroaryl is independently selected from: pyridyl, thienyl, furanyl, indolyl, N-methyl indolyl, thiazolyl, and pyrimidinyl;

and the pharmaceutically acceptable salts and individual diastereomers thereof.

3. The compound of claim 2 where F is not present.

4. The compound of claim 3 of the formula:

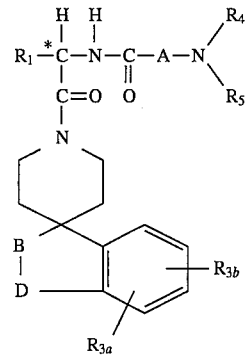

wherein:

$R_1$ is selected from:
$C_1-C_{10}$ alkyl, aryl ($C_1-C_4$ alkyl), heteroaryl ($C_1-C_4$ alkyl), $C_5-C_6$cycloalkyl ($C_1-C_4$ alkyl) or ($C_1-C_4$ alkyl)-K-$C_1-C_2$alkyl-, aryl($C_0-C_2$alkyl)-K-($C_1-C_2$ alkyl), heteroaryl($C_0-C_2$alkyl)-K-($C_1-C_2$ alkyl), $C_3-C_6$cycloalkyl ($C_0-C_2$alkyl)-K-($C_1-C_2$alkyl), where K is $O,S(O)_m$ and the aryl and heteroaryl may be further substituted by 1 to 2 $C_1-C_4$ alkyl, 1 to 2 $OR_2$, $C(O)OR_2$, $S(O)_mR_2$ or 1 to 3 halogen;

$R_2$ is selected from:
hydrogen, $C_1-C_4$ alkyl, $C_3-C_6$ cycloalkyl, and, if two $C_1-C_4$ alkyls are present on one atom, they may be optionally joined to form a $C_5-C_6$ cyclic ring optionally including oxygen or $NR_{2a}$;

$R_{2a}$ is hydrogen or $C_1-C_4$ alkyl;

$R_{3a}$ and $R_{3b}$ are independently selected from:
hydrogen, halogen, $C_1-C_4$ alkyl, hydroxy, C(O)OR, $C_1-C_4$ alkoxy, $S(O)_mC_1-C_4$ alkyl or $CF_3$;

$R_4$ and $R_5$ are independently selected from:
hydrogen, $C_1-C_4$ alkyl, substituted $C_1-C_4$ alkyl where the substituents may be 1 to 2 hydroxy or $S(O)_m(C_1-C_3$alkyl);

A is:

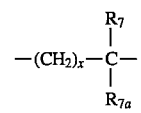

where x is 0 or 1;

$R_7$ and $R_{7a}$ are independently selected from:
hydrogen, $C_1-C_3$ alkyl; or $R_7$ and $R_{7a}$ can independently be joined to one or both of the $R_4$ and $R_5$ groups to form an alkylene bridge between the terminal nitrogen and the alkyl portion of the $R_7$ or $R_{7a}$ groups to form 5 or 6 membered rings containing the terminal nitrogen;

B and D are independently $C(R_8)(R_{10})$, or C=O, or B and D taken together may be $CR_8=CR_{10}$;

$R_8$ and $R_{10}$ are independently selected from:
hydrogen, $R_2$, $(CH_2)_q$aryl, $(CH_2)_q$heteroaryl, $(CH_2)_qOR_2$, $(CH_2)_qO(CH_2)_t$aryl, $(CH_2)_qO(CH_2)_t$heteroaryl, $(CH_2)_qOC(O)R_2$, $(CH_2)_qC(O)OR_2$, $(CH_2)_qC(O)O(CH_2)_t$aryl, $(CH_2)_qC(O)O(CH_2)_t$heteroaryl, $(CH_2)_qC(O)N(R_2)(R_2)$, $(CH_2)_qC(O)N(R_2)(CH_2)_t$aryl, $(CH_2)_qC(O)N(R_2)(CH_2)_t$heteroaryl, $(CH_2)_qN(R_2)C(O)R_2$, $(CH_2)_qN(R_2)C(O)(CH_2)_t$aryl, (CH₂)_qN(R₂)C(O)(CH₂)_theteroaryl,
(CH₂)_qN(R₂)C(O)N(R₂)(R₂),
(CH₂)_qN(R₂)C(O)N(R₂)(CH₂)_taryl,
(CH₂)_qN(R₂)C(O)N(R₂)(CH₂)_theteroaryl,
(CH₂)_qN(R₂)SO₂R₂,  (CH₂)_qN(R₂)SO₂(CH₂)_taryl,
(CH₂)_qN(R₂)SO₂(CH₂)_theteroaryl, (CH₂)_qS(O)_mR₂,
(CH₂)_q(1H-tetrazol-5-yl), (CH₂)_qC(O)NHSO₂R₂,
(CH₂)_qC(O)NHSO₂(CH₂)_taryl,
(CH₂)_qC(O)NHSO₂(CH₂)_theteroaryl,
(CH₂)_qSO₂NH(CH₂)_taryl,
(CH₂)_qSO₂NH(CH₂)_theteroaryl,
(CH₂)_qSO₂NHC(O)R₂,
(CH₂)_qSO₂NHC(O)(CH₂)_taryl and
(CH₂)_qSO₂NHC(O)(CH₂)_theteroaryl, and where the (CH₂)_t and (CH₂)_q may be substituted by 1 to 2 C₁–C₂ alkyl and the R₂ and aryl groups may optionally be substituted by 1 to 2 halogens, OR_{2a}, C(O)OR_{2a}, C(O)O(CH₂)_taryl, S(O)_mR_{2a}, 1 to 2 C₁–C₃ alkyl or 1H-tetrazol-5-yl;

q is 0 to 2;

t is 0 to 2; and aryl is independently selected from: phenyl and napthyl, and heteroaryl is independently selected from: indolyl, N-methyl indolyl, and pyrimidinyl;
and the pharmaceutically acceptable salts and individual diastereomers thereof.

5. A compound of the formula

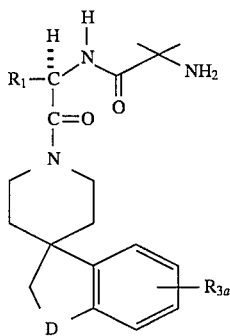

wherein:

R₁ is selected from:

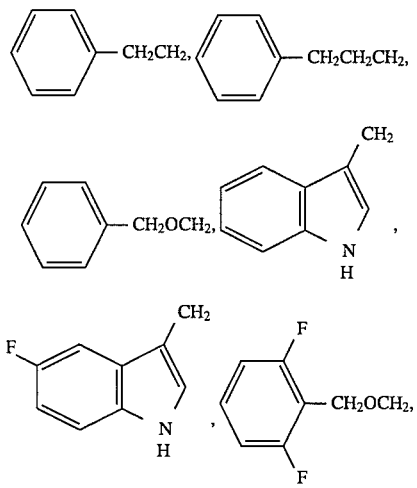

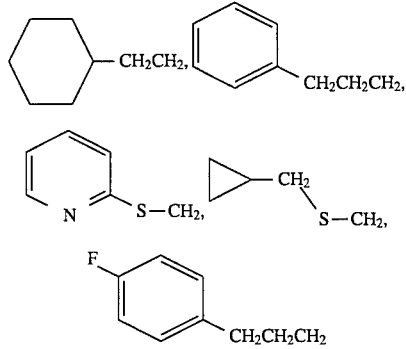

R_{3a} is hydrogen or fluoro,
D is selected from the group consisting of:

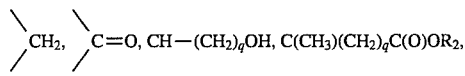

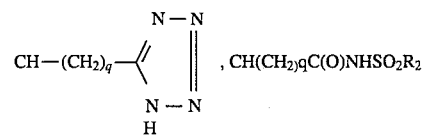

R₂ is hydrogen or C₁–C₄ alkyl;

q is 0, 1, or 2;
and the pharmaceutically acceptable salts and individual diastereomers thereof.

6. A compound which is selected from the group consisting of:

N-[1(R)-[(2,3-dihydrospiro[1H-indene-1,4'piperidin]-1'-yl)-carbonyl]-2-(1H-indol-3-yl)ethyl]-2-amino-2-methylpropanamide;

N-[1(RS)-[(2,3-dihydrospiro[1H-indene-1,4'-piperidin]-1'-yl)carbonyl]-2-(5-fluoro-1H-indol-3-yl)ethyl]-2-amino-2-methyl-propanamide;

N-[1(RS)-[(2,3-dihydro-3-oxospiro[1H-indene-1,4'-piperidin]-1'-yl)-carbonyl]-2-(1H-indol-3-yl)ethyl]-2-amino-2-methylpropanamide;

N-[1(RS)-[(2,3-dihydro-3(RS)-hydroxyspiro[1H-indene-1,4'-piperidin]-1'-yl)carbonyl]-2-(1H-indol-3-yl)ethyl]-2-amino-2-methyl-propanamide;

N-[1(R)-[(2,3-dihydro-6-fluorospiro[1H-indene-1,4'-piperidin]-1'-yl)carbonyl]-2-(indol-3-yl)ethyl]-2-amino-2-methylpropanamide;

N-[1(R)-[(2,3-dihydrospiro[1H-indene-1,4'-piperidin]-1'-yl)-carbonyl]-2(phenylmethyloxy)ethyl]-2-amino-2-methylpropanamide;

N-[1(R)-[(2,3-dihydro-3-oxospiro[1H-indene-1,4'-piperidin]-1'-yl)-carbonyl]-2-(phenylmethyloxy)ethyl]-2-amino-2-methylpropanamide;

N-[1(R)-[(2,3-dihydro-3(RS)-hydroxyspiro[1H-indene-1,4'-piperidin]-1'-yl) carbonyl]-2-(phenylmethyloxy)ethyl]-2-amino-2-methyl-propanamide;

N-[1(R)-[(2,3-dihydrospiro[1H-indene-1,4'-piperidin]-1'-yl)-carbonyl]-2-(2',6'-difluorophenylmethyloxy)ethyl]-2-amino-2-methyl-propanamide;

N-[1(RS)-[(2,3-dihydro-3(RS)-hydroxyspiro[1H-indene-1,4'-piperidin]-1'-yl) carbonyl]-3-phenylpropyl]-2-amino-2-methyl-propanamide;

N-[1(R)-[(2,3-dihydro-3-oxospiro[1H-indene-1,4-piperidin]-1'-yl)carbonyl]-3-cyclohexylpropyl]-2-amino-2-methylpropanamide;

N-[1(R)-[(2,3-dihydro-3-(RS)-hydroxyspiro[1H-indene-1,4'-piperidin]-1'-yl)carbonyl]-3-cyclohexylpropyl]-2-amino-2-methyl-propanamide;

N-[1(R)-[(2,3-dihydro-3-oxospiro[1H-indene-1,4'-piperidin]-1'-yl)carbonyl]-4-phenylbutyl]-2-amino-2-methylpropanamide; or N-[1(R)-[(2,3-dihydro-3(RS)-hydroxyspiro[1H-indene-1,4'-piperidin]-1'-yl)carbonyl]-4-phenylbutyl]-2-amino-2-methyl-propanamide;

1'-[2(R)-[(2-amino-2-methyl-1-oxopropyl)amino]-3-(indole-3-yl)-1-oxopropyl]-2,3-dihydrospiro[1H-indene-1,4'-piperidine]-3-carboxylic acid;

1'[2(R)-[(2-amino-2-methyl-1-oxopropyl)amino]-3-(indole-3-yl)-1-oxopropyl]-2,3-dihydrospiro[1H-indene-1,4'-piperidine-3-carboxylic acid ethyl ester;

1'-[2(R)-[(2-amino-2-methyl-1-oxopropyl)amino]-5-phenyl-1-oxopentyl]-2,3-dihydrospiro[1H-indene-1,4'-piperidine]-3-carboxylic acid;

1'-[2(R)-[(2-amino-2-methyl-1-oxopropyl)amino]-5-phenyl-1-oxopentyl]-2,3-dihydrospiro[1H-indene-1,4'-piperidine]-3-carboxylic acid ethyl ester;

1'-[2(R)-[(2-amino-2-methyl-1-oxopropyl)amino]-3-(indole-3-yl)-1-oxopropyl]-2,3-dihydrospiro[1H-indene-1,4'-piperidine]-3-acetic acid;

1'-[2(R)-[(2-amino-2-methyl-1-oxopropyl)amino]-3-(indole-3-yl)-1-oxopropyl]-2,3-dihydrospiro[1H-indene-1,4'-piperidine]-3(R)-acetic acid;

1'-[2(R)-[(2-amino-2-methyl-1-oxopropyl)amino]-3-(indole-3-yl)-1-oxopropyl]-2,3-dihydrospiro[1H-indene-1,4'-piperidine]-3(S)-acetic acid;

1'-[2(R)-[(2-amino-2-methyl-1-oxopropyl)amino]-3-(indole-3-yl)-1-oxopropyl]-2,3-dihydrospiro[1H-indene-1,4'-piperidine]-3-acetic acid ethyl ester;

1'-[2(R)-[(2-amino-2-methyl-1-oxopropyl)amino]-3-(indole-3-yl)-1-oxopropyl]-2,3-dihydrospiro[1H-indene-1,4'-piperidine]-3(R)-acetic acid ethyl ester;

1'-[2(R)-[(2-amino-2-methyl-1-oxopropyl)amino]-3-(indole-3-yl)-1-oxopropyl]-2,3-dihydrospiro[1H-indene-1,4'-piperidine]-3(S)-acetic acid ethyl ester;

1'-[2(R)-[(2-amino-2-methyl-1-oxopropyl)amino]-3-(5-fluoro-indole-3-yl)-1-oxopropyl]-2,3-dihydrospiro[1H-indene-1,4-piperidine]-3-acetic acid;

1'-[2(R)-[(2-amino-2-methyl-1-oxopropyl)amino]-3-(5-fluoro-indole-3-yl)-1-oxopropyl]-2,3-dihydrospiro[1H-indene-1,4-piperidine]-3(R)-acetic acid;

1'-[2(R)-[(2-amino-2-methyl-1-oxopropyl)amino]-3-(5-fluoro-indole-3-yl)-1-oxopropyl]-2,3-dihydrospiro[1H-indene-1,4-piperidine]-3(S)-acetic acid;

1'-[2(R)-[(2-amino-2-methyl-1-oxopropyl)amino]-3-(5-fluoro-indole-3-yl)-1-oxopropyl]-2,3-dihydrospiro[1H-indene-1,4-piperidine]-3-acetic acid ethyl ester;

1'-[2(R)-[(2-amino-2-methyl-1-oxopropyl)amino]-3-(5-fluoro-indole-3-yl)-1-oxopropyl]-2,3-dihydrospiro[1H-indene-1,4-piperidine]-3(R)-acetic acid ethyl ester;

1'-[2(R)-[(2-amino-2-methyl-1-oxopropyl)amino]-3-(5-fluoro-indole-3-yl)-1-oxopropyl]-2,3-dihydrospiro[1H-indene-1,4-piperidine]-3(S)-acetic acid ethyl ester;

1'-[2(R)-[(2-amino-2-methyl-1-oxopropyl)amino]-3-(phenyl-methoxy)-1-oxopropyl]-2,3-dihydrospiro[1H-indene-1,4-piperidine]-3-acetic acid;

1'-[2(R)-[(2-amino-2-methyl-1-oxopropyl)amino]-3-(phenyl-methoxy)-1-oxopropyl]-2,3-dihydrospiro[1H-indene-1,4-piperidine]-3-acetic acid ethyl ester;

1'-[2(R)-[(2-amino-2-methyl-1-oxopropyl)amino]-3-(2,6-difluoro-phenylmethoxy)-1-oxopropyl]-2,3-dihydrospiro[1H-indene-1,4'-piperidine]-3-acetic acid;

1'-[2(R)-[(2-amino-2-methyl-1-oxopropyl)amino]-3-(2,6-difluoro-phenylmethoxy)-1-oxopropyl]-2,3-dihydrospiro[1H-indene-1,4'-piperidine]-3-acetic acid ethyl ester;

1'-[2(R)-[(2-amino-2-methyl-1-oxopropyl)amino]-3-(5-fluoro-indole-3-yl)-1-oxopropyl]-2,3-dihydro-6-fluorospiro[1H-indene-1,4'-piperidine]-3-acetic acid;

1'-[2(R)-[(2-amino-2-methyl-1-oxopropyl)amino]-3-(5-fluoro-indole-3-yl)-1-oxopropyl]-2,3-dihydro-6-fluorospiro[1H-indene-1,4'-piperidine]-3-acetic acid ethyl ester;

1'-[2(R)-[(2-amino-2-methyl-1-oxopropyl)amino]-5-phenyl-1-oxopentyl]-2,3-dihydrospiro[1H-indene-1,4'-piperidine]-3-propanoic acid;

1'-[2(R)-[(2-amino-2-methyl-1-oxopropyl)amino]-5-phenyl-1-oxopentyl]-2,3-dihydrospiro[1H-indene-1,4'-piperidine]-3-propionic acid ethyl ester;

1'-[2(R)-[(2-amino-2-methyl-1-oxopropyl)amino]-5-phenyl-1-oxopentyl]-2,3-dihyphospiro[1H-indene-1,4'-piperidine]-3-acetic acid;

1'-[2(R)-[(2-amino-2-methyl-1-oxopropyl)amino]-5-phenyl-1-oxopentyl]-2,3-dihydrospiro[1H-indene-1,4'-piperidine]-3(S)-acetic acid;

1'-[2(R)-[(2-amino-2-amino-2-methyl-1-oxopropyl)amino]-5-phenyl-1-oxopentyl]-2,3-dihydrospiro[1H-indene-1,4'-piperidine]-3(R)-acetic acid;

1'-[2(R)-[(2-amino-2-methyl-1-oxopropyl)amino]-5-phenyl-1-oxopentyl]-2,3-dihydrospiro[1H-indene-1,4'-piperidine]-3-acetic acid ethyl ester;

1'-[2(R)-[(2-amino-2-methyl-1-oxopropyl)-amino]-5-phenyl-1-oxopentyl]-2,3-dihydrospiro[1H-indene-1,4'-piperidine]-3(S)-acetic acid ethyl ester;

1'-[2(R)-[(2-amino-2-methyl-1-oxopropyl)amino-5-phenyl-1-oxopentyl]-2,3-dihydrospiro[1H-indene-1,4'-piperidine]-3(R)-acetic acid ethyl ester;

N-ethyl-1'-[2(R)-[(2-amino-2-methyl-1-oxopropyl)amino]-5-phenyl-1-oxopentyl]-2,3-dihydrospiro[1H-indene-1,4'-piperidine]-3-acetamide;

N-ethyl-1'-[2(R)-[(2-amino-2-methyl-1-oxopropyl)amino]-5-phenyl-1-oxopentyl]-2,3-dihydrospiro[1H-indene-1,4'-piperidine]-3(S)-acetamide;

N-ethyl-1'-[2(R)-[(2-amino-2-methyl-1-oxopropyl)amino]-5-phenyl-1-oxopentyl]-2,3-dihydrospiro[1H-indene-1,4-piperidine]-3(R)-acetamide;

1'-[2(R)-[(2-amino-2-methyl-1-oxopropyl)amino]-5-phenyl-1-oxopentyl]-2,3-dihydro-6-fluorospiro[1H-indene-1,4-piperidine]-3-acetic acid;

1'-[2(R)-[(2-amino-2-methyl-1-oxopropyl)amino]-5-phenyl-1-oxopentyl-2,3-dihydro-6-fluorospiro[1H-indene-1,4'-piperidine]-3-acetic acid ethyl ester;

1'-[2(R)-[(2-amino-2-methyl-1-oxopropyl)amino]-5-phenyl-1-oxopentyl]-2,3-dihydrospiro[1H-indene-1,4'-piperidine]-3-propanoic acid;

1'-[2(R)-[(2-amino-2-methyl-1-oxopropyl)amino]-5-phenyl-1-oxopentyl]-2,3-dihydrospiro[1H-indene-1,4'-piperidine]-3-propanoic acid ethyl ester;

1'-[2(R)-[(2-amino-2-methyl-1-oxopropyl)amino]-3-(indole-3-yl)-1-oxopropyl]-2,3-dihydro-6-fluorospiro[1H-indene-1,4'-piperidine]-3-acetic acid;

and pharmaceutically acceptable salts thereof.

7. A compound of claim 1 which is selected from:

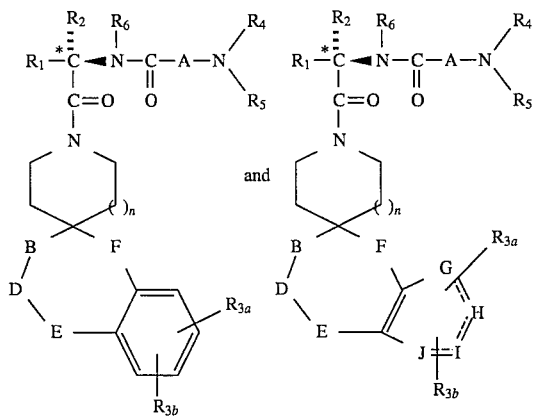

wherein $R^1$, $R^2$, $R^{3a}$, $R_{3b}$, $R^4$, $R_5$, $R_6$, A, B, D, E, F, G, H, I, J, and n are as defined in claim 1.

8. A process for the preparation of a compound of claim 1 which comprises reacting a compound having the formula:

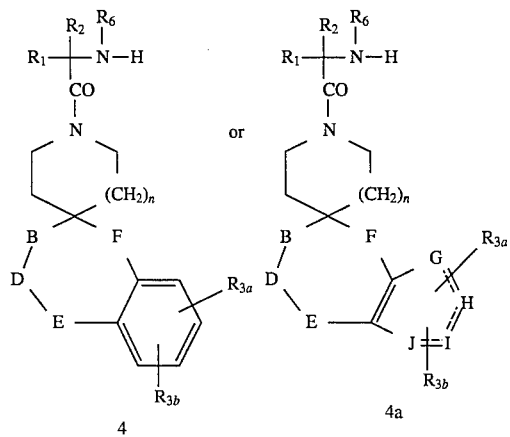

with a compound having the formula

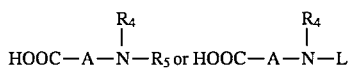

where $R_1$, $R_2$, $R_{3a}$, $R_{3b}$, $R_4$, $R_5$, $R_6$, A, B, D, E, F, G, H, I, J and n are as defined in claim 1.

9. A process for the preparation of a compound of claim 1 which comprises reacting a compound having the formula:

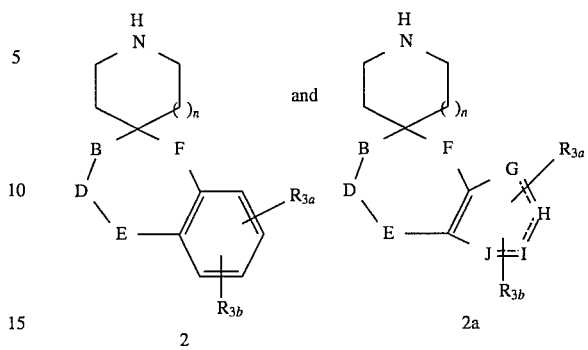

with a compound having the formula

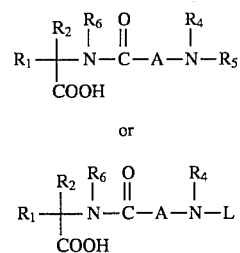

where $R_1$, $R_2$, $R_{3a}$, $R_{3b}$, $R_4$, $R_5$, $R_6$, A, B, C, D, E, F, G, H, I, J, and n are as defined in claim 1 and L is a protecting group which is subsequently removed if present and salts are formed if desired.

10. A pharmaceutical composition which comprises an inert carrier and an effective amount of the compound of claim 1.

11. A pharmaceutical composition which comprises an inert carrier; an effective amount of a compound of claim 1; and another growth hormone secretagogue.

12. The pharmaceutical composition of claim 11 where the other growth hormone secretagogue is selected from the group consisting of: GHRP-6, GHRP-1, GHRP-2, growth hormone releasing factor, an analog of growth hormone releasing factor, IGF-1, and IGF-2.

13. A pharmaceutical composition which comprises an inert carrier; a bisphosphonate compound; and a compound of claim 1.

14. The pharmaceutical composition of claim 13 where the bisphosphonate compound is alendronate.

15. A method for increasing levels of endogenous growth hormone in a human or an animal which comprises administering to such human or animal an effective amount of a compound of claim 1.

16. A method for the treatment of osteoporosis which comprises administering to a patient with osteoporosis a bisphosphonate compound in combination with an effective amount of the compound of claim 1.

17. The method of claim 16 where the bisphosphonate compound is alendronate.

* * * * *